(12) United States Patent
Middleman et al.

(10) Patent No.: US 7,722,626 B2
(45) Date of Patent: *May 25, 2010

(54) METHOD OF MANIPULATING MATTER IN A MAMMALIAN BODY

(75) Inventors: Lee M. Middleman, Portola Valley, CA (US); Walter R. Pyka, Redwood City, CA (US); Michael Buhler, Los Gatos, CA (US); Philippe Poncet, Fremont, CA (US); Karl Van Dyk, Fremont, CA (US); James Jervis, Atherton, CA (US)

(73) Assignee: Medtronic, Inc., Minneapolis, MN (US)

( * ) Notice: Subject to any disclaimer, the term of this patent is extended or adjusted under 35 U.S.C. 154(b) by 1291 days.

This patent is subject to a terminal disclaimer.

(21) Appl. No.: 11/196,944

(22) Filed: Aug. 4, 2005

(65) Prior Publication Data

US 2006/0052799 A1 Mar. 9, 2006

Related U.S. Application Data

(60) Continuation of application No. 10/238,813, filed on Sep. 9, 2002, now Pat. No. 6,986,774, which is a division of application No. 08/914,081, filed on Aug. 18, 1997, now Pat. No. 6,447,523, which is a division of application No. 08/398,629, filed on Mar. 3, 1995, now Pat. No. 6,004,330, and a continuation-in-part of application No. 07/774,016, filed on Oct. 9, 1991, now Pat. No. 5,486,183, which is a continuation-in-part of application No. 07/394,463, filed on Aug. 16, 1989, now abandoned, and a continuation-in-part of application No. 07/594,768, filed on Oct. 9, 1990, now abandoned, and a continuation-in-part of application No. 07/608,117, filed on Nov. 1, 1990, now abandoned, and a continuation-in-part of application No. 07/594,769, filed on Oct. 9, 1990, now abandoned, and a continuation-in-part of application No. 07/608,121, filed on Nov. 1, 1990, now abandoned, and a continuation-in-part of application No. 07/594,871, filed on Oct. 9, 1990, now abandoned, and a continuation-in-part of application No. 07/594,896, filed on Oct. 9, 1990, now abandoned, and a continuation-in-part of application No. 07/594,874, filed on Oct. 9, 1990, now abandoned, and a continuation-in-part of application No. 07/594,873, filed on Oct. 9, 1990, now abandoned, and a continuation-in-part of application No. 07/656,651, filed on Feb. 15, 1991, now abandoned.

(51) Int. Cl.
 *A61F 11/00* (2006.01)
(52) U.S. Cl. ...................................... 606/113; 606/127
(58) Field of Classification Search .................... 606/1, 606/108, 113, 114, 127, 159, 200, 21; 128/898
See application file for complete search history.

(56) References Cited

U.S. PATENT DOCUMENTS 1,609,014 A 11/1926 Dowd (Continued)

FOREIGN PATENT DOCUMENTS

EP 0145166 6/1985

*Primary Examiner*—Kevin T Truong
(74) *Attorney, Agent, or Firm*—Marc Karrish

(57) ABSTRACT

The invention provides a method of using an apparatus for manipulating matter in a confined or inaccessible space, comprising providing an apparatus having manipulator means at least partly constructed of one or more bent or twisted elongate shape memory alloy members having pseudoelasticity at the intended manipulation temperature, and a hollow housing or cannula capable of holding at least the shape memory alloy member(s) in a relatively straightened state, and actuating means for extending the shape memory alloy member(s) from the housing to manipulate matter within the space and for withdrawing the shape memory alloy member(s) into the housing, the arrangement being such that the shape-memory alloy member(s) bend(s) or twist(s) pseudoelastically in a lateral or helical sense to manipulate the matter on extending from the housing at the manipulation temperature, and become(s) relatively straightened on withdrawal into the housing at the temperature.

20 Claims, 100 Drawing Sheets

U.S. PATENT DOCUMENTS

| | | | |
|---|---|---|---|
| 2,114,695 A | 4/1938 | Anderson | |
| 2,137,710 A | 11/1938 | Anderson | |
| 2,670,519 A | 3/1954 | Recklitis | |
| 3,404,677 A | 10/1968 | Springer | |
| 3,472,230 A | 10/1969 | Fogarty | |
| 3,868,956 A | 3/1975 | Alfidi et al. | |
| 3,877,434 A | 4/1975 | Ferguson et al. | |
| 4,174,715 A | 11/1979 | Hasson | |
| 4,190,042 A | 2/1980 | Sinnreich | |
| 4,222,380 A | 9/1980 | Terayama | |
| 4,249,533 A | 2/1981 | Komiya | |
| 4,347,846 A | 9/1982 | Dormia | |
| 4,425,908 A | 1/1984 | Simon | |
| 4,469,100 A | 9/1984 | Hardwick | |
| 4,505,767 A | 3/1985 | Quin | |
| 4,509,517 A | 4/1985 | Zibelin | |
| 4,557,255 A | 12/1985 | Goodman | |
| 4,616,656 A | 10/1986 | Nicholson | |
| 4,655,219 A | 4/1987 | Petruzzi | |
| 4,657,020 A | 4/1987 | Lifton | |
| 4,665,906 A | 5/1987 | Jervis | |
| 4,691,705 A | 9/1987 | Okada | |
| 4,710,181 A | 12/1987 | Fugua | |
| 4,738,666 A | 4/1988 | Fugua | |
| 4,741,335 A | 5/1988 | Okada | |
| 4,744,363 A | 5/1988 | Hasson | |
| 4,768,505 A | 9/1988 | Okada et al. | |
| 4,776,844 A | 10/1988 | Ueda | |
| 4,799,474 A | 1/1989 | Ueda | |
| 4,898,156 A | 2/1990 | Gattuma | |
| 4,899,743 A | 2/1990 | Nicholson | |
| 4,909,789 A | 3/1990 | Taguchi et al. | |
| 4,926,860 A | 5/1990 | Stice | |
| 4,935,068 A | 6/1990 | Duerig | |
| 4,946,468 A | 8/1990 | Li | |
| 4,997,435 A | 3/1991 | Demeter | |
| 5,057,114 A | 10/1991 | Wittich et al. | |
| 5,064,428 A | 11/1991 | Cope et al. | |
| 5,074,867 A | 12/1991 | Wilk | |
| 5,084,054 A * | 1/1992 | Bencini et al. | 606/113 |
| 5,103,804 A | 4/1992 | Abele et al. | |
| 5,123,906 A | 6/1992 | Kelman | |
| 5,147,371 A | 9/1992 | Washington | |
| 5,171,233 A * | 12/1992 | Amplatz et al. | 606/127 |
| 5,171,314 A | 12/1992 | Dulebohn | |
| 5,190,561 A | 3/1993 | Graber | |
| 5,231,989 A | 8/1993 | Middleman et al. | |
| 6,004,330 A | 12/1999 | Middleman et al. | |
| 6,551,327 B1 | 4/2003 | Dhindsa | |
| 6,755,779 B2 | 6/2004 | Vanden Hoek et al. | |

\* cited by examiner

METHOD OF MANIPULATING MATTER IN A MAMMALIAN BODY

CROSS-REFERENCES TO RELATED APPLICATIONS

This application is a continuation-in-part of U.S. application Ser. No. 10/238,813, filed Sep. 9, 2002, now U.S. Pat. No. 6,986,774, which is a divisional application of U.S. application Ser. No. 08/914,081, filed Aug. 18, 1997, now U.S. Pat. No. 6,447,523, which is a divisional application of U.S. application Ser. No. 08/398,629, filed Mar. 3, 1995, now U.S. Pat. No. 6,004,330, and a continuation-in-part of U.S. application Ser. No. 07/843,775, filed Feb. 28, 1992, now U.S. Pat. No. 5,632,746, and which is a continuation-in-part of U.S. application Ser. No. 07/774,016, filed Oct. 9, 1991, now U.S. Pat. No. 5,486,183, which is a continuation-in-part application of U.S. applications Ser. Nos.: 07/394,463, filed Aug. 16, 1989, now abandoned; 07/594,768, filed Oct. 9, 1990, now abandoned, 07/608,117, filed Nov. 1, 1990, now abandoned; 07/594,769, filed Oct. 9, 1990, now abandoned; Ser. No. 07/594,871, filed Oct. 9, 1990, now abandoned; Ser. No. 07/594,873, filed Oct. 9, 1990, now abandoned; Ser. No. 07/594,874, filed Oct. 9, 1990, now abandoned; Ser. No. 07/594,896, filed Oct. 9, 1990, now abandoned; Ser. No. 07/608,117, filed Nov. 1, 1990, now abandoned; Ser. No. 07/608,121, filed Nov. 1, 1990, now abandoned; 07/594,871, filed Oct. 9, 1990, now abandoned; 07/594,896, filed Oct. 9, 1990, now abandoned; 07/594,874, filed Oct. 9, 1990, now abandoned; 07/594,873, filed Oct. 9, 1990, now abandoned; and 07/656,651, filed Feb. 15, 1991, now abandoned. The entire disclosures of these applications are hereby incorporated by reference for all purposes.

BACKGROUND OF THE INVENTION

1. Field of the Invention

This invention relates to a device or apparatus for manipulating matter within a confined or inaccessible space, especially during surgery in a living body.

2. Description of the Prior Art

Matter may be manipulated in such circumstances in various ways, for example by application of a ligature, by suturing, by cutting with a knife or scissor action, or by capture and retrieval in devices such as screens, baskets, barriers, pouches, or retractors. Such manipulation may be difficult when operating in the confined space of a very deep wound or through a small arthroscopic or other endoscopic incision or body aperture.

Many forms of apparatus for performing surgical operations have been proposed previously using flexible steel wires which spring apart when extended from the distal end of a tube and which can be brought together again on withdrawal back into the tube. Examples of such known devices may be seen in U.S. Pat. Nos. 2,114,695; 2,137,710; 2,670,519; 3,404,677; 4,174,715; 4,190,042; 4,222,380; 4,249,533; 4,347,846; 4,655,219; 4,691,705; 4,741,335, 4,768,505; and 4,909,789. However, these devices may not be completely satisfactory for various reasons, especially after repeated use or long storage which may fatigue the materials used.

Attempts have been made to use shape memory metals in surgical apparatus, but these suffer from inconvenience and from the risk of damage to living tissues resulting from the need either to cool the memory metal while positioning it in the body so that body heat thereafter actuates the shape memory effect, or to heat the metal above body temperature to actuate it after positioning. Examples of such attempts are described in U.S. Pat. Nos. 4,509,517; 3,868,956; and 4,425,908.

SUMMARY OF THE INVENTION

The present invention uses pseudoelastic materials, preferably pseudoelastic shape memory alloys, which bend pseudoelastically to perform manipulations which may be difficult or impossible to achieve reliably with previously known devices. Pseudoelastic alloys have previously been described for non-manipulative devices such as lesion marker probes, bone anchors, heart valves, intrauterine devices, dental arch wire, coil stents and filters, as described in U.S. Pat. No. 4,665,906 (Jervis), U.S. Pat. No. 4,616,656 (Nicholson), U.S. Pat. No. 4,898,156 (Gattuma), U.S. Pat. No. 4,899,753 (Nicholson), and U.S. Pat. No. 4,946,468 (Li). In one case, U.S. Pat. No. 4,926,860 (Stice) describes a straight suturing needle made of such alloy which ensures the needle emerges straight after being inserted through a curved cannula. None of these known uses in any way suggests the present ingenious use of the power of pseudoelastic bending on extending a pseudoelastic manipulator means from a cannula to perform manipulations in difficult locations.

The present invention accordingly provides a device or apparatus for manipulating matter in a confined or inaccessible space, comprising:

(i) manipulator means at least partly constructed of one or more bent or twisted elongate shape memory alloy members having pseudoelasticity at the intended manipulation temperature, and (ii) a hollow housing (preferably of elongate tubular form) or cannula capable of holding at least the shape memory alloy member(s) in a relatively straightened state, and (iii) actuating means for extending the shape memory alloy member(s) from the housing to manipulate matter within the said space and for withdrawing the shape memory alloy member(s) into the housing, the arrangement being such that the shape-memory alloy member(s) bend(s) or twist(s) pseudoelastically in a lateral or helical sense to manipulate the matter on extending from the housing at the said manipulation temperature, and become(s) relatively straightened on withdrawal into the housing at the said temperature.

Preferably the invention provides such a device or apparatus which is of elongate form for surgical manipulation of matter within a living body, and which has the manipulator means at its distal end with the shape memory alloy member(s) having pseudoelasticity at the temperature to be encountered within that body, and wherein the actuating means is operable from the proximal end of the device.

Various forms of device or apparatus will now be described independently, it being understood that all may be inventive in themselves, although all are preferably within the scope of at least the first (more preferably both) of the two immediately preceding paragraphs, Non-surgical uses may be appropriate for some forms.

Any elastic material may be used in some of the embodiments of this invention, but it is generally preferred to use a pseudoelastic material. Many different materials exhibit pseudoelasticity and can be used in any embodiment of this invention. It is preferred to use a pseudoelastic shape memory alloy.

The term "elastic material" is used herein to mean a material that has spring-like properties, that is, it is capable of being deformed by an applied stress and then springing back, or recovering, to or toward its original unstressed shape or configuration when the stress is removed. The elastic material is preferably highly elastic. The material can be polymeric or metallic, or a combination of both. The use of metals, such as shape memory alloys, is preferred. Shape memory alloys that exhibit pseudoelasticity, in particular superelasticity, are especially preferred. The elastic materials herein exhibit greater than 1% elastic deformation, more generally greater than 2% elastic deformation. Preferably, the elastic materials herein exhibit greater than 4% elastic deformation, more preferably greater than 6% elastic deformation.

Preferably, the elastic member is at least partially formed from a pseudoelastic material, such as a shape memory alloy that exhibits pseudoelasticity. Shape memory alloys which exhibit superelasticity (also referred to in the literature as non-linear pseudoelasticity), are especially preferred.

U.S. Pat. No. 4,935,068 to Duerig, which is commonly assigned with the present application and incorporated herein by reference, teaches the fundamental principles of shape memory alloys. Some alloys which are capable of transforming between martensitic and austenitic phases are able to exhibit a shape memory effect. The transformation between phases may be caused by a change in temperature. For example, a shape memory alloy in the martensitic phase will begin to transform to the austenitic phase when its temperature rises above $A_S$ and the transformation will be complete when the temperature rises above $A_f$. The forward transformation will begin when the temperature drops below $M_S$ and will be complete when the temperature drops below $M_f$. The temperatures $M_S$, $M_f$, $A_S$, and $A_f$ define the thermal transformation hysteresis loop of the shape memory alloy.

Under certain conditions, shape memory alloys exhibit pseudoelasticity, which does not rely on temperature change in order to accomplish shape change. A pseudoelastic alloy is capable of being elastically deformed far beyond the elastic limits of conventional metals.

The property of pseudoelasticity of certain shape memory alloys, which preferably is used in the devices of this invention, is the subject of a paper entitled "An Engineer's Perspective of Pseudoelasticity", by T. W. Duerig and R. Zadno, published in Engineering Aspects of Shape Memory Alloys, page 380, T. W. Duerig, K Melton, D. Stoeckel, and M. Wayman, editors, Butterworth Publishers,. 1990 (proceedings of a conference entitled "Engineering Aspects of Shape Memory Alloys", held in Lansing, Mich. in August 1988). As discussed in the paper, the disclosure of which is incorporated herein by reference, certain alloys are capable of exhibiting pseudoelasticity of two types.

"Superelasticity" arises in appropriately treated alloys while they are in their austenitic phase at a temperature which is greater than $A_S$ and less than $M_d$ ($A_S$ is the temperature at which, when a shape memory alloy in its martensitic phase is heated, the transformation to the austenitic phase begins, and $M_d$ is the maximum temperature at which the transformation to the martensitic phase can be induced by the application of stress). Superelasticity can be achieved when the alloy is annealed at a temperature which is less than the temperature at which the alloy is fully recrystallized. Alternative methods of creating superelasticity in shape memory alloys, such as solution treating and aging, or alloying, are also discussed in "An Engineer's Perspective of Pseudoelasticity", referenced above. An article may be provided with a desired configuration by holding it in that configuration during annealing, or during solution treatment and aging. An article formed from an alloy which exhibits superelasticity can be deformed substantially reversibly by 11% or more. In contrast, "linear pseudoelasticity", is believed not to be accompanied by a phase change. It is exhibited by shape memory alloys which have been cold worked or irradiated to stabilize the martensite, but have not been annealed in the manner discussed above. An article formed from an alloy which exhibits linear pseudoelasticity can be deformed substantially reversibly by 4% or more. The treatment of shape memory alloys to enhance their pseudoelastic properties is also discussed in above-mentioned U.S. Pat. No. 4,935,068 to Duerig, incorporated herein by reference.

While the alloy that is used in the devices of this invention may exhibit either linear pseudoelasticity or superelasticity (which is sometimes referred to as non-linear pseudoelasticity), or pseudoelasticity of an intermediate type, it is generally preferred that it exhibit superelasticity because of the large amount of deformation that is available without the onset of plasticity. U.S. Pat. No. 4,665,906 to Jervis, which is commonly assigned with the present application and is incorporated herein by reference, teaches the use of pseudoelastic shape memory alloys in medical devices.

The pseudoelastic material will be selected according to the characteristics desired of the article. When a shape memory alloy is used, it is preferably a nickel titanium based alloy, which may include additional elements which might affect the yield strength that is available from the alloy or the temperature at which particular desired pseudoelastic characteristics are obtained. For example, the alloy may be a binary alloy consisting essentially of nickel and titanium, for example 50.8 atomic percent nickel and 49.2 atomic percent titanium, or it may include a quantity of a third element such as copper, cobalt, vanadium, chromium or iron. Alloys consisting essentially of nickel, titanium and vanadium, such as disclosed in U.S. Pat. No. 4,505,767, the disclosure of which is incorporated herein by reference, are preferred for some applications, particularly since they can also exhibit superelastic properties at or around body temperatures, and because they are stiffer and/or can store more elastic energy. Copper based alloys may also be used, for example alloys consisting essentially of copper, aluminum and nickel; copper, aluminum and zinc; and copper and zinc.

An article exhibiting superelasticity can be substantially reversibly deformed, by as much as eleven percent or more. For example, a 1.00 meter length of superelastic wire may be stretched to 1.11 meters in length, wherein its alloy will undergo a phase change to at least a partially more martensitic phase known as stress-induced-martensite. Upon release of the stress, the wire will return substantially to its 1.00 meter length, and its alloy will, correspondingly, return at least substantially toward its more austenitic phase. By way of contrast, a similar wire of spring steel or other conventional metal may only be elastically stretched approximately one percent, or to 1.01 meter in length. Any further stretching of the conventional wire, if not resulting in actual breakage of the wire, will result in a non-elastic (plastic) transformation such that, upon relief of the stress, the wire will not return to its original length. Linear pseudoelastic and superelastic materials may also be bent, twisted, and compressed, rather than stretched, to a far greater degree than conventional metals.

It is believed that the superelastic property is achieved by phase transformation within the alloy, rather than by the dislocation movements which occur during the plastic deformation of ordinary metals. A superelastic material may be deformed and released thousands of times, without being subject to breakage due to the metal fatigue which limits the number of deformation cycles which an ordinary metal may undergo without failure.

Shape memory alloys have a special feature which is beneficial for certain of the embodiments of this invention. As a superelastic shape memory alloy is increasingly deformed from its unconstrained shape, some of its austenitic phase changes into stress-induced-martensite. The stress/strain curve presents a plateau during this phase change. This means that while the alloy undergoes this phase change, it can deform greatly with only minimal increases in loading. Therefore, elements comprising superelastic shape memory alloys have a built-in safety feature. These elements can be designed (using appropriately treated alloys and appropriate dimensions) such that when they are loaded beyond a certain amount, the elements will tend to deform with a concomitant austenite to stress-induced-martensite phase change, instead of merely presenting a greater resistance or force with limited deformation to the load, which is seen with conventional metals.

Just as the stress strain curves of shape memory alloys present a plateau upon loading, they also present a plateau in the stress strain curve upon unloading. Unloading occurs when an element made of superelastic shape memory alloy is permitted to revert from a significantly deformed shape toward its original unstressed shape. Because of the plateau, such an element can maintain an almost constant force during much of the unloading cycle until just before it is completely unloaded.

One form of the present invention provides a surgical instrument which enables the passage of a ligature around a bone, blood vessel, or other such body member, or the grasping of such a body member, without requiring the surgical instrument to be swept over a wide angle of motion. The apparatus includes a cannula and, within the cannula, a member which is at least partly constructed of an elastic material, preferably a pseudoelastic material and most preferably a pseudoelastic shape memory alloy, such as those disclosed in U.S. Pat. No. 4,665,906 to Jervis, dated May 19, 1987, and U.S. Pat. No. 4,505,767 to Quin, dated Mar. 19, 1985, which are preferred for all forms of this invention and which are incorporated herein by reference.

Although the following detailed description and the accompanying Figures illustrate the cannula as having a straight shape, and the elastic member as being held therein in a straightened configuration, it will be understood that the cannula may advantageously be formed with any desirable shape, such as an arc, and that the elastic member may take on any desirable shape upon extrusion from the cannula.

The straight cannula and curved elastic members are used as examples, only, and should not be interpreted to limit the scope of this invention. It will also be understood that although the cannula is discussed as being fairly rigid, it may be formed of a plastically deformable material, which will allow the surgeon to shape the instrument to any required configuration. The instrument may also be flexible to be used within the working channel of a flexible endoscope, the lumen of a catheter or to function as a catheter itself.

Furthermore the elastic member may be coated with a suitable material, such as a polymer.

The elastic member has a distal end portion with a specific curved shape when not subject to mechanical stress. In a first embodiment, the elastic member is of sufficient strength and rigidity to enable a surgeon to grasp and manipulate a body structure, such as a bone, thereby. In the first embodiment, the elastic member includes a distal end structure which may be a pointed tip or a structure which serves to protect the patient's body and to prevent complete withdrawal of the elastic member into the cannula. As the elastic member is distally extended from the cannula, it curves around the body structure sufficiently for grasping and manipulating the body structure.

In a second embodiment, the elastic member may be of less substantial construction and its distal end portion is adapted to retain a ligature. In order to pass the ligature around a blood vessel or bone, the surgeon need only place the distal end of the apparatus near the vessel or bone, and extend the elastic member from the cannula without any required lateral angular motion of the cannula. The elastic member returns to its specific curved shape as it extends beyond the catheter, wrapping itself around the blood vessel or bone. The ligature may then be attached to the distal end of the elastic member, and the elastic member may be withdrawn into the cannula, to pull the ligature around the vessel or bone. By pre-attaching the ligature to the elastic member, the ligature may be passed around the vessel or bone upon extension rather than retraction of the elastic member. The apparatus may further include a means for automatically attaching the ligature to or unattaching the ligature from the elastic member.

The elastic member, if made of pseudoelastic material, will not readily break during repeated use, since metal fatigue does not occur under pseudoelastic use conditions. The instrument operates even though the cannula is not swept over any degree of motion. The instrument is of a simple design, and is of relatively low production cost.

BRIEF DESCRIPTION OF THE DRAWINGS

FIG. 1-1a is a cross-sectional diagram, showing the elastic member disposed within the cannula, in a mode in which the elastic member has a distal end structure.

FIG. 1-1b is a cross-sectional diagram, showing a mode in which the elastic member has a pointed distal tip.

FIGS. 1-2a-b illustrates modes of the elastic member, returning toward a curved shape and a corkscrew shape upon extrusion from the cannula, respectively.

FIGS. 1-3a-c illustrate linear, lateral, and axial manipulation of a bone.

FIGS. 1-4- to 1-12 illustrate a second embodiment of the present invention.

FIG. 1-4 is a cross-sectional diagram, showing the elastic member fully disposed within the cannula.

FIGS. 1-5a-b show alternative modes of the ligature retainer.

FIG. 1-6 shows extension of the elastic member of FIG. 1-5a around a blood vessel.

FIGS. 1-7a-f illustrate a means for automatically grasping a ligature which is passed around a blood vessel.

FIGS. 1-8a-d illustrate an alternative mode of automatically grasping the ligature.

FIG. 1-9 illustrates another alternative mode of automatically grasping the ligature.

FIGS. 1-10a-d illustrate how the apparatus may be used to pass the ligature and automatically tie a half-hitch knot therein.

FIG. 1-11 shows a sliding sleeve which aids in tying the half-hitch knot

FIGS. 1-12a-c illustrate how the apparatus may be used to pass the ligature and automatically tie a logger's knot therein.

FIG. 1-13 shows a prior art apparatus, and illustrates the wide angle of access needed therefore.

FIGS. 2-1 to 2-6 illustrate the first embodiment of the present invention, which longitudinally extrudes an elastic needle through the distal end of a cannula.

FIG. 2-1a is a cross-sectional view, showing the elastic needle held inside the cannula in a straightened configuration under mechanical stress.

FIG. 2-1b shows partial extrusion of the elastic needle from the cannula, with the extruded portion of the needle returning toward its curved configuration by elastic shape memory.

FIG. 2-1c shows the needle fully extruded from the cannula, and released from the cannula insert FIGS. 2-2a-e show alternative modes of the distal end portion of the cannula insert.

FIG. 2-3 is a view of the distal end portion of the cannula insert, showing a raised release signal tab formed therein.

FIG. 2-4a illustrates an integrally constructed mode of the distal end portion of the first embodiment, showing the enlarged transverse dimension of the end portion of the cannula insert.

FIG. 2-4b shows an alternative, non-integral mode of the distal end portion of the cannula insert, formed of a compressible material.

FIG. 2-5 is a view of the distal end portion of the cannula insert, showing an indented distal face therein.

FIG. 2-6 is a cross-sectional view of the proximal end portion of the first embodiment showing a suture retention bobbin within the cannula insert.

FIGS. 2-7 to 2-10 illustrate a second embodiment of the present invention, which extrudes the elastic needle laterally rather than longitudinally.

FIG. 2-7a is a cross-sectional view showing a cannula, shaft, and plunger of the second embodiment FIG. 2-7b is a cross-sectional view of an alternative mode of the proximal end portion of the second embodiment FIG. 2-7c is a cross-sectional view of another alternative mode of the proximal end portion of the second embodiment.

FIG. 2-7d is an enlarged cutaway view of the proximal end portion of the alternative mode shown in FIG. 2-7b.

FIG. 2-7e is a perspective view of the proximal end cap of the alternative mode shown in FIG. 2-7c.

FIG. 2-8 is a cross-sectional view of the distal end portion of the second embodiment, showing a suture retention bobbin therein.

FIG. 2-9 is a cross-sectional view of the second embodiment, taken at line 9-9 of FIG. 2-7 a, showing grooves in the shaft and cannula, and groove engaging tabs in the plunger, for causing rotation of the shaft.

FIG. 2-10 is a cutaway perspective view of the distal end portion of the second embodiment, showing the unwinding of the curved needle through the aperture.

FIG. 2-11a illustrates the present invention being used to deliver the needle to a deep wound for suturing.

FIG. 2-11b illustrates the present invention being used in arthroscopic surgery on a knee.

FIG. 2-12 to 2-15 illustrate a third embodiment of the present invention, which is used to insert ring clips into tissue to hold a wound closed.

FIG. 2-12a is a cutaway view of the third embodiment, illustrating a ring clip held therein.

FIG. 2-12b illustrates extrusion of the ring clip.

FIG. 2-12c illustrates an alternative mode of the third embodiment, adapted for use with an extended ring clip which is held therein.

FIG. 2-13a, 2-13b, 2-13c, and 2-13d, illustrate a marker which indicates a first and a second direction of extrusion of the ring clip, respectively.

FIG. 2-14 is a cross-sectional view of another alternative mode of the third embodiment, adapted for serial extrusion of a plurality of ring clips held therein.

FIG. 2-15a illustrates yet another mode of the third embodiment, with the plurality of ring clips held in a magazine.

FIG. 2-15b illustrates an internal piston return spring.

FIG. 2-16a illustrates manipulation of the extended distal segment of the ring clip of FIG. 2-12c.

FIG. 2-16b illustrates the severing of the extended distal segment of FIG. 2-16a.

FIG. 2-17a-c illustrates various modes of a ring clip.

FIG. 3-1 is a view of an unexpanded barrier device (not shown) within a housing.

FIGS. 3-2 through 3-5 are progressive cross-sectional views through line a-a of FIG. 3-1, showing the use of the device of FIG. 3-1. The figures show, respectively, FIG. 3-2, constrained; FIG. 3-3; expanded (memory); FIG. 3-4, pouched; and FIG. 3-5, withdrawal configurations.

FIGS. 3-6a, b, c and d show alternate embodiments of the device of FIG. 3-1 through line b-b.

FIGS. 3-7 and 3-8 show alternate embodiments of the barrier member in the expanded (memory) configuration.

FIGS. 3-9a, b, and c show cross-sectional embodiments through line b-b of FIG. 3-7.

FIGS. 3-10a and b, 3-11a and b, and 3-12a and b detail alternate expanded loop configurations.

FIG. 3-13 is a schematic representation of another embodiment of a device for deploying an internal drape, and FIGS. 3-14 and 3-15 are schematic representations of yet another embodiment of device for deploying an internal bag, showing the device before and after withdrawal of the drape into the shaft of the instrument.

FIGS. 3-16, 3-17 and 3-18 illustrate the use of a bushing which can be used with any of embodiments 3-1 to 3-15.

FIGS. 3-19, 3-20, 3-21, and 3-22 illustrate a necked-loop configuration which can be incorporated in any of the embodiments, illustrated in FIGS. 3-1 to 3-18.

FIG. 4-1a is a side view of an unexpanded screen device within a duct, placed downstream from the blocking calculus.

FIG. 4-1b shows the screen device, the deployment end of which has been placed upstream from the blocking calculus.

FIG. 4-1c shows a screen device which has been expanded upstream from a blocking calculus.

FIG. 4-1d shows a screen device in place after calculus fragmentation.

FIGS. 4-2a, b, c, and d show various stages of deployment of a tasseled surgical screen.

FIGS. 4-3a through 4-5b show alternate embodiments of the surgical screen portion of a device of this invention.

FIG. 5-1 is a cross-sectional view of a constrained retractor device.

FIGS. 5-2 through 5-6 show alternate top views of expanded (unconstrained) retractor devices.

FIGS. 5-7 through 5-11 show alternate side views of expanded retractor devices.

FIGS. 5-12 and 5-13 show alternate end views of expanded retractor devices.

FIGS. 5-14 and 5-15 show alternate cross sectional views of constrained retractor devices, the cross section taken along line a-a of FIG. 5-1.

FIG. 6-1 is an external view of a device of this invention.

FIGS. 6-2 and 6-3 are alternate cross-sectional views of a sheath of this invention, the cross sections being taken vertically along the longitudinal axis of FIG. 6-1.

FIG. 6-4 is an alternate cross-sectional view of a sheath of this invention, the cross section being taken vertically along the longitudinal axis.

FIG. 6-5 is a cross-sectional view of the device of FIG. 1 taken across the longitudinal axis, along line b-b of FIG. 6-1

FIG. 6-6 is a cross-sectional view of the device of FIG. 6-1 taken across the longitudinal axis, along line c-c of FIG. 6-1.

FIG. 6-7 is a cross-sectional view of a cutting edge of a cutting blade of this invention.

FIGS. 6-8 through 6-12 are alternate side views of the device of FIG. 1 when the cutting blade is deployed.

FIGS. 6-13 through 6-20 are alternate top views of typical elastic blades of this invention.

FIG. 7-1 shows an instrument of this invention.

FIGS. 7-2*a, b, c,* and *d* show the deployment end of a bladed instrument of this invention.

FIGS. 7-3*a, b* and *c* and 7-4*a, b* and *c* are longitudinal cross-sectional views of alternate elastically deployable stems, in longitudinally constrained and longitudinally unconstrained configurations.

FIGS. 7-5*a* and *b,* 7-6*a* and *b* and 7-7*a, b* and *c* each show alternate views of an elastically deformable stem of this invention.

FIGS. 7-8*a, b, c, d, e* and *f* and 7-9*a, b, c, d, e, f, g, h,* and *i* show alternate elastic members suitable for use in an elastically deformable stem of this invention.

FIGS. 7-10*a* and *b* show alternate views of a device of this invention having two pivoted blades, each blade having a longitudinal slot proximal the pivot.

FIGS. 7-11*a, b,* and *c* show alternate views of a device of this invention having two blades, two bars, and four pivots.

FIGS. 7-12*a, b, c, d, e,* and *f* show alternate cross-sections of the device of FIG. 7-1, taken through line 12-12.

FIGS. 7-13*a, b, c, d,* and *e* show various blades suitable for use herein.

FIGS. 7-14*a, b, c, d,* and *e* show various blade cross-sections, taken through line 14-14 of FIG. 7-13.

FIG. 8-1 is an isometric view of a device of the invention;

FIGS. 8-2*a,* 8-2*b* and 8-2*c* are cross-sections through the device shown in FIG. 8-1, taken at lines A-A, B-B and C-C respectively;

FIGS. 8-3*a,* 8-3*b,* 8-3*c,* 8-3*d* and 8-3*e* are elevational views of a first embodiment of the device shown in FIG. 8-1 at various stages during a cutting operation;

FIGS. 8-4*a,* 8-4*b* and 8-8*c* are elevational views, partially in section, of another embodiment of the device at various stages during a cutting or grasping operation.

FIGS. 8-5*a,* 8-5*b,* 8-5*c,* 8-5*d* and 8-5*e* illustrate an embodiment of a device in accordance with this invention in which the end portions and body portions of the elongate elements are integral and are moved by a rotational actuator made of a material other than a pseudoelastic material.

FIGS. 8-6*a,* 8-6*b,* 8-6*c,* 8-6*d* and 8-6*e* illustrate representative cross sections of end portions of the elements adapted to grasp or cut an obect.

FIGS. 8-7*a,* 8-7*b;* 8-7*c,* 8-7*d* and 8-7*e* illustrate various actuating means which function to cause the elements to splay apart and come together and, optionally, rotate the elements, and/or withdraw the elements into or out of the hollow component.

FIG. 8-8 illustrates an embodiment of the device of this invention in which the end portions are curved when at least partially unconstrained and pinned together pivotally at their tips.

FIG. 8-9 demonstrates a method of using a grasping device of this invention.

FIGS. 8-10*a,* 8-10*b* and 8-10*c* illustrate an embodiment of the device of this invention in which the elements are splayed and in which the body portions of the elements are bent when the elements are unconstrained.

FIGS. 8-11*a* and 8-11*b* illustrate a device of this invention in which the elements have end portions beyond a pivot point, and in which the body portions of the elements are of pseudoelastic material and when unconstrained are bent to splay the end portions and position them at a desired angle with respect to the hollow component. The body portions act as actuating means to open and close the end portions of the elements to dissect, grasp and/or cut an object.

FIG. 8-12 illustrates a device similar to the device in FIG. 8-11*b,* but in which the body portions of the elements are made of a pseudoelastic material and have a bend of about 90 degree.

FIG. 8-13 illustrates another device in accordance with this invention.

DETAILED DESCRIPTION

Figure 1:
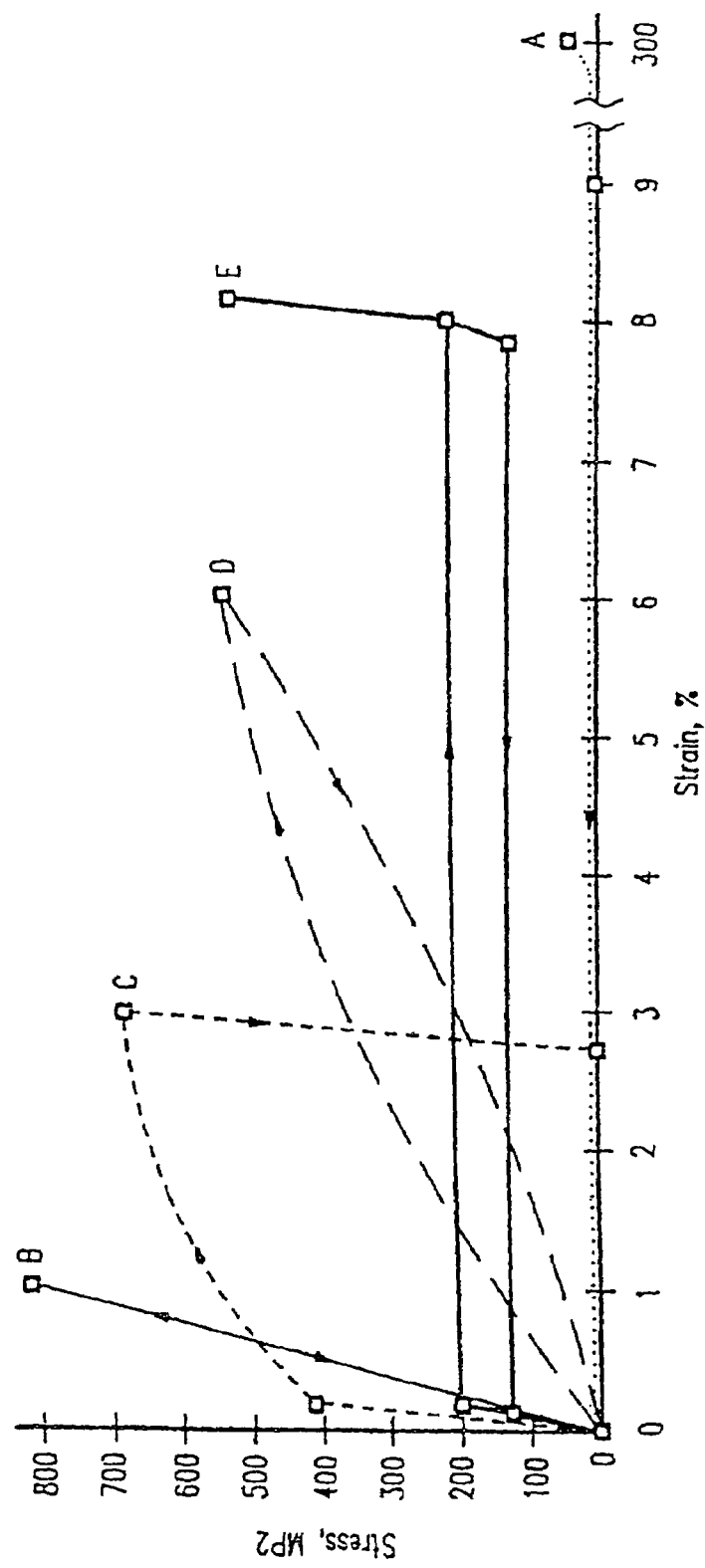
FIGS. 1-1- to 1-3 illustrate a first embodiment of the present invention.

FIG. 1-13 shows the use of a prior art apparatus 700 for passing a ligature (not shown) around a particular blood vessel 703 which is situated among other blood vessels 704. In order to place the operative distal end 710 into a position 715 from which the end 710 is directly accessible, it is necessary to swing the entire apparatus 700 through a very wide angle of motion 720. This wide angle requires a very large entry wound 740 through the patient's tissues 730. It will be understood that such a wide angle of motion is impossible to achieve if the apparatus 700 is being used through an arthroscopic or other small endoscopic surgical entry wound 735 through the patients tissues 730.

As will be understood from the following description and from the accompanying drawings, the present invention is an apparatus usable through such a small entry wound.

In a first embodiment 100, shown in FIGS. 1-1- to 1-3, the present invention includes a cannula 10 and a member 12. Although the present invention may be practiced with a member 12 which is fashioned of another appropriate material, such as spring steel, the preferred material is a pseudoelastic material, preferably a shape memory alloy and in particular a shape memory alloy that exhibits superelasticity. The member 12 will hereinafter be referred to as a elastic member 12, and its distal segment 14 will be referred to as a elastic distal segment 14. In a preferred embodiment the member is made of a superelastic shape memory alloy and the elastic distal segment 14 has a first shape when the alloy of the elastic distal segment 14 is in a substantially austenitic phase and the distal segment 14 is extended distally from the cannula 10 and is not subject to mechanical stress. The elastic distal segment 14 may be mechanically stressed into a second shape (i.e., when the distal segment 14 is held within the cannula 10), wherein at least a portion of the alloy has changed to a stress-induced-martensite phase.

Figures 1, 1A:
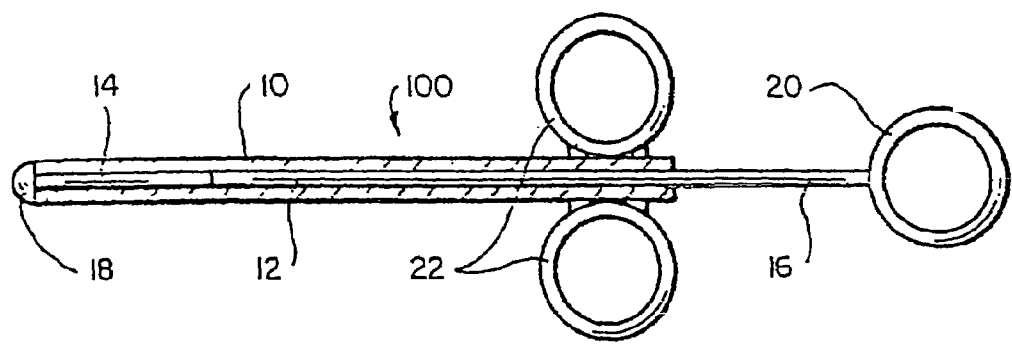

FIGS. 1-1*a-b* show the elastic distal segment 14 elastically deformed into a second, straight shape within the cannula 10. FIG. 1-2*a* shows one mode of the first shape, with the elastic distal segment 14 returning toward an arced first shape upon extrusion from the cannula 10. FIG. 1-2*b* shows an alternative mode of the first shape, wherein the elastic distal segment 14 returns toward a corkscrew first shape upon extrusion from the cannula.

As shown in FIG. 1-1*a,* the elastic member 12 also includes a proximal segment 16 which is relatively straight, to allow its easy insertion into the proximal end of the cannula 10.

The distal and proximal segments may, suitably, be integrally formed of a unitary wire or rod, or the proximal segment may be formed of a different material and coupled end-to-end with a elastic distal segment. If the segments 14 and 16 are formed of a unitary construction, the proximal segment 16 does not, preferably, have a curved shape when it is in an unstressed condition, unlike the elastic distal segment 14. Although the member 12 is referred to herein as a elastic member 12, it will be understood that, as explained, only the distal end segment 14 need be elastic. It will be further understood that the distal end segment 14 as well as the proximal segment 16 may be formed of any suitable material, which may or may not be the same.

The elastic member 12 may also include a distal end structure 18, as shown in FIG. 1-1a. The distal end structure 18 is a contact or grip means which improves the grip of the apparatus 100 upon an object. The distal end structure 18 also prevents the complete withdrawal of the elastic member 12 through the cannula 10, to preserve the apparatus 100 as an integral unit. The smooth surface and shape of the distal end structure 18 serve as a safety means which helps to reduce issue damage upon insertion of the apparatus 100 into a wound, or through tissue, or through an arthroscopic or other such endoscopic surgical entry wound. In the illustrated embodiment, the distal end structure 18 is substantially semi-spherical, with a diameter roughly equal to that of the cannula 10. This protects the patient's tissues from the blunt distal end of the cannula 10, while also preventing complete withdrawal of the elastic member 12 from the cannula 10. The distal end structure 18 may be either unitarily constructed with the elastic distal segment 14, or may be formed of a different material and coupled thereto in any conventional manner. It is to be understood that the distal end structure 18 can have any blunted shape, and may even be spherical or bullet shaped.

Figures 1, 1B:
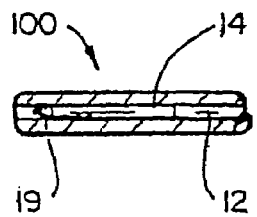
Figures 1, 2, 2A:
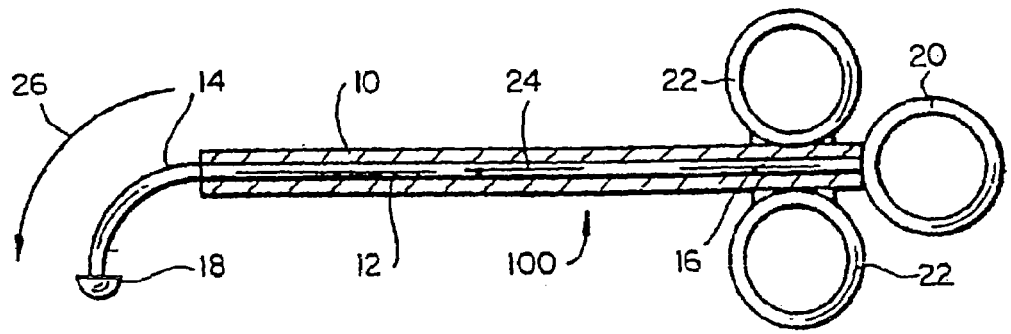
Figures 1, 2, 2B:
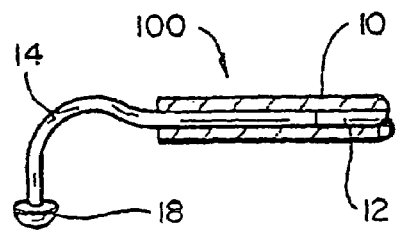

As shown in FIG. 1-1b, the elastic member may have a pointed distal end structure 19, which, like the distal end structure 18 of FIG. 1-1a, improves the mechanical gripping of the apparatus upon a bone or other object. It may be preferred that distal end structure 19 be integral with the elastic member.

The apparatus 100 may, suitably, be further adapted with a handle structure for extending the elastic member 12 through the cannula. In one mode, the handle structure may include a thumb ring 20 coupled to the proximal end of the elastic member 12, and one or more finger rings 22 coupled near the proximal end of the cannula 10. The surgeon inserts the elastic member 12 through the cannula 10 by pressing on the thumb ring 20 while holding the finger rings 22 stationary, and withdraws the elastic member 12 into the cannula by pulling the thumb ring 20 in the opposite direction. Of course, other handle devices are within the scope of all of the embodiments of this invention, such as a pistol grip, or a scissor-action apparatus, or the like. Withdrawal of the elastic member 12 may be assisted by a spring (not shown).

As shown in FIG. 1-2a, when the elastic member 12 is inserted through the cannula 10 with motion 24, the elastic distal segment 14 emerges from the distal end of the cannula 10. In a preferred embodiment in which superelastic shape memory alloy is utilized, the elastic distal segment 14 has its stress-induced-martensite condition at least partially relieved of stress by the absence of any restraining cannula. The alloy of the elastic distal segment 14 undergoes at least a partial reversion toward the austenitic phase, and the elastic distal segment 14 returns toward its first shape with motion 26.

It will be understood that the curvature of the elastic distal segment 14 need not necessarily be circular, nor coplanar with the axis of the cannula 10, within the scope of this invention. For example, the distal segment 14 might be formed to curve radially about the axis of the cannula upon extrusion therefrom, in a corkscrew fashion, as shown in FIG. 1-2b. As will be understood, the elastic distal segment 14 may be formed to have any desired shape or arc or radius of curvature, to suit the apparatus for a given purpose.

As shown in FIGS. 1-3a-c, the apparatus 100 may be used to manipulate a bone 3 or other structure in a patient, or any other suitable object. The specific body members which are discussed herein are listed solely to aid in the understanding of the invention, and do not affect the scope of the invention.

It will be understood that the first embodiment 100 may be constructed in a variety of sizes and with an elastic member of a variety of lateral dimensions, cross-sectional configurations, and strengths, for suitable use in manipulating a wide variety of body members or other objects. For example, a very small apparatus with a very thin elastic member may be desirable in manipulating small or delicate body members such as individual nerves or terminal arteries. On the other hand, a large apparatus with a thick elastic member having great strength may be required in order to manipulate a larger body member such as a broken femur, or a bulky organ, or a prosthesis or other mechanical object. Also the apparatus may be long and/or flexible, so that it can be used in the channel of an endoscope (rigid or flexible), in the lumen of a catheter, or as a catheter itself.

The elastic distal segment 14 of the elastic member 12 may be inserted into or wrapped around the body structure 3, and the apparatus 100 may be moved, to manipulate the structure 3. Extension of the elastic member 12 into grasping connection with the body member 3 does not require any lateral movement of the apparatus 100, but only requires linear insertion of the elastic member 12 through the cannula 10. This permits the apparatus 100 to be used in closely confined surgical sites, or through a very small surgical opening such as may typically be used to gain arthroscopic access to a knee joint, for example.

By forming the elastic distal segment 14 to have a non-stressed shape which curves in a particular direction, the apparatus 100 may be constructed for suitable hooking of a body member which has a given orientation. With the curvature shown in FIG. 1-3a, the apparatus 100 may be suited for linear pulling or pushing of the body structure 3 in the direction 28 shown. With the curvature shown in FIG. 1-3b, the apparatus 100 may be suited for lateral manipulation of the body structure 3 in the direction 30, as shown. As shown in FIG. 1-3c, if the elastic distal segment 14 curves in a corkscrew shape, the apparatus 100 may be readily used to push or pull the body structure 3 along the axis of the body structure 3, in direction 32 as shown.

The apparatus 100 may be adapted with a marker 31, as shown in FIG. 1-3a, for indicating the direction and orientation in which the particular elastic member 12 will curve upon extrusion. The marker 31 may be, for example, printed upon the cannula 10, or may be a raised or indented portion thereof. As it is desirable that the marker 31 not cause any trauma to an entry wound, a printed marker may be the preferred mode. It will be understood that the marker may be placed at any desired point along the length of the cannula. For example, a marker placed immediately adjacent to the distal tip of the apparatus will likely be visible to an arthroscopic surgeon through his or her arthroscopic viewing apparatus. On the other hand, or in addition, a marker placed near the proximal end of the apparatus will remain in plain sight during surgery, as it will remain outside the patient's body. The apparatus 100 may include any suitable means for ensuring that the elastic member 12 curve in the indicated direction. For example, the distal segment 16 may be formed of a square cross-section, with the proximal end opening (not shown) of the cannula 10 being formed of a similar shape, such that the elastic member 12 cannot rotate within the cannula 10. Alternatively, the cannula 10 may have a peg (not shown) which engages a longitudinal slot (not shown) in the elastic member 12, or the elastic member 12 may have a peg (not shown) to engage a longitudinal slot (not shown) in cannula 10.

FIGS. 1-4- to 1-12 illustrate a second embodiment 200 of the present invention. In this embodiment, the elastic member 12 need not include a distal end structure, and may be fully withdrawn into the cannula 10. Although the second embodiment 200 is hereinafter described as being used for passing a ligature around a blood vessel, it will be understood that the ligature may be passed around any other body structure or other object, within the scope of this invention. If the non-deformed shape of the distal segment of the elastic member is substantially circular, this has the important advantage that, during extension and withdrawal of the elastic distal segment, that portion of the elastic distal segment which is already extruded from the cannula and adjacent the blood vessel will not apply any lateral or radial forces upon the blood vessel. It will, therefore, be understood that it is advantageous to form differing modes of the second embodiment, wherein each has an elastic member whose distal segment is of a given radius of curvature in its non-deformed first shape. This allows the surgeon to select an appropriately sized apparatus for passing a ligature around any size of blood vessel, and is within the scope of this invention. It will be understood that the same principle applies equally to the first embodiment described above with regard to FIGS. 1-1- to 1-3. Also the apparatus may be long and/or flexible, so that it can be used in the channel of an endoscope (rigid or flexible), in the lumen of a catheter, or as a catheter itself.

Figures 1, 2, 3, 3A:
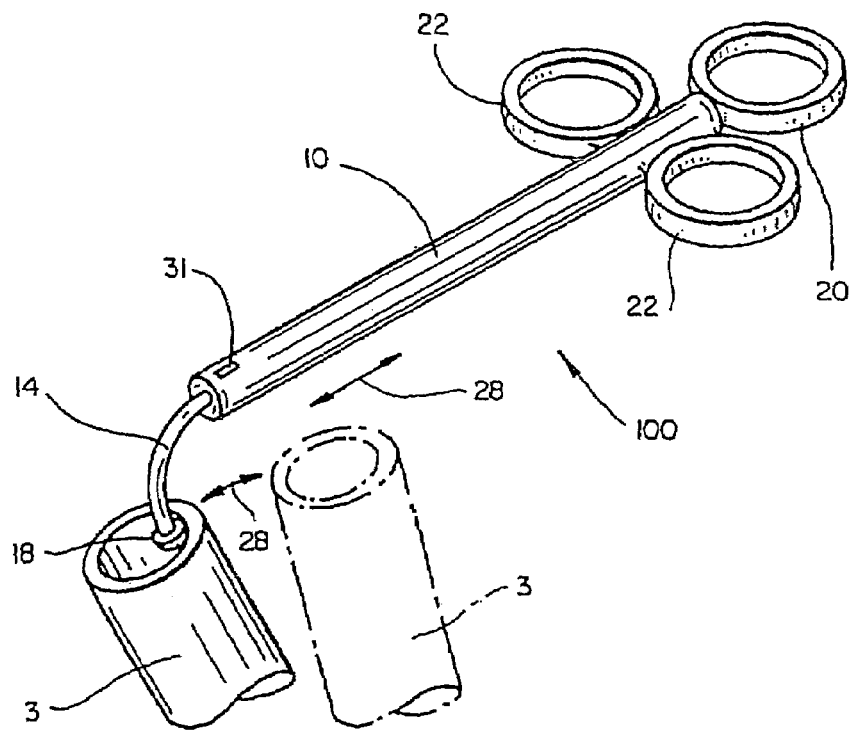
Figures 1, 2, 3, 3C:
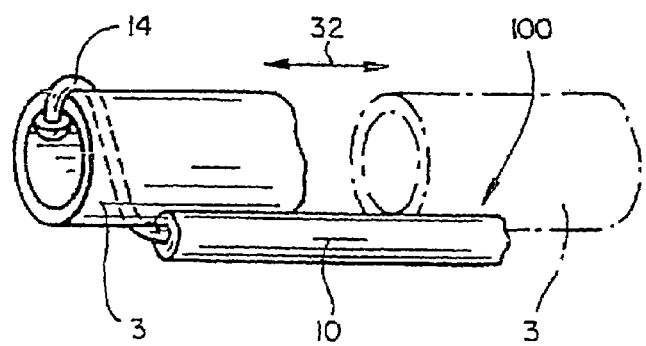
Figures 1, 2, 3, 3B:
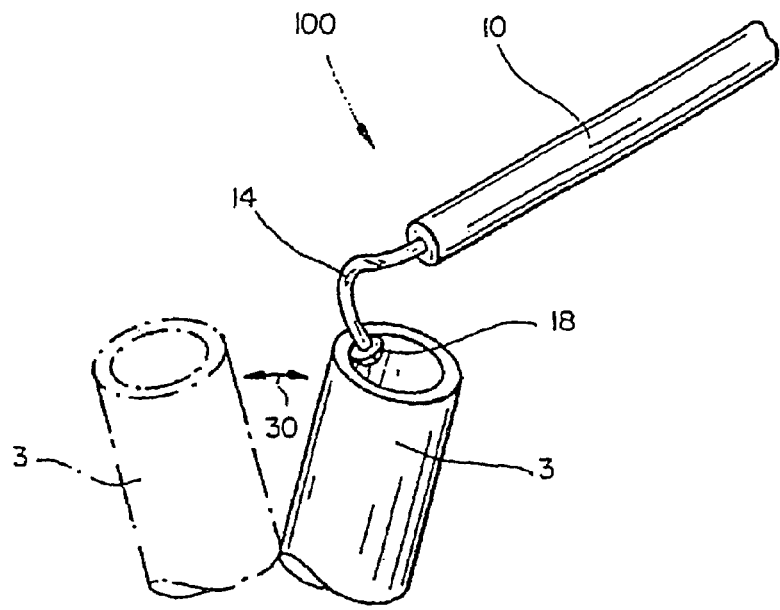
Figures 1, 2, 3, 4:
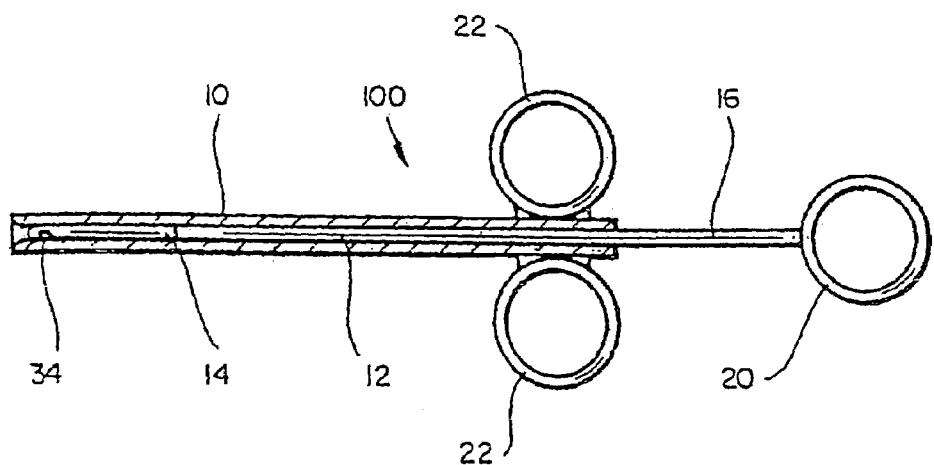
Figures 1, 2, 3, 4, 5, 5A:
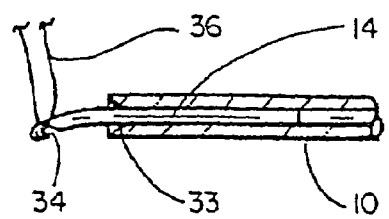
Figures 1A, 2:
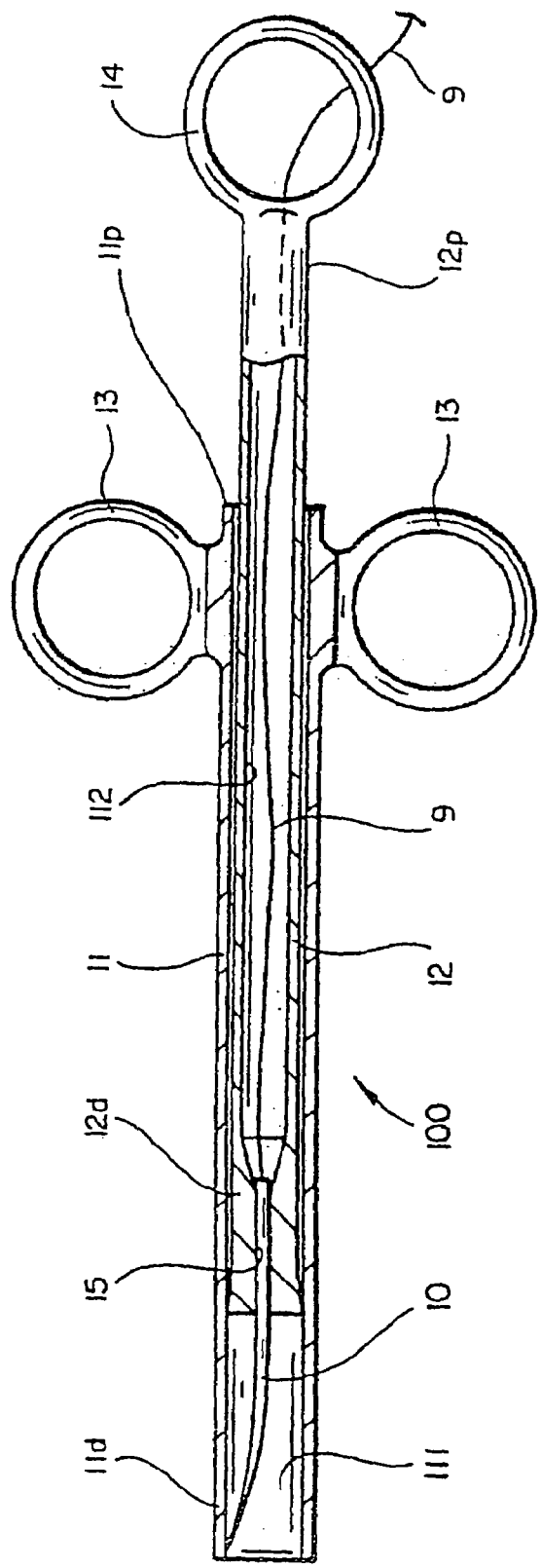
Figures 1B, 2:
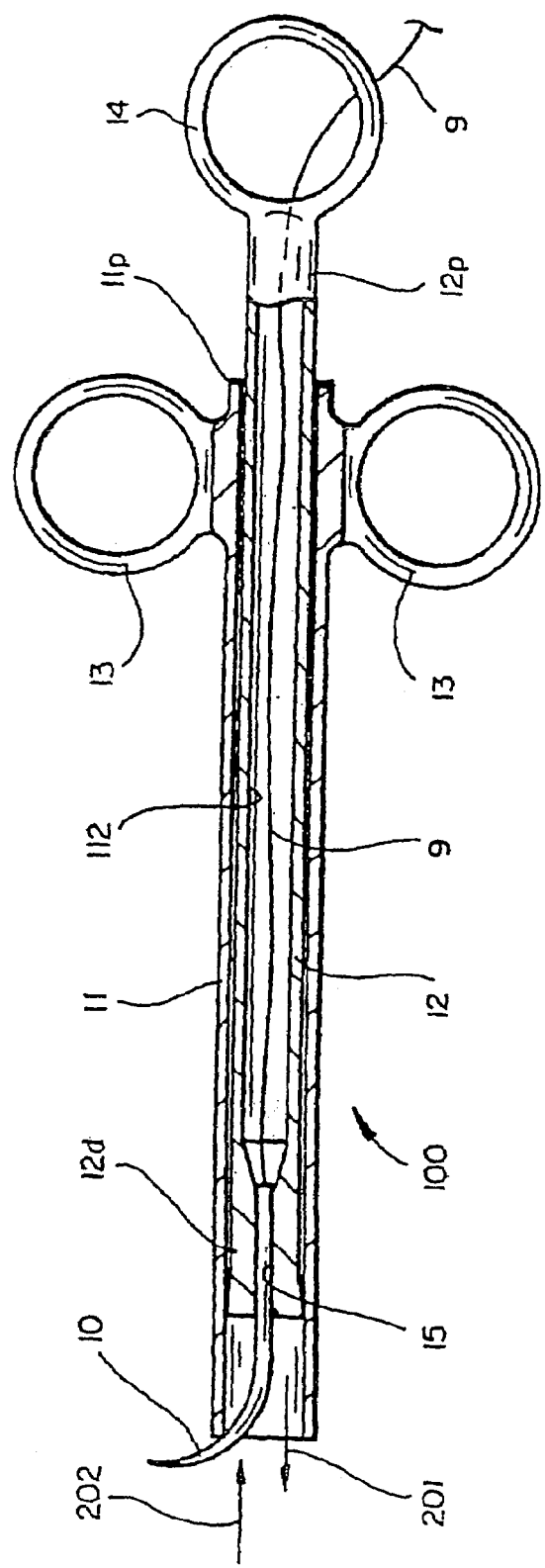
Figures 1C, 2:
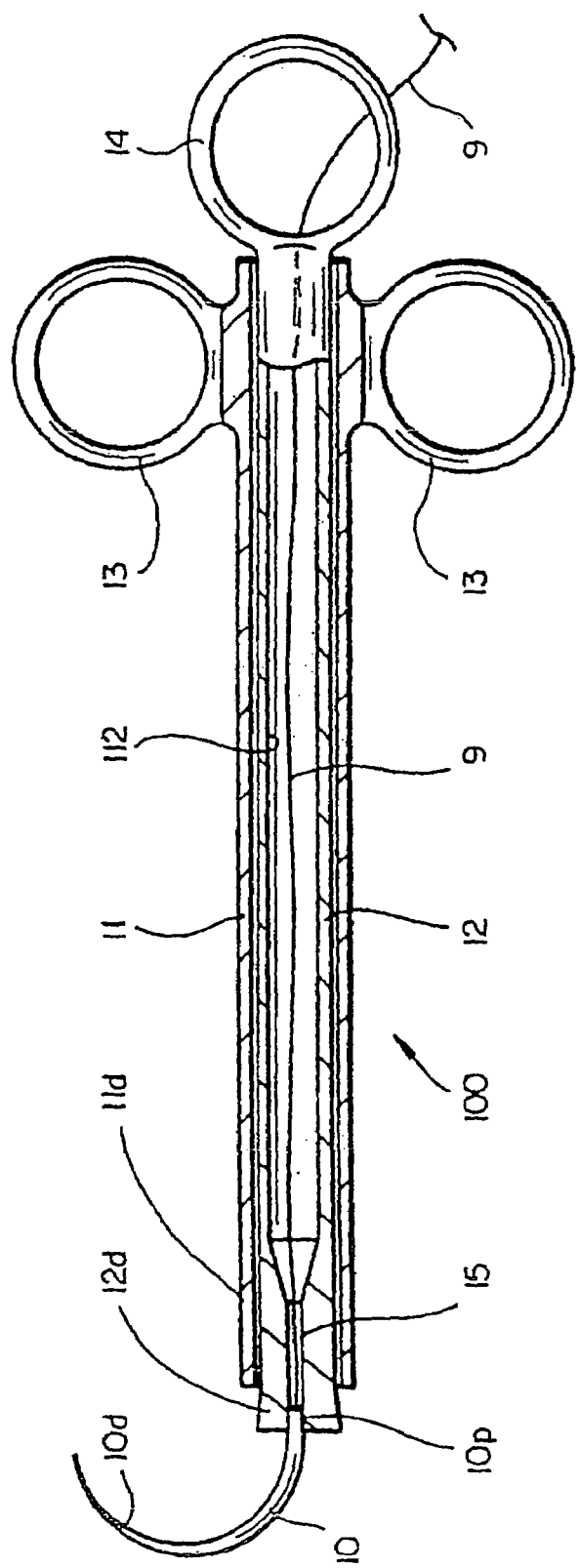
Figures 2, 2A:
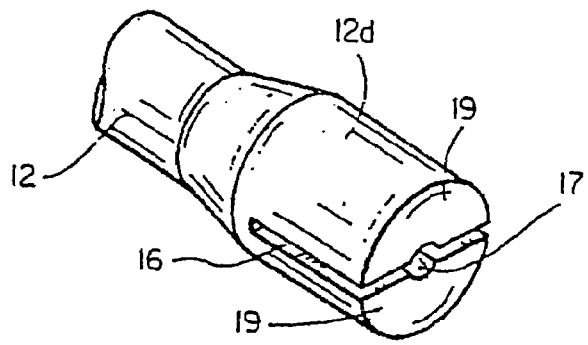
Figures 2, 2B:
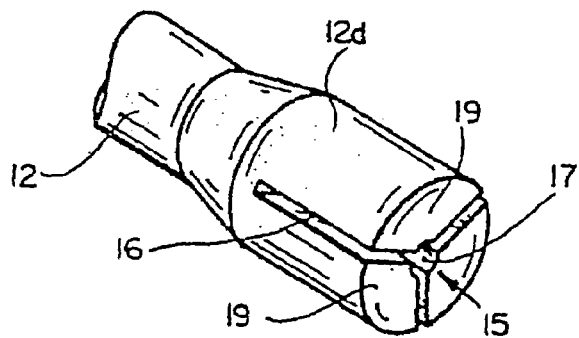
Figures 2, 2C:
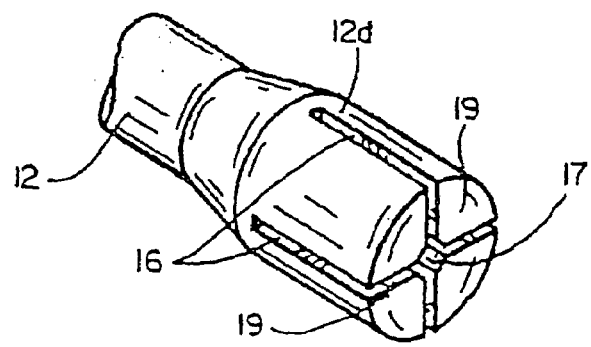
Figures 2, 2D:
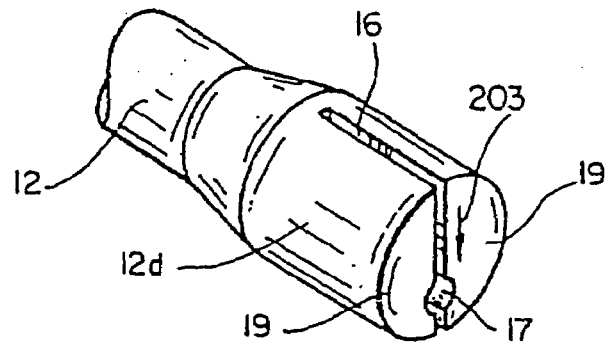
Figures 2, 2E:
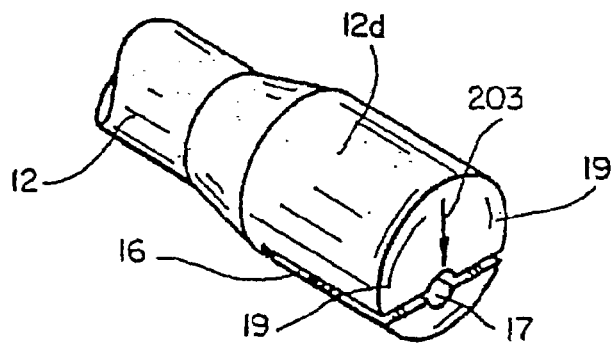
Figures 2, 3:
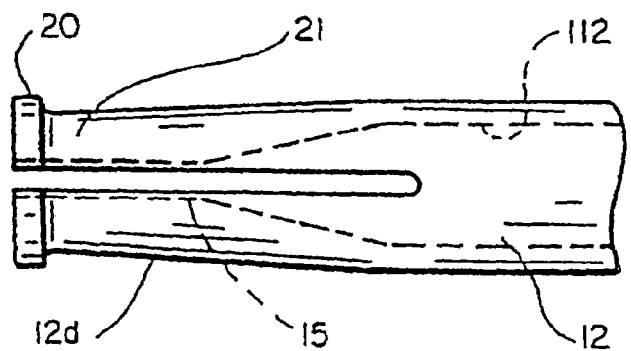
Figures 2, 3, 4, 4A:
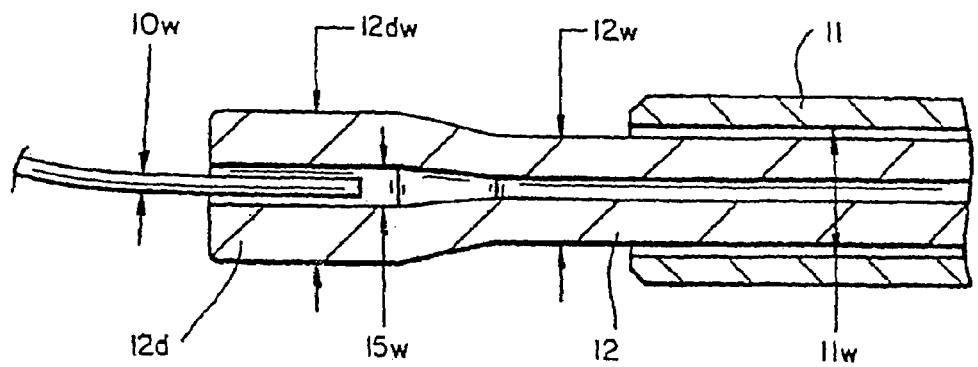
Figures 2, 3, 4, 4B:
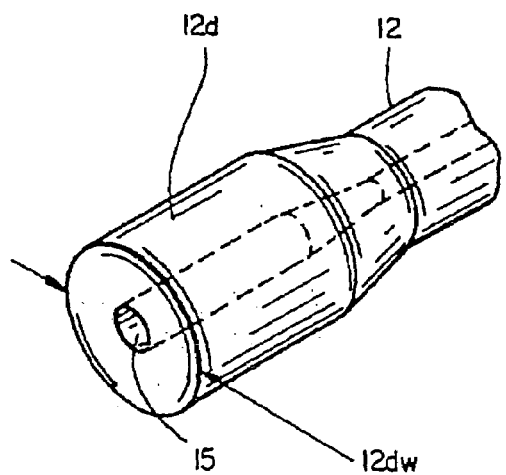
Figures 2, 3, 4, 5:
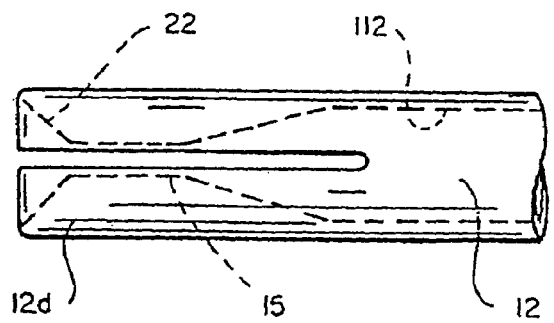
Figures 2, 3, 4, 5, 6:
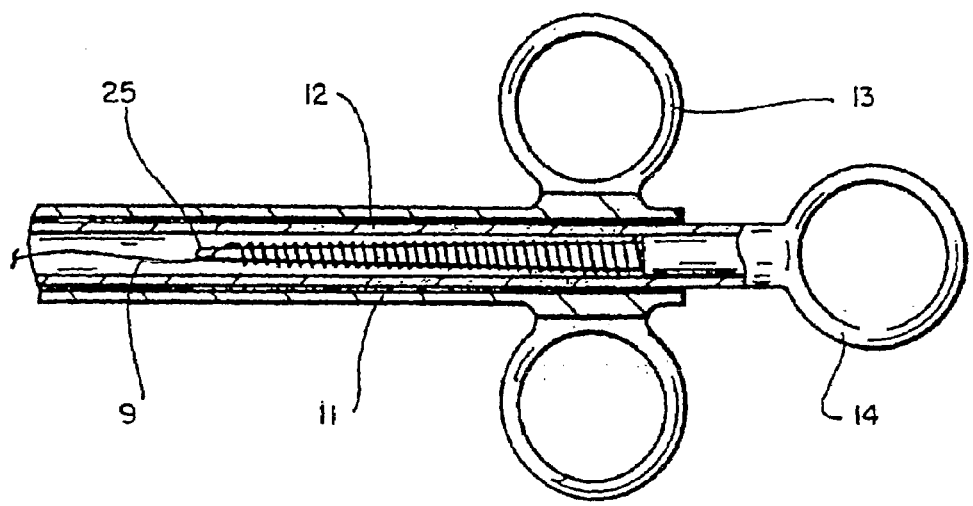
Figures 2, 3, 4, 5, 6, 7, 7A:
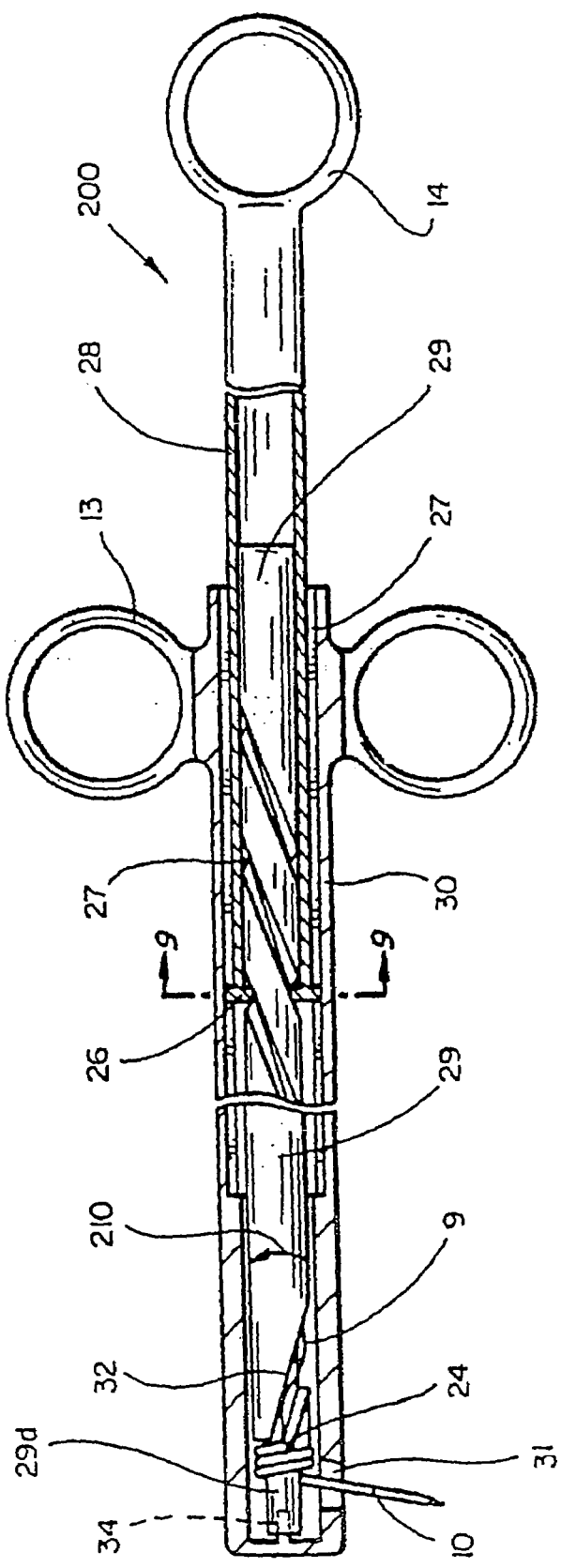
Figures 2, 3, 4, 5, 6, 7, 7B:
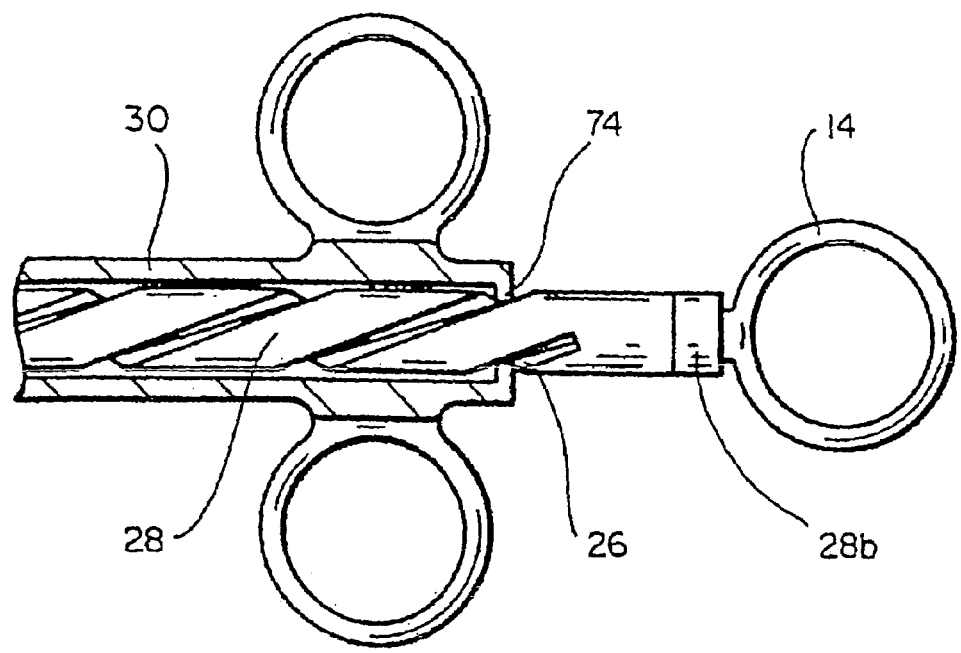
Figures 2, 3, 4, 5, 6, 7, 7C:
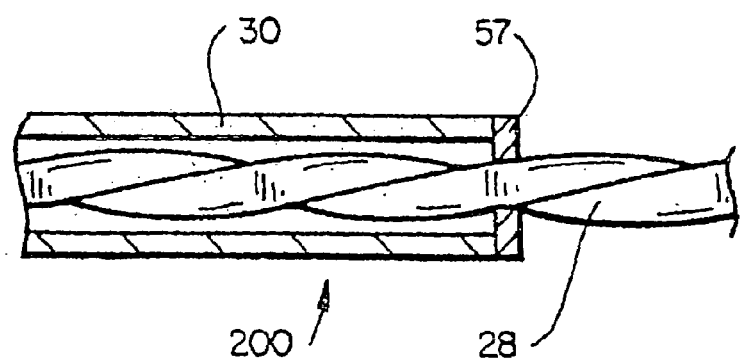
Figures 2, 3, 4, 5, 6, 7, 7D:
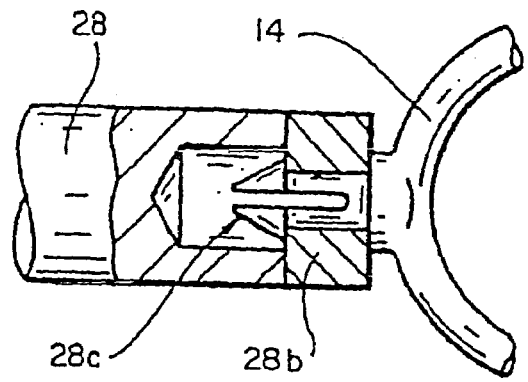
Figures 2, 3, 4, 5, 6, 7, 7E:
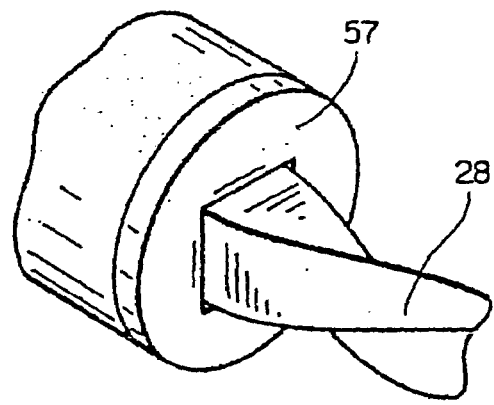
Figures 2, 3, 4, 5, 6, 7, 8:
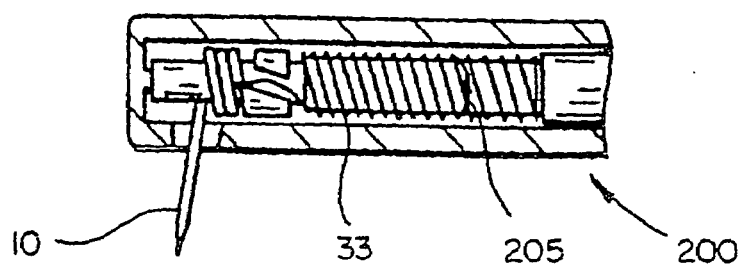
Figures 2, 3, 4, 5, 6, 7, 8, 9:
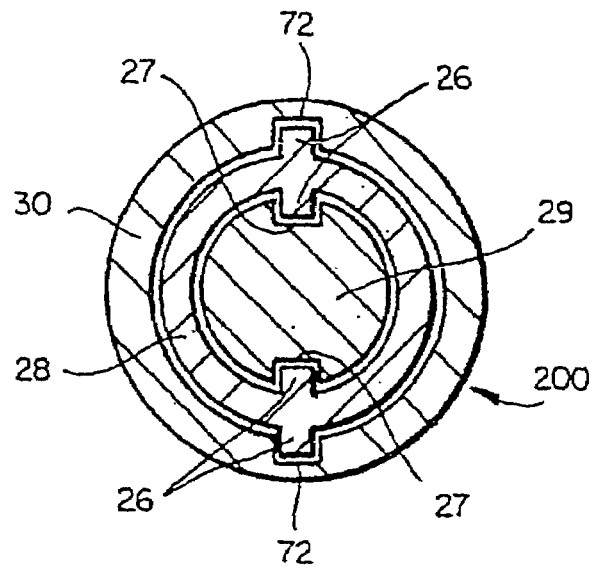
Figures 2, 3, 4, 5, 6, 7, 8, 9, 10:
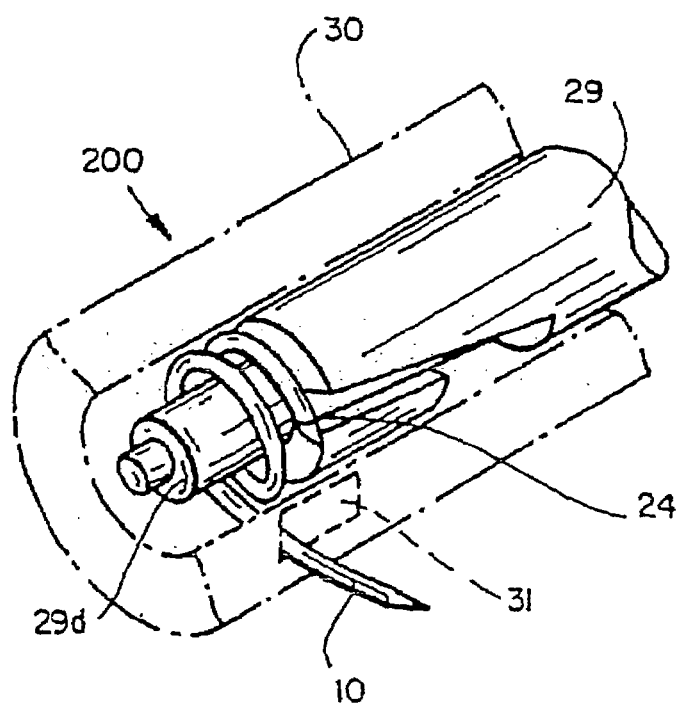
Figures 2, 3, 4, 5, 6, 7, 8, 9, 10, 11, 11A:
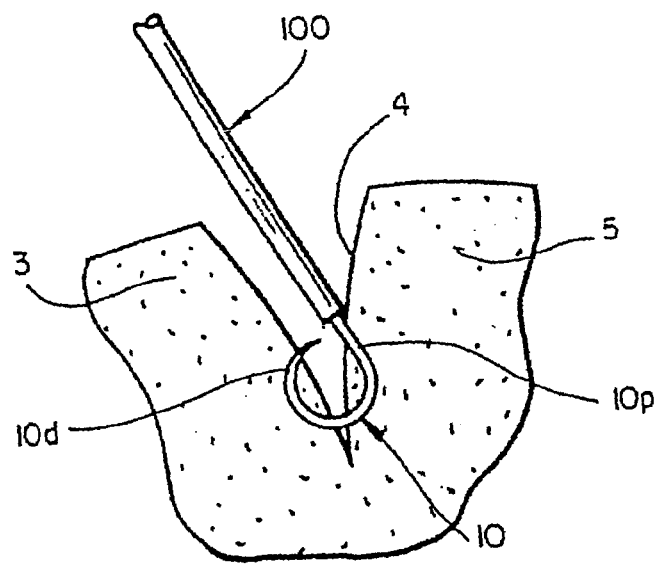
Figures 2, 3, 4, 5, 6, 7, 8, 9, 10, 11, 11B:
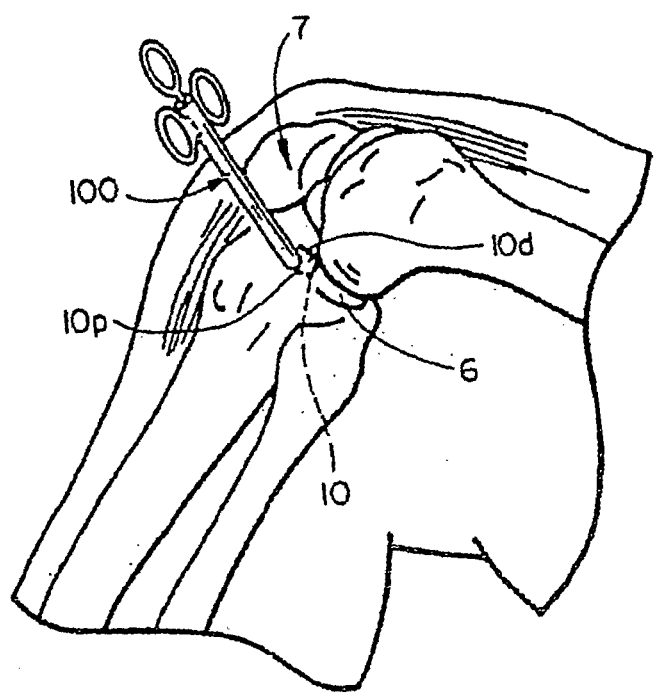
Figures 2, 3, 4, 5, 6, 7, 8, 9, 10, 11, 12, 12A:
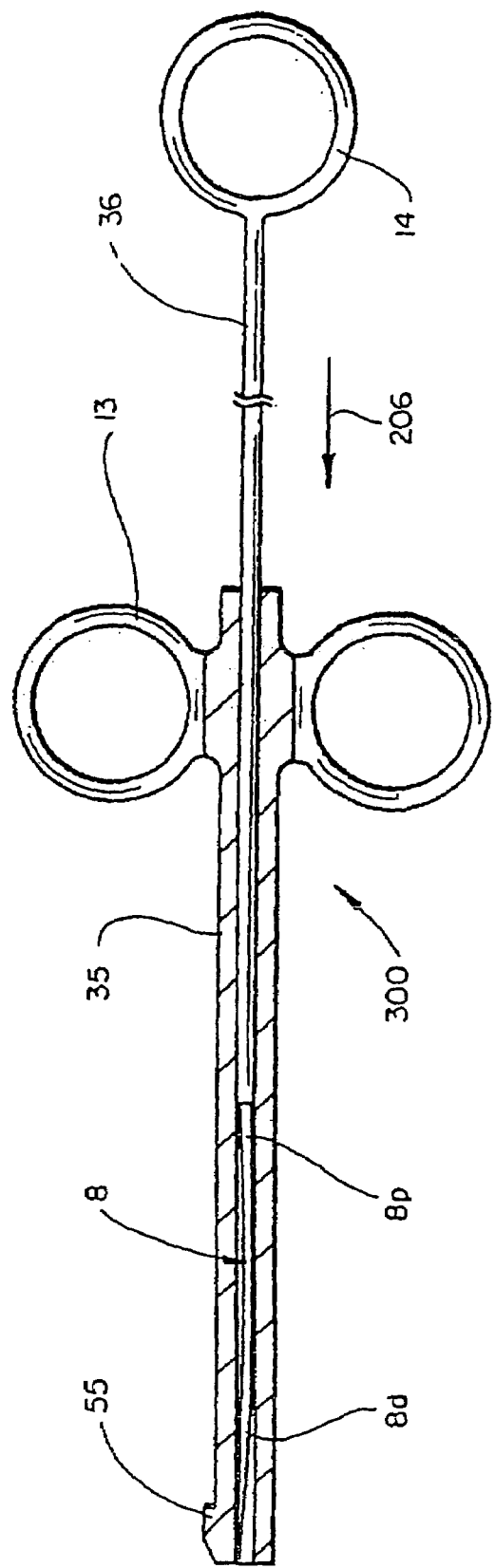
Figures 2, 3, 4, 5, 6, 7, 8, 9, 10, 11, 12, 12B:
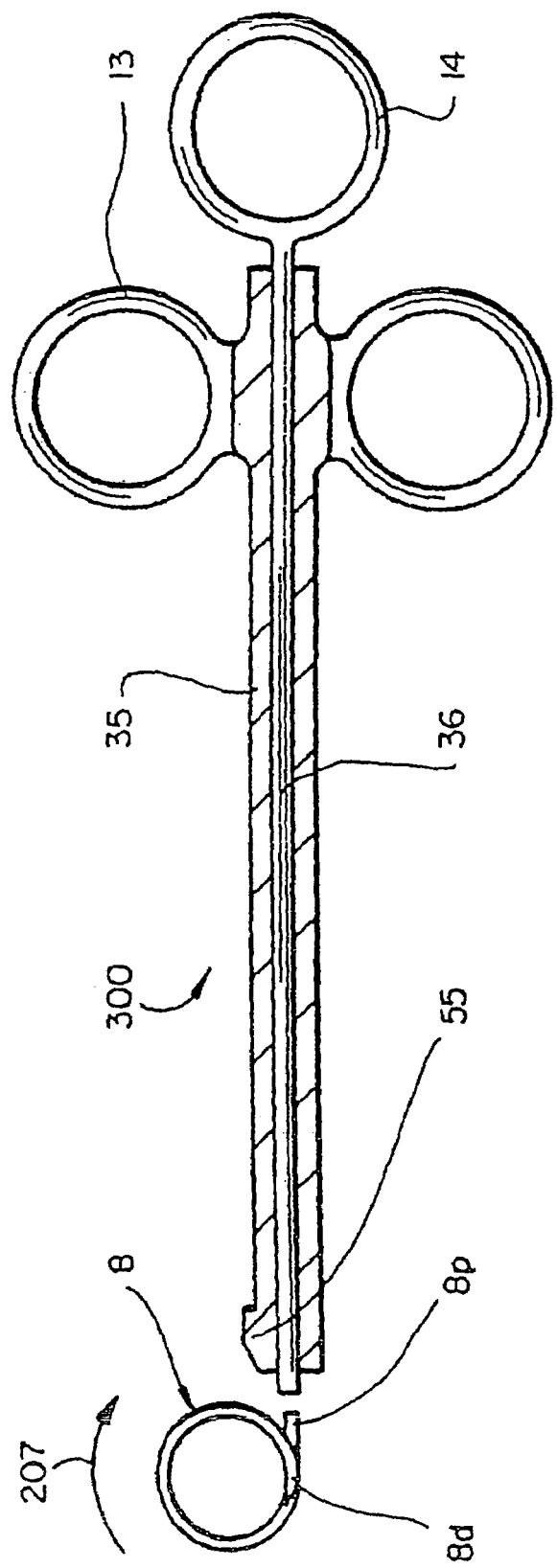
Figures 2, 3, 4, 5, 6, 7, 8, 9, 10, 11, 12, 12C:
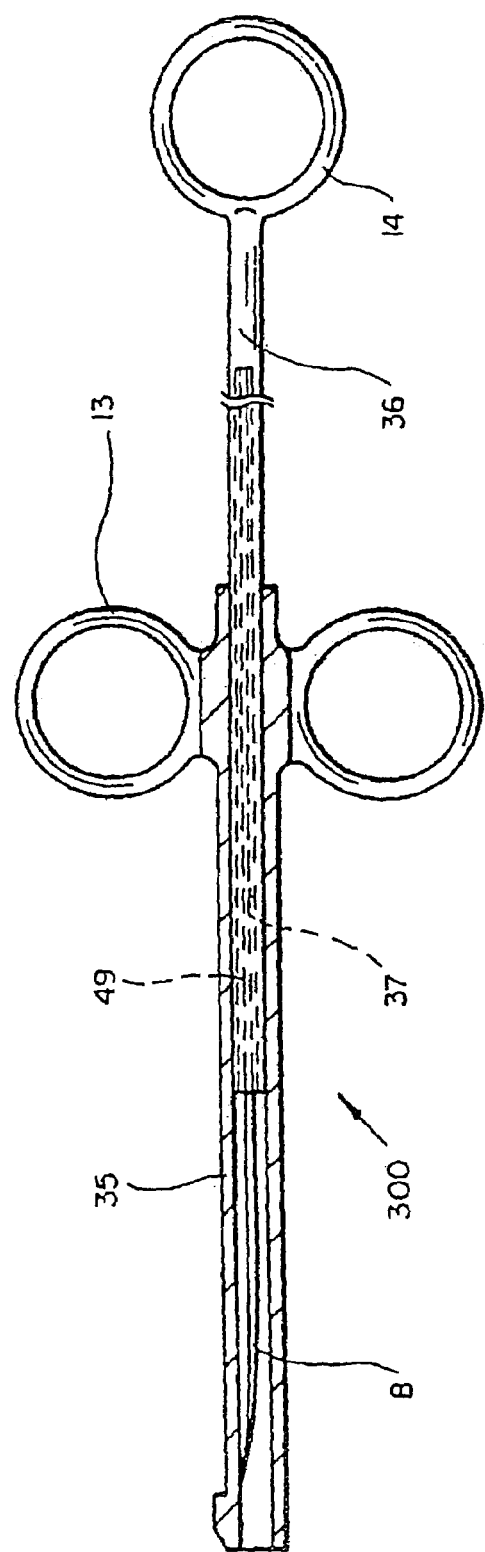
Figures 2, 3, 4, 5, 6, 7, 8, 9, 10, 11, 12, 13, 13A:
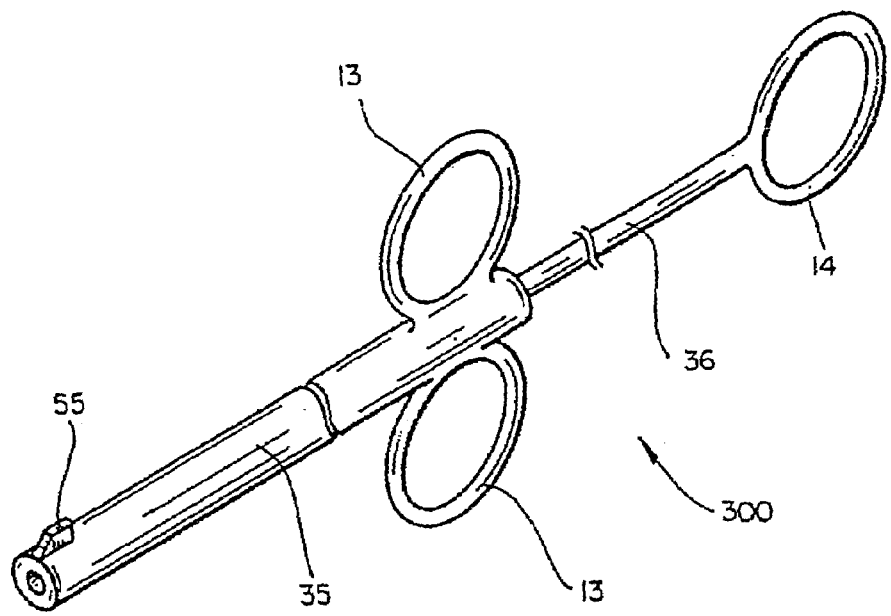
Figures 2, 3, 4, 5, 6, 7, 8, 9, 10, 11, 12, 13, 13B:
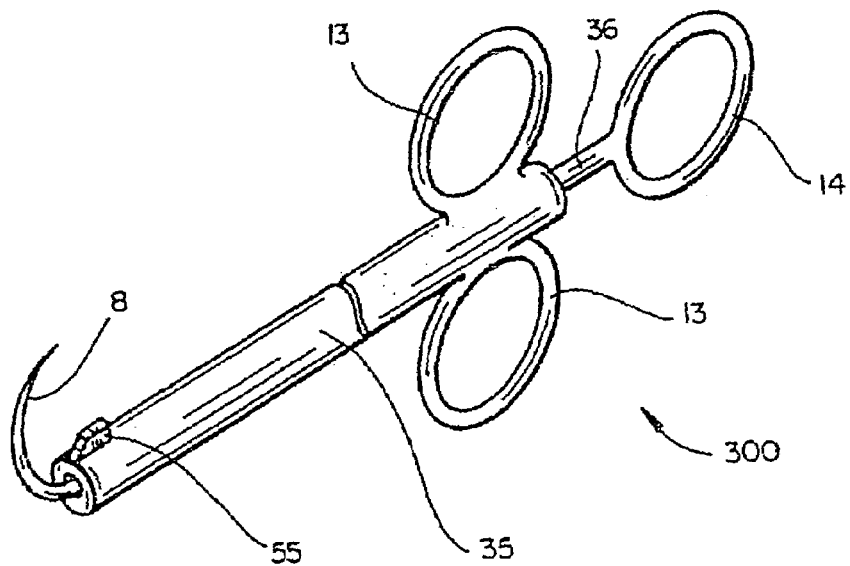
Figures 2, 3, 4, 5, 6, 7, 8, 9, 10, 11, 12, 13, 13C:
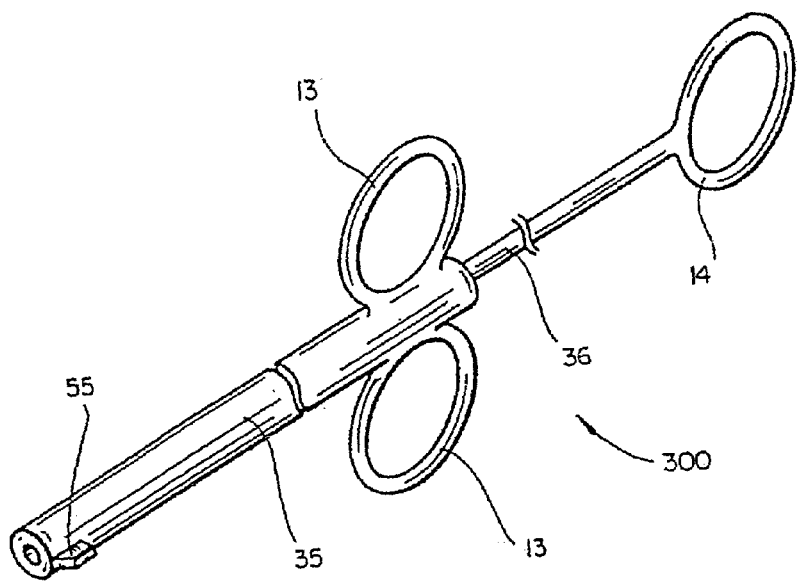
Figures 2, 3, 4, 5, 6, 7, 8, 9, 10, 11, 12, 13, 13D:
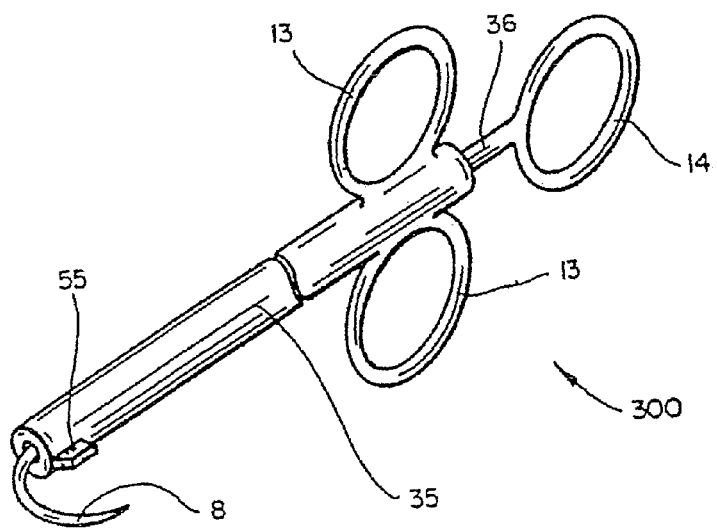
Figures 2, 3, 4, 5, 6, 7, 8, 9, 10, 11, 12, 13, 14:
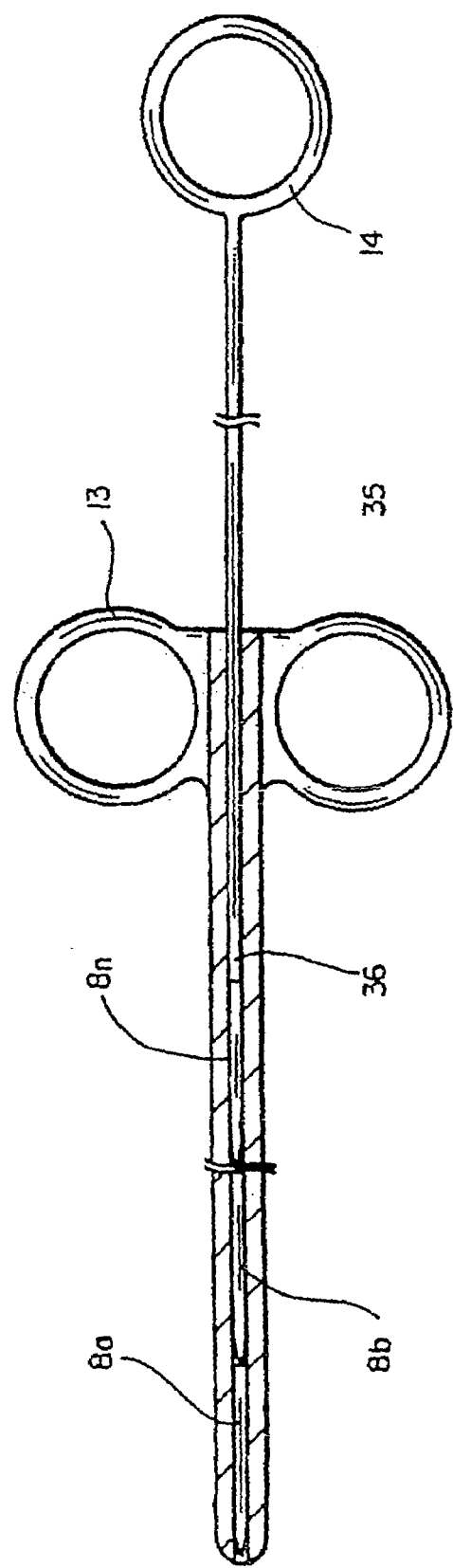
Figures 2, 3, 4, 5, 6, 7, 8, 9, 10, 11, 12, 13, 14, 15, 15A:
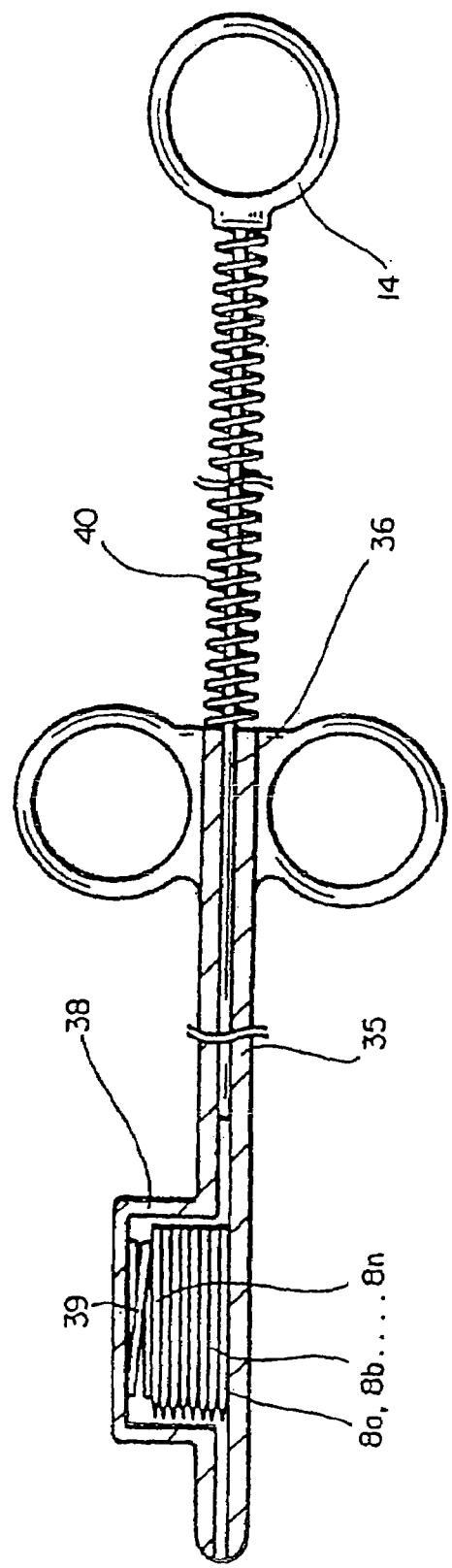
Figures 2, 3, 4, 5, 6, 7, 8, 9, 10, 11, 12, 13, 14, 15, 15B:
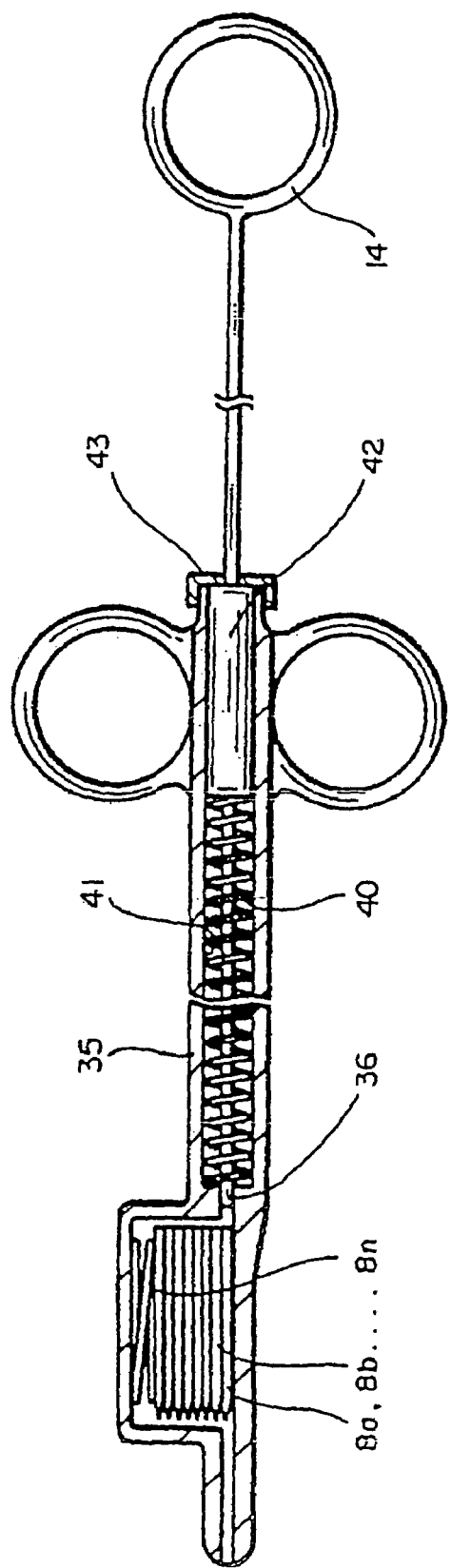
Figures 2, 3, 4, 5, 6, 7, 8, 9, 10, 11, 12, 13, 14, 15, 16, 16A:
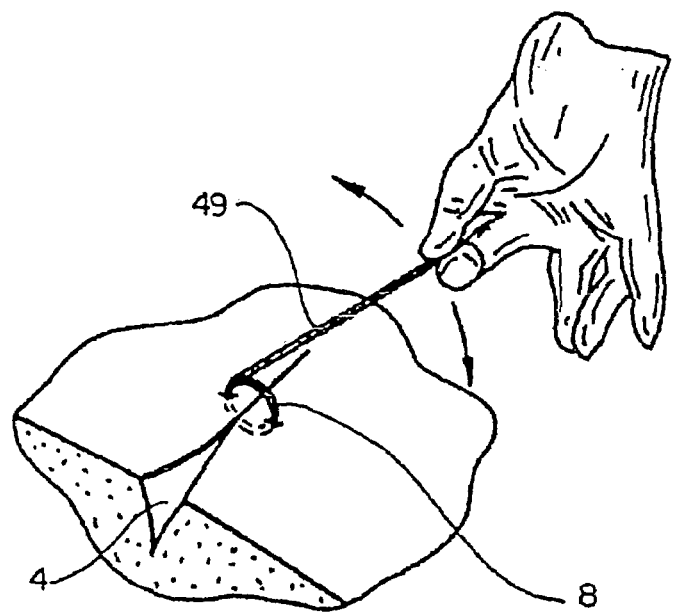
Figures 2, 3, 4, 5, 6, 7, 8, 9, 10, 11, 12, 13, 14, 15, 16, 16B:
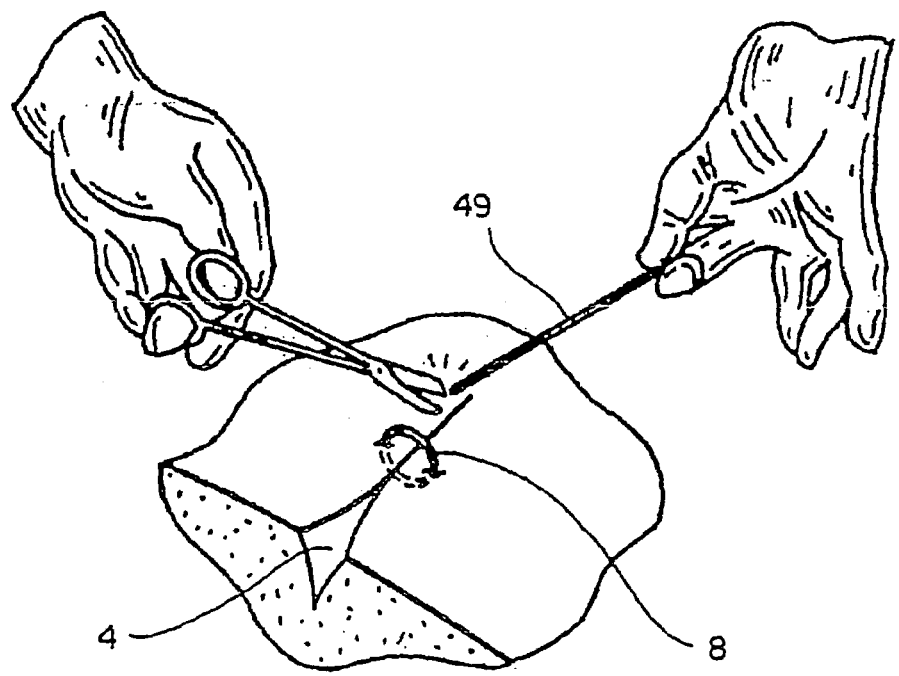
Figures 2, 3, 4, 5, 6, 7, 8, 9, 10, 11, 12, 13, 14, 15, 16, 17, 17A:
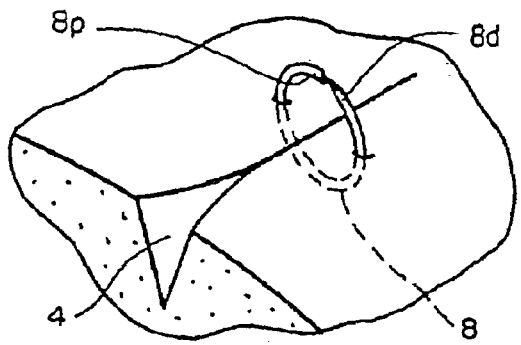
Figures 2, 3, 4, 5, 6, 7, 8, 9, 10, 11, 12, 13, 14, 15, 16, 17, 17B:
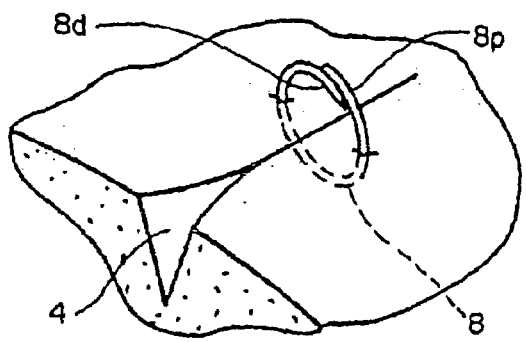
Figures 2, 3, 4, 5, 6, 7, 8, 9, 10, 11, 12, 13, 14, 15, 16, 17, 17C:
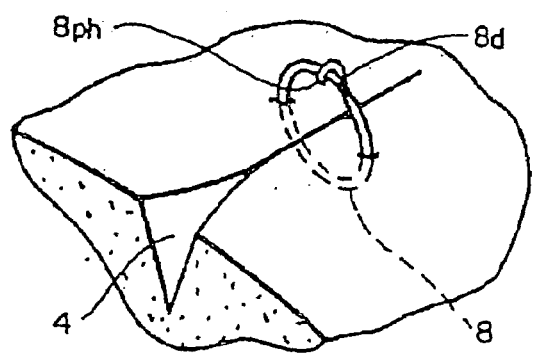

The elastic distal segment 14 of FIG. 16 is adapted with a ligature retainer means 34 which releasably retains the ligature 36. FIGS. 1-5a-b show the ligature retainer 34 as a hook and a hole, respectively. In either mode, the ligature retainer 34 may either be cut into the wire of the elastic distal segment 14, or may be bent thereinto by plastically deforming the wire of the elastic distal segment 14. Other suitable means may be employed without departing from the scope of this invention. It will be understood that the ligature retainer 34 may be fashioned in any desired orientation relative to the plane of curvature of the elastic distal segment 14. If the hook mode of the ligature retainer 34 is used, in order to prevent the hook 34 from catching on the inner lip 33 of the distal opening of the cannula 10 upon withdrawal, the lip 33 may be rounded off, as shown in FIG. 1-5a.

The second embodiment 200, like the first, may be adapted with at least one marker 31 for indicating a predetermined direction of curvature of the elastic member, and with suitable handles 20 and 22 or other means for extending and retracting the elastic member. A spring may be used to assist retraction of the elastic member 12.

As shown in FIG. 1-6, upon extrusion from the cannula 10, the elastic distal segment 14 curves around the vessel 5 with motion 38. It will be understood that the elastic distal segment 14 need not actually touch the vessel 5, but is shown in such contact for convenience. With the elastic member 12 wrapped around the blood vessel 5, the ligature (not shown) may be inserted into the ligature retainer 34 using tweezers, forceps, or the like. Withdrawal of the elastic distal segment 14 into the cannula 10 draws the ligature around the blood vessel 5 with motion 40. As will be understood, the ligature may also be inserted into the ligature retainer 34 before the elastic distal segment 14 is passed around the blood vessel 2, in which instance the ligature is passed around the blood vessel 5 upon extension of the elastic member 12 around the blood vessel 5 with motion 38, if the ligature retainer 34 is appropriately formed.

The apparatus 200 may further be adapted with means for automating the ligature's attachment to, or unattachment from the elastic member. FIGS. 1-7a-f illustrate one mode of this means. One end 35 of the ligature 36 is coupled to the cannula 10, for example by being tied or otherwise coupled to a post 44. Upon extension from the cannula 10, the elastic distal segment 14 curves with motion 38 around the vessel 5, as shown in FIG. 1-7b. The elastic distal segment 14 is constructed such that its return toward the unconstrained first shape brings the ligature retainer 34 into grasping contact with the held portion 35 of the ligature 36, as shown in FIG. 1-7c.

Upon retraction, the elastic member 12 draws the ligature 36 around the vessel 5 with motion 40 (the reverse of motion 38), and the ligature 36 slides through the ligature retainer 34, as shown in FIG. 1-7d. Upon full retraction, shown in FIG. 1-7e, the ligature 36 will be doubled around the vessel 5. If it is desired that only a single loop of ligature 36 pass around the vessel 5, this may be accomplished by simply releasing the trailing end 37 of the ligature 36, and withdrawing the apparatus 200 until the trailing end 37 passes around the vessel 5, as shown in FIG. 1-7f. Alternatively, a doubled suture (not shown) can be placed over the post and held by the post such that only one strand of the suture is hooked by ligature retainer 34.

The post 44 in the embodiments shown in FIGS. 1-7, 1-9, 1-10, 1-11, and 1-12, and the loop grabber 42 shown in FIGS. 1-8 and 1-9, are shown to be rigidly attached to the cannula 10. However, both post 44 and loop grabber 42 could consist of a tongue (not shown) or a cam (not shown) to which sutures may be attached. Such a tongue or cam would preferably be biased flush with the wall of the cannula 10 initially, but would be mechanically forced to extend in a direction sideways from the cannula when the elastic member 12 is extended from the end of the cannula. In this fashion, a suture would be held against the wall of cannula 10 until the elastic member is extended, at which time the post and/or loop grabber would extend sideways from the wall of the cannula 10 such that the post 44 will hold the suture in a better location for the ligature retainer 34, and/or such that the suture can be attached to the loop grabber 42. Upon withdrawal of elastic member 12 the tongue or cam will preferably return to their flush position. It is to be understood that the configuration of a post or a loop grabber can be a tongue, cam or other suitable structure.

In an alternative mode, the second embodiment 200 may be fashioned such that the ligature is passed around the vessel or bone upon extension, rather than retraction, of the elastic member. FIGS. 1-8a-d illustrate one such mode of the apparatus 200. A loop 39 is formed in the ligature 36, and the loop 39 is held in the ligature retainer 34, preferably facing in the direction in which the elastic distal segment 14 will curve upon extension from the cannula 10.

The cannula 10 includes a proximal facing loop grabber 42, which may be a hook. Upon extension, the elastic distal segment 14 curves around the vessel 5 and places the loop 39 of ligature 36 over the loop grabber 42. Upon retraction of the elastic member 12, the loop grabber 42 prevents the ligature retainer 34 from drawing the loop 39 back around the vessel 5. If the ligature retainer 34 is a groove or hook, the loop 39 is simply withdrawn therefrom upon retraction of the elastic member 12. If the ligature retainer 34 is a hole or eye, the ligature 36 slips therethrough upon retraction of the elastic member 12. Forceps can be used, instead of relying on the loop grabber 42, to grasp the ligature 36, if desired. In an alternative embodiment, the ligature 36 may be placed into the ligature retainer 34 as a simple raised strand, to be passed around the vessel and grasped with forceps.

FIG. 1-9 illustrates an equivalent mode of the apparatus 200 which passes the ligature 36 during extension of the elastic member 12. The loop grabber 42 may be elevated such that it has a segment 43 which extends both proximalward and cannulaward. The ligature retainer 34 may be formed as an eye, through which the ligature 36 is positioned. The cannula 10 may, suitably, be adapted with a post 44 to which the ligature 36 may be anchored. It will be understood that, by forming the elastic distal segment 14 to have a curvature upon extension such that the eye 34 is brought into contact with the segment 43 of the loop grabber 42, and by extending the elastic member 12 until the eye 34 extends slightly past the segment 43, the ligature 36 will be forced over the segment 43 as shown. This and other alternative modes of the ligature catching means are within the scope of this invention. Alternatively, a doubled suture (not shown) can be placed over the post and held by the post such that only one strand of the suture is hooked by ligature retainer 34.

In any of the modes, the ligature retainer may include two grooves or eyes on opposite ends of a Y-shaped distal end of the elastic member. In such a mode, a segment of the ligature may be held between the arms of the Y for presentation to the cannula's hook. This may be advantageous if the loop of the ligature is too limp to be easily caught by the cannula's hook. If formed as a hole, the ligature retainer may include a narrowed, slot-like portion at its proximal end, into which the ligature may be wedged. The narrowed portion will provide a fight grip on the loop of ligature during extension about the vessel, while the larger portion of the hole will enable the ligature to easily slip therethrough during retraction of the elastic member. These, and various other modifications may be made to the ligature, retainer, within the scope of this invention.

As shown in FIGS. 1-10a-d, the second embodiment 200 may be used to create a knot in the ligature 36. A loop 39 of the ligature 36 is placed around the cannula 10 in the following manner, as explained with reference to FIG. 1-10a. An end 35 of the ligature 36 is held at some point toward the proximal end (not shown) of the cannula 10. The ligature 36 is passed by a first side (the far side in FIG. 1-10a) of a post 44, then over the cannula 10 toward a second side (the near side in FIG. 1-10a) of the cannula 10 at a point distalward from the post 44. From there, the ligature 36 is passed around the cannula 10 back to the first side, then around the post 44 proximal to loop 39 on the second side. The trailing end 37 of the ligature 36 is then drawn toward the proximal end (not shown) of the apparatus 200 to draw the ligature 36 at least somewhat tight around the cannula 10 and post 44. The post 44 may include a protrusion 46 to keep the trailing end portion 37 of the ligature 36 elevated above the cannula 10, for ease of grasping the ligature 36. The cannula 10 may include an indented or grooved segment 48, to keep the loop 39 of ligature 36 in a given position about the cannula 10.

As seen in FIG. 1-10b, with the apparatus 200 in position at the vessel 5, the elastic member 12 may be extended until the ligature retainer 34 engages the trailing end portion 37 of the ligature 36. Then, the trailing end portion 37 alone may be drawn around the vessel 5 as shown in FIG. 1-10c. Finally, by sliding the loop 39 distally off of the cannula 10, with motion 50, until the loop 39 passes completely over and around the ligature retainer 34, the trailing end 37 may be drawn through the loop 39, to form a half-hitch knot as shown in FIG. 1-10d. The knot may then be tightened, as needed.

FIG. 1-11 illustrates the addition of a sliding sleeve 52, which slides in and out of the cannula 10. The sleeve 52 is disposed within the cannula 10, and the elastic member 12 is, in turn, disposed within the sleeve 52. Extension and retraction of the elastic member 12 may permit the sleeve 52 to slide a short, restricted distance. The loop 39 of the ligature 36 may be placed over the sliding sleeve 52 rather than over the cannula 10 itself. Then, after the trailing end 37 has been pulled around the vessel as described above, the sleeve 52 may be slid into the cannula 10, to dislodge the loop 39. In the final stages of retracting the elastic member 12 back into the sliding sleeve 52, the elastic member 12 may engage the sliding sleeve 52 such that the sliding sleeve 52 is automatically withdrawn into the cannula 10 and automatically releases the loop 39, if the tolerance between cannula 10 and sliding sleeve 52 is small and the loop 39 cannot readily pass between sliding sleeve 52 and cannula 10. If the ligature retainer 34 is kept within the sleeve 52 during the sliding, the loop 39 will not catch on the ligature retainer 34. The sliding sleeve 52 may be biased toward its extended position by a spring (not shown).

Alternatively, in FIGS. 1-10 and 1-11, end 35 of ligature 36 may be fastened to post 44.

FIGS. 1-12a-c illustrate how the apparatus 200, with or without the sliding sleeve, may be used to form a logger's knot around a vessel 5. The ligature 36 is loaded onto the apparatus 200 by simply passing a loop 39 of the ligature 36 over the distal end of the cannula 10, and by placing both ends 37 and 35 of the ligature 36 over the protrusion 46 on the post 44. The elastic member is extended and retracted, to catch and retrieve both ends 35 and 37 of the ligature 36, as described above. Then, both ends 37 and 35 of the ligature 36 are passed around the vessel 5 and are drawn through the loop 39. Other knots may be tied using the apparatus 200, within the scope of this invention. In all of the embodiments described herein, any suitable form of activating means may be utilized, for example, syringe-plunger mechanisms, slider mechanisms, scissor action mechanisms, pistol grip mechanisms or the like.

Various other modifications may be made to the apparatus, including those suggested by the following description of a "Suturing Instrument".

Another form of the present invention discloses an apparatus and method which, through the properties of elastic materials, preferably pseudoelastic materials, such as pseudoelastic shape memory alloys, overcome the prior art's disadvantages listed above. The apparatus is a delivery system for delivering, into a deep wound or into an arthroscopic, endoscopic, laparoscopic, or other such surgery site, a needle which is constructed of an elastic material, preferably a shape memory alloy. Although pseudoelasticity is exhibited in both linear and non-linear variations, the present invention deals preferably with superelasticity: and further references to materials having this property will simply be designated as being "pseudoelastic" or having shape memory. It will be understood, however, that the present invention may employ any appropriate elastic material, preferably shape memory alloy, whether linearly or non-linearly pseudoelastic. The term "needle" as used herein includes solid and hollow needles.

In a first embodiment, the present invention discloses a deep needle delivery apparatus, including a longitudinally extending cannula which may be inserted through an arthroscopic or other such incision or into a deep wound or into a natural body orifice. Inside the cannula, the apparatus has a cannula insert member, whose distal end includes a means for grasping a needle. The needle is held entirely within the cannula, in a straightened configuration.

Holding the needle within the cannula in a straightened configuration offers two advantages in reducing trauma to the patient's tissues: because no portion of the needle extends from the cannula during insertion of the cannula into the patient's body, the apparatus will not snag the tissues upon insertion, and because the apparatus has a minimized transverse dimension, only a small entry incision or site is required. The minimized transverse dimension may also permit the cannula to be used in a channel of an endoscope (rigid or flexible), in the lumen of a catheter, or as a catheter itself.

The apparatus includes a minimum of moving parts and is, therefore, both less subject to failure and less expensive than prior needle delivery apparatuses. The apparatus' simplicity of design results in a unique simplicity of use, as well.

In a second embodiment, the needle is extruded laterally rather than longitudinally, which may permit insertion of the needle into otherwise inaccessible portions of a patient's tissues.

In a third embodiment, the apparatus inserts ring dips (solid or hollow) rather than a needle.

FIGS. 2-1a to 2-6 illstrate the first embodiment of the present inventon, which longitudinally extrudes an elastic needle through the distal end of a cannula.

FIG. 2-1a is a cross-sectional view, showing the elastic needle held inside the cannula in a straightened configuration under mechanical stress.

FIG. 2-1b shows partial extrusion of the elastic needle from the cannula, with the extruded portion of the needle returning toward its curved configuration by elastic shape memory.

FIG. 2-1c shows the needle fully extruded from the cannula, and released from the cannula insert.

FIGS. 2-2a-e show alternative modes of the distal end portion of the cannula insert.

FIG. 2-3 is a view of the distal end portion of the cannula insert, showing a raised release signal tab formed therein.

FIG. 2-4a illustrates an integrally constructed mode of the distal end portion of the first embodiment, showing the enlarged transverse dimenson of the end portion of the cannula insert.

FIG. 2-4b shows an alternative, non-integral mode of the distal end portion of the cannula insert, formed of a compressible material.

FIG. 2-5 is a view of the distal end portion of the cannula insert, showing an indented distal face therein.

FIG. 2-6 is a cross-sectional view of the proximal end portion of the first embodiment, showing a suture retention bobbin within the cannula insert.

FIGS. 2-7 to 2-10 illustrate a second embodiment of the present invention, which extrudes the elastic needle laterally rather than longitudinally.

FIG. 2-7a is a cross-sectional view showing a cannula, shaft, and plunger of the second embodiment.

FIG. 2-7b is a cross-sectional view of an alternative mode of the proximal end portion of the second embodiment.

FIG. 2-7c is a cross-sectional view of another alternative mode of the proximal end portion of the second embodiment.

FIG. 2-7d is an enlarged cutaway view of the proximal end portion of the alternative mode shown in FIG. 2-7B.

FIG. 2-7e is a perspective view of the proximal end cap of the alternative mode shown in FIG. 27C.

FIG. 2-8 is a cross-sectional view of the distal end portion of the second embodiment, showing a suture retention bobbin therein.

FIG. 2-9 is a cross-sectional view of the second embodiment, taken at line 9-9 of FIG. 2-7a, showing grooves in the shaft and cannula, and groove engaging tabs in the plunger, for causing rotation of the shaft.

FIG. 2-10 is a cutaway perspective view of the distal end portion of the second embodiment, showing the unwinding of the curved needle through the aperture.

FIG. 2-11a illustrates the present invention being used to deliver the needle to a deep wound for suturing.

FIG. 2-11b illustrates the present invention being used in arthroscopic surgery on a knee.

FIGS. 2-12 to 2-15 illustrate a third embodiment of the present invention, which is used to insert ring clips into tissue to hold a wound closed.

FIG. 2-12a is a cutaway view of the third embodiment, illustrating a ring clip held therein.

FIG. 2-12b illustrates extrusion of the ring clip.

FIG. 2-12c illustrates an alternative mode of the third embodiment, adapted for use with an extended ring clip which is held therein.

FIGS. 2-13a and 2-13b, and 2-13c and 2-13d, illustrate a marker which indicates a first and a second direction of extrusion of the ring clip, respectively.

FIG. 2-14 is a cross-sectional view of another alternative mode of the third embodiment, adapted for serial extrusion of a purality of ring clips held therein.

FIG. 2-15a illustrates yet another mode of the third embodiment, with the plurality of ring clips held in a magazine.

FIG. 2-15b illustrates an internal piston return spring.

FIG. 2-16a illustrates manipulation of the extended distal seqment of the ring clip of FIG. 2-12c.

FIG. 2-16b illustrates the severing of the extended distal segment of FIG. 2-16a.

FIGS. 2-17a to 2-17c illustrate various modes of a ring clip.

FIGS. 2-1a to 2-1c illustrate the first embodiment of the present invention, a deep needlesuturing apparatus 100. The apparatus 100 has a cannula 11 and a needle delivery member which is a cannula insert 12. Although the drawings and this description specifically show a cannula 11 and cannula insert 12 which are straight and which may be assumed to be rigid, the cannula 11 and cannula insert 12 may be curved, or may even be deformable to some degree, within the scope of this invention. For example, they may be flexible and/or long enough for apparatus 100 to be used within a channel of an endoscope (flexible or rigid), in the lumen of a catheter, or as a catheter itself.

The cannula insert 12 has an outer dimension which allows it to fit coaxially within the cannula 11 and move longitudinally therewithin. The cannula 11 has a proximal end portion 11p to which are affixed cannula handles 13 which, suitably, may be finger rings into which a surgeon may insert his index and middle fingers. The cannula 11 has a bore 111 extending longitudinally therethrough. The bore 111 extends out the distal end portion 11d of the cannula 11, to allow a distal end portion 12d of the cannula insert 12 to extend distally out of the cannula 11. A cannula insert handle 14 is affixed to the proximal end portion 12p of the cannula insert 12. The handle 14 may, suitably, be a thumb ring through which the surgeon may insert his thumb. By pressing on the thumb ring 14 and pulling on the finger rings 13, the surgeon may extend the cannula insert 12 through the cannula 11 with motion 201. It will be understood that, within the scope of this invention, various other means may be employed to extend the cannula insert through the cannula. For example, the apparatus may include a pistol grip with a trigger for extending the cannula insert, or a scissor action mechanism, or the like.

The distal end portion 12d of the cannula insert 12 grasps an elastic needle 10. In the preferred embodiment the needle 10 is of a pseudoelastic shape memory alloy and has an arced shape while the needle's alloy is in a substantially austenitic phase, and the needle 10 may be stressed into a more straight shape in which the needle's alloy enters an at least partially more martensitic phase. When the needle 10 is held entirely within the cannula 11, as shown in FIG. 2-1a, the needle 10 is straightened and contains more stress-induced-martensite phase. As the needle 10 is extruded from the distal end portion 11d of the cannula 11, that portion of the needle 10 which extends beyond the cannula 11 returns toward its original shape by a martensitic-to-austenitic shape memory phase change caused by at least partial relief of the stress-induced-martensite in the needle's alloy.

The cannula insert 12 includes a longitudinal bore 112, which may be used to contain a suture 9 attached to the needle 10. Suitably, the bore 112 may extend longitudinally entirely through the cannula insert 12, to permit an unlimited length of suture 9 to be pulled therethrough. Although in FIGS. 2-1a-c the suture 9 is shown exiting through the proximal end of the cannula insert and laterally out of the thumb ring 14, the suture 9 may, within the scope of this invention, exit the apparatus in a variety of manners. For example, the suture may exit through a small aperture (not shown) in the side wall of the distal end portion of the cannula insert, in which case bore 112 would not have to extend further proximally and the proximal portion of cannula insert 12 would be dimensioned such that there would be room for the suture within bore 111 (i.e., the proximal portion of cannula insert 12 could have a smaller transverse dimension than its distal portion, or it may include a longitudinal slot for the suture). Alternatively, the thumb ring may be hollow, and the suture may pass directly from the interior of the cannula insert Into the interior of the thumb ring, and may exit through an aperture (not shown) at some point about the thumb ring.

The suture may be attached to the needle in a variety of ways. For example, the proximal end of the needle may include a hollow orifice which may be crimped down upon an end of the suture. Alternatively, a ferrule may be used to couple the suture to the needle. Or, a small wedge-shaped groove may be used to pinch the suture into a slot in the proximal end of the needle. If a more complex needle assembly is economically manufacturable, it may be advantageous to form, into the proximal end of the needle, a longitudinal slot or hole which may also communicate with a transverse slot into which a knotted or thickened portion of the suture may be positioned. Or, it may simply suffice to glue the suture onto the needle.

The distal end portion 12d of the cannula insert 12 includes a means for holding 15, which grips the needle 10, and which is connected to the bore 112. As the distal end portion 12d is distally extended from the cannula 11 with motion 201, the means for holding 15 releases the needle 10, permitting the surgeon to manipulate the needle 10 within the patient, to form stitches or perform other procedures. However, if the needle 10 is only partially extended from the cannula 11, the means for holding 15 will not yet have released the needle 10, and the cannula insert 12 and needle 10 may be retracted into the cannula with motion 202, to allow repositioning of the needle 10 in the patient.

FIGS. 2-2a through 2-2e illustrate various designs of the means for holding 15 formed in the distal end portion 12d of the cannula insert 12. The distal end portion 12d is divided by a slot 16 into a plurality of end sections 19. Each end section 19 includes a longitudinal groove 17, which runs substantially parallel to the axis of the cannula insert 12. In one mode, shown in FIG. 2-2a, one slot 16 divides the cannula insert 12 into two end sections 19, each of which has a flat surface into which the respective grooves 17 are formed. The enlargement in the slot 16, which is formed by the adjoining groves 17, constitutes the means for holding 15. In other modes, however, a plurality of slots may divide the distal end portion 12d into three or more end sections 19, as shown in FIGS. 2-2b and 2-2c. If there are three or more end sections 19, the grooves 17 lie at a centermost point of the wedge shaped end sections 19. It will be understood that the exact cross-sectional shape of the grooves 17 is not critical, so long as the grooves 17 remain well adapted to grasp the needle 10. It will be understood that the slot 16 may merely be a slit cut into the cannula insert 12, if the material of the cannula insert 12 reacts to the slit by flaring outward to allow later compression of the distal end portion 12d.

With reference to FIGS. 2-1c and 2-4a, it will be understood how the means for holding 15 grips the needle 10. A proximal, non-piercing end portion 10p of the needle 10 has a transverse dimension 10w, while the means for holding 15 has a transverse dimension 15w sufficiently larger than dimension 10w to accept the needle 10 without gripping it. The distal end portion 12d of the cannula insert 12 has a transverse dimension 12dw perpendicular to the slot 16, and the remainder of the cannula insert 12 has a dimension 12w which is smaller than dimension 12dw. The cannula 11 has an internal transverse dimension 11w, which is sufficiently larger than dimension 12w to allow the cannula insert 12 to move freely therewithin. However, because dimension 11w is smaller than dimension 12dw, in order for the distal end portion 12d of the cannula insert 12 to fit within the cannula 11, the distal end portion 12d must compress. It will be understood that by appropriately sizing various portions of the bore 111, the distal end portion 12d may be caused to compress at a determinable point along the cannula 11. The compression need not occur at the exact distal end of the cannula.

FIGS. 2-2a-e and 2-4a illustrate embodiments of the compressible distal end portion 12d, in which the distal end portion 12d is formed as an integral, unitary member with the cannula insert 12. As the distal end portion 12d is drawn into the cannula 11, the end segments 19 are pressed toward each other, reducing the widths of the slots 16, which causes the grooves 17 to clamp down on the needle 10. However, as shown in FIG. 2-4b, the distal end portion 12d may simply be a separate member made of a compressible material, such as an elastomer, with or without any slots or end sections, which member is coupled to the cannula insert 12. In such a mode, the entire distal end portion 12d elastically compresses onto a needle held in its means for holding 15. In either mode, as the distal end portion 12d of the cannula insert 12 is extended distally out of the open end of the cannula 11, the distal end portion 12d elastically returns toward its original shape, allowing the needle 10 to freely slip from the means for holding 15.

FIGS. 2-2d and e may be better understood with reference to FIG. 2-1a. It will be understood that when the needle 10 is held in the means for holding 15, and the needle 10 is disposed entirely within the cannula 11, the elastic properties of the needle 10 exert lateral forces upon both the cannula 11, and the means for holding 15. The straightened needle 10 exerts lateral force on the distal end of the cannula insert 12 in the direction shown in FIG. 2-2d by arrow 203. The needle 10 has a point which bears on the cannula 11 at a location opposite the direction 203. By forming the means for holding 15 in a position radially removed from the center from the cannula insert 12, in direction 203, the needle 10 may be held in a less stressed and less straightened configuration, without changing the transverse dimension of the cannula 11.

The slot 16 may be radially removed from the center of the cannula insert 12, as shown in FIG. 2-2e, to divide the distal end portion 12d into two asymmetrical end portions 19. A needle 10 held in an orientation so as to curve opposite the direction of arrow 203 (generally upward in FIG. 2-2e) will exert a force which is perpendicular to the slot 16 rather than along the slot 16. This helps prevent the needle 10 from forcing its way out of the means for holding 15 and into another position within the slot 16, and ensures a more firm grasp on the needle 10.

FIG. 2-3 illustrates a needle release indicator formed in the distal end portion 12d of the cannula insert 12. Near the distal end of the cannula insert 12, a raised release signal tab 20 is formed in the distal end portion 12d. A segment 21 immediately proximal to the tab 20 is radially indented relative to the tab 20. Although segment 21 is shown in FIG. 2-3 as having a lateral dimension which is smaller than the remaining portions of the cannula insert 12, this is, in various modes of the cannula insert 12, not mandatory. For example, the remaining portions of the cannula insert 12 may be of smaller, equal, or greater lateral dimension than segment 21, so long as the cannula insert 12 remains longitudinally movable within the cannula 11, and so long as the means for holding 15 remains able to hold and release the needle 10.

When the distal end portion 12d of the cannula insert 12 is extended beyond the distal end of the cannula 11, at the moment the tab 20 completely exits the cannula 11, the distal end portion 12d snaps outward until the segment 21 contacts the cannula 11. This produces a tangible or audible signal to the surgeon, indicating that the cannula insert 12 is emerging from the distal end of the cannula 11, and, depending on the placement of the tab 20 relative to the means for holding 15, may indicate to the surgeon that the needle 10 has just been or is about to be, released. It will be understood that, by appropriately sizing various segments of the cannula 11 and by appropriately placing the tab 20, the release signal may be made to occur at any given stage of needle extension. In an alternative embodiment (not shown), tab 20 can be replaced by one or more elastic tabs directed proximally which spring out as distal end portion 12d emerges from the distal end of cannula 11.

Once the needle 10 has been released from the cannula insert 12, the surgeon may use the needle 10 to insert running stitches or regular stitches into the patient's tissues. Once the stitching procedure is finished, the needle 10 must be withdrawn from the patient's body with a minimum of trauma to the patient. The apparatus 100 of the first embodiment can also be used in the withdrawal of the needle 10. By maneuvering the cannula insert 12 until an end of the needle 10 enters the means for holding 15, and then distally extending the cannula 11 onto the cannula insert 12, the surgeon may recompress the distal end portion 12d of the cannula insert 12, which presses the means for holding 15 onto the needle 10. Then, by withdrawing the cannula insert 12 into the cannula 11, the needle 10 may be restraightened and drawn entirely inside the cannula 11. The cannula 11 may then be withdrawn from the patient's body with an absolute minimum of trauma. This same process may be used if the needle 10 is badly placed when extruded from the cannula 11. The surgeon may simply regrasp the needle 10 in the cannula insert 12, retract the needle 10, and re-extrude the needle 10 into a better position. The same process may even be used repeatedly in the suturing process itself.

In order to ease the process of manipulating the cannula insert 12 back onto the needle 10 for withdrawal, the distal end of the cannula insert 12 may include a concave face 22, as shown in FIG. 2-5. The means for holding 15 enters through the distal end of the cannula insert 12 at the deepest point of the indented face 22. Thus, if the surgeon maneuvers the cannula insert 12 near enough to the needle 10, so that an end of the needle 10 is within the indented face 22, during further distalward motion of the cannula insert 12, the indented face 22 will guide the needle 10 into the means for holding 15.

In order to provide a more self-contained apparatus 100, the cannula insert 12 may include a means for containing a length of suture. In one mode, the means for containing may be a suture release bobbin 25 around which a length of suture 9 is wound, as shown in FIG. 2-6. As the surgeon uses the needle 10 to make stitches in the patient, the suture 9 is pulled from the distal end of the bobbin 25. By forming the bobbin 25 with a slightly conical shape, the suture 9 may be pulled from the bobbin 25 with reduced friction. Reducing the friction between the apparatus 100 and the suture 9 is not only desirable to make suturing easier for the surgeon, but also to prevent accidental movement of a needle 10 which has been released within the patient. Such unwanted movement might be caused by friction between the suture 9 and the apparatus 100 if the apparatus 100 is moved or inadvertently bumped by the surgeon.

FIG. 2-11a shows how the first embodiment 100 of the present invention may be used to repair a deep wound 4 in tissues 3 and 5. The surgeon positions the apparatus 100 near the wound to be repaired, and extrudes the needle 10 from the apparatus, as described above. The needle's piercing distal end 10d first pierces the tissue 5 on one side of the wound 4. Then, as the needle 10 is further extruded from the cannula 11, the needle 10 returns toward its unstressed shape. This curves the needle 10 through the tissue 5 beneath or near the bottom of the wound 4. The piercing distal end 10d of the needle 10 eventually penetrates and then protrudes from the tissue 3 at the opposite side of the wound 4. The distal end 10d of the needle may then be grasped to pull the needle through the tissue 5 and 3 to draw the suture across the wound 4. Knots may then be tied in the suture, or the needle 10 may be repeatedly withdrawn and extruded from the apparatus 100 to form multiple stitches. The means for holding 15 may be used to grasp the distal end 10d of the needle during this process, in the same manner described above for withdrawal of the needle 10. After the distal end 10d emerges from the tissue 3, the surgeon may grasp the distal end 10d in the cannula insert's means for holding, as described. The surgeon may then pull the needle 10 and suture through the tissues 5 and 3. The surgeon may release the needle 10, then grasp its proximal end 10p in the means for holding and partially or fully resheath the needle 10 inside the cannula 11 preparatory to forming another stitch.

FIG. 2-11b illustrates the first embodiment 100 of the present invention being used in arthroscopic surgery to repair a torn meniscus 6 in a knee 7, in much the same manner. It will be understood that, because the needle 10 provides its own curving suture path as it pierces the meniscus 6, the apparatus 100 need not be swept over any degree of motion in order to suture the meniscus 6. The apparatus 100 is capable of performing suturing through an entry wound which is of a minimal size. The entry wound need only be big enough so that the apparatus 100 may slip inside the knee. In other words, the entry wound need only be as big as the lateral dimension of the apparatus 100.

As shown in FIG. 2-7a, a second embodiment of the present invention is an apparatus 200 which extrudes a needle 10 laterally rather than distally. The second embodiment 200 includes a cannula 30 which is substantially similar to the cannula of the first embodiment. Apparatus 200, which is preferably rigid, can be long and/or flexible enough for apparatus 200 to be used in a channel of an endoscope (flexible or rigid), in the lumen of a catheter, or as a catheter itself. However, the second embodiment's cannula 30 does not have an open distal end. Rather, the second embodiment 200 extrudes the needle 10 through an aperture 31 which is located through a side wall of the cannula 30 near its distal end. In this application, it is intended that the term "adjacent the distal end", when applied to the location of the aperture or of other equivalent means, indicates that the aperture may open either through the side wall of the cannula or actually through the distal end of the cannula.

Inside its distal end, the cannula 30 includes a pivot 34, about which a shaft 29 rotates. The distal end portion of the shaft 29 is a spool portion 29d about which the needle 10 is wrapped. When used with the second embodiment 200, the needle 10 is stressed into a more curved, rather than a more straightened, shape when disposed within the apparatus. Relief of the stress in needle 10 held in the more curved configuration, then, results in the needle 10 returning toward its more straight shape which may be a curve suitable for suturing.

Much of the remainder of the shaft 29 includes spiral grooves 27. A plunger 28 is disposed about the shaft 29 and within the cannula 30, and has tabs 26 which engage the spiral grooves 27 of the shaft 29. When the plunger 28 is moved into the cannula 30, the tabs 26 and grooves 27 impart rotating motion 210 to the shaft 29 and needle 10. When the plunger 28 is withdrawn, the shaft 29 rotates in the opposite direction.

FIG. 2-9 is a cross sectional view of the apparatus 200, taken across line 9-9 of FIG. 2-7 a, and illustrates the special relationship between the cannula 30, the plunger 28 with its tabs 26, and the shaft 29 with its spiral grooves 27. As will be understood, a functionally identical equivalent may be constructed by affixing the tabs 26 to the shaft 29, and adapting the plunger 28 with the spiral groves 27. As further shown in FIG. 2-9, the groove-engaging tabs 26 of the plunger 28 may also extend outward from the plunger 28, and the inner surface of the cannula 30 may also be adapted with grooves 72. By forming the grooves 72 in the cannula 30 to run substantially linear to the axis of the cannula 30, the plunger 28 will be prevented from rotating upon insertion into and withdrawal from the cannula 30.

As shown in FIG. 2-7b, the tabs 26 may be constructed as a part of the cannula 30. The thumb ring 14 is coupled to the plunger 28 by a swiveling means. In one mode, the swiveling means may be the simple snap-lock mechanism 28c shown in FIG. 2-7d, which is held in place by an end cap 28b. In this mode, the shaft 29 slidably engages the plunger 28 by any non-circular cross-section instead of having spiralled grooves.

With reference to FIGS. 2-7c and 2-7e, it will be understood that the exact means for imparting rotation to the shaft 29 may be formed in a variety of ways within the scope of this invention. For example, the tabs and grooves may be eliminated by simply forming the plunger 28 of a spiral-twisted rod of square cross-section, and providing the cannula 30 with an appropriate end cap 57 which has an opening suited for permitting the plunger 28 to pass therethrough only by appropriate rotation. Other non-circular cross-sections are, of course, within the scope of this invention. Again, shaft 29 slidably engages plunger 28 by any non-circular cross-section instead of having spiralled grooves. It is to be understood that any suitable activating means, such as syringe-plunger mechanisms, slidings mechanisms, pistol grip action mechanisms, scissor action mechanisms or the like can be used to depress plunger 28 into cannula 30.

With reference again to FIG. 2-7a, the shaft 29 may contain a repository 32 which is a means for containing a length of suture 9. The shaft 29 includes a needle stop 24, which prevents the needle 10 from rotating backward relative to the shaft 29. In one embodiment, the needle stop 24 may simply be a lip on one side of the repository 32, which lip forms a means for abutting a non-piercing end of the needle 10.

FIG. 2-8 illustrates an alternative mode of the repository 32, in which the repository may be a bobbin 33 which contains a length of suture. The bobbin 33 rotates freely about the shaft 29 with motion 205. This, too, reduces friction between the suture and the apparatus 200, to prevent unwanted movement of the needle 10 via the suture, once the needle 10 has been completely extruded from the cannula 30.

FIG. 2-10 is a cutaway cross-sectional view of the distal end portion of the second embodiment 200, and illustrates the unwinding of the needle 10 through the aperture 31. The aperture 31 must have a dimension sufficient to allow the needle 10 to freely pass therethrough in its entirety without binding. As the spool portion 29d of the shaft 29 rotates relative to the cannula 30, the needle 10 unwinds through the aperture 31 and returns to its unstressed shape. It will be understood that the alternative modes shown in FIGS. 2-7b-e are not complete, and must include appropriate components at their distal ends, much like those shown in FIG. 2-7a.

As will be understood, the second embodiment 200 may be used in a substantially similar fashion as described for the first embodiment of the deep needle suturing apparatus 100 with reference to FIGS. 2-11a and 2-11b, above. The second embodiment 200, however, may be used to provide surgical access to various suturing sites not accessible with the first embodiment.

In some surgical procedures, stitches are not implanted in a wound. In a third embodiment 300 of the present invention, illustrated in FIGS. 2-12a-c, the unstressed shape of the needle may be substantially circular to form the needle into a ring clip 8. Only after the wound has healed are the ring clips removed, if at all.

FIG. 2-12a shows the third embodiment 300 of the present invention, adapted for inserting ring clips 8 (which can be hollow or solid) rather than needles. The third embodiment 300 includes a cannula or cylinder 35 which is substantially similar to the cannula of the first embodiment. Apparatus 300, which is preferably rigid, can be long and/or flexible enough for apparatus 300 to be used in a channel of an endoscope (flexible or rigid), in the lumen of a catheter, or as a catheter itself. However, the cylinder 35 has an internal dimension which may be more similar to the outer dimension of the wire of the ring clip 8 than is the inner dimension of the first embodiment's cannula to the needle. By forming both the wire from which the ring clip is made and the internal bore of the cylinder to have a non-circular cross-section, the ring clip may be prevented from rotating within the bore. The third embodiment 300 further includes a piston 36, whose transverse dimension is substantially equal to the inner dimension of the cylinder 35. The piston 36 need not necessarily contain any means for grasping the ring clip 8, as it is only used to extrude the ring clip 8 from the cylinder 35. However, adaptations of the third embodiment 300 which provide means for holding and retracting the ring clip 8, similar to those provided for holding and retracting the needle in the first embodiment, are certainly within the scope of this invention.

The ring clip 8 is disposed within the cylinder 35, with its distal end 8d facing toward the open distal end of the cylinder 35. The piston 36 is disposed within the cylinder 35, with the distal end of the piston 36 abutting the proximal end 8p of the ring clip 8. Insertion of the piston 36 through the cylinder 35 with motion 206 expels the ring clip 8 from the cylinder 35 as shown in FIG. 2-12b. As the ring clip 8 is expelled, it returns to its unstressed shape with coiling motion 207, as described above for the needle of the first embodiment. Suitably, the ring clip 8 may have an unstressed shape which is substantially circular, in order that it may pass through a patient's soft tissues with a minimum of lateral pressure, to cause a minimum of structural damage to the tissues.

The third embodiment 300 (as well as any of the embodiments of this invention) may be adapted with at least one marker means 55. The marker 55 may be, suitably, a raised or embossed portion of the cylinder 35, or may simply be printed thereon. With the ring clip 8 loaded into the cylinder 35 in an appropriate orientation, the marker 55 will indicate the direction in which the ring clip 8 will curl when extruded. This aids the surgeon in properly clipping a wound. It will be understood that any of the various embodiments described herein may also be advantageously adapted with a suitable marker means. FIGS. 2-13a-b, and FIGS. 2-13c-d, illustrate proper alignment of the marker 55 indicating two respective directions of extrusion of a ring clip 8. The respective positions of the marker 55 in FIGS. 2-13a or c indicate that the ring clip 8 will exit the cylinder 35 in the direction as shown in FIGS. 2-13b or d, respectively. Marker 55 may be positioned at any suitable location along the cylinder. More that one marker may be present In another mode, shown in FIGS. 2-12c and 2-16a, the ring clip 8 includes an extended proximal segment 49, whose unstressed shape is relatively straight. This proximal segment 49 may be grasped by the surgeon in any manner and manipulated, in order to adjust the ring clip 8 within the soft tissues. In this mode, the piston 36 has an enlarged diameter and includes a bore 37 extending into the piston 36. Adapting the piston 36 with the bore 37 allows the third embodiment 300 to contain the lengthened and extended ring clip 8. This obviates the need to lengthen the cylinder 35, making the apparatus 300 easier for the surgeon to handle. As shown in FIG. 2-16b, after the surgeon has manipulated the extended ring clip 8, the extended end segment 49 may be removed by any conventional method, such as cutting it off with wire cutters. It will be understood that the proximal segment 49 need not be of an elastic material, but may be any conventional material affixed to the elastic segment 8 in order to minimize the cost of the apparatus 300.

The cylinder and piston of the third embodiment of the apparatus may be used with a variety of different ring clips, such as are shown in FIGS. 2-17a-c. As shown in FIG. 2-17 a, the ring clip 8 may be formed such that, in its unstressed configuration, its distal end 8d and proximal end 8p come into end-to-end abutting alignment. Alternatively, as shown in FIG. 2-17b, the ends 8d and 8p may come into side-by-side overlapping alignment. Locking of the ring clip may be permitted by having a small barb or barbs (not shown) on end 8d which fit(s) into a recess or recesses (also not shown) on end 8p or vice versa.

A slightly modified ring clip may include a proximal coupling hook 8ph. In such a configuration, in the ring clip's unstressed configuration, the hook 8ph remains somewhat separated from the piercing end 8d, such that the ring clip does not form a complete circle. The surgeon may stress the ring clip into a tighter arc, and engage the hook 8ph with the piercing end 8d, as shown. The elasticity in the ring clip 8 will cause the hook 8ph to remain engaged under mechanical stress. Such a mode of the ring clip is taught in U.S. Pat. No. 5,002,563 (Pyka et al).

As shown in FIG. 2-14, the third embodiment 300 may have a lengthened cylinder 35, within which may be disposed a plurality of ring clips 8a-8n. Injection of the piston 36 through the cylinder 35 then causes serial extrusion of the ring clips 8a-8n.

Serial extrusion of ring clips 8a-8n may also be accomplished by adapting the third embodiment 300 as shown in FIGS. 2-15a or b. In this mode, the third embodiment 300 includes a magazine 38 which holds the plurality of ring clips 8a-8n. The magazine 38 includes a magazine spring 39, which presses on the ring clips 8a-8n to keep them in their stressed and more straightened shape, and which introduces them serially into the cylinder 35, in position for extrusion by the piston 36. The magazine 38 may be separately attachable, and may also be refillable. It will be understood that any suitable means may be used to keep the plurality of ring clips in any favored orientation, if it is desired that they exit the cylinder 35 in a predetermined orientation of curvature. For example, the ring clips 8a-8n may be formed of a rectangular cross section, or they may be releasably glued together, to prevent their rotation, within the magazine 38, away from their preferred orientation.

The third embodiment 300 may further be adapted with a piston return spring 40, which is compressed upon injection of the piston 36, and which automatically returns the piston 36 to a position allowing introduction of the next ring clip into the cylinder 35. As shown in FIG. 2-15b, the piston return spring 40 may be disposed within the cylinder 35. In this mode, the cylinder 35 includes an enlarged chamber 41, within which the spring 40 is disposed. The piston 36 may include an enlarged segment 42, which is disposed within the cylinder 35, and which is kept inside the cylinder 35 by an end cap 43 on the cylinder 35. This maintains the apparatus 300 as a more integral unit, and prevents the complete withdrawal of the piston 36 from the cylinder 35. This also allows for a precompressed piston return spring 40 to be used, which provides greater return strength and speed for the piston 36. It is to be understood that any of the embodiment of this invention may be activated by any suitable activating means, such as syringe-plunger mechanisms, slidings mechanisms, pistol grip action mechanisms, scissor action mechanisms or the like.

A third form of the present invention provides an endoscopic or laparoscopic surgical device which provides an internal drape, and facilitates tissue collection. The surgical device comprises a housing having an axial bore with a distal deployment opening; and a barrier member which is constrainable within the axial bore. The barrier member comprises a loop of elastically recoverable material, preferably a shape memory alloy, and a barrier membrane loosely spanning the loop. Remote means are provided to project and retract, and optionally to rotate, the barrier member relative to the distal end of the housing. A preferred embodiment uses a shape memory alloy material, especially a pseudoelastic shape memory alloy material, and more preferably a superelastic shape memory alloy material.

The barrier member is moveable between a first position wherein the barrier member is constrained within the housing, and a second position wherein the barrier member is extended past the distal deployment opening of the housing, and assumes an expanded shape. In the expanded shape, the barrier member acts as a surgical drape and/or as a surgical collector. The barrier member is preferably moveable to a third position wherein the barrier member is partially or fully retracted, and at least a portion of it is constrained within the housing.

The loop of elastically recoverable material may be partially or wholly formed of elastically recoverable material. Thus for example two or more parts of the loop, e.g. two substantially semi-circular halves of the loop, may be connected to each other by another member which may or may not be elastically recoverable. In one embodiment two or more elastically recoverable parts of the loop are connected to each other by a flexible heat-shrinkable sleeve, which preferably comprises a polymeric material. In this case the elastically recoverable parts may comprise a shape memory alloy as described hereinbefore, or traditional resiliently deformable materials such as spring metals. The heat recoverable connecting sleeve, being flexible can bend e.g. by acting as a hinge to allow the loop parts to fold together to be compressed into the housing, and also to spring apart when extended from the housing. The connecting member may itself be resilient, causing the arms of the loop to spring apart when the loop is deployed outside the housing.

In one advantageous embodiment the connecting member, can be removed to release the barrier membrane, e.g. the bag or drape, spanning the loop.

In preferred embodiments according to the invention, especially where the barrier member is acting as a collecting pouch, a bushing is included in the housing. This bushing is arranged to be pushed out from the distal end of the housing at the same time or after the barrier member is deployed, and then to snap against the outside of the distal end of the housing. Since it is snapped against the housing the bushing can not then be withdrawn back into the housing. This hollow bushing may serve two functions. Firstly, the dimensions of the hollow bushing are preferably such that it allows complete withdrawal back into the housing of the elastically deformable loop, but not a filled barrier membrane, which may now be of larger volume, being filled, for example, with body samples. Thus the bushing ensures that the barrier member remains suspended outside the housing, as desired for some applications. Secondly the bushing is preferably shaped to provide a smooth entrance so that the barrier member is not torn by contact with the ends of the housing.

In the above embodiments, where a loop or a frame of an elastically deformable material is constrained within a housing such as a cannula or the like it is particularly advantageous to modify the design of the loop in order to minimize or, to suppress any possibe risk of plastic deformation. Therefore in preferred embodiments the elastically deformable loop preferaby comprises a necked portion, preferably towards the distal end of the loop. The "necked portion" is formed where the sides or arms of the loop come towards each other and then divert outwards of the loop before turning towards each other again to join to each other. A bulbous portion, or second loop portion, is thereby formed adjacent to the main loop portion. The bulbous portion is preferaby of significantly smaller dimensions than the main loop portion. The advantage of the necked-loop design is that when the loop is constrained within the housing any severe deformation is absorbed by the necked region and therefore the risk of any plastic deformation to the main loop portion is substantially eliminated or at least minimized.

The necked portion may, for example, be formed in the following two ways. First the sides of the loop may come toward each other, overlap, and then curve outwards in the opposite sense to join to each other. In this case the overall shape is a double loop configuration, similar to a figure "8". In the second case the sides of the loop divert outwards without overlapping to form a bulbous region, or "nipple" configuration adjacent the main loop.

One advantage of the preferred necked-loop configuration is that it allows severe constraints to be put on the elastically deformable loop without introducing any plastic deformation into the main body of the loop. This allows smaller diameter housings to be used to constrain the loop than would be possible without the necked configuration. This can be particularly advantageous, for example, in less invasive surgery. The design also allows the thickness of the loop to be increased without risking plastic deformation. Thus the loop rigidity may be increased which may be advantageous for some applications, especially for example where large bops are to be used.

FIG. 3-1 is a view of an unexpanded barrier device (not shown) within a housing.

FIG. 3-2 through FIG. 3-5 are progressive cross-sectional views through line a-a of FIG. 3-1, showing the use of the device of FIG. 3-1. The figures show, respectively, FIG. 3-2, constrained; FIG. 3-3, expanded (memory); FIG. 3-4, pouched; and FIG. 3-5, withdrawal configurations.

FIG. 3-6 shows alternate embodiments of the device of FIG. 3-1 through line b-b.

FIG. 3-7 and FIG. 3-8 show alternate embodiments of the barrier member in the expanded (memory) configuration.

FIG. 3-9 shows cross-sectional embodiments through line b-b of FIG. 3-7.

FIGS. 3-10, 3-11 and 3-12 detail alternate expanded loop configurations.

FIG. 3-13 is a schematic representation of another embodiment of a device for deploying an internal drape, and FIGS. 3-14 and 3-15 are schematic representations of yet another embodiment of device for deploying an internal bag, showing the device before and after withdrawal of the drape into the shaft of the instrument.

FIGS. 3-16 to 3-18 illustrate the use of a bushing which can be used with any of embodiments 3-1 to 3-15.

FIGS. 3-19 to 3-22 illustrate a necked-loop configuration which can be incorporated in any of the embodiments, illustrated in FIGS. 3-1 to 3-18.

During surgery, especially "least invasive surgery" (LIS), it is frequently necessary to remove diseased tissue. This tissue may be infected, contain inflammatory secretions (e.g., bile), or contain tumor cells. In any of these situations it is desirable to perform surgery without contaminating surrounding healthy tissues with any of the diseased tissue. Expandable internal barriers of this invention minimize or prevent such contamination. The expandable barrier member comprises (a) a flexible membrane which loosely spans (b) a loop of elastically deformable material. The elastically deformable loop is preferably a pseudoelastic shape memory alloy which defines an expanded loop in its "memory" shape. The expandable barrier is constrained within a housing, and the deployment end of the housing is placed within a body. The barrier is deployed from the housing and expands to its memory shape.

The barrier can be placed under diseased tissue, so that undesired materials spill into the barrier by gravity and/or irrigation flow, without contaminating surrounding tissues. The undesired materials can be aspirated from the surface of the barrier prior to withdrawal of the device. Alternatively, the barrier is placed so that it substantially surrounds and encloses the diseased tissue and sequesters it from healthy tissue during surgery. The tissue sample is severed (if necessary). In a preferred embodiment, when the elastically deformable loop is first withdrawn back into the housing the barrier membrane remains suspended outside the housing. The upper edge of the barrier membrane closes to form a pouch as the elastically deformable loop is retracted into the housing. Within the pouch is a tissue sample or other material which has been enclosed by the membrane. The housing, barrier and enclosed materials are removed from the patient.

The figures are drawn for purposes of clarity and are not drawn to scale. Like numbers represent like structures.

FIG. 3-1 is a lateral external view of a device according to the subject invention. The housing 10 includes a deployment end 12 which is inserted into the patient and which houses the expandable barrier member (not shown) in a constrained configuration; a shaft portion 14 which may be partially or completely inserted within the patient body; and an actuator end 16 opposite the deployment end, which is retained substantially outside the patient. The housing 10 can be flexible or rigid, and its rigidity can vary along its length. A remote actuator means 18 is used to project and/or retract, and, optionally, to rotate the barrier member relative to the distal deployment opening 24.

FIGS. 3-2 through 3-5 show the use of a device of this invention to obtain a tissue sample. They are simplified cross sectional representations of the device shown in FIG. 3-1, the cross section being taken along line a-a. In use, the device is partially inserted into a human or animal patient (not shown). The housing can be inserted directly into a patient, or the device can be emplaced using an instrument channel of a standard endoscope, laparoscope, catheter, or the like.

FIG. 3-2 shows a cross-section of the device of FIG. 3-1 with the expandable barrier member 22 in a first, constrained configuration.

The housing 10 is preferably an elongate sheath, having an axial bore 20 therethrough, the axial bore being sized to receive the expandable barrier member 22 in a constrained configuration. The axial bore 20 opens to the environment at the deployment opening 24. In one embodiment (not shown), the axial bore also opens to the environment at the activator opening 26, and access for additional laparoscopic or endoscopic devices, and/or fluid access or withdrawal, is provided. A seal (not shown) may be added at the activator opening 26, to minimize or prevent fluid (i.e., liquid or gas) leakage.

The specific configuration and dimensions of the axial bore 20 will vary with the use of the device, the parameters of the barrier member 22, and whether access for additional laparoscopic or endoscopic devices is provided. In general the axial bore 20 will have an internal diameter of from less than about 0.3 cm to about 2 cm or greater, preferably from about 0.25 cm to about 2.5 cm. In one embodiment (not shown), the axial bore comprises a working channel of an endoscope. Such an endoscope can also provide surgical implements such as lasers, scalpels, irrigation and aspiration means, visualization means, and the like.

The outer diameter of the housing 10 will vary with the application, the size of the expandable barrier, and whether additional working channels are included in the device. The housing in a laparoscopic device will have a diameter of from less than about 1 mm to about 3 cm or greater, preferably from about 0.4 cm to about 1.5 cm. The length of laparoscopic devices will be from less than about 10 cm to about 30 cm or greater, more generally from about 20 cm to about 30 cm. The housing 10 of a device intended for endoscopic use will have a diameter of from less than about 1 mm to about 3 cm or greater. The length of endoscopic devices will be from less than about 10 cm to about 1 meter or greater.

The barrier member 22 is extended through the deployment opening 24 remotely. The barrier member 22 can be attached through the actuator opening 26 of the housing 10 by a connecting means 28. The connecting means 28 can be, for example, soldered or otherwise affixed to the barrier member 22, as shown. Alternatively, it can be a continuation of the elastic material used in forming the elastically deformable loop 36. In the shown configuration, the barrier member 22 is attached to the remote actuator means 18 by the connecting means 28. Longitudinal axial movement of the activator means 18 relative to the housing 10 causes the barrier member 22 to be extended from, or retracted into, the housing 10, via the deployment opening 24. Rotational movement of the activator means 18 relative to the housing 10 causes the barrier member 22 to be rotated. If rotational movement is not desirable, a means to prevent rotation can be employed.

In the depicted configurations, the remote actuator means 18 slidably engages the activator opening 26. The remote actuator means 18 can be an extension of the elastically deformable loop 36, or of the connecting means 28, and be substantially independent of the housing 10. Alternatively, the remote actuator means 18 can be connected to the connecting means 28.

The housing 10 includes, or provides integration with, a surgical handling apparatus to deploy and retract the barrier member. In one embodiment, as shown, two finger rings 30 are part of the actuator end 16. An additional thumb ring 32 is part of the remote actuator means 18. These rings are for ease of handling. Knobs or ridges, for example, can be provided for ease of integration with a separate actuator means (not shown). Suitable actuator means include slider mechanisms, pistol grip or thumb actuated mechanisms, scissors handles, and syringe-plunger mechanisms (similar to the configuration shown in FIGS. 3-2 through 3-6). These and others are well known to the art. The specific type of actuator mechanism is generally determined by the personal preference of the surgeon.

In use, the deployment end 12, and possibly the shaft portion 14, is inserted into the patient. The housing can be inserted directly into the patient, or it can be introduced using the instrument channel of a standard LIS device. The deployment end 12 possesses lateral integrity such that it is not significantly deformed by the pressure exerted by the constrained barrier member 22. In a device having a rigid housing (the usual case for a laparoscopic device), the deployment end 12 of the housing can be integral to the shaft portion 14 of the housing, such that there is no obvious demarcation between the functional zones. When a device of this invention functions as a catheter (typical with endoscopic use) and there is little lateral support, the deployment end 12 may require reinforcement to provide consistent constraint of the expandable barrier member.

The shaft portion 14 of the housing is located between the actuator (non-inserted) end 16 and the deployment (inserted) end 12 of the device. The shaft portion 14 of the housing may be inserted into the patient (not shown) partially or completely. The shaft portion 14 of a device which is used in laparoscopy must have sufficient structural integrity that it is easily inserted through a surgical opening into the body of the patient without undue deformation. Materials with sufficient structural rigidity include stainless steel and rigid polymeric materials such as plastics.

The material of the shaft portion 14, and the material of the deployment end 12, can be the same, or can have different physical properties. For example, the shaft portion 14 of an expandable barrier device housing used in endoscopic surgery will generally be flexible, to allow insertion through naturally occurring orifices, ducts, and/or passages, or to allow insertion through the working channel of an endoscope. Suitable polymeric material includes polytetrafluorethylene, polyurethane, polyethylene, Teflon, and the like. The material of such a flexible housing may be reinforced at the deployment end 12 with fibers, rings, or longitudinal ribs, for example, to enable it to withstand the forces exerted on it by the barrier member 22 while it is constrained within and deformed by the housing.

The barrier member 22 has two components: the barrier membrane 34, and the elastically deformable loop 36.

When expanded, the barrier member 22 can have a diameter of from about 1 cm or less to about 5 cm or greater, more generally from about 2 cm to about 4 cm. The barrier membrane 34 spans the elastically deformable loop 36 loosely, forming a rounded plate or bowl. The depth of arc described by the barrier membrane 34 when suspended from the elastically deformable loop 36 is from less than about 1 cm to about 7 cm or greater. In general, the preferred depth of the pouch formed by the barrier membrane 34 will be less when the barrier membrane 34 is used primarily as a tissue protecting surgical drape, and will be correspondingly greater when the barrier membrane is used as a pouch to collect tissue or to remove tissue in toto from the surgery site. In those embodiments in which a relatively deep bow-like pouch is present, it may be desirable to reinforce the barrier membrane. Reinforcing stays or ribs, made of, for example, plastic, thickened barrier membrane material, or a shape memory alloy, provide reinforcement, and assist the barrier membrane to deploy fully into the desired shape.

The barrier member 22 is compressed and loaded within the axial bore 20. In this constrained configuration, the barrier device can be sterilized, packaged and stored for later use. Preferably at least one expandable barrier device is available during surgery: when needed, the surgeon can visually assess the size of the barrier member necessary for tissue protection and/or collection, and select an appropriate expandable barrier device.

When constrained, the barrier membrane 34 is collapsed, and may be furled around the elastically deformed loop 36. The barrier membrane is preferably made of a flexible and impermeable biocompatible material. The composition of the barrier membrane will reflect the specific use of the expandable barrier. The barrier membrane is sufficiently thin that it can be folded or gathered, together with the elastically deformable loop, to fit within the axial bore 20.

In one preferred embodiment the barrier membrane material is substantially impermeable to body fluids and other liquids, such as normal saline solution, which might be present during surgical procedures. The thickness of the membrane is sufficient to provide an effective barrier to noxious or contaminated materials such as bile, spillage from inflamed or infected tissues, or tumor cells. Suitable materials include polyethylene, polyvinyl chloride, urethane, silicone rubber, and the like.

In an alternate preferred embodiment, the barrier membrane material is substantially impermeable to tissue samples, but is generally permeable to body fluids and other liquids, such as normal saline solution, which might be present during surgical procedures. In this embodiment, the barrier membrane material can be a net, web, or grid. Suitable materials include perforated, webbed or netted polyethylene, polyvinyl chloride, urethane, silicone rubber, and the like. A similar construct can be made of, or contain, shape memory materials.

The elastically deformable loop 36 is a wire, or a strip of elastic material. The term "elastic material" is used herein to mean a metallic material that has spring-like properties, that is, it is capable of being deformed by an applied stress and then springing back, or recovering, to or toward its original unstressed shape or configuration when the stress is removed. The elastic material is preferably highly elastic. The material are metallic. The use of metals such as shape memory alloys is preferred. Shape memory alloys that exhibit pseudoelasticity, in particular superelasticity, are especially preferred. The elastic materials herein exhibit greater than 1% elastic deformation, more generally greater than 2% elastic deformation. Preferably, the elastic materials herein exhibit greater than 3% elastic deformation, more preferably greater than 4% elastic deformation.

FIG. 3-3 shows the device of FIG. 3-2 in an expanded position. The remote actuator means 18 has been moved distally along the axial bore 20. The elastically deformable loop 36 extends past the confines of the deployment opening 24. Once the elastically deformable loop 36 is released from the compression of the housing 10, the loop regains its unconstrained, memory, shape and the barrier member 22 attains its deployed configuration. While the elastically deformable loop 36 is shown as generally circular or oval, other shapes are also possible. Elliptical, rounded, square, and irregular shapes are also possible, and may be desirable for a particular application.

The barrier membrane 34 is connected to the elastically deformable loop 36. As the loop expands, the barrier membrane 34 unfurls to form a generally plate-like or bowl-like enclosure having a mouth 38. The perimeter, or the mouth 38, of the barrier membrane 34 is defined by the intersection of the elastically deformable loop 36 and the barrier membrane 34.

The more bowl-like configuration, shown in FIG. 3-3, is generally preferred when the device is used to collect or retrieve tissue samples. In use, the expanded barrier member 22 is suspended internally at or near the surgical site. The barrier can be manipulated to underlie the surgical site, so that fluids or other materials which are released at the surgical site flow gently downhill into the expandable barrier by means of irrigation flow and/or gravity. When the barrier membrane 34 is bowl-like, it can substantially contain a tissue sample 40 to be excised and removed during surgery.

FIG. 3-4 shows the device of FIG. 3-3 in a pouched configuration, partially between the expanded configuration of FIG. 3-3 and the withdrawal configuration of FIG. 3-5. The remote actuator means 18 has been moved proximally along the inside of the axial bore 20. The elastically deformable loop 36 extends only partially past the confines of the deployment opening 24, and constraining force of the housing 10 has forced the elastically deformable loop 36 into a deformed semi-constrained shape. The barrier membrane 34 can preferably slide relative to the elastically deformable loop 36. The barrier membrane 34 is preferably not retracted into the housing 10 with the elastically deformable loop 36, and remains substantially outside of the housing 10. As the elastically deformable loop 36 is withdrawn into the housing 10, the barrier membrane 34 catches on the deployment opening 24 of the deployment end 12 of the housing 10. Therefore, the diameter of the mouth 38 of the barrier membrane 34 becomes reduced as compared to the expanded configuration shown in FIG. 3-3, and the barrier membrane 34 forms a pouch. The tissue sample 40 is substantially enclosed in the pouch.

FIG. 3-5 shows the device of FIG. 3-4 in a configuration for withdrawal from the body. The remote actuator means 18 has been moved further along the axial bore 20 in the proximal direction, and is in approximately the position from which it started. The elastically deformable loop 36 is substantially fully retracted into the axial bore 20, and constraint of the housing 10 has deformed the elastically deformable loop 36 to fit within the axial bore 20. The mouth 38 of the barrier membrane 34 is retracted into the housing 10 with the elastically deformable loop 36, preventing any undesired loss of tissue or fluids from within the pouch. The body of the barrier membrane 34, containing the tissue sample 40, remains substantially outside of the housing 10. In this configuration the device is withdrawn. As the filled pouch of the barrier membrane 34 is generally larger than the deployment opening 24, there is a tendency for the barrier membrane 34 to seal against the deployment opening 24 of the housing 10. This tendency can be enhanced by placing a seal or gasket means (not shown) at the deployment opening 24.

While the demonstration of the device as shown in FIG. 3-1 through FIG. 3-5 is representative of one embodiment of a device of this invention, other embodiments are also within the scope of the invention. For example, in an alternate embodiment, not shown, the barrier membrane 34 is adhered to the elastically deformable loop 36, so that as the mouth of the barrier membrane 34 is withdrawn into the housing 10 it is only collapsed transversely as the elastically deformable loop 36 is withdrawn into and contained within the axial bore. In yet another embodiment, the barrier membrane and tissue sample are completely withdrawn into the housing for removal from the body.

The pouched barrier membrane can provide a transfer means for tissues which have been removed from a patient and are to be delivered, for example, to a pathology laboratory. The entire barrier device can be delivered, or the distal end of the device including the pouched barrier membrane can be separated from the rest of the device and delivered (not shown). If such a transfer is desired, the barrier membrane can be lined with, can contain, or can be filled with a tissue preservative.

FIG. 3-6 shows representative embodiments of a cross-section through the housing, taken along line b-b of FIG. 3-1. A barrier membrane would normally be enclosed within the housing in a folded, bunched, or furled configuration. For simplicity, however, the barrier membrane is not shown.

FIG. 3-6a shows a housing 110 having a circular cross-section. This is a preferred cross-section for an expandable barrier device of this invention. A circular housing cross-section has the advantage of being deformable in any radial direction. A circular housing cross-section also permits delivery of an expandable barrier of this invention through a standard laparoscopic trocar, or through the instrument channel of a standard endoscope. However, other cross-sections may be preferable.

Within the axial bore 120 is the elastically deformable loop 136, which has been constrained to fit within the axial bore 120. The elastically deformable loop 136 is shown having an elongated oval cross-sectional shape. This is a preferred cross-sectional shape, as it permits structural rigidity of the expanded loop in a direction perpendicular to the general plane of the loop, but does not compromise the lateral compressibility of the loop within the general plane of the loop. However, the elastically deformable loop 136 can have any appropriate cross-sectional shape.

The axial bore 120 can provide access for auxiliary implements such as an electrocautery device, laser, knife, probe, or other surgical implement an imaging means, or an irrigation or aspiration means. Auxiliary implements can be an integral part of the device as manufactured, or can be introduced as needed through the axial bore 120.

FIG. 3-6b shows a housing 110 which has an oval cross-sectional shape. Within the axial bore 120 is the elastically deformable loop 136, which has been constrained to fit within the axial bore 120. The elastically deformable loop 136 is shown with a rounded cross-sectional shape. A lumen 142 is present. The lumen 142 can have any desired cross-sectional shape. The lumen 142 is used to introduce auxiliary implements to the surgical site. Auxiliary implements can include, for example, an electrocautery device, laser, knife, probe, or other surgical implement an imaging means, or an irrigation or aspiration means. Auxiliary implements can be an integral part of the device as manufactured, or can be introduced as needed through a provided lumen 142.

FIG. 3-6c represents an embodiment in which a cautery wire 144 is provided as an integral part of the expandable barrier device. Various cautery wires are known in the art and are suitable for use with this invention. In the pictured embodiment the cautery wire 144 is a loop through which electrical current can flow. It is located adjacent to the mouth of the barrier membrane when both the expandable barrier and the cautery wire are deployed. Insulation 146 can be provided around sections of the cautery wire, for protection of tissues and of the housing. The cautery wire 144 is used to sever and/or cauterize tissues, which are preferably collected within the expanded barrier member. The deployment and retraction of the cautery wire can be controlled using the same actuator as that which deploys and retracts the expandable barrier element. Alternatively, a second actuator mechanism can be supplied for deployment of the cautery wire.

The cautery device can be made of any suitable material. If the cautery device is rigid, then the size of the cautery device is either limited to the size of the lumen 142, or it protrudes from the deployment end of the lumen at all times. However, the cautery wire can comprise an elastic material. In a preferred embodiment, the cautery wire is a loop of wire, and the loop is constrained within the lumen 142 while the expandable barrier device is placed within the body. In an alternate embodiment, the cautery wire is a hook-shaped span of elastic material which can be linearly constrained within the lumen 142.

It has been discovered that an improved cautery device can be made of a shape memory alloy. The use of an SMA which exhibits pseudoelasticity has the advantage that the amount of elastic deformation that is available is large compared with that available from many other electrically conductive materials. The large amount of elastic deformation of the alloy allows the loop to have a small transverse dimension when it is constrained within a housing.

FIG. 3-6d shows the cautery wire 144 located within the elastically deformable loop 136. This arrangement permits the cautery wire 144 to be within the mouth of the barrier membrane. It also permits the cautery wire and the elastically deformable loop to be contained in the same lumen of the housing. The deployment of the cautery wire can be controlled using the same actuator as that which deploys and retracts the expandable barrier element. Alternatively, a second actuator mechanism can be supplied for deployment of the cautery wire. Other embodiments (not shown) include adhering the cautery wire to the mouth portion of the expandable barrier, or having the elastically deformable loop itself function as a cautery wire, with the barrier membrane being perforated at specific locations to permit electricity or heat flow to the issue. Alternatively, a conductive polymer which can be electrically heated from outside the body can be used to line the mouth portion of the barrier membrane, or the barrier membrane itself can support the flow of heat or electricity through its body. Insulation 146 can be provided within the housing, for protection of the housing.

FIG. 3-7 and FIG. 3-8 demonstrate alternative embodiments of the expandable barrier of this invention.

FIG. 3-7 shows a shallow barrier member 222 wherein the depth of the barrier membrane 234 is a fraction of the diameter of the mouth 238. The connecting means 228 fastens to a circular elastically deformable loop 236 which forms a closed ring. This type of expandable barrier member can function as an internal surgical drape. The housing 210 is shown.

FIG. 3-8 shows another embodiment of this invention. The barrier member 222 is relatively deep: the depth of the barrier membrane 234 is greater than the diameter of the mouth 238. The connecting means 228 are wires which are continuations of the elastically deformable loop 236. The elastically deformable loop 236 is retained within an enclosure 248 formed of the barrier membrane 234. The barrier membrane 234 is preferably folded over itself, and self-adhered to form the enclosure 248. The elastically deformable loop 236 enters the enclosure through openings 250. Each end of the elastically deformable loop 236 can independently enter the enclosure at opening 250, as shown. Alternatively, both ends of the elastically deformable loop 236 can enter the enclosure through one opening 250, not shown. The elastically deformable loop 236 slidably engages the loop enclosure 248: in an especially preferred embodiment, the barrier membrane forms a closed pouch upon retraction of the elastically deformable loop within the housing when the barrier member is used to collect a tissue sample, as shown in FIG. 3-5.

Also shown in FIG. 3-8 is a cautery wire 244 which, when deployed, is located proximal the mouth 238 of the barrier member 222. An insulating sheath 252 is located within the axial bore which houses the cautery wire and projects slightly from the distal end of the housing 210.

While a self-adhered barrier membrane 234 is shown, alternate embodiments are possible. FIG. 3-9 presents some of the alternatives in cross-sectional view, the cross-section being taken through line b-b of FIG. 3-7. The barrier membrane 234 can be a doubled sheet with the elastically deformable loop 236 between the two surfaces, as shown in FIG. 3-9*a*. The doubled sheet can be self-adhered if desired. The barrier membrane 234 can include rings 260 formed either of the membrane material or of some other material as shown in FIG. 3-9*b*. The barrier membrane 234 can be punctured by the elastically deformable loop 236, as shown in FIG. 3-9*c*. Alternately, the barrier membrane 234 can be affixed to the elastically deformable loop 236 so that sliding of the membrane material over the elastically deformable loop is substantially impeded (not shown).

FIGS. 3-10, 3-11 and 3-12 show some alternate top and side views of the elastically deformable loop in the expanded, "memory" configuration. FIG. 3-10 shows a closed circular loop 336, with a connecting means 328. The housing 310 is shown. The elastically deformable loop is flat in side view. FIG. 3-11 shows a circular loop 336, in which the connecting means 328 is a continuation of the loop. The loop is flat in side view, and the elastic connecting bar is sharply angled. FIG. 3-12 shows an oval loop 336 in top view, in which the connecting means 328 is a continuation of the elastically deformable loop. The loop is curved in side view, and the connecting bar is gently angled.

The devices of this invention, including the housing and the barrier member, can be reusable. Preferably the device is disposable or semidisposable. The barrier member and the housing are generally disposable, and the remote actuator means is either reused or discarded.

A possibly advantageous variation of this form of the invention is shown in FIG. 3-13, which shows an arrangement which can be used to insert a catch bag 434 through a trocar entry, deploy the bag, and allow the removal of the insertion device prior to removal of the bag itself. Other devices have not allowed for dissociation of the bag and insertion device.

The principle feature of this variation is the replacement of the closed loop of metal in the cuff 448 of the bag by two curved arms 436, joined in the shaft 410 of the instrument, with their tips meeting at the distal portion of the cuff. Also in the cuff 448 is a drawstring 490 looping completely around the cuff, with ends passing through the shaft 410 of the instrument, and fastened to the actuation handle 448, in a manner which lets the drawstring move with the arms keeping the drawstring essentially taut.

Initial insertion of the device is accomplished with the bag 434 disposed around the straightened arms 436, all situated in the instrument shaft 410.

Separating the ends 491 of the strings 490 from the insertion tool external to the body will allow the insertion tool to be withdrawn. The arms 436 will slide out of the cuff 448, and the drawstring ends 491 will pass through the shaft 410. This will leave the bag 434 behind with the drawstring ends coming out of the trocar. An internal pressure seal may be affected at the proximal end of the shaft 410 or within the shaft.

FIGS. 3-14 and 3-15 show yet another arrangement which can be used to deploy a catch bag 460 through a trocar entry.

In this case, as in the embodiment of FIG. 3-13 the closed loop of metal is replaced by two curved arms 462 which are joined in the shaft of the instrument. In this case however the arms 462 are connected at their distal end by a heat-shrink polymeric sleeve 464. This acts both as a connector for the distal ends of arms 462, and as a hinge, allowing the arms to fold towards each other. Thus FIG. 3-14 shows the device in its operating position with the loop extending from the distal end of the instrument. In this position the arms 462 spring apart from each other into their unstressed configuration, fexible sleeve 464 allowing this movement. FIG. 3-15 shows the device when the loop is retracted into the instrument's shaft e.g. for insertion or withdrawal of the device from the patient. In this case the arms 462 are folded toward each other about sleeve 464 which acts as a hinge, to allow the loop easily to be retracted into the shaft. In this embodiment the arms 462 may comprise a regular resiliently deformable material e.g. a spring metal, or a material exhibiting pseudoelastic, especially superelastic behavior, especially a shape memory alloy.

FIGS. 3-16 to 3-18 illustrate the additional use of a bushing 470 to prevent accidental withdrawal of a deployed filled barrier member, e.g. collecting pouch, back into the housing 472 and also to prevent tearing of the barrier member. FIG. 3-16 illustrates the embodiment before deployment of the barrier, and FIG. 3-17 illustrates the embodiment after deployment of the barrier.

Referring to FIG. 3-16, a bushing 470 that is substantially funnel shape, comprising a hollow tubular portion 474, and a frustoconical shaped flange portion 482 is positioned on the connecting member or deployment rod 476. The flange portion 482 is resiliently biased radially outward and the tubular portion 474 is a push fit on rod 476 but slidably relative thereto when subjected to sufficient force. On the distal side of the bushing 470 a barrier, comprising a superelastic loop 478 and a barrier member 480, is secured to the deployment rod 476, as in the previous figures.

Referring now to FIG. 3-17, when the barrier is deployed outside the housing 472 by extending the deployment rod 476, the bushing 470 is carried with the rod (because of the push fit tubular portion 474) towards the distal end of the housing 472 until it projects from the end of the housing 472. In this position the flange portion 482, which is resiliently biased, snaps against the distal end of the housing so that complete withdrawal of the bushing 470 back into the housing is prevented by the flange 482. Withdrawal of the rod 476 is however possible, the rod sliding relative to the tubular portion 474 of the bushing 470.

Operation and body sample collection by the deployed barrier member 480 can then take place as before, and then the elastically deformable loop retracted back into the housing 472 as illustrated in FIG. 3-18. The bore of the bushing 470 is however sufficiently small that the barrier membrane 480, which is now filled with body samples, is blocked from re-entry into the housing. It therefore remains suspended outside the housing 472, which is desirable for some applications. The funnel shaped ends of the bushing also act to provide a smooth transition substantially to prevent tearing of the barrier membrane 480 by the housing 472.

It will be appreciated that bushings with shapes other than that illustrated in FIGS. 3-16 through 3-18 can be used. The preferred features to be incorporated in any other shaped bushing are a small diameter bore to prevent barrier member re-entry, a resilient distal end to snap against the housing, and a smooth opening to avoid tearing of the barrier membrane.

FIGS. 3-19 and 3-20 show a modified necked loop design for use in situations where an elastically deformable loop is to be constrained within a housing. In these figures, FIGS. 3-19 and 3-20 show the modified loop in the pre-constrained and the constrained configuration respectively. The sides 500 of the loop come toward each other, overlap at part 502 ("the necked portion" which is at the distal end of the loop), and then divert outwards, curving in the opposite sense to that previously to join to each other. The result is a smaller loop portion 504 adjacent to the main loop portion 506, in a roughly figure "8" configuration. The advantage of this necked configuration is that when the loop is constrained as shown in FIG. 3-20, substantially all the severe deformation is absorbed by the small loop portion 504, especially the overlap point 502. Thus if the loop is deployed again, at least main loop 502 will regain the prestrained configuration, i.e. the same configuration as illustrated in FIG. 3-19 which showed the loop before constraining.

FIGS. 3-21 and 3-22 show an alternative design, in pre-constrained and constrained condition respectively. In this case the sides 508 of the loop turn outwards at points 510 towards the distal end of the loop before they meet or overlap. The sides then turn towards each other again to join. The result is a general nipple shape, with a small bulbous section 512 adjacent the main loop region 514. As before, a necked region is formed, in this case by the outward diversion of the sides of the loop at points 570. The necked region absorbs substantially all the severe deformation on constraining as before (FIG. 3-22).

In a fourth form of the present invention, a remotely operated device comprises an elongate housing, and an elastic surgical screen which can be constrained within the housing. The surgical screen is deployable from within the housing to assume an expanded memory shape. In the expanded shape the surgical screen can have any of several functions. The screen can act as a duct screen, to collect calculi or calculus fragments, and to prevent the movement of calculus fragments in an undesired direction. The screen can act as an emboli screen, to prevent the movement of emboli at or near an operative site. The screen can act as a surgical tool, to hold or maintain a mass, such as a tissue mass, in a localized area. Generally, the screen is removed from the patient in its expanded memory shape, simultaneously removing calculi or residual calculus fragments, emboli or emboli fragments, or other internal masses. The surgical screen is preferably moveable to a third position wherein the surgical screen is partially or fully retracted, and at least a portion of it is constrained within the housing.

The surgical screens of this invention are deployed with radial asymmetry from the mouth of the delivering catheter, and are able to traverse substantially the entire width of a duct with a screening means. The elastic screen comprises, for example, one or more loops of elastic material, which may be partially or completely spanned by a semipermeable material; a graduated series of a loops; or a tassel. Remote means are provided to project, retract and/or rotate the screen means relative to the distal end of the housing.

A method of this invention for removing an internal obstruction comprises (a) inserting a catheter end beyond an obstruction; (b) deploying a surgical screen from the catheter end; and (c) retracting the surgical screen to remove the obstruction.

A further method of this invention comprises (a) inserting a catheter end beyond an obstruction; (b) deploying a surgical screen from the catheter end; (c) fragmenting the obstruction; and (d) removing the surgical screen to remove obstruction fragments.

An alternate method of this invention comprises (a) inserting a catheter end beyond an obstruction; (b) deploying a surgical screen from the catheter end; (c) fragmenting the obstruction; (d) retracting the surgical screen into the catheter; and (e) removing the catheter.

Yet another method of this invention comprises (a) inserting a catheter end beyond an obstruction; (b) deploying a surgical screen from the catheter end; (c) fragmenting the obstruction; (d) removing obstruction fragments from the operative site; (e) retracting the surgical screen into the catheter; and (f) removing the catheter.

Figures 1A, 4:
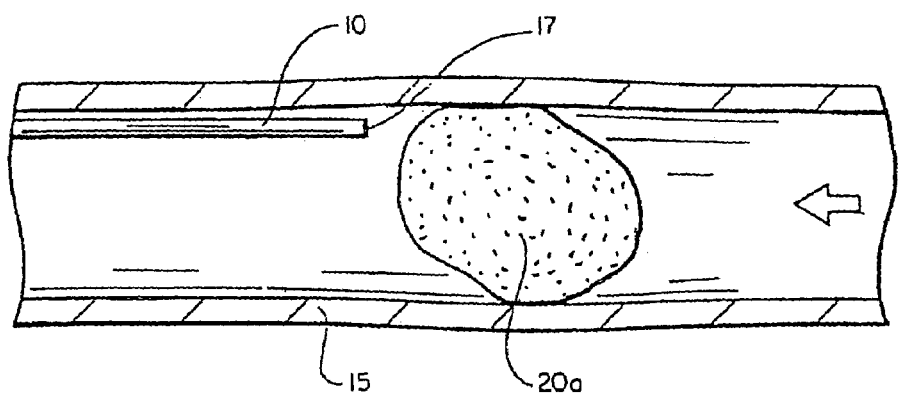
Figures 1B, 4:
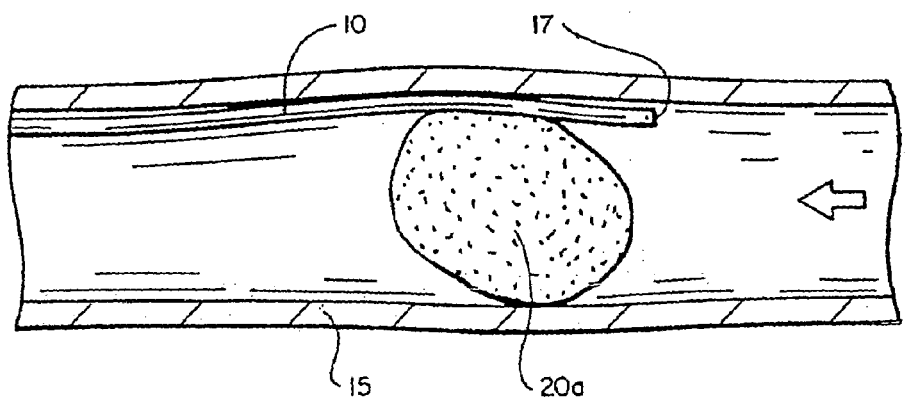
Figures 1C, 4:
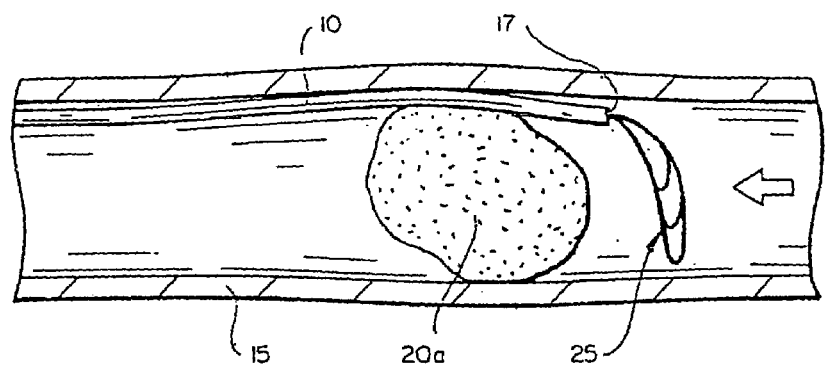
Figures 1D, 4:
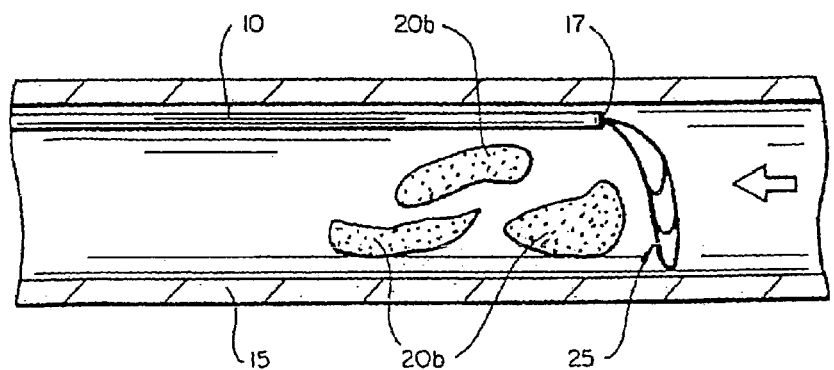
Figures 2A, 4:
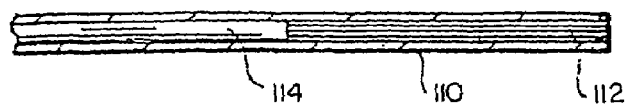
Figures 2B, 4:
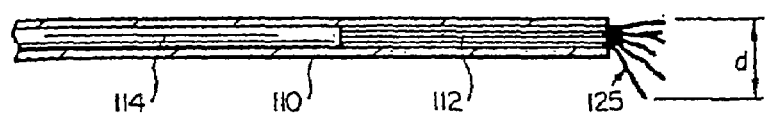
Figures 2C, 4:
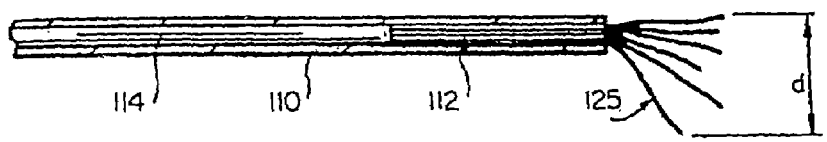
Figures 2D, 4:
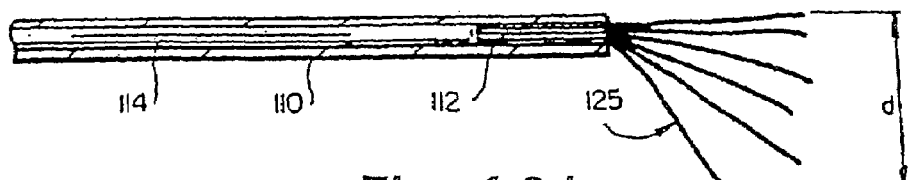
Figures 3A, 4:
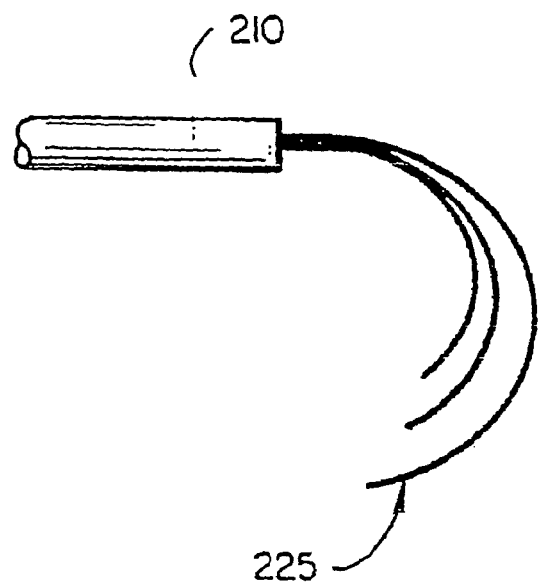
Figures 3B, 4:
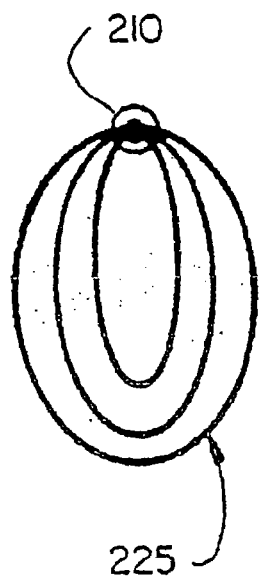
Figure 4:
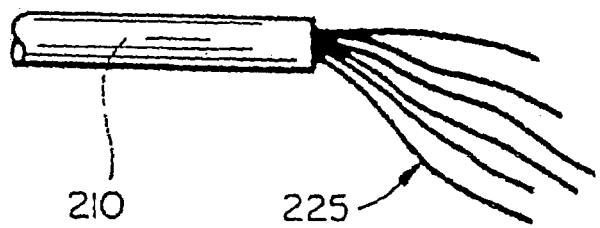
Figures 4, 4A:
Figures 4, 4B:

FIG. 4-1*a* is a side view of an unexpanded screen device within a duct, placed downstream from a blocking calculus. FIG. 4-1*b* shows the screen device, the deployment end of which has been placed upstream from the blocking calculus. FIG. 4-1*c* shows a screen device which has been expanded upstream from a blocking calculus. FIG. 4-1*d* shows a screen device in place after calculus fragmentation.

FIG. 4-2 shows various stages of deployment of a tasseled surgical screen.

FIG. 4-3 through FIG. 4-5 show alternate embodiments of the surgical screen portion of a device of this invention.

The devices of this invention have a variety of potential uses. A surgical screen of the invention herein can be used to capture an undesired mass from within a duct, for example, for removing a gallstone from the bile ducts; for removing a kidney stone from the urinary system; or for removing an emboli from a blood vessel. Alternatively, the surgical screens can be used during an operative procedure, such as to contain or hold a discrete mass for further procedures or for removal. For purposes of example only, and not as a limitation, reference will be made to calculi produced by a kidney and removed from a ureter using an endoscopic device. It is to be understood that this is for simplicity of example only, and that the apparatus, methods and teachings will be similarly applicable to a variety of uses.

As used herein, the term "screen" refers to a structure which is screened, perforated, tasseled, or sieve-like, or which functions to separate larger particulate matter from smaller particulate matter, or, more preferably, to separate solid matter from fluids.

As used herein, the term "surgical screen" refers to a screen means which is comprised of an elastic material, preferably a shape memory alloy, and more preferably a pseudoelastic shape memory alloy. The surgical screen is compressible for delivery to the operative site. The "operative site" can be, for example, a surgical site, a biopsy site, the site of an angioplasty procedure, the site of a diagnostic procedure, and the like. Once present at the operative site the surgical screen is deployed from the housing, expands to its memory shape, and substantially spans the width of the duct. A tissue "mass" refers to a discrete unit of tissue, a calculus, an embolus, a prosthetic device, and the like.

The surgical screen preferably demonstrates radial asymmetry: it is not deployed radially from the housing opening. When deployed from the catheter, the surgical screen is unconstrained, and expands to traverse the duct. In general, at least 80% of the width of the duct will be within the perimeter of the surgical screen. More preferably, the surgical screen is slightly larger than the diameter of the duct, and gently expands apart against the walls of the duct when in the expanded configuration. When the surgical screen is used to localize a tissue mass outside a duct the mass is preferably contained at the surface of the surgical screen. Preferably two or more surgical screen devices of different sizes are available during a procedure. When needed, the surgeon assesses the size of screen necessary for tissue protection and/or internal mass collection, and selects a screen which has an appropriate size, shape and/or filter pore size.

The surgical screen is one or more wire or a strip of elastic material. The term "elastic material" is used herein to mean a material that has spring-like properties, that is, it is capable of being deformed by an applied stress and then springing back, or recovering, to or toward its original unstressed shape or configuration when the stress is removed. The elastic material is preferably highly elastic. The material can be polymeric or metallic, or a combination of both. The use of metals, such as shape memory alloys, is preferred. Shape memory alloys that exhibit pseudoelasticity, in particular superelasticity, are especially preferred. The elastic materials herein exhibit greater than 1% elastic deformation, more generally greater than 2% elastic deformation. Preferably, the elastic materials herein exhibit greater than 3% elastic deformation, more preferably greater than 4% elastic deformation.

The surgical screen differs from the prior art in several key aspects. The surgical screen is not radially deployed from the housing, nor is the housing preferably centered in a duct when the screen is expanded, as has been the case in the prior art. Prior art stone baskets, for example, provide a radially deployed basket, into which the stone is snagged. Removal of the stone is dependent upon the successful engagement of the calculus within the body of the device, so that the calculus is substantially enclosed within the basket. The devices require manipulation of the deployed basket to ensnare the stone for removal. Stone removal is directly related to the ability of the operator to snag the stone with the basket. In contrast, the surgical screen traverses the diameter of a duct, and the inserted end of the catheter remains near the perimeter of duct. Using a device of this invention, the stone does not have to be caught within the screen, but is removed at the surface of the screen as the catheter and screen are withdrawn from the duct. This provides more control and requires less manipulation than prior art devices. The devices of this invention are therefore less likely to damage duct walls during stone withdrawal than those of the prior art. Devices of this invention are retractable back into the housing for withdrawal, if desired.

Similar numbers refer to similar function throughout the Figures. The Figures are drawn for clarity and are not drawn to scale.

FIG. 4-1 shows (1*a*) the introduction of a surgical screen housing 10, in this case a catheter, into the occluded duct 15; (1*b*) placement of the distal end 17 of the housing beyond the calculus 20*a*; (1*c*) deployment of the surgical screen 25; and (1*d*) fragments 20*b* of the calculus 20*a*. The calculus fragments 20*b* can be retracted from the duct with the withdrawal of the catheter housing 10. In an alternative embodiment (not shown) the calculus 20*a* is retracted from the duct without fragmentation.

The surgical screen, when expanded, will have a diameter substantially similar to the inside diameter of the duct being cleared. For example, when used within a ureter, the diameter of the surgical screen will be from about 1 mm to about 1 cm. When used within a bile duct, the diameter of the surgical screen will be from about 1 mm to about 1 cm. When used within a blood vessel, the diameter of the surgical screen will be from about 1 mm to greater than about 5 cm. When used to remove a tissue mass which is not within a duct, the surgical screen will be from about 1 mm or smaller to about 8 cm or greater. The preferred diameter of the surgical screen will vary with the specific application and with the specific anatomy of the patient. In general, the diameter of a surgical screen will be from about 1 mm or less to about 5 cm or greater, more generally from about 2 mm to about 3 cm.

The housing 10 is preferably an elongate sheath, having an axial bore therethrough. The housing 10 can be flexible or rigid, and the rigidity can vary by region. Standard catheters and laparoscopic devices well known to the art are appropriate. The axial bore is sized to receive the surgical screen 25 in a constrained configuration. The axial bore opens to the environment at the inserted deployment end 17. Opposite the inserted deployment end 17 is the actuator end (not shown). The actuator end can include rings, knobs or ridges, for example, for ease of integration with a separate actuator means (not shown). Suitable actuator means include slider mechanisms, pistol grip or thumb actuated mechanisms, scissors handles, and syringe-plunger mechanisms. These and others are well known to the art. The specific type of actuator mechanism is generally determined by the personal preference of the surgeon.

The specific configuration and dimensions of the housing will vary with the use of the device, the parameters of the surgical screen 25, and whether access for additional laparoscopic or endoscopic devices is provided. In general the axial bore, into which the surgical screen is constrained, will have an internal diameter of from less than about 1 mm to about 2 cm or greater.

The outer diameter of the housing 10 swill vary with the application and the size of the expandable screen. The housing in an endoscopic device will have a diameter of from less than about 0.7 mm to about 4.5 cm or greater. The length of endoscopic devices will be from less than about 10 cm to about 3 meters or greater. The housing in a laparoscopic device will have a diameter of from less than about 3 mm to about 1.5 cm or greater. The length of laparoscopic devices will be from less than about 5 cm to about 20 cm or greater.

The end of the surgical screen housing possesses sufficient lateral integrity that it is not significantly deformed by the pressure exerted by the constrained surgical screen. When an endoscopic device of this invention functions as a catheter and there is little lateral support in the main body of the catheter, the inserted end of the catheter may require reinforcement to provide consistent constraint of the surgical screen element For example, the surgical screen of this invention can be delivered to the operative site using the instrument channel, or working channel, of standard endoscopic devices. Such standard endoscopic devices may also include other devices, especially a laser, lithotriptor, visualization means, or crushing stone basket in separate lumen. In a device having a rigid housing, such as a laparoscopic device, the inserted end of the housing can have the same physical attributes as the remainder of the body of the housing.

As shown in FIG. 4-2, the surgical screen is moveable between a first position (FIG. 4-2*a*) wherein the screen is constrained within the housing and assumes a constrained shape, and a second position (FIGS. 4-2*b*, FIG. 4-2*c* and FIG. 4-2*d*) wherein the screen means extends past the distal deployment end and assumes an expanded memory shape. In the expanded memory shape the screen means acts as a surgical screen. After use, the surgical screen and the housing are removed from the patient. If desired, the surgical screen can be removed in its expanded memory shape, simultaneously removing, for example, calculi or residual calculus fragments. Alternatively, the surgical screen is retracted into the housing, assumes a constrained shape, and is replaced within the axial bore before the constrained surgical screen and the housing are removed from the patient. This method can be used when residual calculus fragments, for example, have been removed by irrigation and/or aspiration.

FIG. 4-2 shows a longitudinal cross sectional view of a tasseled surgical screen. As FIG. 4-2a shows, the housing 110 maintains the constrained surgical screen 112 in a compressed configuration. Attached to the constrained surgical screen 112 is a connecting means 114. The connecting means 114 can be, for example, a bar, flexible wire, sheath, and the like. If a guide wire is to be used, the connecting means 114 can include a lumen for placement of the guide wire. Alternatively, a guide wire can be introduced using a separate lumen. The connecting means 114 connects the surgical screen to the remote means (not shown) which project, retract, or rotate the surgical screen relative to the distal deployment opening. FIGS. 4-2b, 4-2c, and 4-2d show the expanded surgical screen 125 in various degrees of deployment. By varying the amount of deployment, and thus the diameter of the surgical screen, d, the operator can maximize the screening effects of the surgical screen while minimizing potential damage to the duct wall due to surgical screen expansion, or due to the withdrawal of the expanded screen from the body.

FIG. 4-3 shows one embodiment of a surgical screen 225 of this invention. Three elastic strips or wires form concentric loops in their expanded configurations. These strips or wires form a surgical screen 225 suitable for removal of entire calculi, or of calculus fragments. It will be obvious to one skilled in the art that while three loops which are curved along their length are pictured, other configurations are also appropriate for use with this invention. One, two, four, or more loops can be used. The loops can be fairly regular (as shown), or they can be eccentric, scalloped, rounded, oval or irregularly shaped. The degree of longitudinal curvature, and curvature across the width of the screen, can be varied to suit the desired application. The loops can be spaced relatively widely, especially where an unfragmented calculus is to be removed, or they can be spaced fairly closely together, especially where a calculus is to be fragmented and/or calculus fragments are to be removed. A perforated sheet can be suspended across a loop of a multiloop surgical screen, similar to the configuration shown in FIG. 4-5. Alternatively, a perforated sheet can be suspended between any two loops of a multiloop surgical screen (not shown).

FIG. 4-4 shows a side view of a tasseled surgical screen 225 of this invention. Enlargements show various end treatments for the tassels. Pictured are (a) an elastic wire which terminates in a self-closing loop; (b) an elastic wire that terminates in a blunted or truncated end; (c) an elastic wire that terminates in a knob of added material, such as a plastic; and (d) an elastic wire that terminates in a knob formed of the elastic material itself. Each individual strand which makes up a tassel filter can be substantially straight along its length, or it can be curved, wavy, or undulating in two or three dimensions. The strands can be substantially similar in configuration, or they can be different.

FIG. 4-5 shows a surgical screen which includes an elastic loop 236, an elastically deformable ring or loop of elastic material, which is spanned by a barrier material 234. The elastic loop 236 is preferably pseudoelastic, and more preferably a shape memory alloy. As shown, a connector 228 can be used to orient the surgical screen sharply across the duct. The pictured connector 228 is an extension of the elastic loop 236. Alternatively, the connector 228 can integrate with, but be separate from the elastic loop 236.

The diameter of the elastic loop 236 will vary with the diameter of duct for which it is intended, as discussed above. The depth of arc described by the barrier material 234 when suspended from the memory loop is from less than about 1 mm to about 1 cm or greater. The surgical screen can provide a sack-like structure which substantially encloses a calculus. The calculus can then be removed without fragmentation, or it can be fragmented. If the calculus is fragmented, the pieces can be removed within the surgical screen, they can be aspirated or irrigated from the face of the surgical screen, or the surgical screen can be retracted and the fragments can be washed from the site by normal duct fluid flow.

The barrier material is a flexible and biocompatable material. When constrained, the barrier material 234 is collapsed and furled around the constrained elastic loop 236. The barrier material is sufficiently thin that it can be folded, furled, or gathered, together with the elastic loop 236, to fit within the housing. The composition of the barrier material will reflect the specific use of the surgical screen. In one embodiment the barrier material is substantially permeable to fluids. In such an embodiment, the barrier material is a web, net or grid, perforated sheet, and the like, and is substantially permeable to body fluids and other liquids, such as normal saline solution or gases, which might be present during surgical procedures. Suitable materials include nylon or Dacron netting or screen, or a grid of elastic material.

The surgical screen is compressed and loaded within the housing. In this constrained configuration, the screen device can be sterilized, packaged and stored for later use. The screen device (i.e., surgical screen and housing) is preferably a disposable device.

In one preferred embodiment, a device of this invention comprises (a) a housing having a distal deployment opening; (b) a surgical screen which is constrainable within the housing, the surgical screen comprising an elastic material; and (c) remote means to project, retract and/or rotate the surgical screen relative to the distal deployment opening; the surgical screen being moveable between a first position wherein the surgical screen is constrained within the housing, and a second position wherein the surgical screen is extended past the distal deployment end and assumes an expanded shape.

A device of this invention can be used in a variety of procedures, such as the capture an undesired mass from within a duct. For example, a device of this invention can be used to remove a gallstone from the bile ducts; to remove a kidney stone from the urinary system; or to remove an embolus from a blood vessel. A surgical screen of this invention can be used during an operative or surgical procedure, to contain or hold a discrete tissue body for further procedures or for removal. For purposes of example only, and not as a limitation, reference will be made to methods for removal of a calculus from a ureter, wherein the device housing is a catheter. It is to be understood that this is for simplicity of example only, and that the apparatus, methods and teachings will be similarly applicable a variety of such uses.

In one method, the deployment end of a housing containing a surgical screen is partially inserted into a human or animal patient. A guide wire may or may not be used for placement of the device. When a guide wire is used, it is introduced into the ureter and placed appropriately, e.g., beyond an obstruction. A catheter is slipped over the guide wire. The guide wire is then removed, and the surgical screen is extended beyond the deployment end of the catheter. The guide wire preferably passes through a separate lumen in the catheter. Alternatively, the guide wire can pass through the catheter lumen which houses the surgical screen, in which case the connecting means can be tubular and provide an internal bore to accept the guide wire. Alternatively, the guide wire can pass through the axial bore of the housing adjacent the connecting means, or the guide wire can be introduced through a bore or slot within the connecting means. The surgical screen can be radiopaque for ease of placement at the operative site.

A method for removing an internal obstruction comprises (a) inserting an end of an elongate housing, such as a catheter end, beyond a mass, such as a calculus; (b) deploying a surgical screen from the housing end; and (c) retracting the housing and surgical screen to remove the mass. Alternately, the calculus can be fragmented before removal. Calculus fragmentation can be by, for example, lithotripsy (ultrasound), mechanical fragmentation, or laser fragmentation. This method comprises (a) inserting a catheter end beyond a mass; (b) deploying a surgical screen from the catheter end; (c) fragmenting the mass; and (d) retracting the catheter and surgical screen to remove mass fragments.

Yet another method of this invention comprises (a) inserting a catheter end beyond a mass; (b) deploying a surgical screen from the catheter end; (c) fragmenting the mass; (d) removing mass fragments from the operative site; (e) retracting the surgical screen into the catheter, and (f) removing the catheter. The use of this method prevents calculus fragments from migrating from the fragmentation site where they cannot be retrieved and can act as nucleation sites for further obstructions. Fragments of the obstructing mass which remain can be removed, for example, by flushing the operative site with normal saline or other liquids, by aspiration of the fragments, by mechanical means, or by a combination of means.

As a separate embodiment of this invention, it has been discovered that stone baskets of the prior art can be advantageously made of a shape memory alloy, preferably a pseudoelastic shape memory alloy, and more preferably a superelastic shape memory alloy. The attributes of, and processes for obtaining, such shape memory alloys have been discussed above.

Stone baskets use a trap, or cage, effect. They facilitate passage of the obstruction (e.g., a calculus or other mass) inside the basket, but then prevent escape of the obstruction when it is in place in the basket. The basket and obstruction are then withdrawn. Prior art stone baskets include baskets of helically deployed wires (U.S. Pat. No. 4,347,846, to Dormia), baskets of flat spring strips (U.S. Pat. No. 4,590,938 to Segura et al.), baskets which facilitate the insertion of a prosthesis (U.S. Pat. No. 4,592,341 to Omagari et al.), baskets which are used to capture and then crush the calculus (U.S. Pat. Nos. 4,691,705 and 4,741,335 to Okada, and U.S. Pat. No. 4,768,505 to Okada et al.).

Stone baskets generally are classed as medical retriever devices. They are adapted for delivery and use through a catheter, or through the working channel of an endoscope. Stone baskets generally comprise a narrow, elongated sheath; a basket of relatively large diameter extendible from the distal end of the sheath and collapsible when withdrawn into the sheath; and a remote means to project, retract, and/or rotate the basket relative to the distal end of the sheath. The basket is defined by a multiplicity of spaced apart, outwardly bowed spring arms or wires which extend generally axially from the sheath, and are joined at each of the distal and proximal ends of the basket.

The use of shape memory alloys which exhibit pseudoelasticity in the stone baskets of the prior art allow the use of thinner arms (wires or strips, as the case may be) in the makeup of a basket having a desired expanded diameter, or permit a much greater deformation of the basket upon deployment. This permits the use of catheters or working channels having a significantly decreased diameter than those of the prior art Introduction of a thinner shape memory alloy stone basket catheter beyond a calculus is easier than introducing the stone basket catheters of the prior art. The increased diameter and/or thinner wires produce a stone basket which is easier to use than those of the prior art. The thinner wires and/or larger diameter provide more unimpeded area into which the blocking calculus can be captured for removal.

In a fifth form of the present invention, a remotely operated device of this invention comprises an elongate housing, and a retractor of a shape memory alloy. Remote means are provided to project retract and/or rotate the retractor means relative to the distal end of the housing. The retractor preferably comprises one or more loops of a shape memory material. The retractor is preliminarily constrained within a housing, such as a laparoscope or an endoscope. It is deployed from within the housing at an operative site. The retractor is generally used to manipulate organs or other tissues. The retractor can be replaced within the housing. The housing is then withdrawn from the patient.

The shape memory retractor means is a strip or wire of a shape memory material which forms one or more loop in the expanded configuration. All or part of the retractor can be spanned by a semipermeable or permeable membrane.

FIG. 5-1 is a cross-sectional view of a constrained retractor device. FIGS. 5-2 through 5-6 show alternate top views of expanded (unconstrained) retractor devices. FIGS. 5-7 through 5-11 show alternate side views of expanded retractor devices. FIGS. -12 and 5-13 show alternate end views of expanded retractor devices. FIGS. 5-14 and 5-15 show alternate cross sectional views of constrained retractor devices, the cross section taken along line a-a of FIG. 5-1.

A remotely operated device of this invention comprises an elongate housing having a distal end and a proximal end; a retractor of a shape memory alloy; and remote means to project, retract and, optionally, to rotate the retractor means relative to the distal end of the housing. The retractor comprises one or more loops of a shape memory material. A loop can be substantially round, oval, or shaped like a teardrop, for example, or it can be eccentric in its shape. When two or more loops are present, they can be of similar shape, or they can be dissimilar in shape. Two or more fingers or lobes can be present. One or more loop can be partially or completely spanned by a membrane. The proximal ends of the retractor loop can integrate with, or function as, the remote means to project, retract and rotate the retractor means relative to the distal end of the housing.

The retractor is preliminarily constrained within the housing. The retractor is deployed at an operative site, where the retractor is used, for example, to manipulate organs or other tissues. The retractor can be moved back to the preliminary position, so that the retractor is again constrained within the housing. The device can then be repositoned and the retractor redeployed at an alternate site, or the housing can be withdrawn from the patient.

The operative site can be, for example, a surgical site, biopsy site, the site of diagnostic procedures, and the like. For purposes of example only, and not as a limitation, reference will be made to a housing which is a catheter. It is to be understood that this is for simplicity of example only, and that the apparatus, methods and teachings will be similarly applicable to devices in which the housing is, for example, a laparoscopic or alternate endoscopic device.

As used herein, the term "retractor" refers to a looped retractor means which is comprised of a shape memory alloy.

The retractor is preferably a pseudoelastic shape memory alloy, and most preferably a superelastic shape memory alloy. The shape memory alloy can have a biocompatable coating, if desired.

The retractor differs from the prior art in several key aspects. The elastically compressible retractor material makes use of the property of shape memory to achieve its desired effect. Materials which are deformable and which return to a predetermined shape demonstrate shape memory. Spring steel and plastic materials, for example, can demonstrate shape memory. Preferably, the compressible retractor material is a shape memory alloy (SMA) which demonstrates pseudoelasticity when deformed under an applied stress. Articles made of a pseudoelastic shape memory alloy can be deformed from an original undeformed configuration to a second deformed configuration. Such articles revert to the undeformed configuration under specified conditions and are said to have "shape memory."

The use of an SMA which exhibits pseudoelasticity has the advantage that the amount of elastic deformation that is available is large compared with that available from many other materials. The large amount of elastic deformation of the elements allows the device to be used to form retractors of relatively large dimension and relatively eccentric shape, while simultaneously ensuring that the device has a small transverse dimension when the retractor elements are constrained within a housing, allowing the device to pass through small passages or surgical entry sites.

FIG. 5-1 shows a cross-sectional view of the distal end of a retractor device of this invention. The retractor 8 is constrained within the housing 10. The distal (inserted) deployment end 12 is shown. Remote means to project and retract, and optionally to rotate, the retractor is located at the proximal end of the device (not shown), and is in the direction of the arrow. The housing 10 is preferably an elongate sheath, having an axial bore 14 therethrough. Standard catheters, endoscopic and laparoscopic devices well known to the art are appropriate. The axial bore 14 is sized to receive the retractor 8 in a constrained configuration. The axial bore 14 opens to the environment at the deployment end 12.

The specific configuration and dimensions of the housing will vary with the use of the device, the parameters of the operative site, the size of the retractor, the mass of tissue or the prosthetic device which is to be manipulated, and whether access for additional laparoscopic or endoscopic devices is provided within a retractor device. In general the axial bore 14, into which the retractor is constrained, will have an internal diameter of from less than about 1 mm to about 2 cm or greater. The outer diameter of the housing 10 will vary with the application, the diameter of the axial bore, and whether access for additional or alternate instruments is provided within the housing. For example, the housing in an endoscopic device will have a diameter of from less than about 0.7 mm to about 4.5cm or greater. The length of endoscopic devices will be from less than about 10 cm to about 3 meters or greater. The housing in a laparoscopic device will have a diameter of from less than about 3 mm to about 1.5 cm or greater. The length of laparoscopic devices will be from less than about 5 cm to about 30 cm or greater.

The end of the retractor device possesses sufficient lateral integrity that it is not significantly deformed by the pressure exerted by the constrained retractor. The housing 10 may be rigid or flexible, and its rigidity can vary along its length. When an endoscopic device of this invention functions as a catheter, and there is little lateral support in the main body of the catheter, the inserted end of the catheter may require reinforcement to provide consistent transverse compression of the retractor element. A retractor of this invention can be delivered to the operative site using the instrument channel, or working channel, of a standard laparoscopic or endoscopic device. Such a standard device may also include other devices, especially a cautery device, laser, lithotriptor, visualization means, scalpel means, and the like, in one or more separate lumens.

FIG. 5-2 shows a top view of an expanded retractor of this invention. The retractor 108 has three loops 116 which fan out from the housing 110 upon deployment. One or more of the loops can be spanned by a membrane (see FIG. 5-4). While three loops are shown, it will be apparent to one skilled in the art that one, two, four, or more loops can be provided to form the retractor. While the loops 116 pictured are substantially drop-shaped, other configurations are easily imagined. The loop or loops 116 can be, for example, round, oval, triangular, square, rectangular, irregularly shaped, and the like. When two or more loops are present the loops can be substantially similar in shape, or they can be dissimilar in shape.

The loops 116 can overlap, or they can be substantially independent from one another. In such a case a deforming pressure placed upon one loop perpendicular to the general plane of the loop will deform that loop, but will not affect the other loops. In a preferred embodiment, the loops 116 are interconnected and/or overlapping, and a deforming pressure placed upon one loop perpendicular to the general plane of the loop will be transmitted to the other loops. All loops thus act together, providing strength across the width of the retractor. The loops can be coated with a biocompatable material. The coated or uncoated loops can have a surface that prevents slippage of the retracted tissue. For example, the biocompabtble coating can provide a roughened or non-slippery texture to the loops. Alternatively, the loops can have gentle ridges or serrations upon all or part of the exposed surface.

FIG. 5-3 shows a top view of an expanded retractor of this invention. This preferred retractor 108 has three lobes, or finger means 118 which fan out from the housing 110 upon deployment. One or more of the finger means can be spanned by a membrane (see FIG. 5-4). Alternatively, one or more of the spaces between fingers can be spanned by a membrane (see FIG. 5-5).

FIG. 5-4 shows a top view of another expanded retractor of this invention. This retractor 108 has one loop means 116 which expands upon deployment from the housing 110. As shown, the loop is spanned by a permeable, semipermeable or substantially impermeable membrane 120. The membrane 120 is preferably made of a flexible and impermeable biocompatable material. The membrane is sufficiently thin that it can be folded or gathered, together with the elastically deformable retractor means 108, to fit within the housing 110. Suitable membrane materials include sheets of polyethylene, polyvinyl chloride, urethane, silicone rubber, and the like.

In an alternative embodiment, the membrane 120 is substantially impermeable to tissue, but is generally permeable to body fluids and other liquids which might be present during surgical procedures. In this embodiment, the membrane 120 can be a grid of shape memory material, a net, a web, and the like. Suitable materials include perforated, webbed or netted polyethylene, polyvinyl chloride, urethane, silicone rubber, and the like.

FIG. 5-5 shows a top view of yet another expanded retractor of this invention. This retractor 108 has two lobes, or finger means 118 which fan out upon deployment from the housing 110. The space between the fingers is spanned by a membrane 120.

FIG. 5-6 shows a top view of an alternate expanded retractor of this invention. Emerging from the housing 110 is a retractor 108 which has two loops 116. As shown, a smaller loop 116a is nested within a larger loop 116b. In the pictured embodiment, the smaller loop 116a is spanned by a membrane 120. It will be apparent to one skilled in the art that any number of such loops, in various configurations, whether or not spanned by a membrane 120 either across or between loops, can be provided to form the retractor.

FIGS. 5-7 through 5-11 show side views of a deployed retractor of this invention.

Figures 1, 2, 3, 4, 5, 5B:
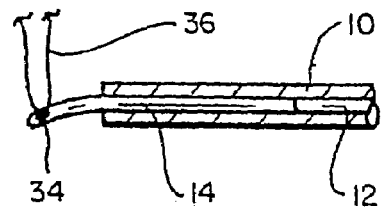
Figures 1, 2, 3, 4, 5, 6:
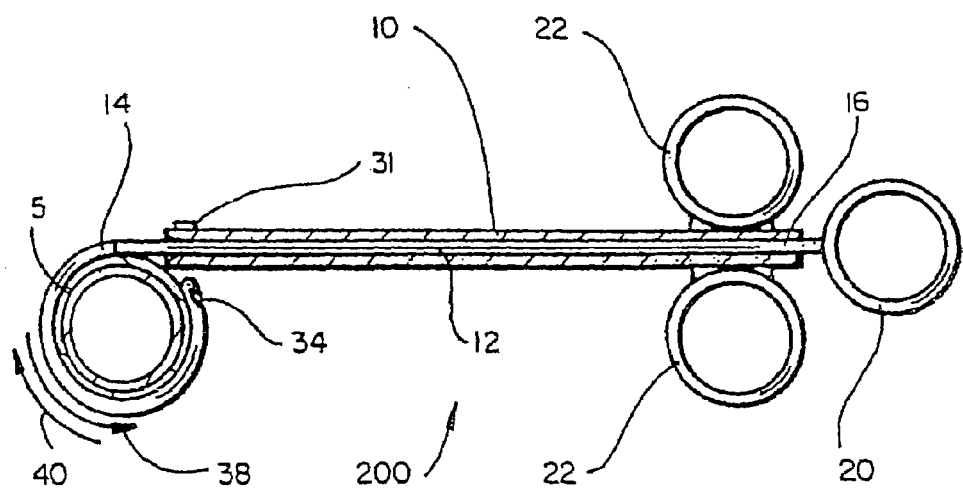
Figures 1, 2, 3, 4, 5, 6, 7, 7A:
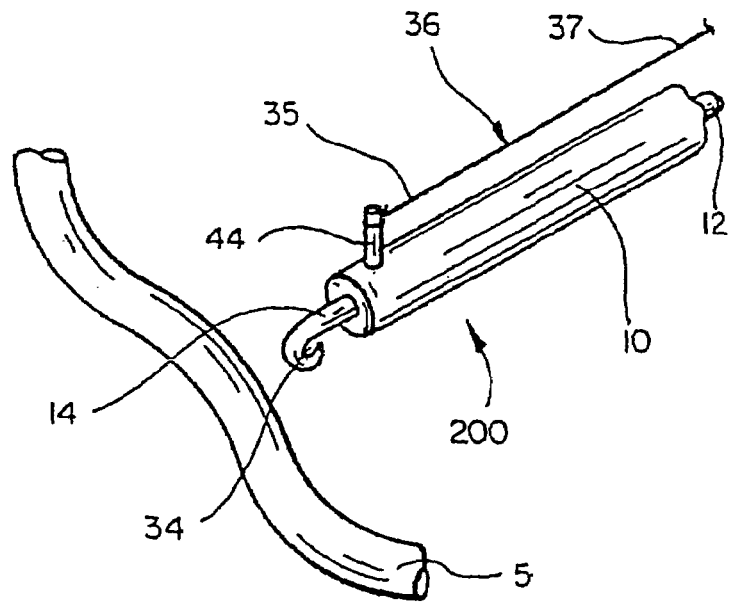

FIG. 5-7 shows a side view of a deployed retractor of this invention. The amount of elastic curvature of the retractor 208 is greatest at the base of the retractor, where the retractor emerges from the housing 210.

FIG. 5-8 shows an alternate side view of a deployed retractor of this invention. The amount of elastic curvature of the retractor 208 is fairly consistent across the length of the retractor 208.

FIG. 5-9 shows yet another side view of a deployed retractor of this invention. The retractor 208 has the smallest radius of curvature at its distal end.

In FIG. 5-10, the retractor 208 is substantially straight upon deployment from the housing 210.

FIG. 5-11 shows a retractor 208 which is gently curved.

FIGS. 5-12 and 5-13 show alternate end views of an expanded (unconstrained) retractor, such as shown by arrow E in FIG. 5-10. In end view, the expanded retractor can be flat. However, using the shape memory material retractors of this invention, other configurations are possible. FIG. 5-12 shows a retractor which is gently curved across its width. FIG. 5-13 shows a retractor 308 which is asymmetrical: it is flattened on one side, and curved or hooked on the other side. These configurations find particular application when the mass to be gently manipulated by the retractor is substantially parallel to the length of the retractor device or retractor housing. As used herein, the term "mass" refers to a tissue mass, or to a prosthetic device. Other configurations in addition to the flattened silhouette, and the curved configurations shown in FIGS. 5-12 and 5-13, will be readily apparent to one skilled in the art. For example, the retractor may be sharply angled, or it may be twisted along its length. The retractor may also have curvature in two or more directions in any of the planes described, such that the retractor may have a zig-zag or undulating appearance.

The various embodiments shown in FIGS. 5-2 through 5-13 can be combined as desired. A retractor of this invention can comprise, for example, the three-fingered shape of FIG. 5-3, curved along its length as shown in FIG. 5-8, and curved along its width as shown in FIG. 5-12. Such a retractor is generally cup-shaped.

FIGS. 5-14 and 5-15 show alternate cross-sectional views of a constrained retractor, taken at line a-a of FIG. 5-1. FIG. 5-14 shows a retractor made of wires 408 having a circular cross section, the retractor being constrained within the housing 410. FIG. 5-15 shows a retractor of strips 408 having an oval cross section. It will be clear to one skilled in the art that many other wire or strip cross-sections are equally appropriate for use in the retractors of this invention. For example, the retractor can be made of a strip member which is squared, rectangular, triangular, and the like. A cross-section such as the oval shape of FIG. 5-15 is generally preferred for the refractors of this invention. Such a cross-section provides strength upon the application of force which is perpendicular to the general plane in which the retractor is elastically deployed, but provides minimized dimensions and resistance upon constraint of the retractor within the housing 410.

In one preferred embodiment, a device of this invention comprises (a) a housing having an axial bore with a distal deployment opening; (b) a retractor which comprises a loop shape, the retractor being constrainable within said axial bore, and the retractor comprising a shape memory alloy; and (c) remote means to project and retract, and, optionally, to rotate, said retractor relative to the distal deployment opening. The retractor is moveable between a first position wherein the retractor is housed within the axial bore and assumes a constrained shape, and a second position wherein the retractor is extended past the distal deployment end and assumes an expanded memory shape.

The retractor is compressed and loaded within the housing. In this constrained configuration, the retractor device can be sterilized, packaged and stored for later use. The retractor device (i.e., retractor, housing, and deployment means) is preferably a disposable device. When needed, the surgeon visually assesses the size of retractor necessary for tissue manipulation, and selects a retractor which has an appropriate diameter, curvature and/or membrane.

In use, the device is partially inserted into a human or animal patient and used to manipulate organs or other tissues at an operative site. A guide wire may or may not be used for placement of the device. When a guide wire is used, it is introduced into the operative site and placed appropriately. A catheter containing a retractor is slipped over the guide wire. The guide wire is then removed, and the retractor is extended beyond the deployment end of the catheter. The guide wire preferably passes through a separate lumen in the catheter. Alternatively, the guide wire can pass through the catheter lumen which houses the retractor. The retractor can be radiopaque for ease of identification and use at the operative site.

A sixth form of the present invention provides a sheath-protected blade wherein the sheath is substantially straight. When it is constrained within the sheath, the blade is substantially linear. Upon deployment from the sheath, the blade is unconstrained, and assumes a configuration which is elastically deflected away from the longitudinal axis of the sheath. The blade is an elastically deformable material, preferably a pseudoelastic material, and more preferably a shape memory alloy.

One or more exposed edge of the elastic blade can provide a cutting edge. Exposed surfaces which are blunted can provide a means for manipulation of tissues or artificial devices.

FIG. 6-1 is an external view of a device of this invention.

FIGS. 6-2 and 6-3 are alternate cross-sectional views of a sheath of this invention, the cross sections being taken vertically along the longitudinal axis of FIG. 6-1.

FIG. 6-4 is an alternate cross-sectional view of a sheath of this invention, the cross section being taken vertically along the longitudinal axis.

FIG. 6-5 is a cross-sectional view of the device of FIG. 6-1 taken across the lonqitudinal axis, along line b-b of FIG. 6-1. FIG. 6-6 is a cross-sectional view of the device of FIG. 6-1 taken across the longitudinal axis, along line c-c of FIG. 6-1.

FIG. 6-7 is a cross-sectional view of a cutting edge of a cutting blade of this invention.

FIGS. 6-8 through FIG. 6-12 are alternate side views of the device of FIG. 6-1 when the cutting blade is deployed.

FIG. 6-13 through FIG. 6-20 are alternate top views of typical elastic blades of this invention.

A remotely operated device of this invention comprises an elongate housing, and an elongate blade which can be linearly constrained within the housing. The elastic blade is deployable from within the housing, and assumes a curved unconstrained shape upon deployment. Remote means are provided to project and retract, and optionally to rotate, the elastic blade relative to the distal end of the housing. Alternatively, remote means are provided to project and retract the sheath relative to the elastic blade.

The sheathed blade device of this invention differs from the prior art in several key aspects. The sheath is substantially straight along its length. When constrained within the sheath, the elastic blade is also substantially straight along its length. When deployed from the sheath the elastic blade assumes, as much as possible, its curved unconstrained shape.

The blades of this invention are curved (e.g., curled or twisted) along their length to a greater or lesser degree. The degree of curvature can be consistent along the length of the blade, or the curvature can vary in degree and/or in direction. A cutting surface can be provided at any desired exposed edge of the blade. When the unconstrained shape of the elastic blade is generally semicircular (such as shown in FIG. 6-8) a cutting surface can be provided along the sides of the blade (such as shown in FIGS. 6-13, 6-14, and 6-19). Alternatively, a cutting surface can be provided at the tip of the blade (such as shown in FIGS. 6-15, 6-16, and 6-17) to provide a scalpel which has a cutting surface directed 180° from the opening of the sheath. Varying the amount of deployment of the blade varies the cutting angle, so that a blade can be provided in which the cutting surface is angled from 0° to 180° or greater from the axis of the sheath.

The elastic nature of the blade allows for a complete retraction of the blade into the sheath for a complete protective enclosing of the blade, protecting both the blade and the body tissue during both the insertion and removal of the instrument. The sheath not only protects the blade but also guides and directs the blade whereby the extension of the blade from the sheath can comprise a cutting movement of the blade, rather than merely a means for exposing the blade for subsequent manipulation. The user, upon selection of the appropriate elastic blade (i.e., a blade having a desired curvature and position of cutting edge), orients the sheath, and then extends the blade. The blade is extended either by moving the blade outward from the sheath, or retracting the sheath relative to the blade.

Similar numbers refer to similar function throughout the Figures. The Figures are drawn for clarity and are not drawn to scale.

FIG. 6-1 is an external view of a device of this invention. The housing 10 is an elongate member, having an axial bore therethrough. The housing has a distal end 12, which acts as a sheath for the elastic blade, and a proximal end 14, which provides integration with a means to project and retract the elastic blade relative to the distal end of the housing 10. Between the distal end 12 and the proximal end 14 is the housing body 16.

The housing preferably also includes a remote means 18, the actuation of which causes the elastic blade to be deployed from the housing, or the housing to be retracted from the blade. The remote means 18 can be actuated by any manual or motorized means (not shown). In one embodiment, as pictured, two finger rings 20 are part of the proximal end 14. An additional thumb ring 22 is part of the remote means 18. When the thumb ring 22 is depressed, the elastic blade (not shown) is deployed from the housing at the distal end 12. The pictured rings are for ease of handling. Alternatively, knobs or ridges, for example, can be provided for ease of integration with a separate actuator means (not shown). Separate actuator means include slider mechanisms, pistol grip or thumb actuated mechanisms, scissors handles, and pistol-grip mechanisms. These and others are well known to the art. The specific type of actuator mechanism is generally determined by the personal preference of the surgeon. The orientation of the blade relative to the actuator mechanism can be configured to suit the specific application or the preference of the surgeon.

The distal end 12 of the housing acts as a sheath which constrains the elastic blade in a substantially linear configuration. It possesses sufficient lateral integrity that it is not significantly deformed by the pressure exerted by the constrained elastic blade. When an endoscopic device of this invention is a catheter and there is little lateral support in the housing body 16, the distal end 12 of the catheter may require reinforcement to provide consistent constraint of the elastic blade (not shown). In a device having a rigid housing, such as a laparoscopic device, the distal end 12 of the housing can have the same physical attributes as the remainder of the housing. Standard endoscopic and laparoscopic devices well known to the art are appropriate for use with the elastic blades of this invention.

The housing body 16 of a device which is used in laparoscopy must have sufficient structural integrity that it is easily inserted through a surgical opening into the body of the patient without undue deformation. Materials with sufficient structural rigidity include stainless steel and rigid polymeric materials such as plastics. The material of the proximal end of the housing 14, the material of the housing body 16, and the material of the distal end 12, can be the same, or can have different physical properties. For example, the housing body 16 used in endoscopic surgery will generally be flexible, to allow insertion through naturally occurring orifices, ducts, and/or passages, or to allow insertion through the working channel of an endoscope. Suitable polymeric material includes polytetrafluorethylene, polyurethane, polyethylene, Teflon, and the like. The material of such a flexible housing may be reinforced at the distal end 12 with fibers, rings, or longitudinal ribs, for example, to enable it to withstand the forces exerted on it by the elastic blade while it is constrained within, and deformed by, the housing.

The specific configuration and dimensions of the housing 10 will vary with the use of the device, the parameters of the elastic blade, and whether access for additional laparoscopic or endoscopic devices is provided. The housing 10 can be substantially uniform along its length, as shown in FIG. 6-1, or it can vary in diameter or shape, as shown in FIG. 6-4. Preferably, the housing 10 has a circular cross-section. A circular cross-section permits delivery of an elastic blade of this invention through a standard laparoscopic trocar, or through the instrument channel of a standard endoscope. However, other cross-sections may be preferable, for example, to adapt an endoscopic device to the orifice through which it will enter the body.

In general, the housing in an endoscopic device will have an outside diameter of from less than about 0.7 mm to about 4.5 cm or greater. The length of endoscopic devices will be from less than about 10 cm to about 3 meters or greater. The housing in a laparoscopic device will have an outside diameter of from less than about 0.3 mm to about 1.5 cm or greater. The length of laparoscopic devices will be from less than about 5 cm to about 30 cm or greater.

FIGS. 6-2 and 6-3 are alternate cross-sectional views of a device of this invention, the cross section being taken vertically along the longitudinal axis of the distal end 12 of FIG. 6-1.

FIG. 6-2 shows the distal end 112 of a housing 110 which is made as one unit. An axial bore 130 runs axially through the housing. At the proximal end 132 of the axial bore 130, the axial bore can have any convenient size and shape. In general the axial bore will have an internal diameter of from less than about 0.5 mm to about 2 cm or greater. At the distal end, the axial bore becomes flattened, and forms the sheath bore 134 for the constrained elastic blade 136. The sheath bore 134 is sized to slidably accept the constrained elastic blade 136, and to constrain the elastic blade 136 in a substantially linear configuration. When the elastic blade 136 is fully housed within the sheath bore 134, the sheath bore 134 contains at least those portions of the elastic blade 136 which have cutting edges. Preferably the cutting edges of the elastic blade 136 do not touch or rub against the sheath bore 134 when stored, or upon deployment or retraction, as such contact can dull the cutting edges.

In general the proximal end 132 of the axial bore 130 will be circular and relatively large, to facilitate the loading of the connecting means 138 and the elastic blade 136 within the sheath. A circular conformation is for general ease of manufacture and handling, and alternate conformations can be used, as desired. The proximal end 132 of the axial bore 130 houses the connecting means 138. The connecting means 138 can be, for example, soldered or otherwise affixed to the elastic blade. Alternatively, it can be a continuation of the elastic material used to form the elastic blade 136.

FIG. 6-3 shows the distal end 112 of a housing 110 which is made as two units. One unit is a tube 140 through which extends an axial bore 130. A bushing 142 is fitted within the tube, for example by press fit or by thread. The bushing 142 provides the sheath bore 134 for the constrained elastic blade 136. The bushing 142 can be made of any suitable material, polymeric and/or metallic. It may be desirable to pass an electric current through the elastic blade 136, so that the elastic blade 136 acts as an electrocautery device. In such an embodiment the bushing can be a non-conducting polymer, and it can act to keep the elastic blade 136 electrically insulated from the housing 110. The elastic blade 136 is held for reciprocal motion by the connecting means 138.

FIG. 6-4 is an alternate cross-sectional view of the distal end 112 of a housing 110 of this invention, the cross section being taken vertically along the longitudinal axis. In this embodiment the housing 110 is a metal or plastic tube which has been flattened at one end. The flattened end provides the sheath bore 134 in which the elastic blade is slidably constrained. The elastic blade 136 is held for reciprocal motion by the connecting means 138.

If the housing 110 is a tubular structure having a flattened end, as shown in FIG. 6-4, it may be desirable to provide a covering of any suitable material (not shown). The covering provides a uniform outer dimension for the device. A covering which provides a substantially uniform circular cross-section is advantageous if the blade device is to be introduced into the body through a standard laparoscopic trocar, or through the instrument channel of a standard endoscope. The covering acts to minimize the escape of fluids (either liquid or gas) from the body. The covering can be made of a polymeric material such as polyurethane, polyethylene, and the like.

FIG. 6-5 is a cross-sectional view of the device of FIG. 6-2 taken across the longitudinal axis at line b-b. The housing 210 surrounds the axial bore 230. Within the axial bore is the connecting means 238. The connecting means 238 can have any suitable cross-sectional shape. In the shown embodiment the connecting means 238 spans axial bore 230 to minimize lateral motion as the sheath and elastic blade (not shown) are moved longitudinally relative to each other. If an electric current is passed through the connecting means 238 and the elastic blade, so that the elastic blade acts as an electrocautery device, it may be desirable to include a layer of a non-conducting material (not shown) around connecting means 238 to insulate the connecting means 238 from the housing 210.

FIG. 6-6 is a cross-sectional view of the device of FIG. 6-2 taken across the longitudinal axis at line c-c. The housing 210 surrounds the sheath bore 234. Within the sheath bore is the elastic blade 236.

One or more edges of the elastic blade 236 can remain dull, and can aid the non-cutting manipulation of tissues or artificial devices during surgery. For instance, the blade can have no cutting edges. This minimizes the amount of trauma to surrounding tissues upon manipulation of the blade. More generally, the elastic blade 236 has one or more sharpened edges 240. The sheath bore 234 is substantially flattened, and holds the elastic blade 236 so that the elastic blade 236 is constrained linearly. In a preferred embodiment, the sheath bore 234 is slightly enlarged in the region of the sharpened edges 240. This acts to protect the sharpened blade from wear as it is deployed from, and withdrawn into, the housing. Alternatively, the sheath bore 234 closely mimics the outer shape of the elastic blade 236. Other embodiments are also possible, such as a sheath bore 234 which is substantially rectangular or eccentric, and such embodiments will be readily apparent to one skilled in the art.

FIG. 6-7 is a cross-sectional view of a cutting edge of a cutting blade of this invention. A cutting edge can be provided at any edge of the elastic blade. In a preferred embodiment, the edge of the elastic material is beveled, and provides a cutting blade. FIG. 6-7 shows a cutting edge which is beveled on both sides. The bevel or bevels can be at any appropriate angle from the plane of the blade. When two bevels are present, they can have the same angle of bevel, or different angles of bevel. In FIG. 6-7, the bevels are β and .phi degrees from the plane of the blade. Alternatively, only one bevel may be present (not shown). The honing of an edge to form a cutting blade is well known in the art. If desired, the cutting blade can be serrated. The cutting edge is preferably derived from the beveled elastic material itself. However, it may be desirable or necessary to provide a honed blade edge to the elastic material. This additional blade can be added mechanically, as shown in FIG. 6-12. Alternatively, two or more elastic materials can be used to form the blade. For example, a non-cutting elastic blade can be combined with an elastic alloy blade having a cutting edge.

FIGS. 6-8 through 6-11 are side views of the device of FIG. 6-1 when the elastic blade is deployed. A cutting surface can be provided at any desired exposed edge of the blade.

FIG. 6-8 shows an elastic blade 336 which is substantially semicircular upon deployment from the housing 310. The degree of curvature can be substantially consistent along the length of the blade, as shown, or the curvature can vary, i.e., the elastic blade can have a uniform or non-uniform radius of curvature.

FIG. 6-9 shows an elastic blade 336 which describes an S-shaped curve upon deployment from the housing 310.

FIG. 6-10 shows an elastic blade 336 which is twisted along its longitudinal axis upon deployment from the housing 310. The elastic blade is shown having a clockwise spiral, but counterclockwise spirals, and combinations of the two, are also appropriate for use herein.

FIG. 6-11 shows an elastic blade 336 which is sharply curved in the region closest the housing 310, and substantially linear in the region furthest from the housing 310.

FIG. 6-12 shows a standard surgical blade 350, which is attached to a strip of elastic material 352 by a mechanical means 354. The standard surgical blade 350 is not curved. However, the strip of elastic material 352 is strongly bent and upon deployment from the housing it acts to bend the surgical blade 350 sharply away from the housing 310.

FIGS. 6-13 through 6-19 are each a top view of an alternate elastic blade of this invention.

FIG. 6-13 shows a top view of an elastic blade 436 which has one longitudinal sharpened (cutting) edge 460.

FIG. 6-14 shows a top view of an elastic blade 436 in which the entire perimeter of the blade provides the sharpened edge 460.

FIG. 6-15 shows a top view of an elastic blade 436 in which only the most distal surface provides the sharpened edge 460.

FIG. 6-16 shows a top view of an elastic blade 436 in which only the most distal surface provides the sharpened edge 460. The sharpened edge 460 has two angled sections, 460a and 460b, each of which is angled relative to the longitudinal axis of the blade. The angled sections can have any desired degree of angle relative to the longitudinal axis of the blade, and the degree of angle for each section can be similar to, or dissimilar to, that of the other section.

FIG. 6-17 shows a top view of an elastic blade 436 in which an outwardly curved surface provides the sharpened edge 460.

FIG. 6-18 shows a top view of an elastic blade 436 in which an inwardly curved surface provides the sharpened edge 460.

FIG. 6-19 shows a top view of a preferred embodiment of the elastic blade 436 in which the distal perimeter of the blade provides the sharpened edge 460, and the proximal edges of the blade are unsharpened. The width of distal section of the elastic blade 436 is somewhat less than the width of the proximal section. The distal portion of the elastic blade having the sharpened edge 460 is narrower than proximal unsharpened portion, so that the sharpened edge 460 will not touch the sides of the sheath bore. The sharpened edge 460 is therefore protected during the process of deployment and retraction of the elastic blade 436.

FIG. 6-20 shows a top view of an embodiment of the elastic blade 436 in which all edges of the blade are unsharpened. This embodiment is preferred when the blade is not used to cut tissues, and can function to manipulate tissues or artificial devices.

The elastic blade is compressed and loaded within the sheath. In this constrained configuration, the blade and sheath can be sterilized, packaged and stored for later use In one preferred embodiment, a device of this invention comprises (a) a housing having a distal deployment opening; (b) a curved elastic blade which is linearly constrainable within the housing; and (c) remote means to project and retract the elastic blade relative to the distal deployment opening; the elastic blade being moveable between a first position wherein the elastic blade is linearly constrained within the housing, and a second position wherein the elastic blade is extended past the distal deployment end and assumes a memory shape.

In a preferred embodiment, a blade of this invention comprises an elastically deformable curved blade.

According to a seventh form of the present invention, it has now been discovered that a pivoted two-bladed device, such as a forceps, scissors, snips, and the like, can be combined with an elastically deformable stem. Remote blade actuator means are used to cause the blades to splay apart or come together. An elastic member and a constraining member, for deforming the elastically deformable stem, are present. The elastic member and the constraining means are longitudinally slidable relative to one another, causing the angular deformation of the elastically deformable stem.

The elastically deformable stem includes an elastic member which is substantially linear when it is constrained, and assumes a substantially non-linear shape when it is unconstrained. When a constraining elongate housing is present and serves as the constraining member, the elastic member is moveable between a first position wherein the elastic member is linearly constrained within the housing, and a second position wherein the elastic member is deployed from the housing and is unconstrained. Alternatively, the housing is moveable between a first position wherein the elastic member is linearly constrained, and a second position wherein the elastic member is unconstrained. The elastically deformable stem, which includes the elastic member, assume a nonlinear shape. The amount of deformation of the elastically deformable stem can be controlled by adjusting the amount of the elastic member which is not constrained by the elongate housing.

If the device does not include an elongate housing, and in embodiments in which the elongate housing is present but is not a constraining member, an internal constraining member is present. The deformation of the elastically deformable stem can be controlled by moving the elastic member between a first position wherein the elastic member is linearly constrained, and a second position wherein the elastic member is substantially unconstrained. Alternately, the deformation of the elastically deformable stem can be controlled by moving the constraining member between a first position wherein the elastic member is linearly constrained, and a second position wherein the elastic member is substantially unconstrained. Between the first, constrained, position and the second, unconstrained, position, is a range of partial or variable deployment.

The elastic member is formed of an elastic material, preferably a pseudoelastic material such as a shape memory alloy, which is capable of being greatly deformed without permanent deformation. This provides an improved instrument that can be used in applications in which there is a limited amount of space. The instrument can be operated remotely, and at angles to the line of insertion, more conveniently than previous instruments. The instrument, with appropriately configured blade edges and/or tips, can be used to grasp, cut, and/or dissect tissue.

A remotely operated instrument of this invention comprises (a) a bladed element having a first pivoted blade, and a second opposing blade; (b) an elastically deformable stem connected to the bladed element, the elastically deformable stem including an elastic-member; (c) a constraining member which can constrain the elastic member in a substantially linear configuration; (d) a blade actuator means for controlling pivotal motion of the pivotable blade(s); and (e) a stem deforming means for controlling deformation of the elastically deformable stem. A separate blade rotator means, for controlling rotation of the plane through which the blade(s) are pivoted, is preferably included.

An alternate remotely operated instrument of this invention comprises: (a) a bladed element, having opposable blades including a first blade which is mounted for movement relative to the second blade; the first blade being moveable between a closed position wherein the axes of the blades are substantially parallel, and an open position, wherein the axes of the blades are deflected from the parallel; (b) an elastically deformable stem including an elastic member which is substantially non-linear in its unconstrained shape; (c) a constraining member which constrains the elastic member in a substantially linear shape; (d) a blade actuator means, said blade actuator means controlling position of the opposing blades between the open position and the closed position; and (e) a stem deformation controlling means. A rotation means, for controlling the plane of the blades, is preferably included.

The elastically deformable stem includes at least one elastic member which assumes a linear configuration when constrained, and which is curved when unconstrained. The elastic member is held in a constrained configuration by the presence of the constraining member. Elastic materials which are suitable for use in the elastic member include pseudoelastic and superelastic materials, as described below.

When an elongate housing is present and acts as the constraining member, the instrument is moveable between a first position wherein the elastically deformable stem and, optionally, the bladed element, are within the housing, and a second position wherein the bladed element and at least part of the elastically deformable stem are deployed from the housing. The elastically deployable stem includes an elastic member which is curved at a predetermined angle with respect to the elongate housing when the elastically deformable stem is deployed from the housing. When the housing acts as the constraining member, varying the amount of deployment of the elastically deformable stem varies the angle of presentation of the bladed element.

In an alternate embodiment, the elastic member is constrained in a linear configuration by the action of an internal constraining member, such as an internal constraining rod. Movement of the internal constraining member relative to the elastic member causes variable deformation of the elastically deformable stem. An elongate housing may or may not be present in embodiments in which an internal constraining member is present.

The bladed instrument can comprise a grasping device (e.g., a forceps), a cutting device (e.g., a scissors), or a dissecting device.

FIG. 7-1 shows an instrument of this invention.

FIGS. 7-2 show the deployment end of a bladed instrument of this invention.

FIGS. 7-3 and 7-4 are longitudinal cross-sectional views of alternate elastically deployable stems, in longitudinally constrained and longitudinally unconstrained configurations.

FIGS. 7-5 through 7-7 each show alternate views of an elastically deformable stem of this invention.

Figures 1, 2, 3, 4, 5, 6, 7, 7B:
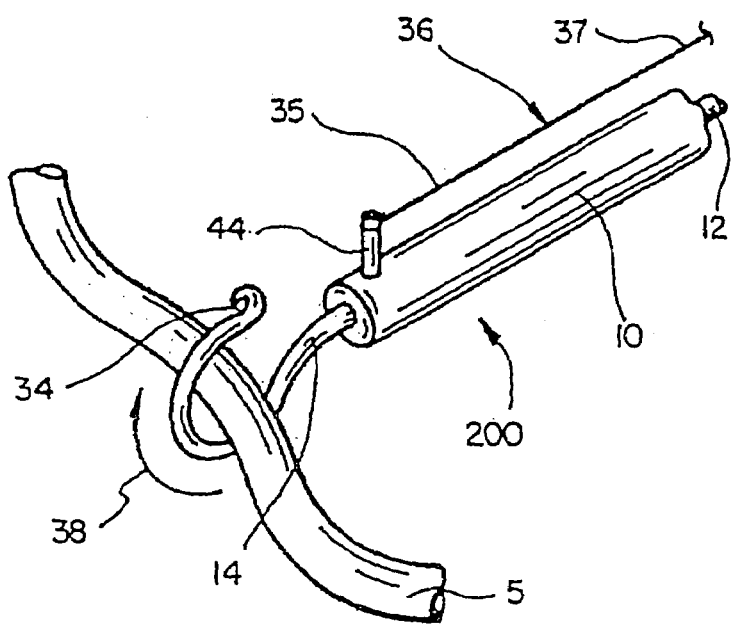
Figures 1, 2, 3, 4, 5, 6, 7, 7C:
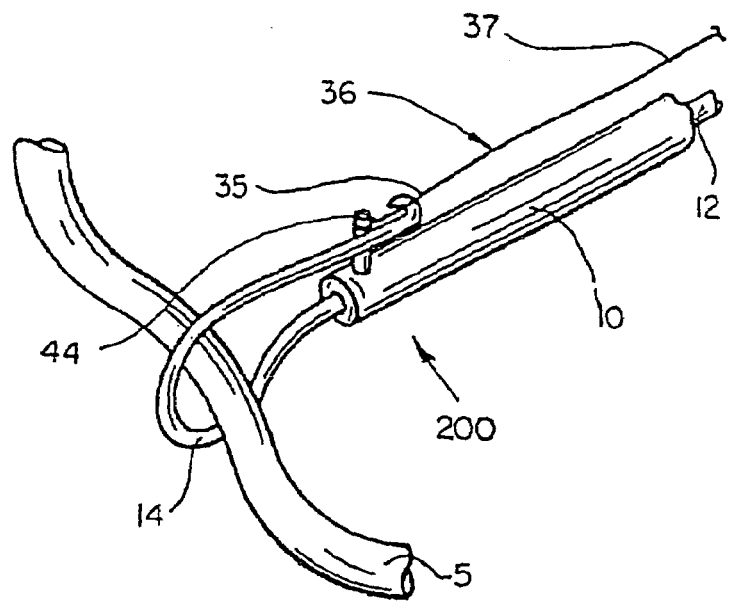
Figures 1, 2, 3, 4, 5, 6, 7, 7D:
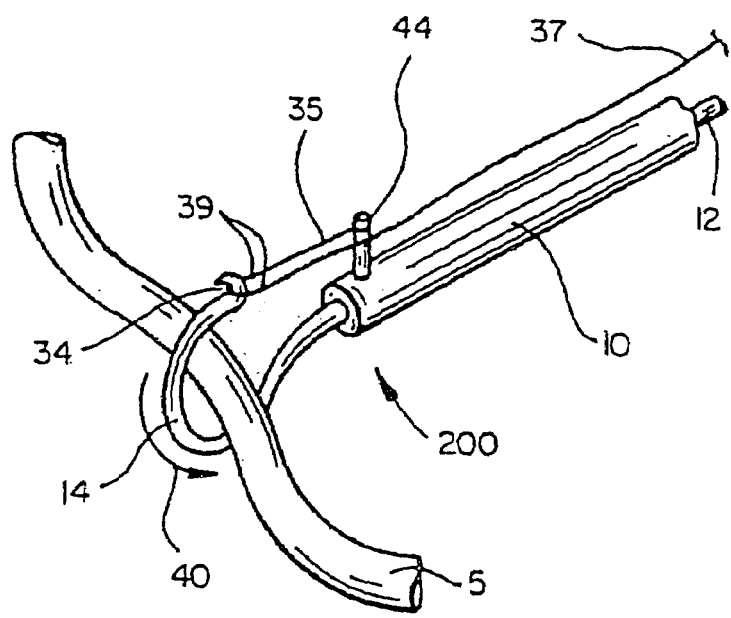
Figures 1, 2, 3, 4, 5, 6, 7, 7E:
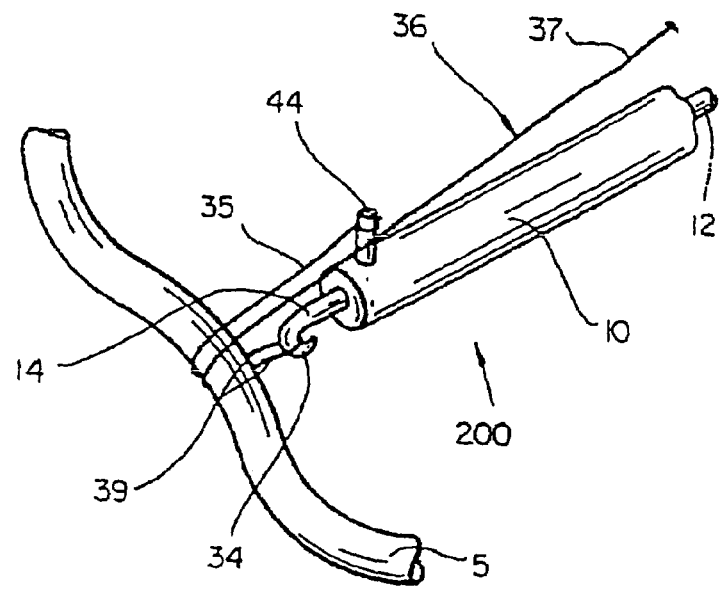
Figures 1, 2, 3, 4, 5, 6, 7, 7F:
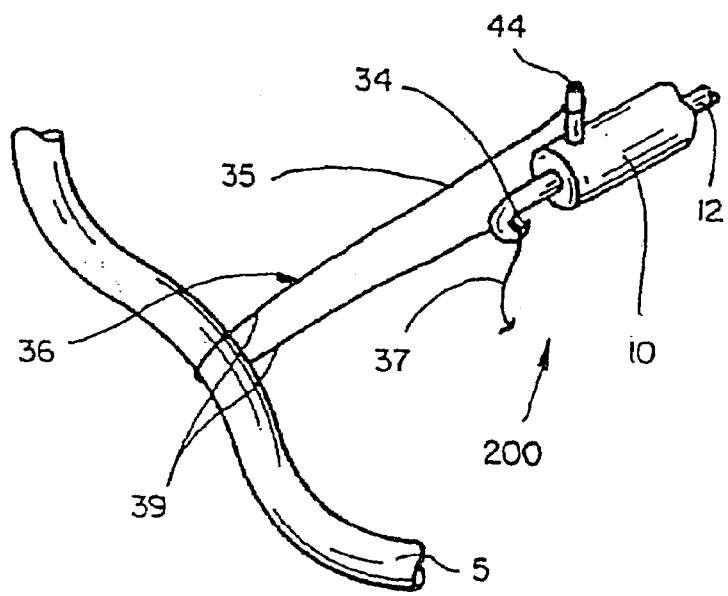
Figures 1, 2, 3, 4, 5, 6, 7, 8, 8A:
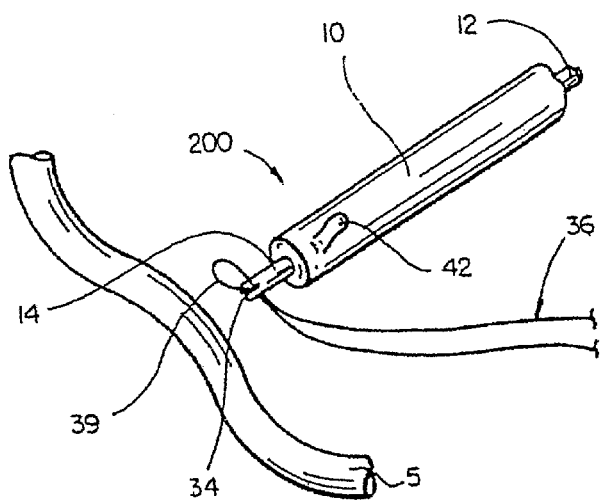
Figures 1, 2, 3, 4, 5, 6, 7, 8, 8B:
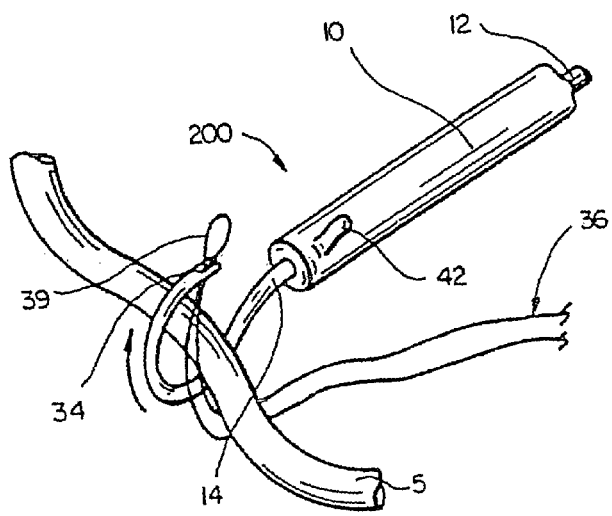
Figures 1, 2, 3, 4, 5, 6, 7, 8, 8C:
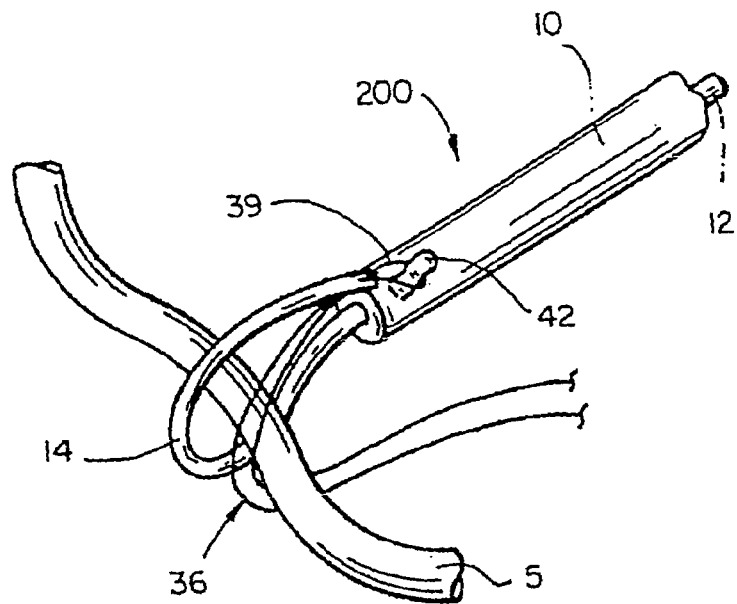
Figures 1, 2, 3, 4, 5, 6, 7, 8, 8D:
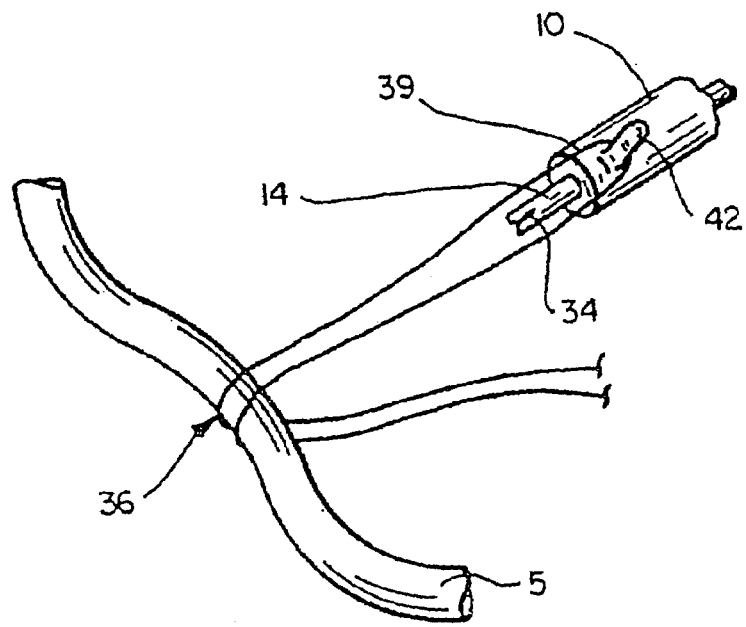
Figures 1, 2, 3, 4, 5, 6, 7, 8, 9:
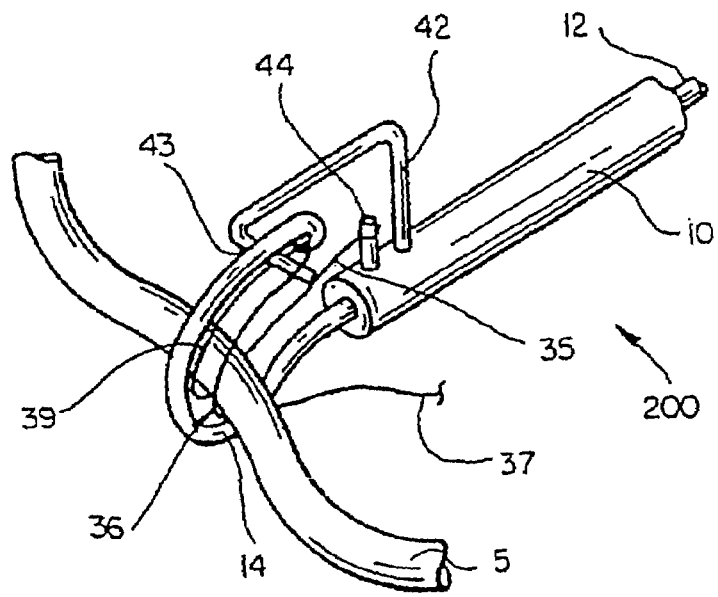
Figures 1, 2, 3, 4, 5, 6, 7, 8, 9, 10, 11:
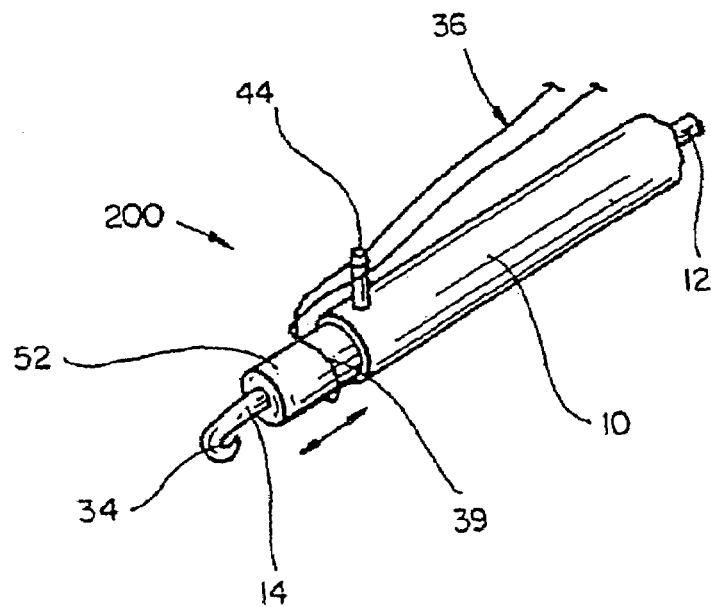
Figures 1, 2, 3, 4, 5, 6, 7, 8, 9, 10, 10A:
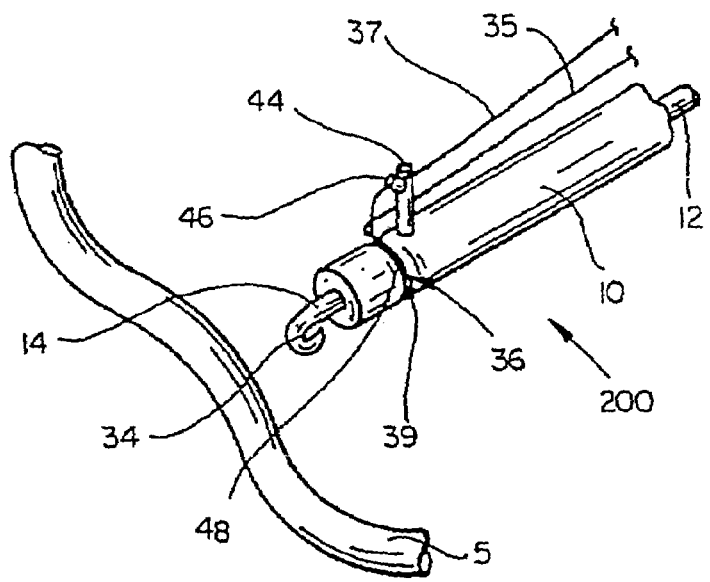
Figures 1, 2, 3, 4, 5, 6, 7, 8, 9, 10, 10B:
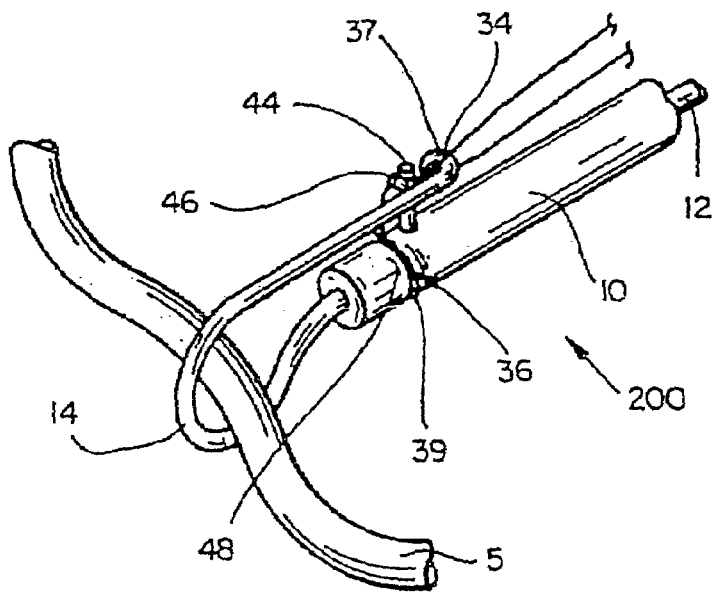
Figures 1, 2, 3, 4, 5, 6, 7, 8, 9, 10, 10C:
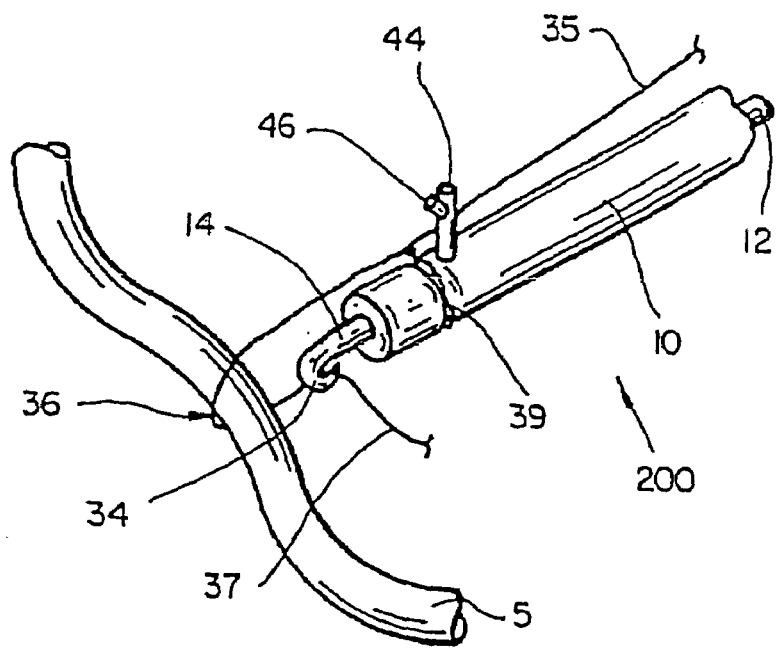
Figures 1, 2, 3, 4, 5, 6, 7, 8, 9, 10, 10D:
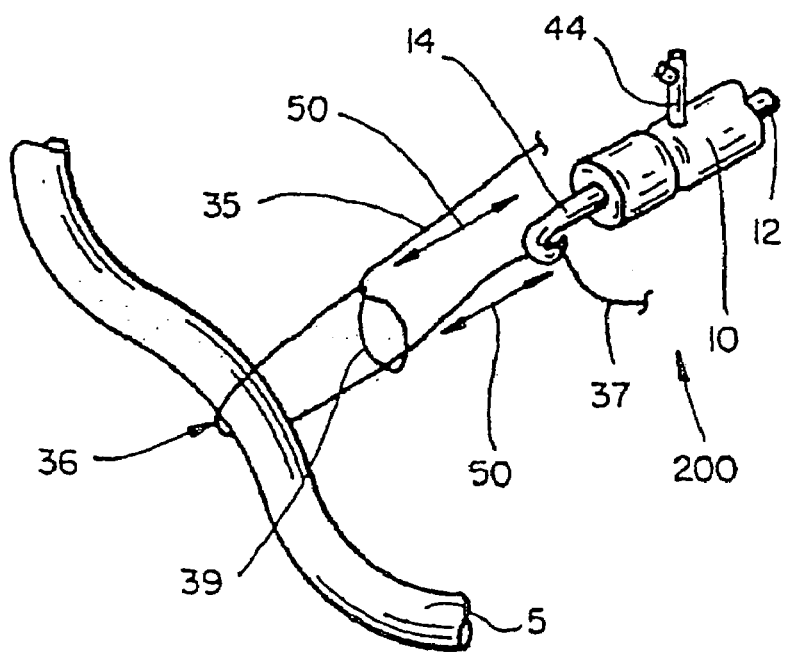
Figures 1, 2, 3, 4, 5, 6, 7, 8, 9, 10, 11, 12, 12A:
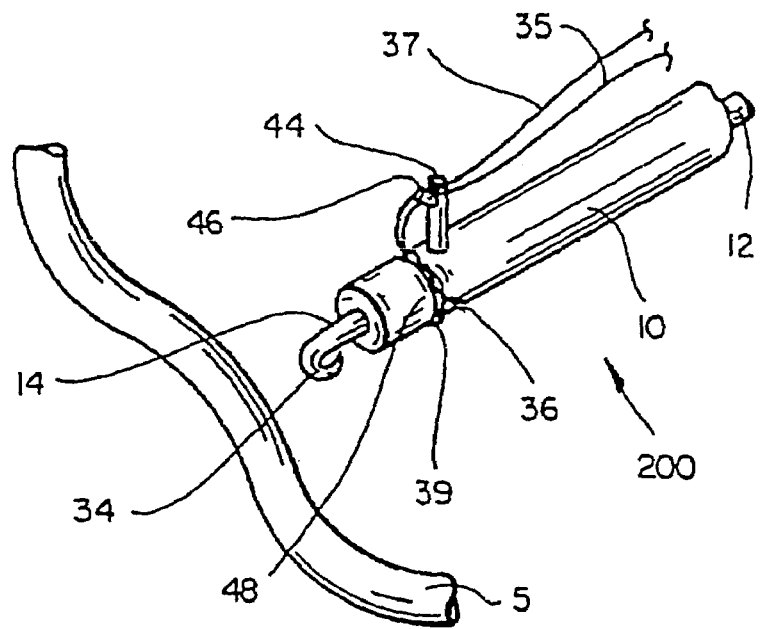
Figures 1, 2, 3, 4, 5, 6, 7, 8, 9, 10, 11, 12, 12B:
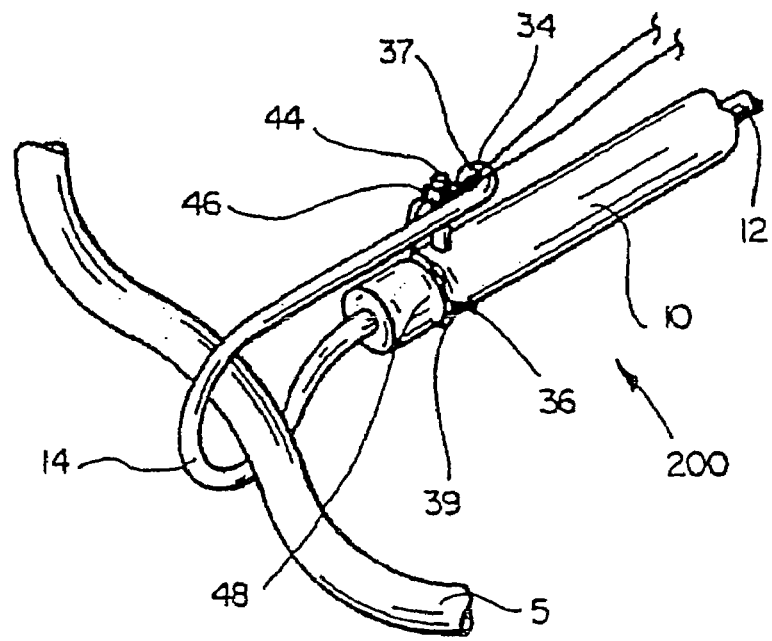
Figures 1, 2, 3, 4, 5, 6, 7, 8, 9, 10, 11, 12, 12C:
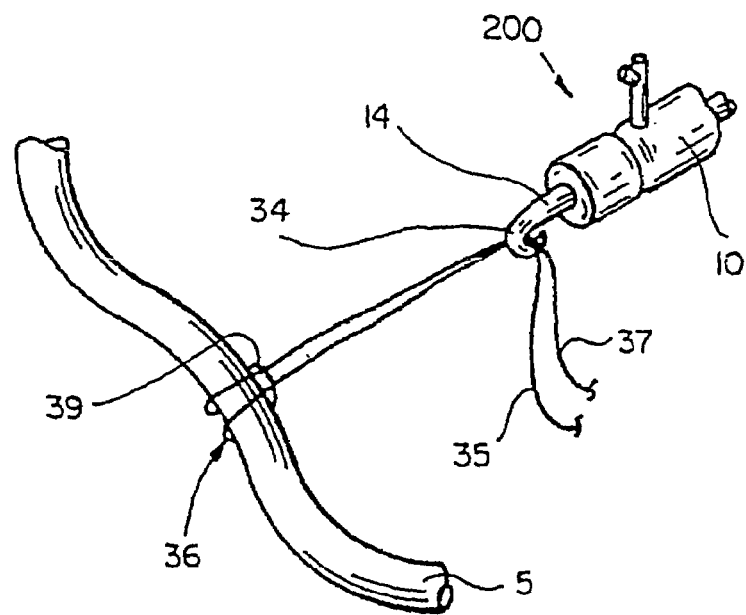
Figures 1, 2, 3, 4, 5, 6, 7, 8, 9, 10, 11, 12, 13:
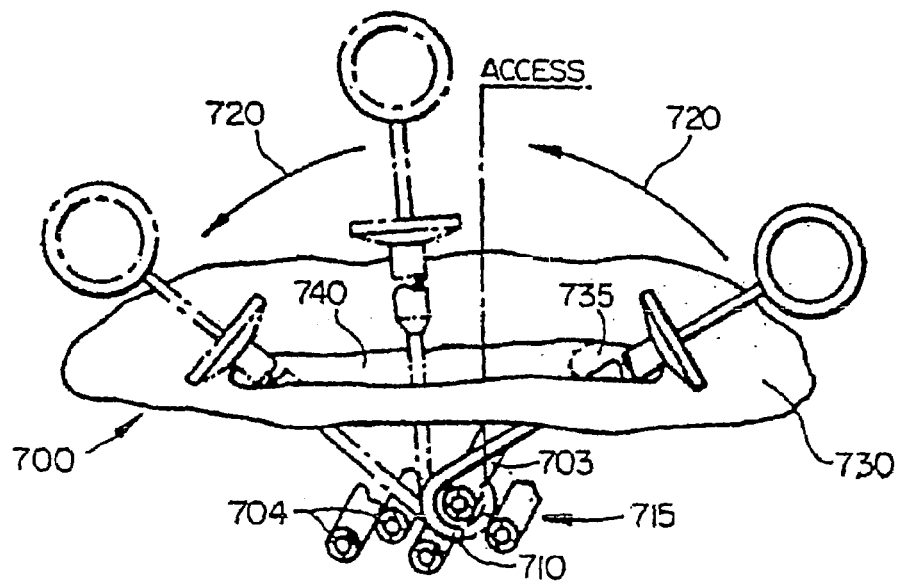

FIGS. 7-8 and 7-9 show alternate elastic members suitabe for use in an elastically deformable stem of this invention.

FIGS. 7-10 show alternate views of a device of this invention having two pivoted blades, each blade having a longitudinal slot proximal the pivot.

FIGS. 7-11 show alternate views of a device of this invention having two blades, two bars, and four pivots.

FIGS. 7-12 show alternate cross-sections of the device of FIG. 7-1, taken through line 12--12.

FIGS. 7-13 show various blades suitable for use herein.

FIGS. 7-14 show various blade cross-sections, taken throuh line 14-14 of FIG. 7-13.

A surgical instrument of this invention consists essentially of a bladed element having opposable blades, at least one of which is pivotally mounted for movement; a blade actuator means for causing pivotal motion of the pivotable blade(s); an elastically deformable stem connected to the bladed element, and a variable constraining means for causing deformation of the elastically deformable stem.

The instrument is particularly useful in applications in which access to an object to be cut, grasped, or dissected is restricted. For example, the instrument is especially useful in medical applications in which the object to be cut, grasped, or dissected is part of a human or animal body. In such applications, the surgical instrument generally includes or is passed through a sheath in the form of a cannula, catheter, or endoscope. The distal end of the sheath is introduced through an opening into a body cavity, duct, or joint, for example during laparoscopic surgery.

The instrument may also be useful in the assembly of mechanical, electrical or other equipment, especially when access to the worksite is limited, or when the worksite is located at an angle to the access.

The instrument includes an elastically deformable stem, so that the bladed element can be variably angled away from the angle of introduction. When an elongate housing (e.g., a sheath) is present, the bladed elements can be arranged such that the axis on which the elements cut, grasp, and/or dissect the object is not coaxial with the axis of at least a significant portion of the elongate housing.

The elastically deformable stem includes at least one elastic member, which is made of an elastic material. The elastic member is manufactured in a non-linear shape. For example, the elastic member is manufactured having one or more (generally one) bend, curve or twist. The bend, curve or twist can describe any desired angle. The angle described by the elastic member is generally less than 270°, more generally less than about 180°. For many applications, an angle of about 90° is preferred. The angle described by the elastic member in its unconstrained shape is the maximum amount of deformation which can be attained by the elastically deformable stem.

The elastic member is deformed (constrained) from the bent configuration towards the straight configuration, and held in the straight (constrained) configuration during positioning of the instrument. Preferably, the bladed element is fully functional when the blades are not housed within the elongate housing, whether or not the elastically deformable stem has been deployed. When the elastically deformable stem is to assume an angled (unconstrained) configuration, the constraining member is removed. When the elastically deformable stem is constrained by an elongate housing, the housing is withdrawn to permit the elastic member to regain its bent (unconstrained) shape, and thus deform the elastically deformable stem. When the elastically deformable stem is constrained by a constraining rod, for example, the rod is preferably withdrawn to permit the elastically deformable stem to regain its bent (unconstrained) shape. Alternately, the elastic member can be deployed beyond the constraining member to permit the elastic member to assume its unconstrained shape and to deform the elastically deformable stem.

The amount of deformation of the elastically deformable stem can be variably controlled between the maximum and the minimum by manipulation of the constraining member. The constraining means is generally a longitudinally slidable rigid member. The constraining member can comprise, for example, a stiff elongate housing, or a substantially linear stiff constraining rod. Alternatively, the constraining member can be fixed, and the elastic member can be slidable relative to the constraining member.

The elastically deformable stem can be, for example, a rod, one or more wires, a hollow tubular element, or the like.

When the instrument includes a housing which acts to constrain the elastic member into a substantially linear shape, the housing and the elastically deformable stem are moved longitudinally relative to each other to release the elastic member from lateral constraint. The elastic member regains its original (unconstrained) non-linear shape, and thus to deform the elastically deformable stem. This approach is shown in graphic cross-section in FIG. 7-3.

Alternatively, the elastically deformable stem can include a substantially linear constraining rod. This constraining rod deforms the elastic member into a substantially linear shape. As the constraining rod and the elastic member are withdrawn relative to one another, the elastic member regains its original non-linear shape and causes the elastically deformable stem to deform. This approach is shown in graphic cross-section in FIG. 7-4.

In yet another embodiment (not shown), the instrument includes a substantially linear constraining means which has a fixed position. This constraining means deforms the elastic member into a substantially linear shape. As the elastic member and the constraining rod are withdrawn relative to one another, the elastic member regains its original non-linear shape and causes the elastically deformable stem to deform.

The elastic member of the elastically deformable stem comprises an elastic material which is substantially linear in its constrained configuration, and is curved in its unconstrained, or "memory", configuration. The term "elastic material" is used herein to mean a material that has spring-like properties, that is, it is capable of being deformed by an applied stress and then springing back, or recovering, to or toward its original unstressed shape or configuration when the stress is removed. The elastic material is preferably highly elastic. The material can be polymeric or metallic, or a combination of both. The use of metals, such as shape memory alloys, is preferred. Shape memory alloys that exhibit pseudoelasticity, in particular superelasticity, are especially preferred. The elastic materials herein exhibit greater than 1% elastic deformation, more generally greater than 2% elastic deformation. Preferably, the elastic materials herein exhibit greater than 4% elastic deformation, more preferably greater than 6% elastic deformation.

Preferably, the elastic member is at least partially formed from a pseudoelastic material, such as a shape memory alloy.

The Figures are drawn for clarity and are not drawn to scale.

FIG. 7-1 shows a bladed instrument of this invention. As shown, a scissors-type blade actuator mechanism 110 controls the pivotal movement of the blades 112. A finger-activated stem deformation controlling means 114 is used to control the deployment of the bladed element 116 and the elastically deformable stem 118 from the elongate housing 120. A rotator mechanism 122 is shown in the form of a knob, and is used to rotate the elastically deformable stem 118 and the bladed element 116 around the long axis of the elongate housing 120. Each of: the actuator mechamism 110, the stem deformation controlling means 114, and the rotator mechanism 122 can take any suitable manually operated configuration. The specific configuration of each of the actuator mechanism 110, the stem deformation controlling means 114, and the rotator mechanism 122 can be the same, or they can be different, as shown. Examples of suitable manually operated mechanisms include one or more slider, pistol grip handle, scissors handle, and/or plunger arrangement. These and other such devices are well known to the art.

An elongate housing 120 maintains, the elastic member 124 in a substantially linear configuration prior to deployment of the elastically deformable stem 118 and the bladed element 116. Upon full deployment from the elongate housing, the bladed element 116 assumes a position which is at an angle from the elongate housing 120. It should be noted that the angle .phi between the elongate housing 120 and the bladed element 116 can be any number of degrees desired. As shown, angle .phi. is approximately 60°. Angle .phi. is defined by the axis of the elongate housing β, and the plane which is perpendicular to the axis of the pivot 126 around which the blades pivot. Angle .phi. can be any desired angle. Preferably a rotator mechanism 122 is provided, and permits rotation of the bladed element 116 and the elastically deformable stem 118 around the long axis of the elongate housing β. The rotation of the bladed element 116 is preferably independent of the amount of deployment of the elastically deformable stem 118.

The elongate housing 120 is an elongate sheath having an axial bore (not shown) therethrough. The axial bore is sized to receive the elastically deformable stem and, optionally, the bladed element, in a constrained configuration. The axial bore can have a consistent dimension through the length of the elongate housing 120, or the axial bore can widen and narrow as necessary to conform to the shape of the elastically deformable stem 118 and, optionally, to the bladed element 116.

In general, the elongate housing 120 can be flexible or rigid, and the rigidity can vary by region. When the elongate housing does not act as the constraining member, an alternate constraining member (such as an internal constraint) must be present. Standard catheters and laparoscopic devices well known to the art are appropriate housings for the bladed element and the elastically deformable stem. The stiff-sheath elongate housing of FIG. 7-1 can be polymeric or metallic, for example stainless steel. A preferred stiff elongate housing is a rigid elongate tube of stainless steel.

The elongate housing 120 can be circular in cross-section, but other cross-sections may be preferable in some situations. For example, squared, oval, or eccentric cross-sections can be used. The elongate housing can be substantially uniform in cross-section along its length, or it can vary.

The specific configuration and dimensions of the elongate housing 120 will vary with the use of the device, the parameters of the bladed element, and whether access for additional surgical devices is provided. The outer diameter of the elongate housing will vary with the application and the size of the bladed element. For example, the elongate housing in a laparoscopic device will have a diameter of from less than about 3 mm to about 1.5 cm or greater; the length of a laparoscopic device will be from less than about 20 cm to about 30 cm or greater.

In any of the embodiments of this invention, a suitable means may be provided for passing a fluid (liquid or gas) through the device for irrigation, aspiration, insufflation, and the like. In any of the embodiments of this invention, electricity may be passed to one or both end portion(s) of the blade(s) for purposes of electrocautery or electrocutting.

FIGS. 7-2a through 7-2d are side views of the distal end of an instrument of this invention. The instrument shown in FIG. 7-2 includes a rigid elongate housing 128 which acts as the constraining means.

As shown in FIG. 7-2, the instrument is moveable between a first position (FIG. 7-2a or FIG. 7-2b) wherein the elastically deformable stem 132 is constrained within the elongate housing 128, and a second position (FIG. 7-2d) wherein the bladed element 130 and the elastically deformable stem 132 extend past the constraint of the elongate housing 128 and assume a memory shape. In one embodiment, both the elastically deformable stem 132 and the bladed element 130 are fully retractable into the elongate housing 128, as shown in FIG. 7-2a. Between the first position and that shown in FIG. 7-2d are degrees of deployment (for example that shown in FIGS. 7-2b and 7-2c) in which the bladed element 130 is deployed sufficiently for use (FIG. 7-2b), and in which the elastically deformable stem 132 is partially deployed (FIG. 7-2c). In an alternate embodiment, the bladed element 130 is not retractable into the elongate housing 128. Such an embodiment is demonstrated in FIGS. 7-2b through 7-2d. These variable degrees of partial deployment allow the operator to choose the angle of deflection that the bladed element assumes relative to the elongate housing 128. (Pivotal actuation of the blades is not shown in this series of figures.)

After use, the instrument is removed from the worksite. When the worksite is within a patient the elastically deformable stem 132 and, optionally, the bladed element 130, are retracted back into the elongate housing 128 before the instrument is removed from the patient: the various elements therefore resume the configuration shown in FIG. 7-2a before removal. If only the elastically deformable stem 132 is retracted back into the elongate housing 128 before the instrument is removed from the patient, the elements resume the configuration shown in FIG. 7-2b before removal.

FIG. 7-2b shows the blades 134 free of the elongate housing 128. The blades 134, the pivot 136, and other elements necessary for pivotal motion of one or more blade (but not including the blade actuator) comprise the bladed element 130. A portion of the elastic member 138 is shown. In the pictured embodiment, the elastic member 138 comprises two strips of elastic material, each strip being secured to the pivot 136. The elastic member 138 can have any desired cross-sectional shape, and the cross-sectional shape can vary along its length. Preferred cross-sectional shapes include a tubular shape or rod shape, and a rectangular or roughly rectangular shape. In the embodiment shown the elastic member 138 comprises two strips which are not in the neutral plane of bending of the elastically deformable stem 132: this is a less preferred configuration. The preferred placement of the elastic member is at or near the neutral plane of bending of the elastically deformable stem 132, and is discussed further below.

FIG. 7-2c shows the bladed element 130 as it is deployed axially from the elongate housing 128. Also shown is a portion of the elastic member 138. Shown next to the elastic member 138 is the blade actuator rod 140. In this embodiment, the elastic member 138 and the blade actuator rod 140 are included within the elastically deformable stem 132. The actuator rod 140 is preferably centrally located within the elastically deformable stem.

The blade actuator rod 140 can comprise a rod, strip, filament, cord, conduit catheter, pipe, lever, or other suitable connecting means which allows the remote pivotal manipulation of the blade(s). More than one such element can be present. The cross-sectional parameters of the blade actuator rod can vary along its length. Any suitable material, including a shape-memory material, can be used to form the blade actuator rod 140. In one embodiment the elastic member also acts as the blade actuator rod 140. The blade actuator rod 140 preferably has sufficient flexibility that it does not interfere with the elastic deformation of the elastic member 138. The blade actuator rod 140 can be positioned as desired within the elastically deformable stem 132. Preferably, the blade actuator rod 140 is located in a position that does not interfere with the longitudinal motion of the elastic member 138 or of the constraining member, and does not interfere with the bending motion of the elastic member 138. At the actuator end of the instrument (not shown), the blade actuator rod 140 can integrate with an actuator means, such as a slider mechanism, pistol grip or thumb actuated mechanism, scissors handle, and/or plunger mechanism. Alternatively, the actuator rod 140 projects proximally from the elongate housing 128, and can be directly manipulated to cause pivotal motion of the opposing blades. The blade actuator means includes the actuator rod 140, any apparatus necessary to integrate with the bladed element and the actuator mechanism (if any). The blade actuator means is used remotely to open and close the bladed element. Illustrative actuating means are described more fully below with reference to the drawings and include rack and pinion means, pin and slot means, four-bar linkages, and the like. In certain embodiments, the actuating means may be formed of a pseudoelastic material. The actuating means may permit the bladed element to be axially rotated. The actuating means can also provide suitable means for irrigating or aspirating the workfield of the bladed elements, or can conduct electrical current to one or both of the blades, if desired.

FIG. 7-2d shows the bladed element 130 in the fully deployed configuration. The elastically deformable stem 132 is fully deployed (i.e., has achieved its fully unconstrained shape), and, as depicted, holds the bladed element 130 in position approximately 90° from the axis of the body of the instrument.

Reconstraining the elastically deformable stem 132 as shown in FIG. 7-2d is accomplished by reversing the process, i.e, by moving the elements to the configuration shown in FIGS. 7-2c, 7-2b, and (optionally) 7-2a, sequentially.

FIG. 7-3 provides cross-sectional views of one segment of an elastically deformable stem 142 in constrained (FIG. 7-3a), partially constrained (FIG. 7-3b), and unconstrained (FIG. 7-3c) configurations.

FIG. 7-3a shows a section of an elongate housing 144 which surrounds the elastically deformable stem 142. The elastically deformable stem 142 is fully constrained by the elongate housing 144, and is in a substantially linear configuration. The elastically deformable stem 142 includes an elastic member 146 in the shape of a tube, and the enclosed blade actuator rod 148.

The elongate housing 144 and the elastically deformable stem 142 are capable of reciprocal longitudinal motion, e.g., are longitudinally slidable relative to one another. For example, the elongate housing 144 can be moved in direction L (arrow) to deploy the elastically deformable stem 142. The same effect can be achieved by moving the elastically deformable stem 142 in direction R (arrow). Alternatively, the elongate housing 144 can be moved in direction L (arrow) while the elastically deformable stem 142 is moved in direction R (arrow), to achieve deployment of the elastically deformable stem 142. Point a is labeled on FIGS. 7-3a, 7-3b and 7-3c, and shows the relative movement of the elastically deformable stem 142 relative to the elongate housing 144.

FIG. 7-3b shows the section of elastically deformable stem 142 in a partially deployed configuration. The elastically deformable stem 142 is partially constrained in a linear configuration by the elongate housing 144, and partially unconstrained.

FIG. 7-3c shows the section of elastically deformable stem 142 in a fully deployed configuration. The elastically deformable stem 142 is unconstrained, and shows the maximum deformation available from the specific elastic member 146.

Reconstraining the elastically deformable stem 142 as shown in FIG. 7-3c is accomplished by reversing the process, i.e., by moving the elements to the configuration shown in FIGS. 7-3b and 7-3a, sequentially.

FIG. 7-4 provides views of one segment of an elastically deployable stem 150 in constrained (FIG. 7-4a), partially constrained (FIG. 7-4b), and unconstrained (FIG. 7-4c) configurations.

FIG. 7-4a shows a section of an elastically deformable stem 150 which is constrained by the constraining rod 152, and is held in a substantially linear configuration. The elastically deformable stem 150 comprises an elastic member 154, the blade actuator rod 156, and the constraining rod 152.

The constraining rod 152 and the elastically deformable stem 150 are longitudinally slidable relative to one another. For example, the constraining rod 152 can be moved in direction L (arrow) to cause deformation of the elastically deformable stem 150. The same effect can be achieved by moving the elastically deformable stem 150 in direction R (arrow). Alternatively, the constraining rod 152 can be moved in direction L (arrow) while the elastically deformable stem 150 is simultaneously moved in direction R (arrow), to achieve deformation of the elastically deformable stem 150. Point b is labeled on FIGS. 7-4a, 7-4b and 7-4c, and shows the relative movement of the elastically deformable stem 150 relative to the constraining rod 152.

FIG. 7-4b shows the section of elastically deformable stem 150 in a partially deployed configuration. The elastically deformable stem 150 is partially constrained in a linear configuration by the constraining rod 152, and partially unconstrained.

Figures 4, 4C:
Figures 4, 4D:
Figures 4, 5, 5A:
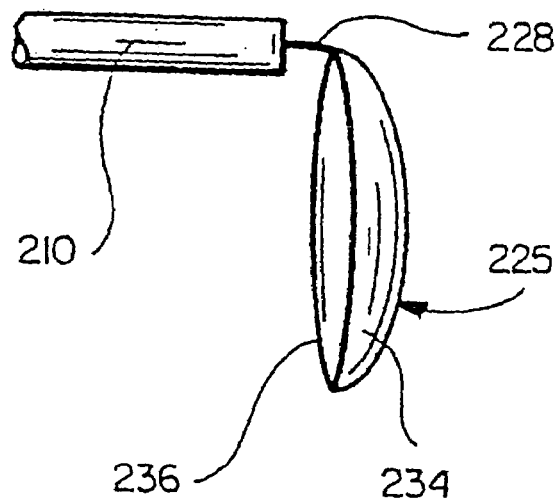
Figures 4, 5, 5B:
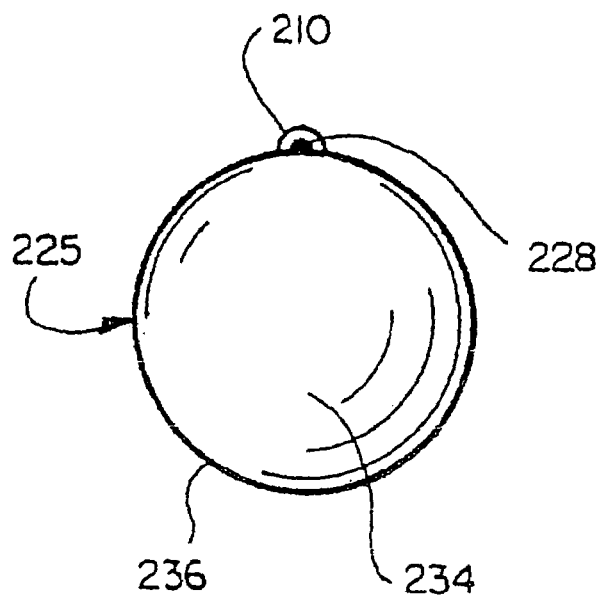
Figures 1, 5:
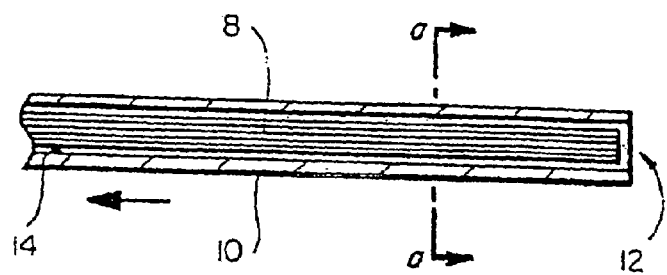
Figures 2, 5:
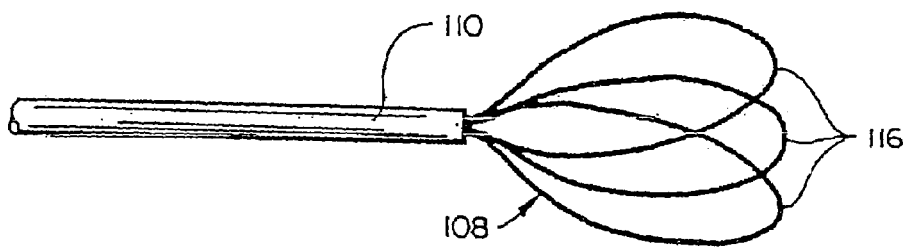
Figures 3, 5:
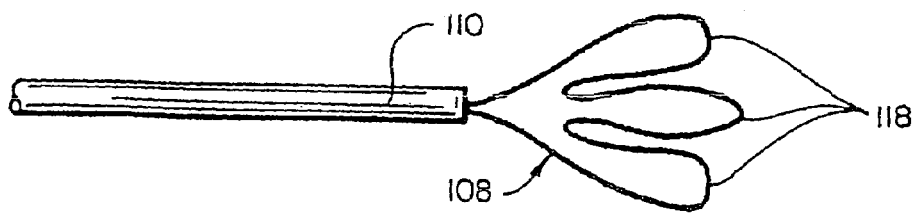
Figures 4, 5:
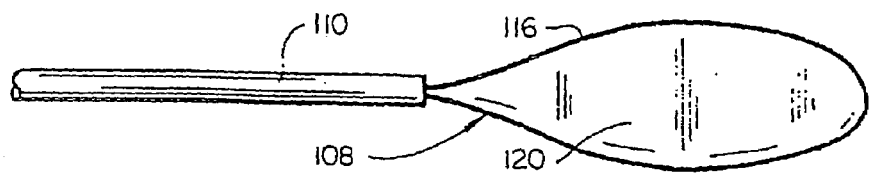
Figure 5:
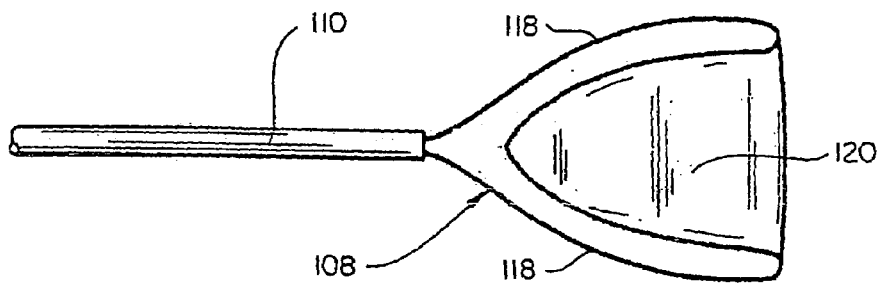
Figures 5, 6:
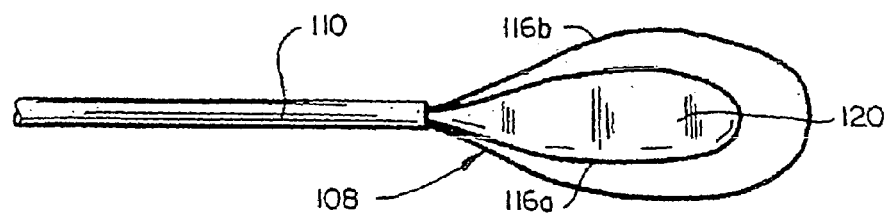
Figures 5, 6, 7:
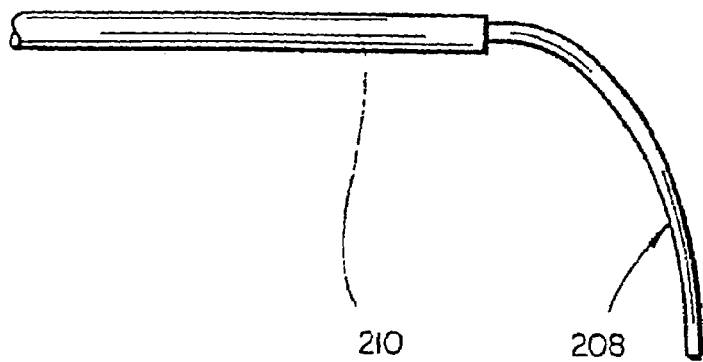
Figures 5, 6, 7, 8:
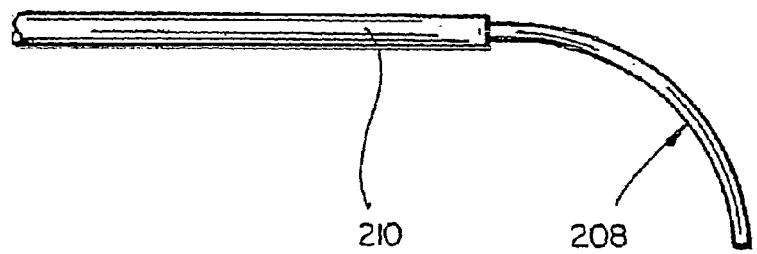
Figures 5, 6, 7, 8, 9:
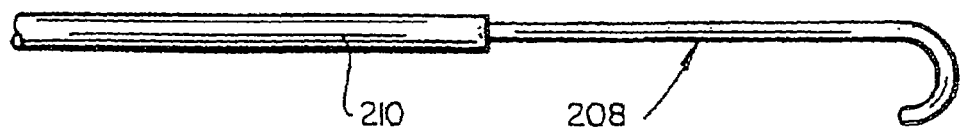
Figures 5, 6, 7, 8, 9, 10:
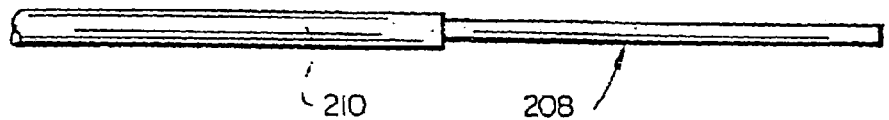
Figures 5, 6, 7, 8, 9, 10, 11:
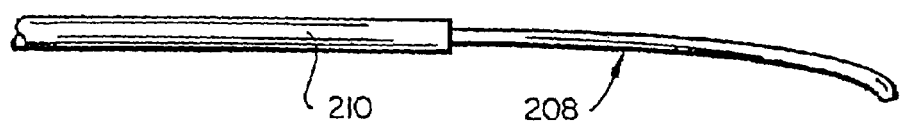
Figures 5, 6, 7, 8, 9, 10, 11, 12:
Figures 5, 6, 7, 8, 9, 10, 11, 12, 13:
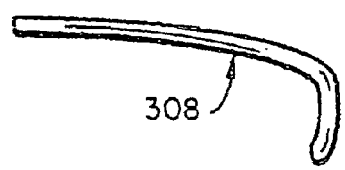
Figures 5, 6, 7, 8, 9, 10, 11, 12, 13, 14:
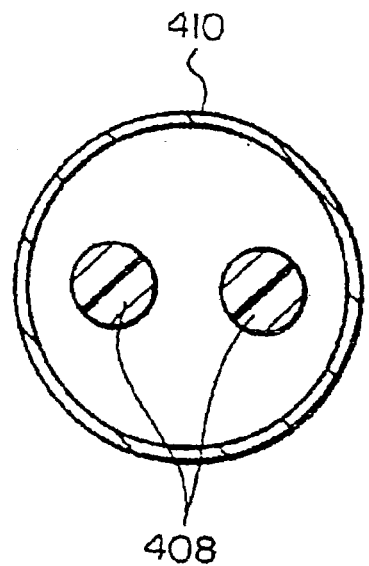
Figures 5, 6, 7, 8, 9, 10, 11, 12, 13, 14, 15:
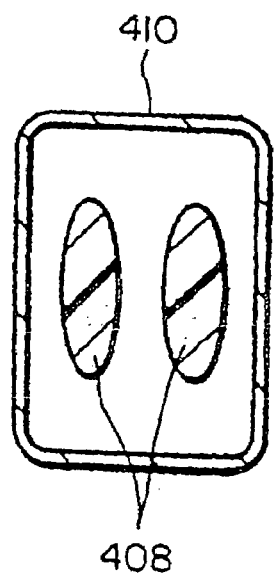
Figures 1, 6:
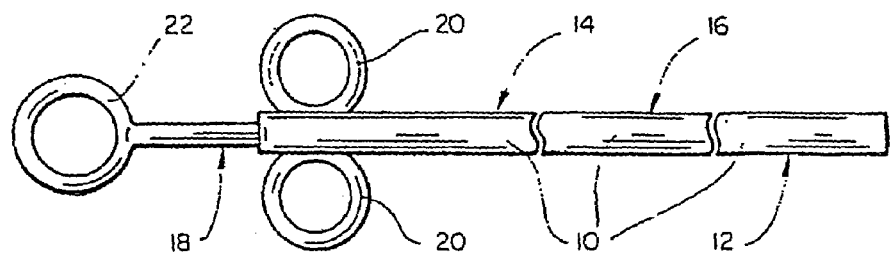
Figures 2, 6:
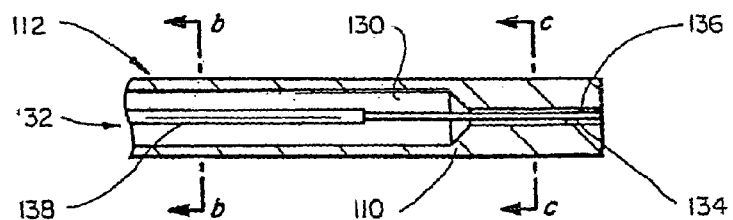
Figures 3, 6:
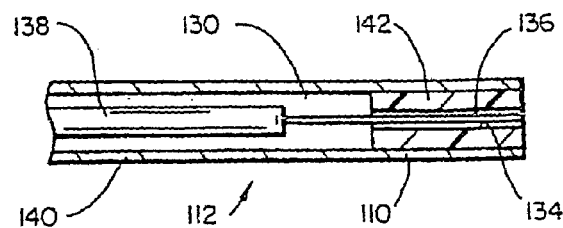
Figures 4, 6:
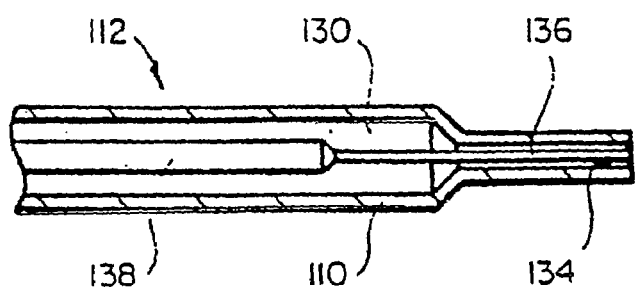
Figures 5, 6:
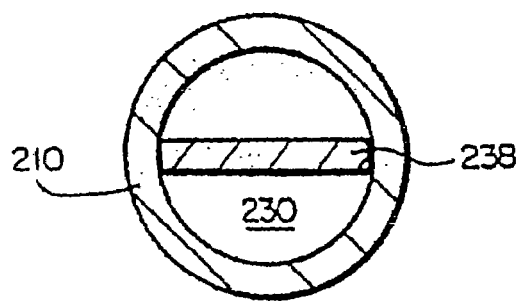
Figure 6:
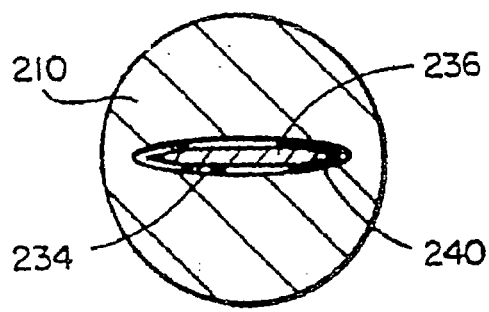
Figures 6, 7:
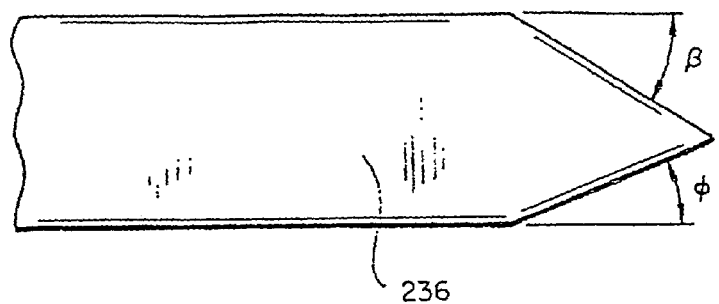
Figures 6, 7, 8:
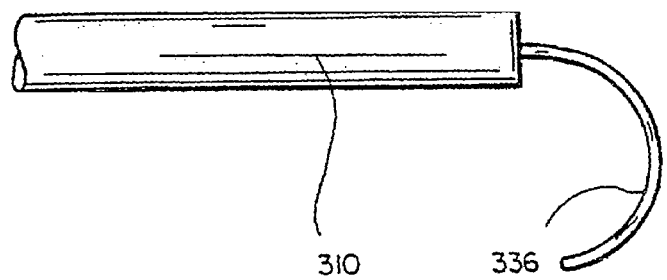
Figures 6, 7, 8, 9:
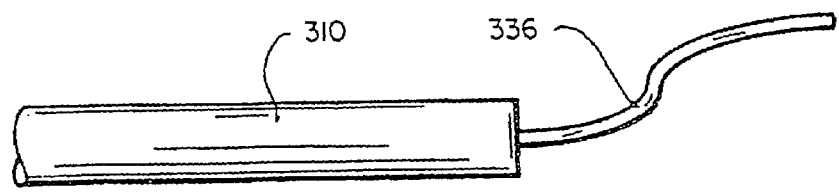
Figures 6, 7, 8, 9, 10:
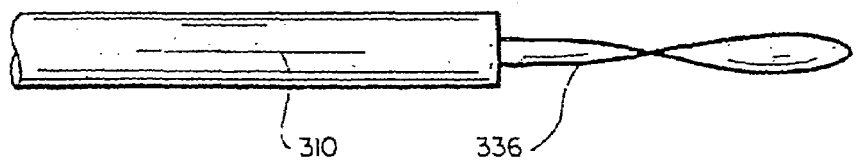
Figures 6, 7, 8, 9, 10, 11:
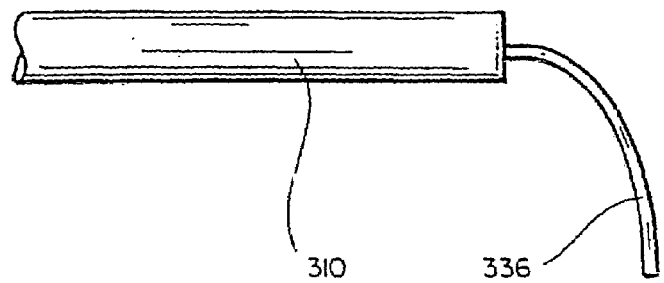
Figures 6, 7, 8, 9, 10, 11, 12:
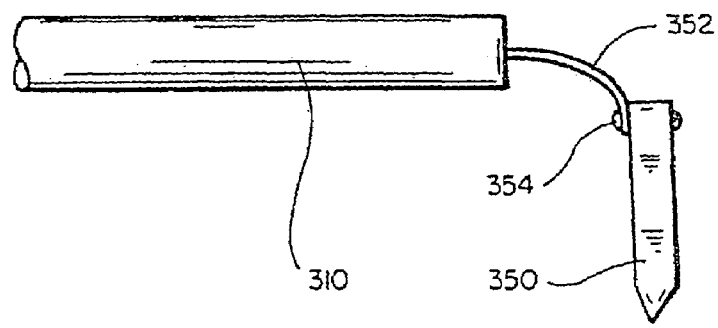
Figures 6, 7, 8, 9, 10, 11, 12, 13:
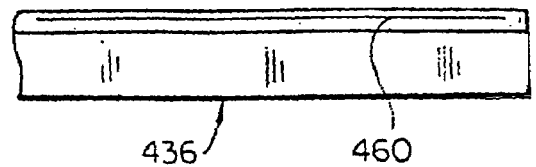
Figures 6, 7, 8, 9, 10, 11, 12, 13, 14:
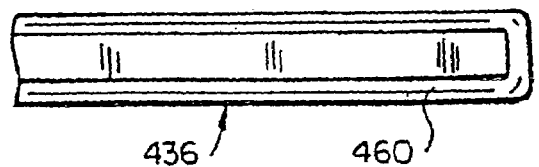
Figures 6, 7, 8, 9, 10, 11, 12, 13, 14, 15:
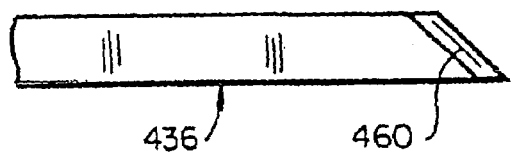
Figures 6, 7, 8, 9, 10, 11, 12, 13, 14, 15, 16:
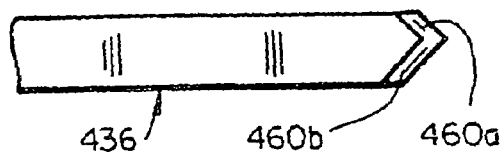
Figures 6, 7, 8, 9, 10, 11, 12, 13, 14, 15, 16, 17:
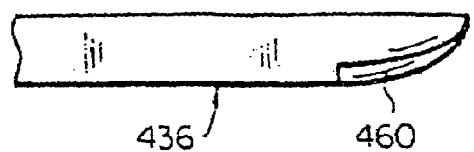
Figures 6, 7, 8, 9, 10, 11, 12, 13, 14, 15, 16, 17, 18:
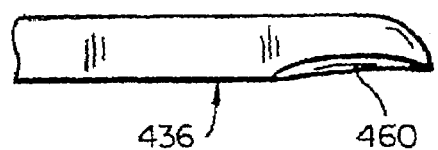
Figures 6, 7, 8, 9, 10, 11, 12, 13, 14, 15, 16, 17, 18, 19:
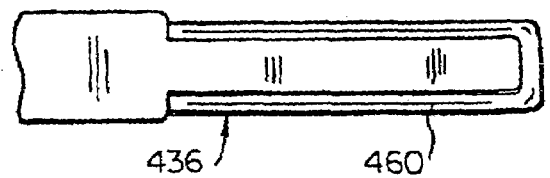
Figures 6, 7, 8, 9, 10, 11, 12, 13, 14, 15, 16, 17, 18, 19, 20:
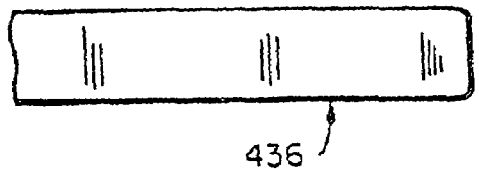
Figures 1, 7:
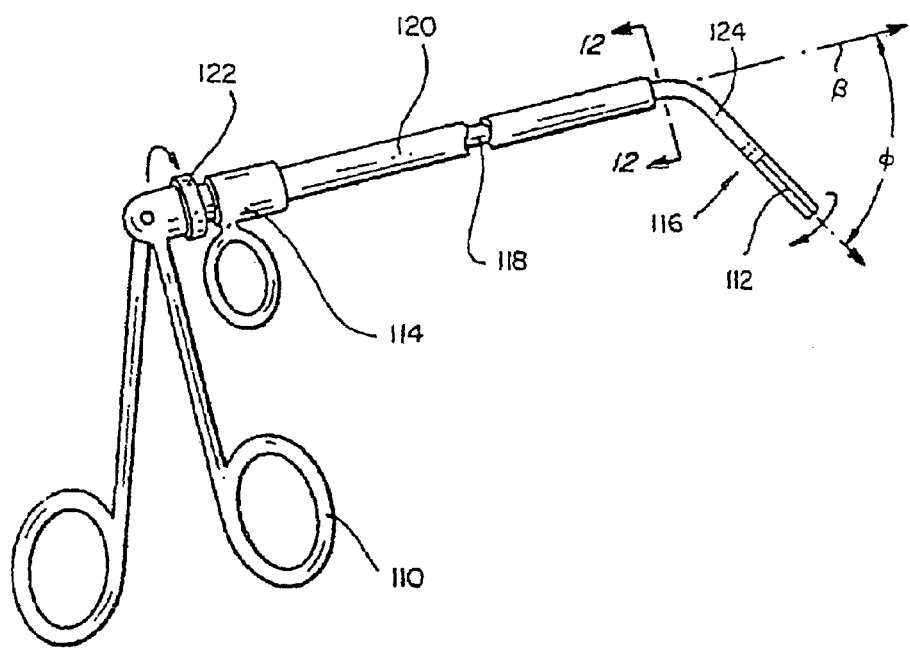
Figures 2A, 7:
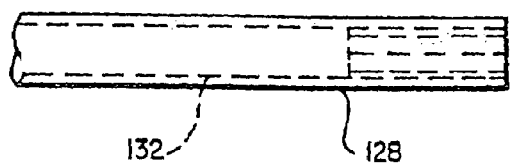
Figures 2B, 7:
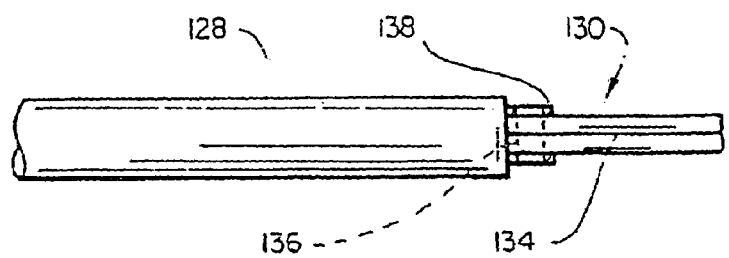
Figures 2C, 7:
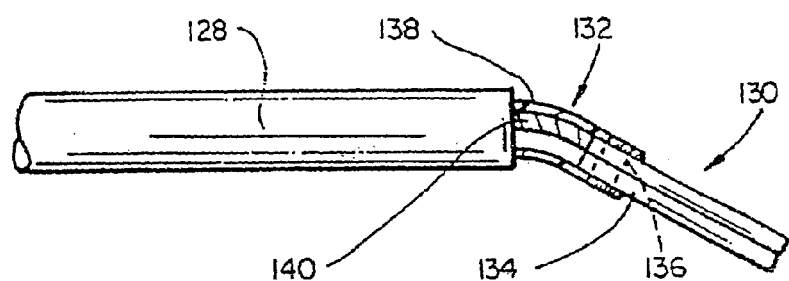
Figures 2D, 7:
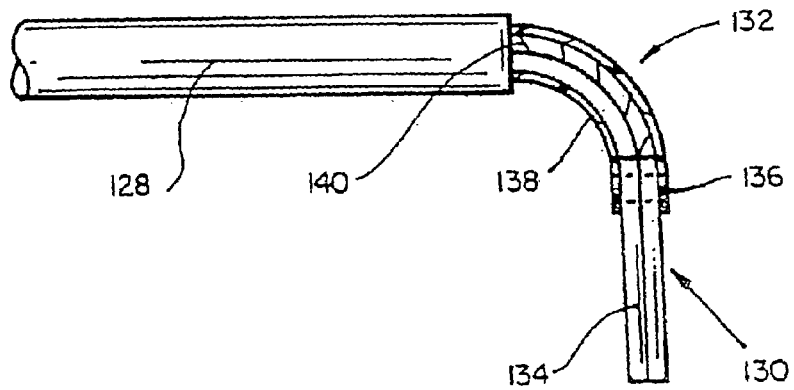
Figures 3A, 7:
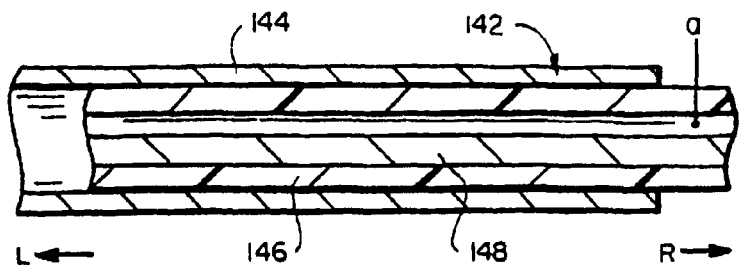
Figures 3B, 7:
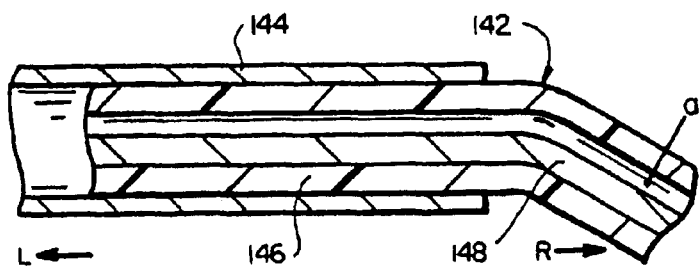
Figures 3C, 7:
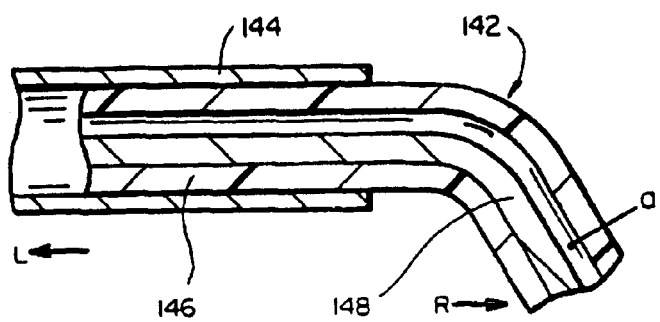
Figures 4A, 7:
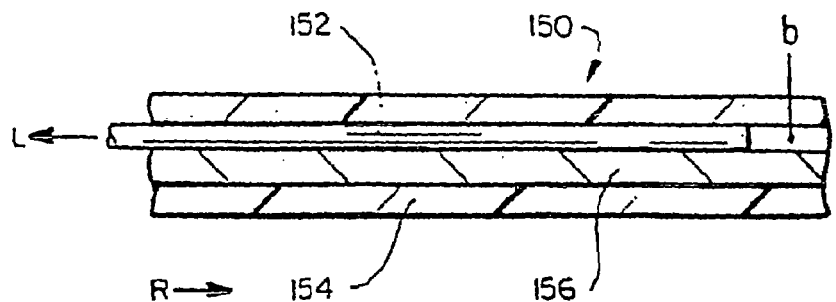
Figures 4B, 7:
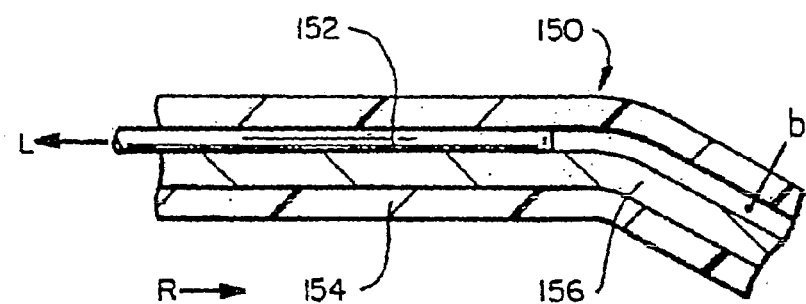
Figures 4C, 7:
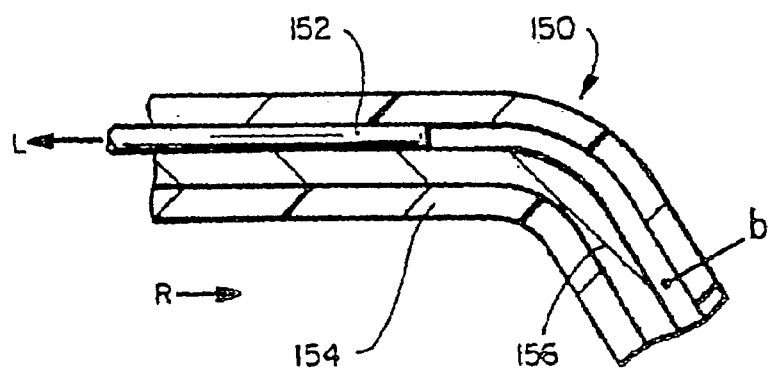
Figures 5A, 7:
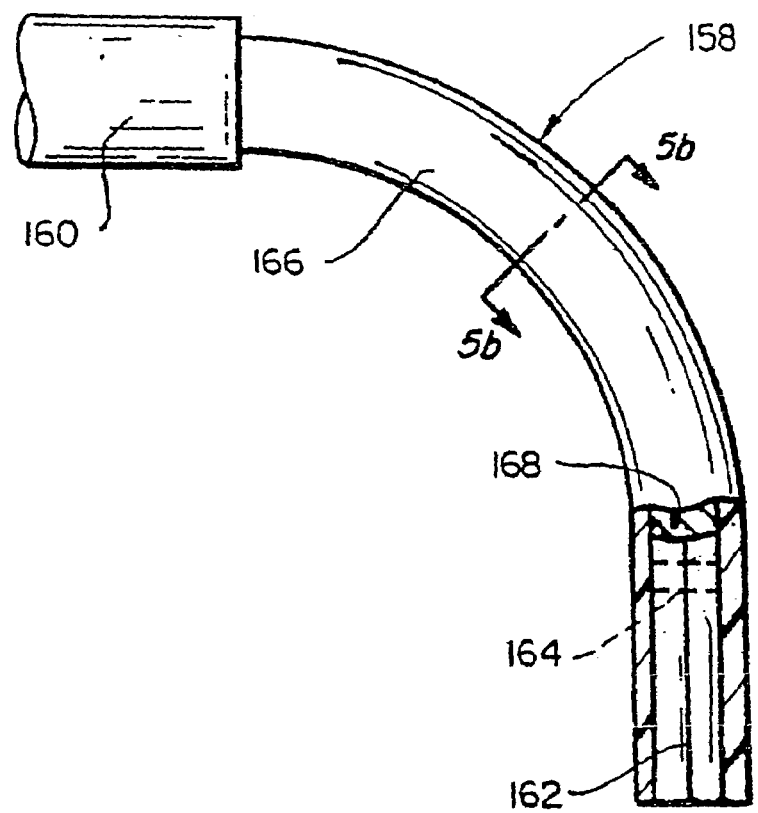
Figures 5B, 7:
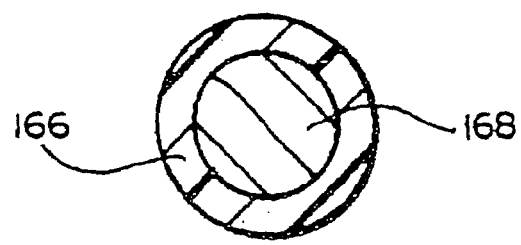
Figures 6A, 7:
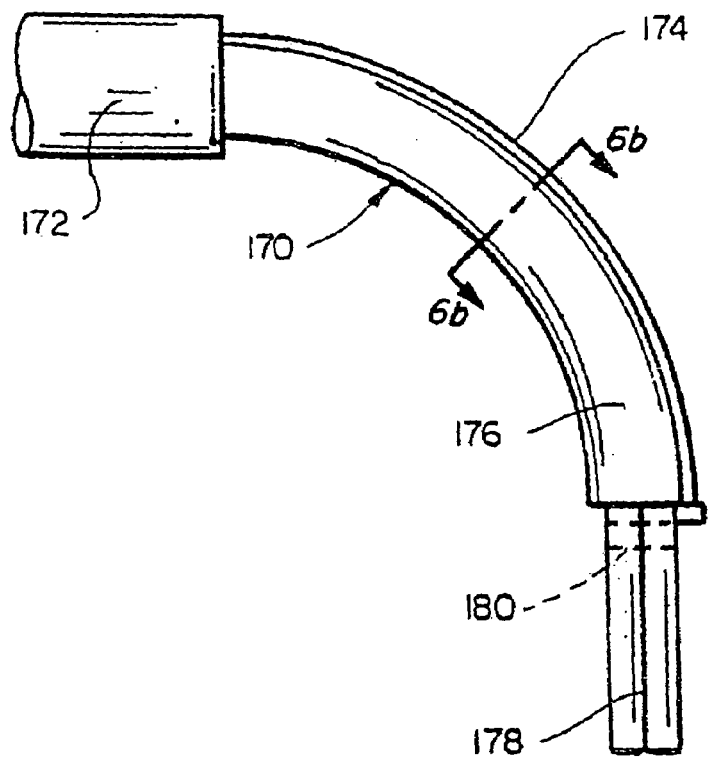
Figures 6B, 7:
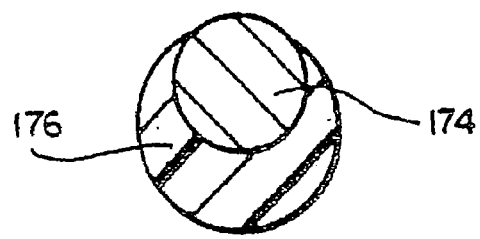
Figures 7, 7A:
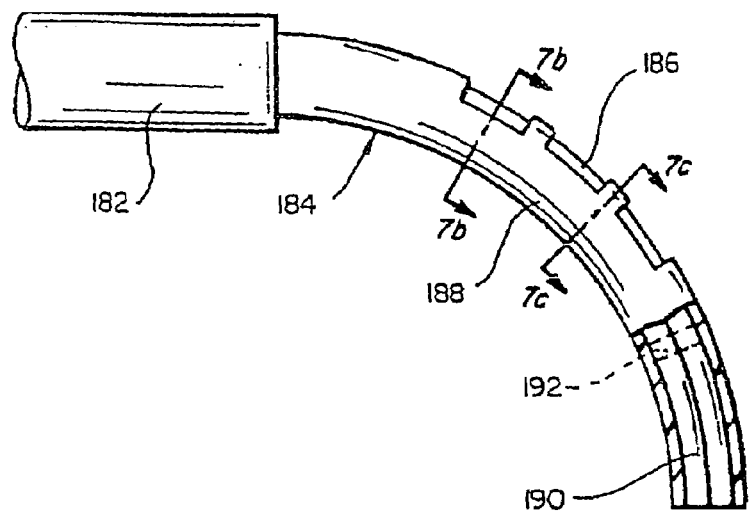
Figures 7, 7B:
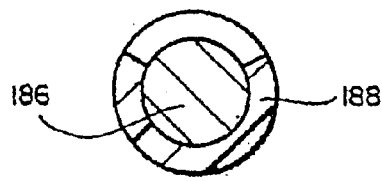
Figures 7, 7C:
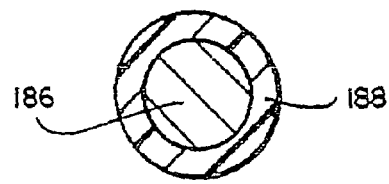
Figures 7, 8, 8A:
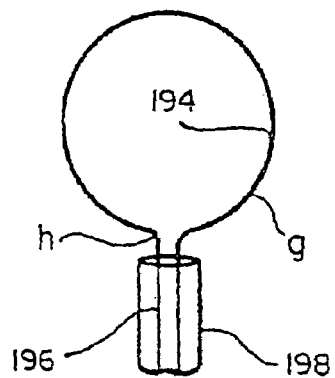
Figures 7, 8, 8B:
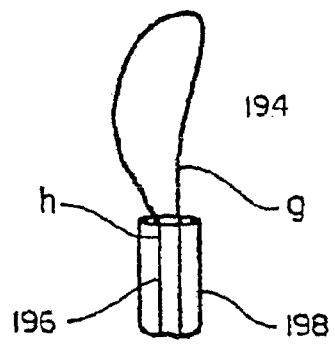
Figures 7, 8, 8C:
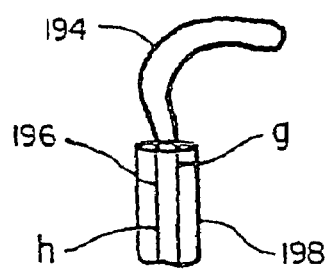
Figures 7, 8, 8D:
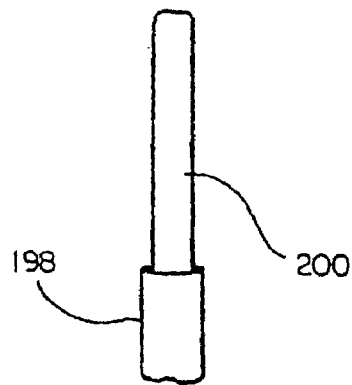
Figures 7, 8, 8E:
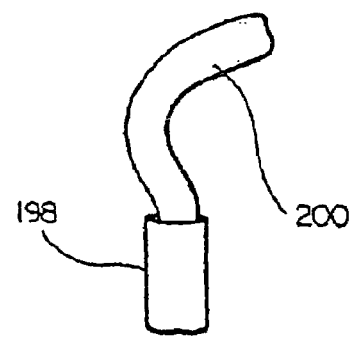
Figures 7, 8, 8F:
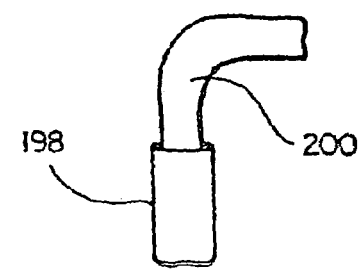
Figures 7, 8, 9, 9A:
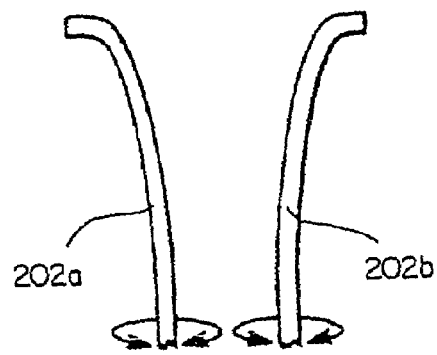
Figures 7, 8, 9, 9D:
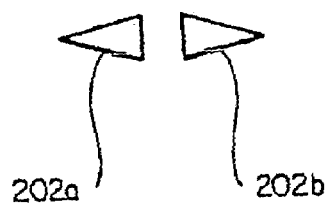
Figures 7, 8, 9, 9G:
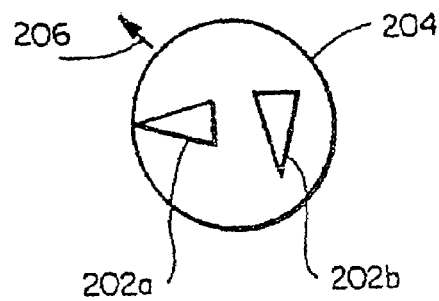
Figures 7, 8, 9, 9B:
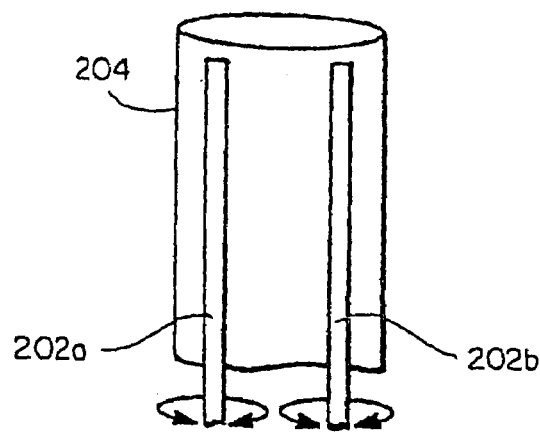
Figures 7, 8, 9, 9E:
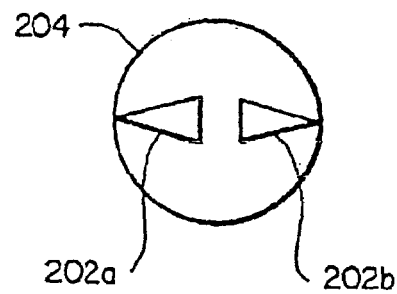
Figures 7, 8, 9, 9H:
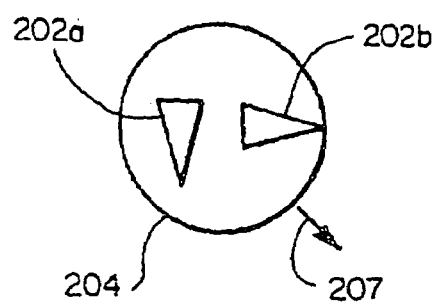
Figures 7, 8, 9, 9C:
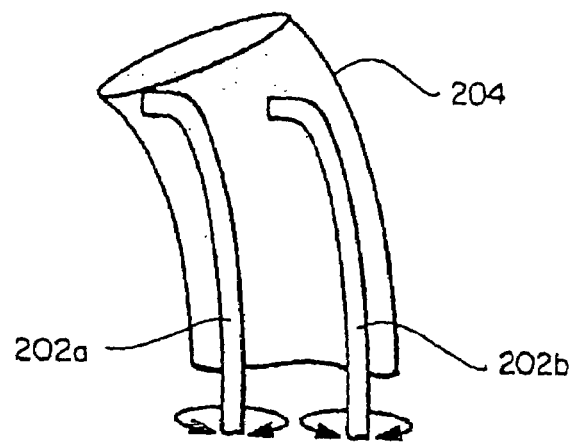
Figures 7, 8, 9, 9F:
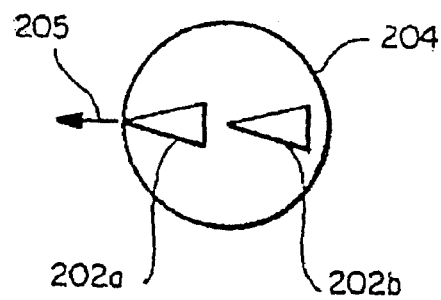
Figures 7, 8, 9, 9I:
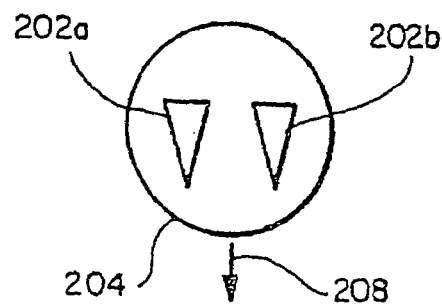
Figures 7, 8, 9, 10, 10A:
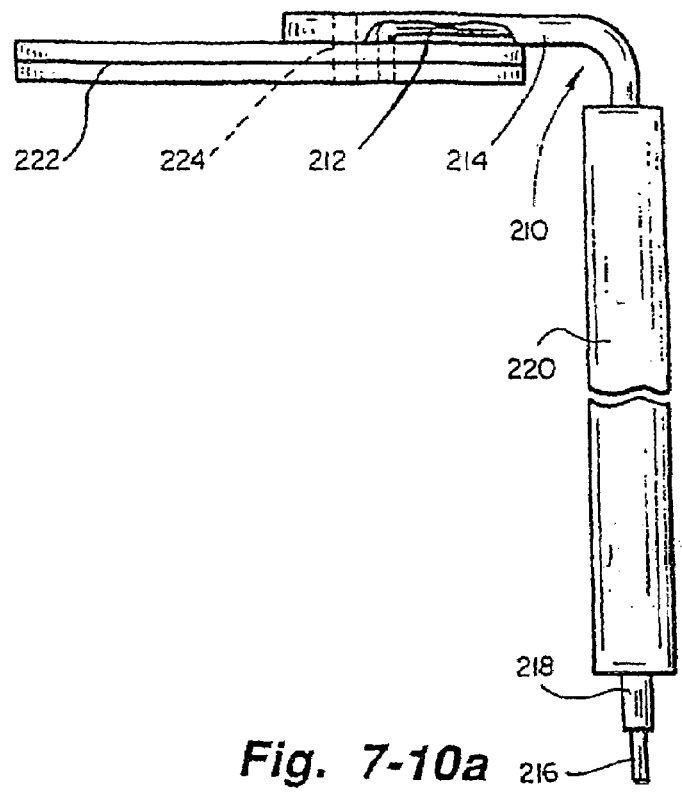
Figures 7, 8, 9, 10, 10B:
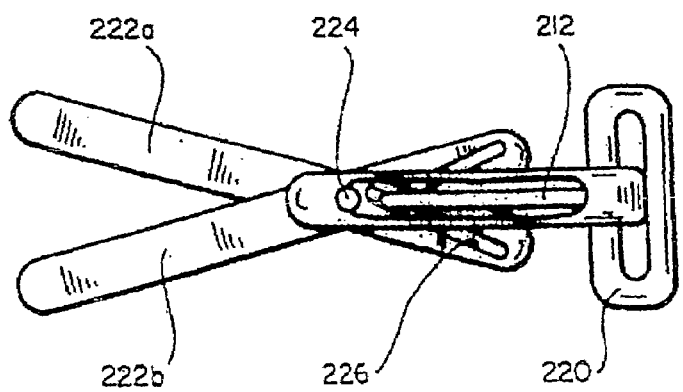
Figures 7, 8, 9, 10, 11, 11A:
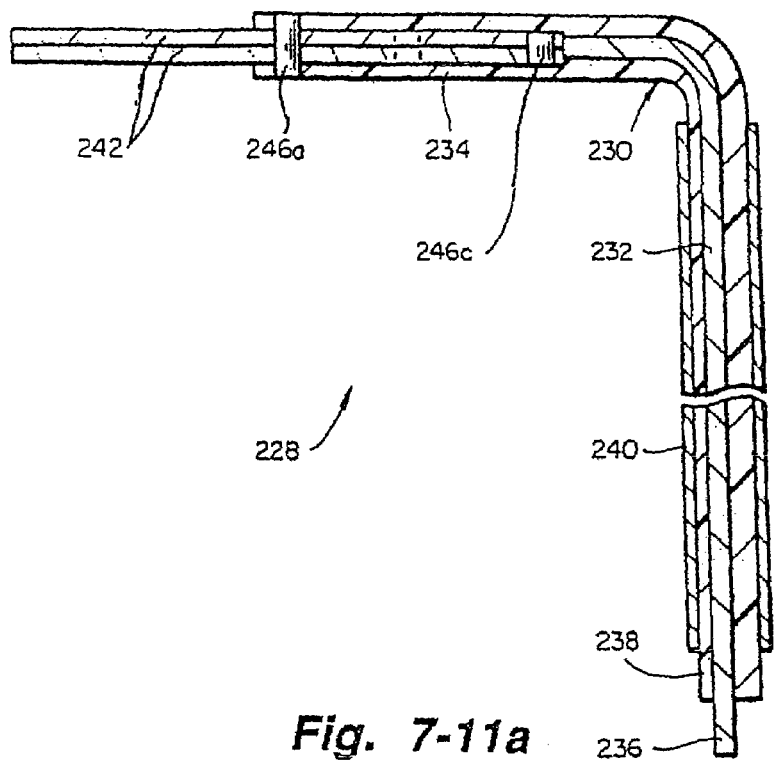
Figures 7, 8, 9, 10, 11, 11B:
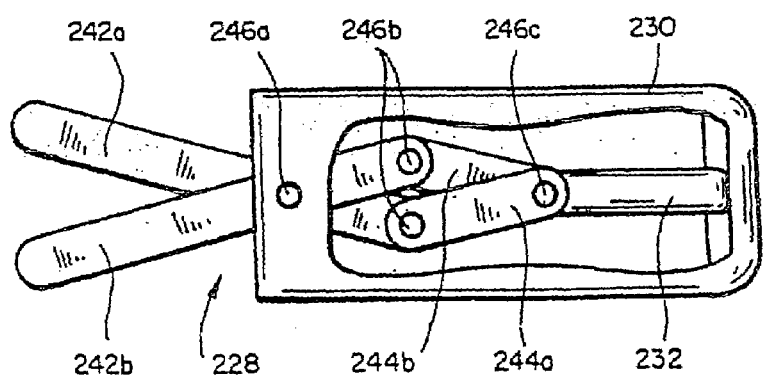
Figures 7, 8, 9, 10, 11, 11C:
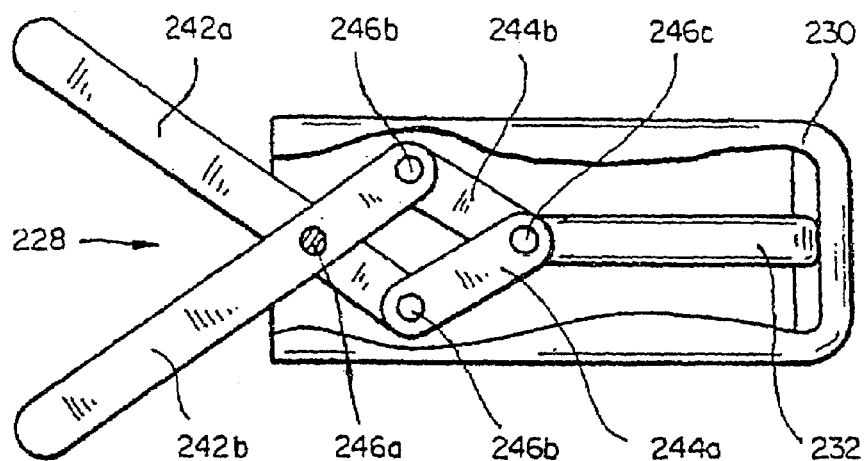
Figures 7, 8, 9, 10, 11, 12, 12A:
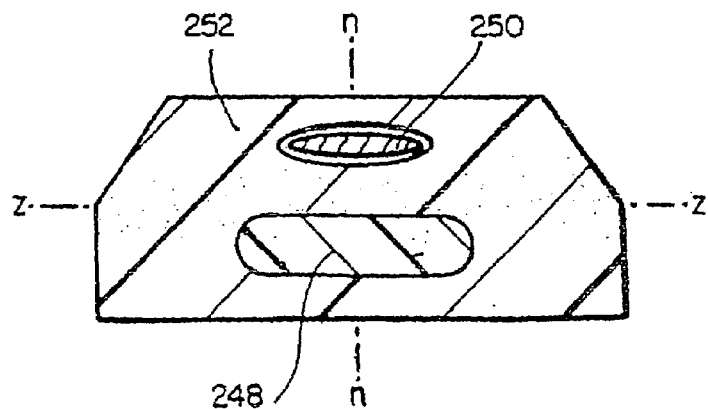
Figures 7, 8, 9, 10, 11, 12, 12B:
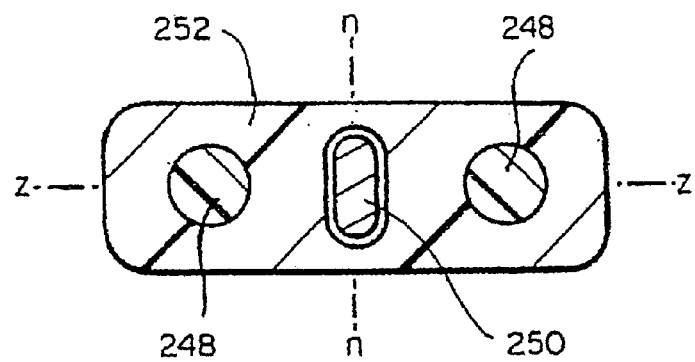
Figures 7, 8, 9, 10, 11, 12, 12C:
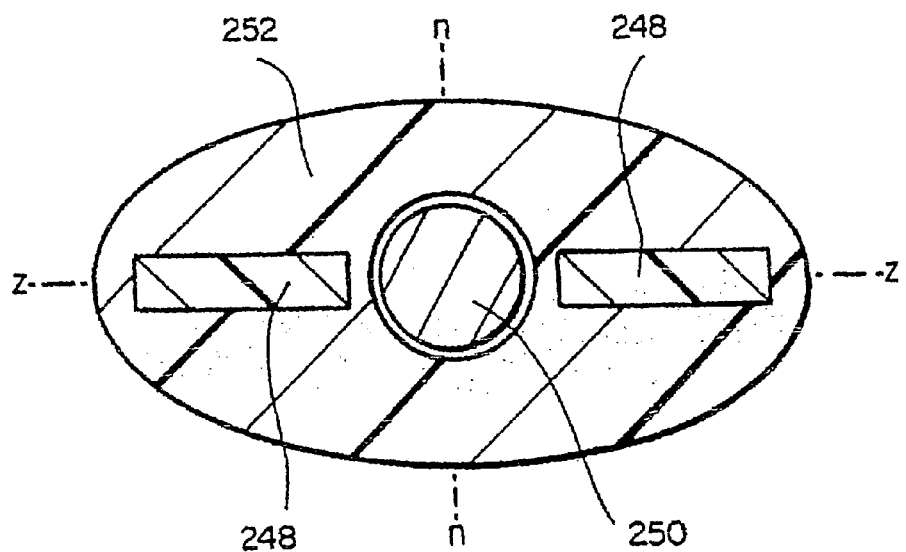
Figures 7, 8, 9, 10, 11, 12, 12D:
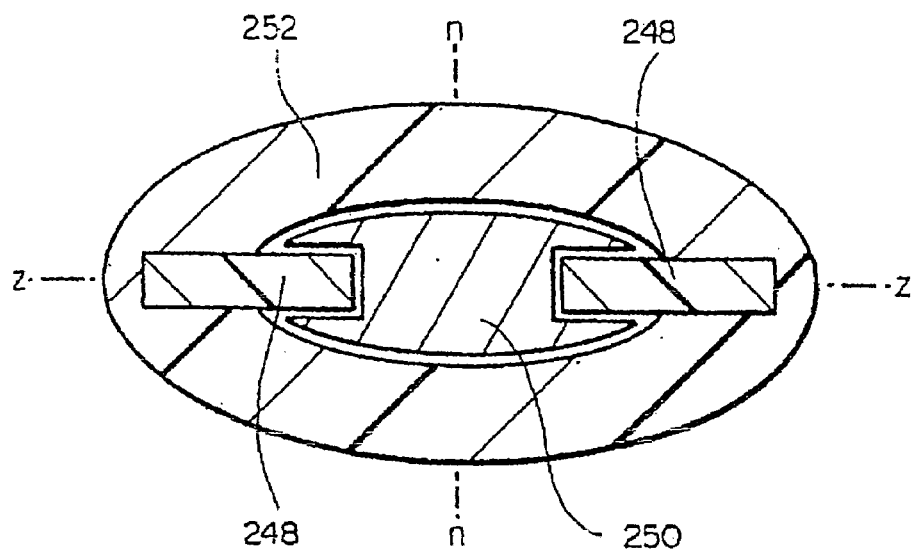
Figures 7, 8, 9, 10, 11, 12, 12E:
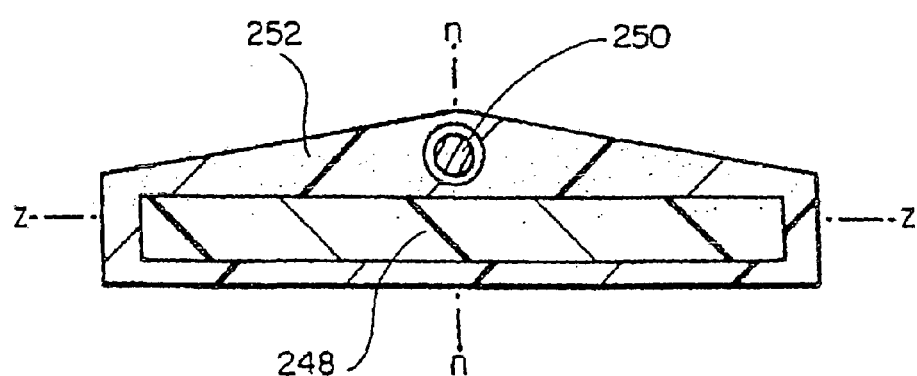
Figures 7, 8, 9, 10, 11, 12, 12F:
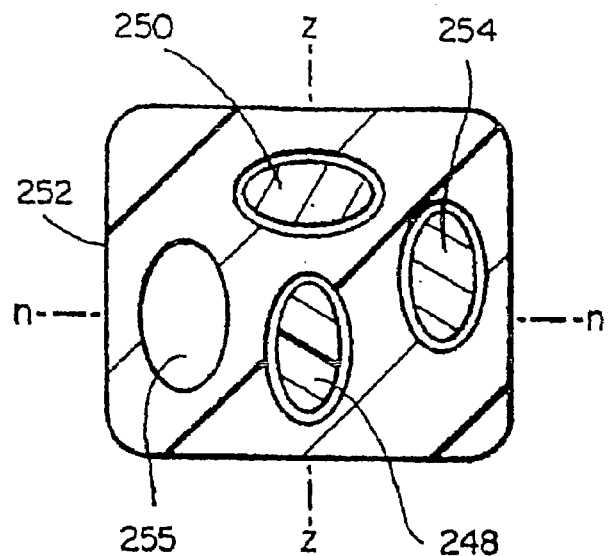
Figures 7, 8, 9, 10, 11, 12, 13, 13A:
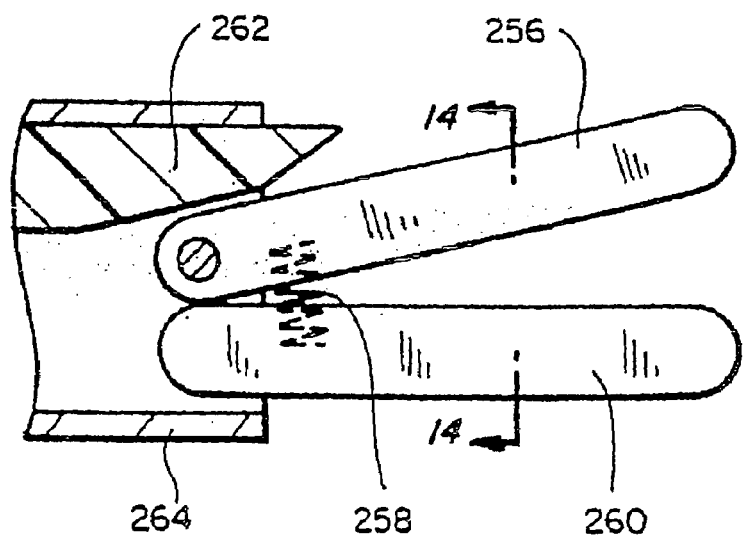
Figures 7, 8, 9, 10, 11, 12, 13, 13B:
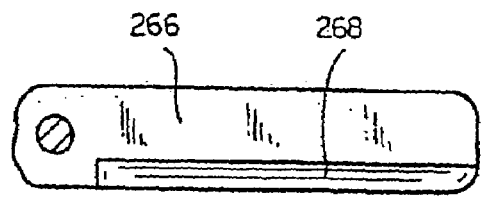
Figures 7, 8, 9, 10, 11, 12, 13, 13C:
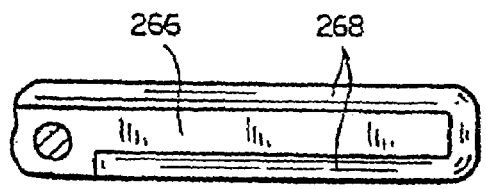
Figures 7, 8, 9, 10, 11, 12, 13, 13D:
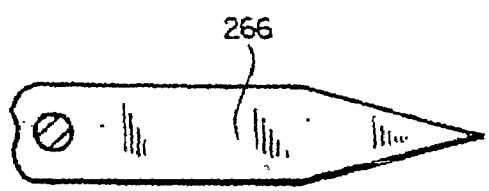
Figures 7, 8, 9, 10, 11, 12, 13, 13E:
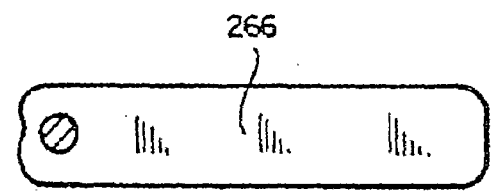
Figures 7, 8, 9, 10, 11, 12, 13, 14, 14A:
Figures 7, 8, 9, 10, 11, 12, 13, 14, 14B:
Figures 7, 8, 9, 10, 11, 12, 13, 14, 14C:
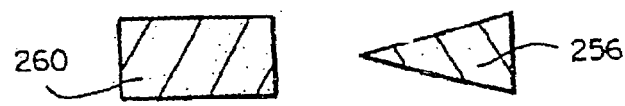
Figures 7, 8, 9, 10, 11, 12, 13, 14, 14D:
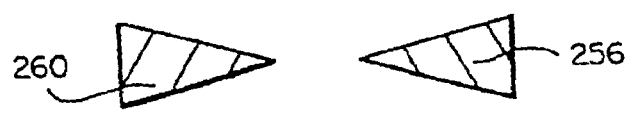
Figures 7, 8, 9, 10, 11, 12, 13, 14, 14E:
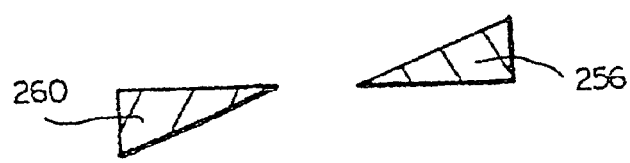

FIG. 7-4c shows the section of elastically deformable stem 150 in a fully deployed configuration. The elastically deformable stem 150 is unconstrained, and shows the maximum deformation available from the specific elastic member 154.

Reconstraining the elastically deformable stem 150 as shown in FIG. 7-4c is accomplished by reversing the process, i.e., by moving the elements to the configuration shown in FIGS. 7-4b and 7-4a, sequentially.

In one embodiment (not shown) the elastically deformable stem and the rigid constraining rod are present only at the distal (introduced) end of the instrument, near the bladed element. The major portion of the introduced body of the instrument is relatively flexible. Such an embodiment finds particular use as an endoscopic device, i.e., a device which can be introduced through naturally occurring openings. In the human body, endoscopic devices are appropriate for use in the respiratory tract (introduced through the mouth or nose), gastrointestinal tract (introduced through the mouth, nose, or rectum), or in the urogenital tract (introduced through the ureter or, in women, the vagina).

The material of the flexible housing of the endoscopic instrument may be polymeric. If made of a flexible polymeric material, the material may be reinforced, for example, with fibers. A suitable polymeric material for the component is, for example, polytetrafluorethylene, reinforced with braided fibers.

The elongate housing in an endoscopic device will have a diameter of from less than about 0.7 mm to about 4.5 cm or greater; the length of endoscopic devices will be from less than about 10cm to about 3 meters or greater.

FIGS. 7-5 through 7-7 each show a different embodiment of the elastically deformable stem of this invention.

FIG. 7-5a shows a portion of an elastically deformable stem 158 and of an elongate housing 160. Shown in cutaway view are the blades 162 and the pivot 164, sheathed within the elastically deformable stem 158. In the shown embodiment, the blades 162 must be deployed from the elastic member 166 prior to pivotal blade movement, controlled by the blade actuator rod 168. The plane through which the blades 162 open can be in any orientation desired relative to the elastically deformable stem 158 or to the elongate housing 160.

FIG. 7-5b shows a cross-sectional view of the elastically deformable stem 158, taken through line 5b-5b of FIG. 7-5a. The blade actuator rod 168 is fully enclosed by the elastic member 166.

Figures 1, 3:
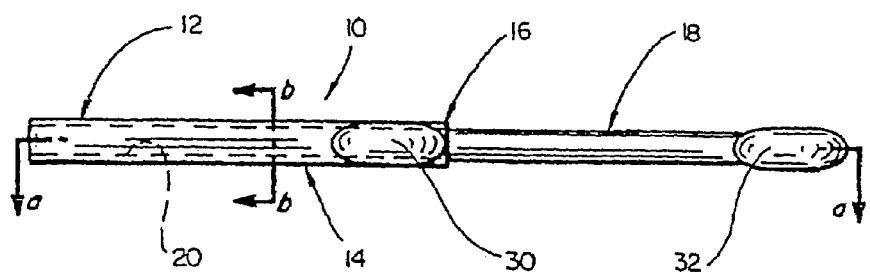
Figures 2, 3:
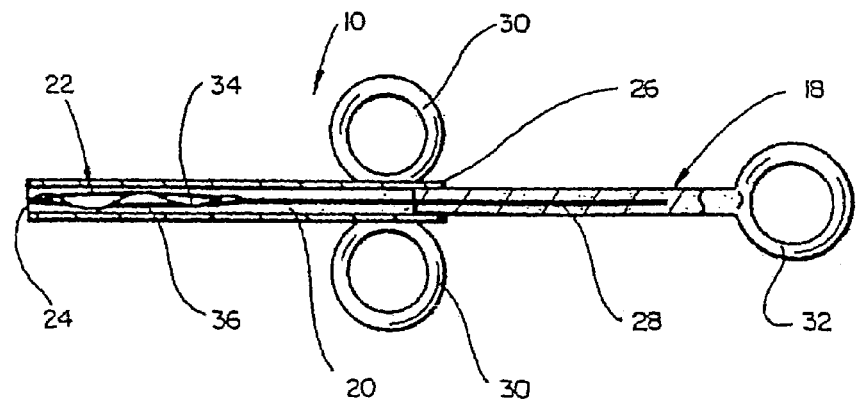
Figure 3:
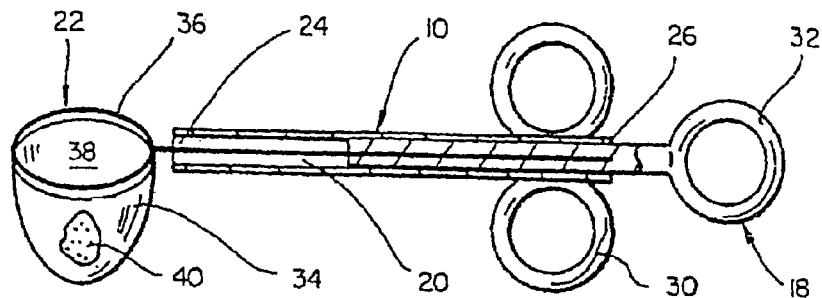
Figures 3, 4:
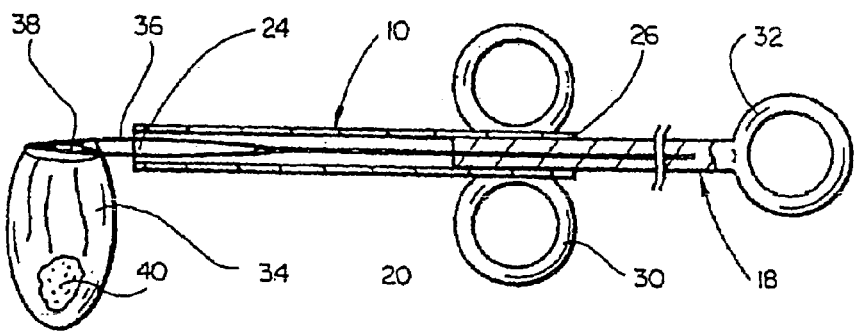
Figures 3, 4, 5:
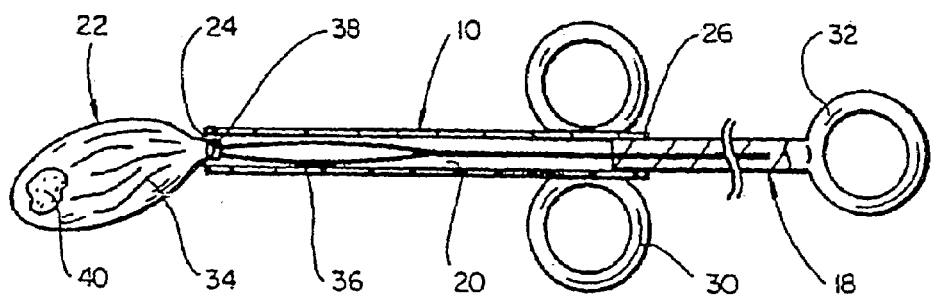
Figures 3, 4, 5, 6, 6A:
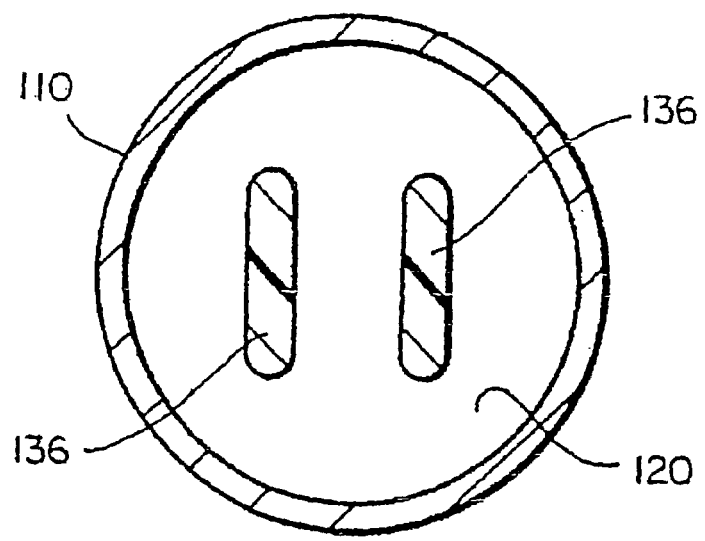

FIG. 7-6a shows a portion of an elastically deformable stem 170 having a rod-and-groove configuration, and of an elongate housing 172. The blade actuator rod 174 is partially enclosed by the elastic member 176, and is partially exposed.

FIG. 7-6a shows an embodiment wherein the blades 178 and the pivot 180 are not substantially sheathed within the elastically deformable stem 170 when the elastically deformable stem 170 is fully withdrawn into the housing 172. The blades 178 do not need to be deployed from the elastic member prior to pivotal blade movement, controlled by the blade actuator rod 174. The plane through which the blades 178 open can be in any orientation desired relative to the elastically deformable stem 170 or to the elongate housing 172.

Figures 3, 4, 5, 6, 6B:
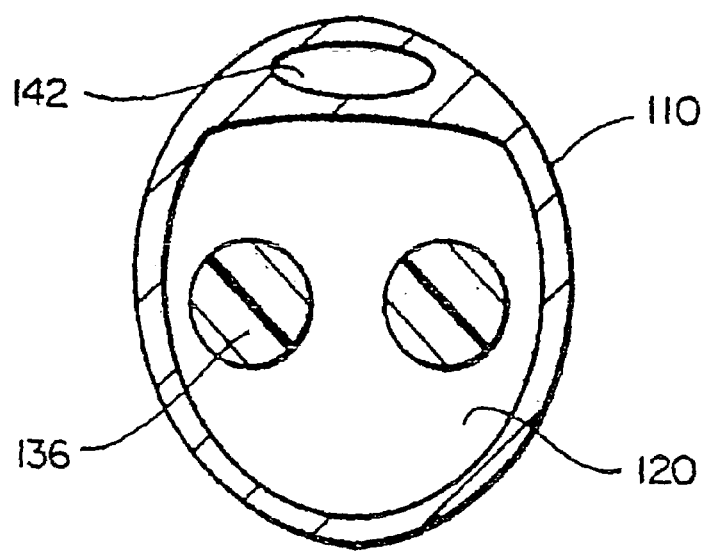

FIG. 7-6b shows a cross-sectional view of the elastically deformable stem 170, taken through line 6b-6b of FIG. 7-6a. The blade actuator rod 174 is partially enclosed in a groove in the elastic member 176.

FIG. 7-7a shows a portion of a housing 182, and an elastically deformable stem 184 with a windowed configuration. The windows are shown on the convex surface of the elastically deformable stem 184. Such windows can be present on any of the concave or lateral surfaces of the elastically deformable stem 184, as desired. Any number of windows can be used, including one, two, or a multiplicity.

Shown in cutaway view are curved blades 190 and the pivot 192, which are substantially sheathed within the elastically deformable stem 184. As shown, the blades 190 must be deployed prior to pivotal blade movement. When the blades 190 are curved, it is generally preferable that the curve of the blades 190 continue the curve of the elastically deformable stem 184, but that is not necessary.

The plane through which the blades 190 open can be in any orientation desired to the elastically deformable stem 184, or to the elongate housing 182. In a currently preferred embodiment, the blades 190 are not retracted into the elongate housing 182 or into the elastically deformable stem 184 even when the blades are fully retracted, a configuration which is shown in FIG. 7-2b.

FIG. 7-7b shows a cross-sectional view of the elastically deformable stem 184, taken through line 7b-7b of FIG. 7-7a. The blade actuator rod 186 is partially enclosed in a groove in the elastic member 188.

FIG. 7-7c shows -a cross-sectional view of the elastically deformable stem 184, taken through line 7c-7c of FIG. 7-7a. The blade actuator rod 186 is fully enclosed by the elastic member 188.

FIG. 7-8 demonstrates the use of an alternate elastic member 194. As shown in FIG. 7-8a, the elastic member 194 is an element such as a wire which describes a closed shape in its unconstrained shape. The elastic member 194 has a stem 196, which can be a continuation of the elastic member 194, as shown, or can be a handle means connected to the elastic member 194. Point g and point h are labeled to show the progression of the loop as it is withdrawn into the constraining housing 198. FIG. 7-8b demonstrates that when the stem 196 and the elastic member 194 are retracted into a constraining housing 198, the circle deforms into a cupped configuration. As shown in FIG. 7-8c, further retraction of the stem 196 and the elastic member 194 into the constraining housing 198 causes further deformation. The closed shape becomes narrowed and sharply angled. This occurs because as the sides of the closed shape take less stress to rotate out of the plane of the undeformed shape than to straighten within the plane of the undeformed shape. The figure thus deforms by bending at the apex, with the sides rotating out of the plane of the undeformed shape.

FIGS. 7-8d, 7-8e and 7-8f show the incorporation of the closed shape of FIGS. 7-8a, 7-8b and 7-8c, respectively, into an enclosing flexible sheath 200. FIGS. 7-8d, 7-8e and 7-8f are side views of the flexible sheath 200 and constraining housing 198 which show the bending which takes place as the stem (not shown) and the circular elastic member (not shown) are drawn into the constraining housing 198.

FIG. 7-9 demonstrates another method of constraining an elastic member. FIG. 7-9a shows two unconstrained elastic members 202a and 202b. Each is curved when it is not constrained. Each is capable of independent rotation. As shown in FIG. 7-9a, the elastic members 202a and 202b are angled away from each other.

FIG. 7-9b shows the elastic members 202a and 202b held within a flexible sheath 204. The sheath causes each elastic member to act as a constraint for the elastic member having an opposite bend. As a result the flexible sheath 204 is straight.

FIG. 7-9c shows the elastic members 202a and 202b held within a flexible sheath 204. Elastic member 202b has been rotated to align its curve to the curve of elastic member 202a. The sheath bends to conform to the bend of the two elastic members 202a and 202b.

Figures 3, 4, 5, 6, 6C:
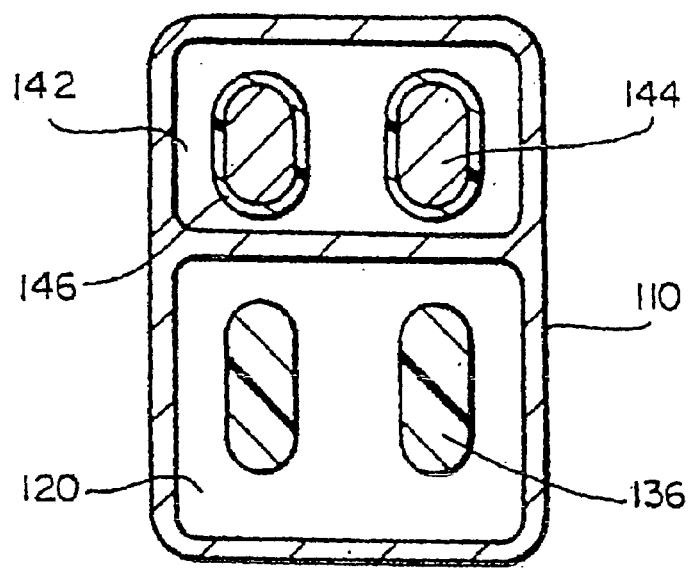
Figures 3, 4, 5, 6, 6D:
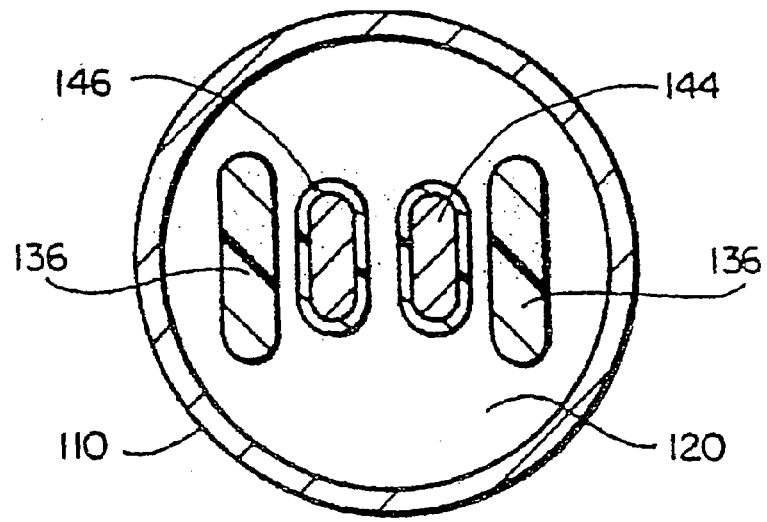
Figures 3, 4, 5, 6, 7:
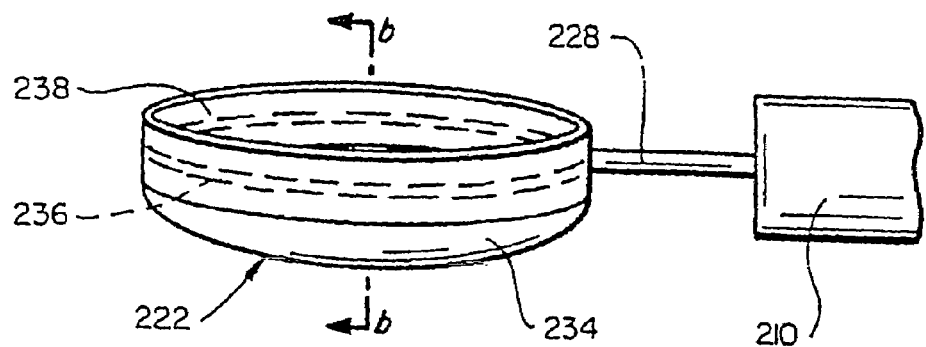
Figures 3, 4, 5, 6, 7, 8:
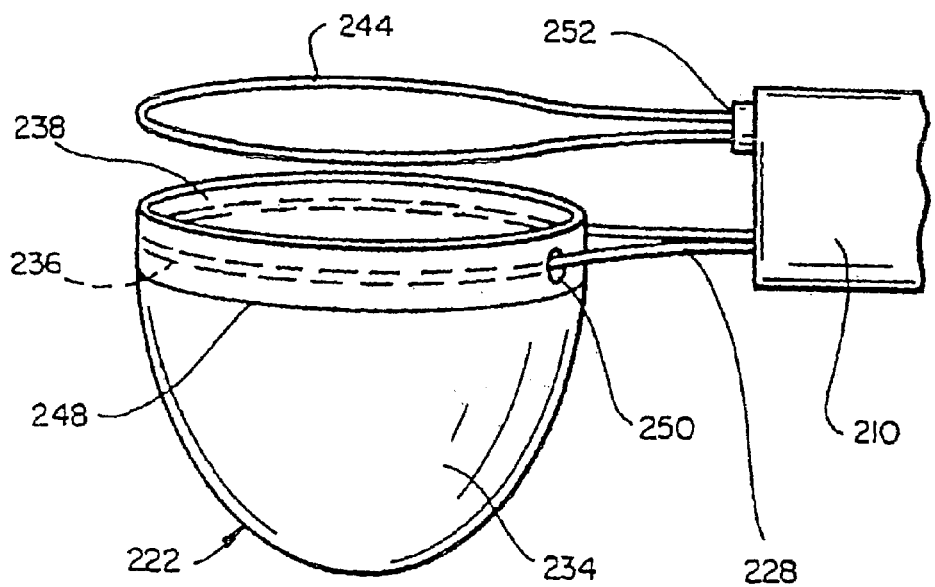
Figures 3, 4, 5, 6, 7, 8, 9, 9A:
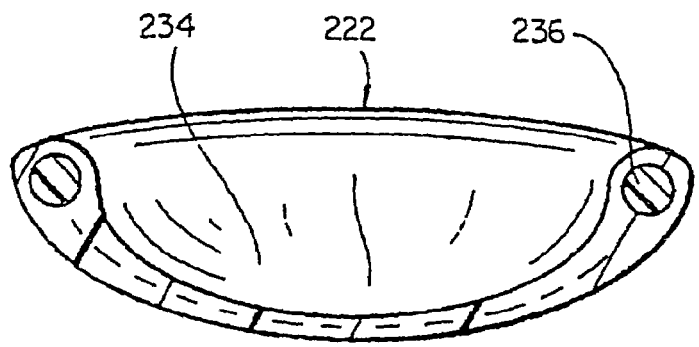
Figures 3, 4, 5, 6, 7, 8, 9, 9B:
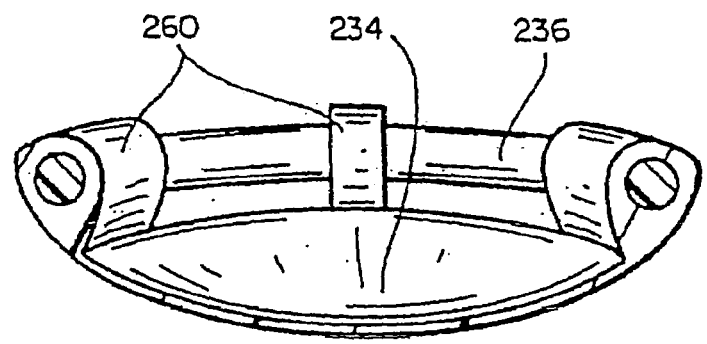
Figures 3, 4, 5, 6, 7, 8, 9, 9C:
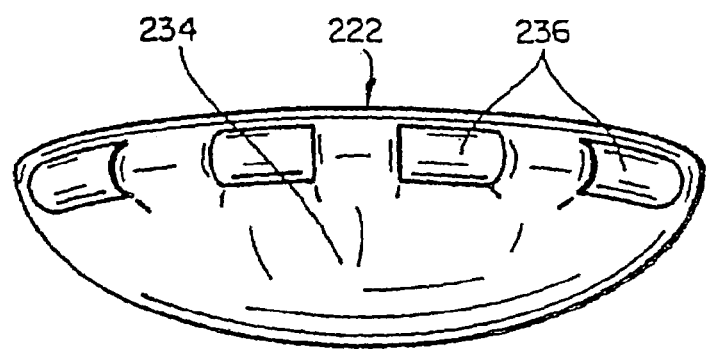
Figures 3, 4, 5, 6, 7, 8, 9, 10, 10A:
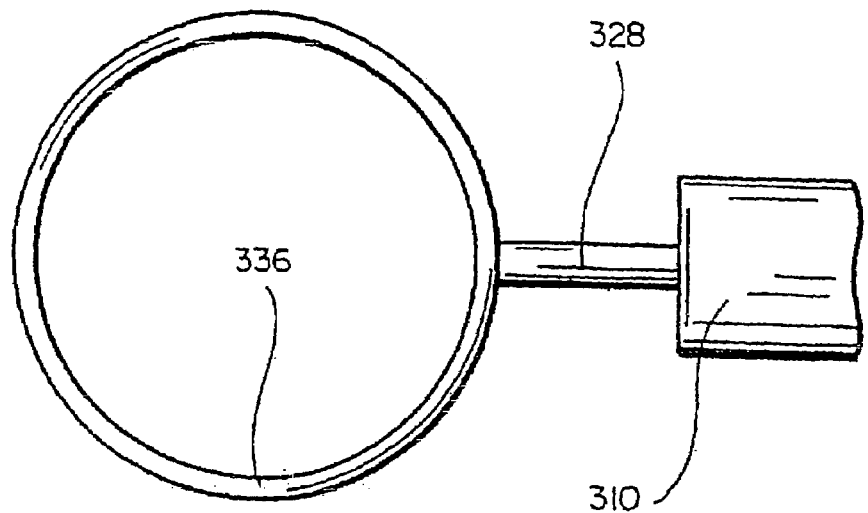
Figures 3, 4, 5, 6, 7, 8, 9, 10, 10B:
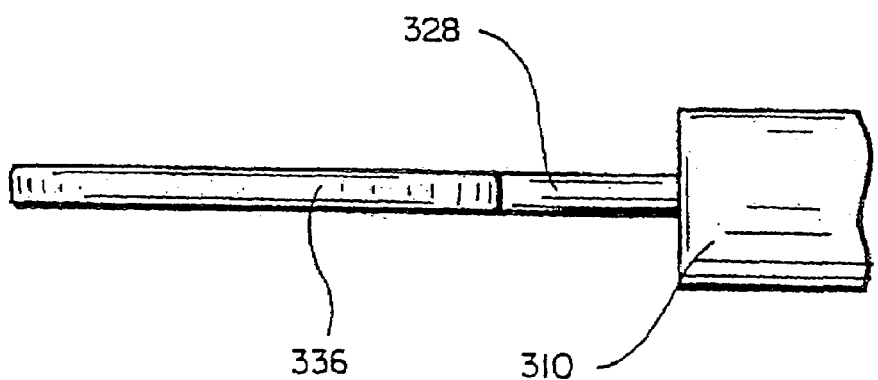
Figures 3, 4, 5, 6, 7, 8, 9, 10, 11, 11A:
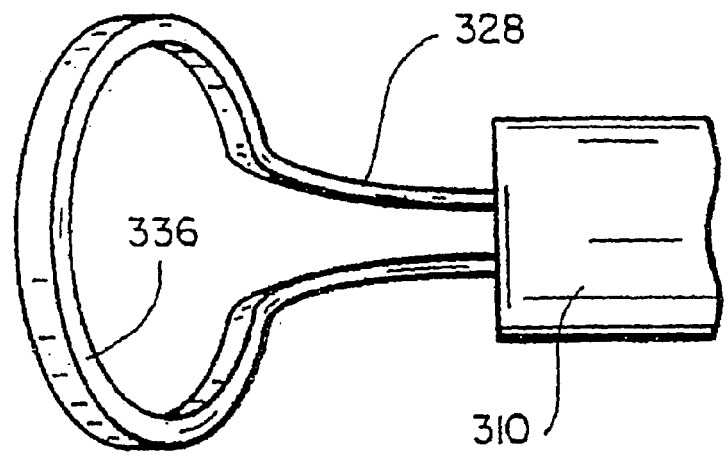
Figures 3, 4, 5, 6, 7, 8, 9, 10, 11, 11B:
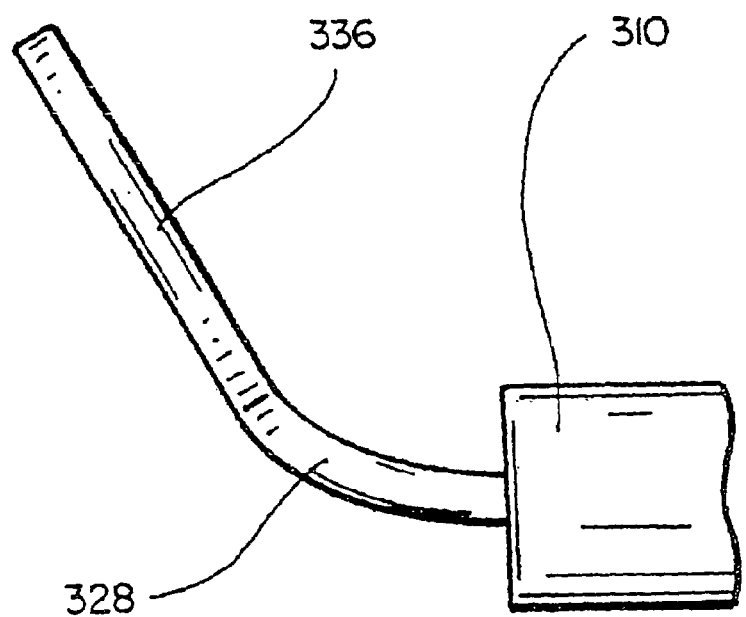
Figures 3, 4, 5, 6, 7, 8, 9, 10, 11, 12, 12A:
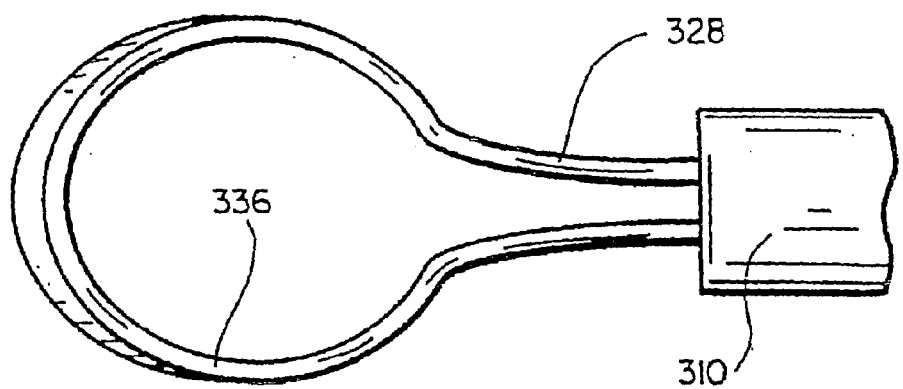
Figures 3, 4, 5, 6, 7, 8, 9, 10, 11, 12, 12B:
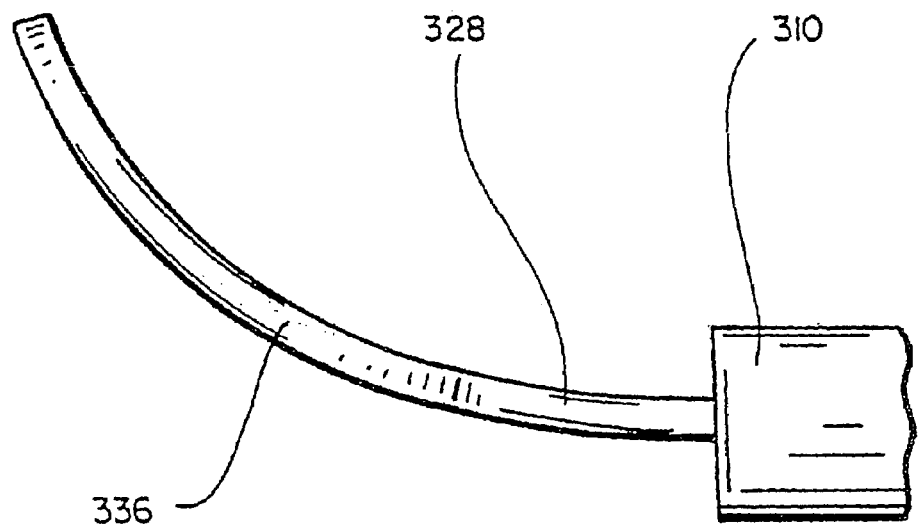
Figures 3, 4, 5, 6, 7, 8, 9, 10, 11, 12, 13:
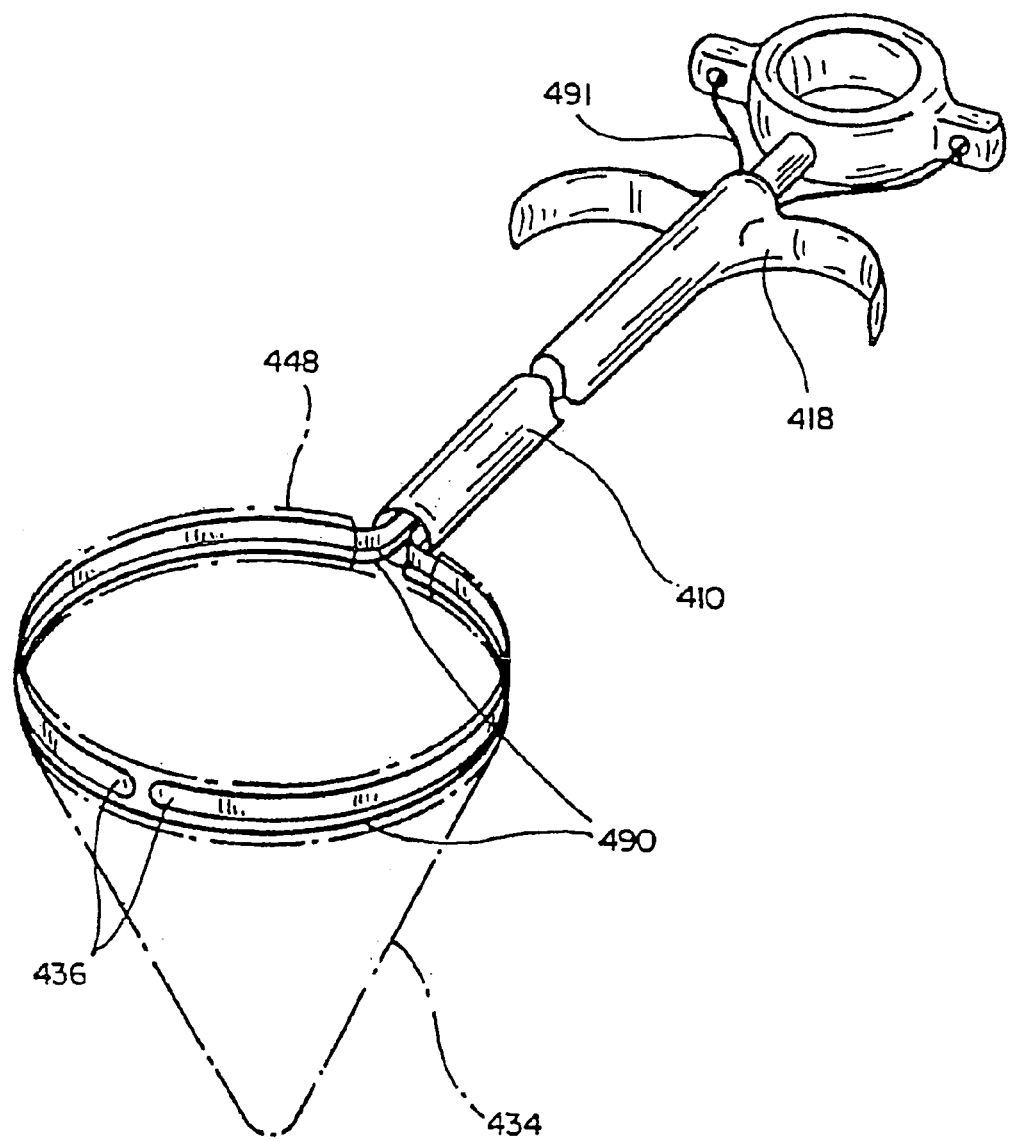
Figures 3, 4, 5, 6, 7, 8, 9, 10, 11, 12, 13, 14:
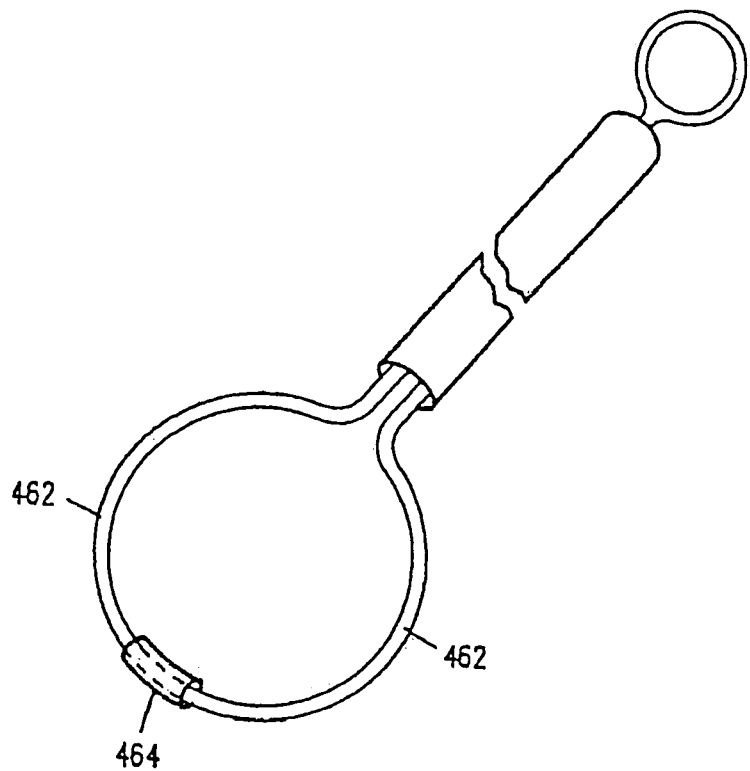
Figures 3, 4, 5, 6, 7, 8, 9, 10, 11, 12, 13, 14, 15:
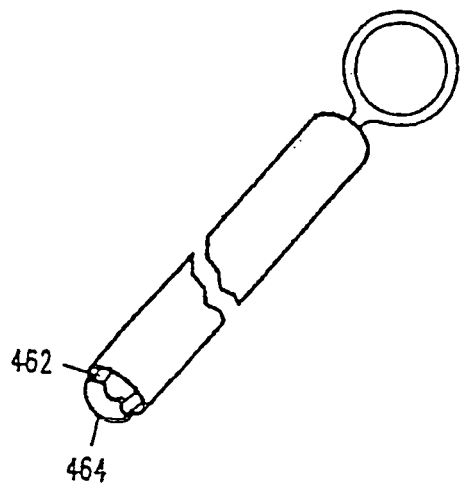
Figures 3, 4, 5, 6, 7, 8, 9, 10, 11, 12, 13, 14, 15, 16:
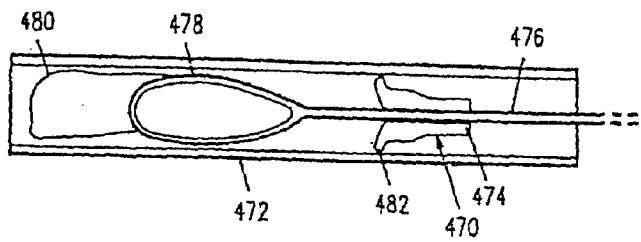
Figures 3, 4, 5, 6, 7, 8, 9, 10, 11, 12, 13, 14, 15, 16, 17:
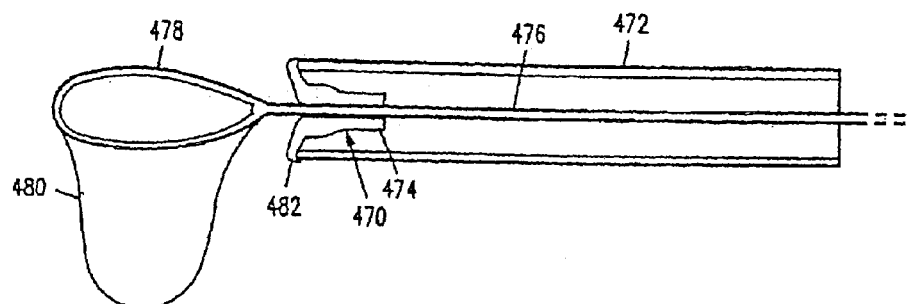
Figures 3, 4, 5, 6, 7, 8, 9, 10, 11, 12, 13, 14, 15, 16, 17, 18:
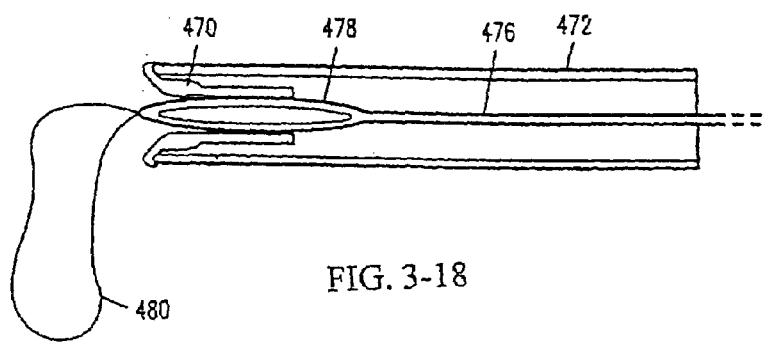
Figures 3, 4, 5, 6, 7, 8, 9, 10, 11, 12, 13, 14, 15, 16, 17, 18, 19:
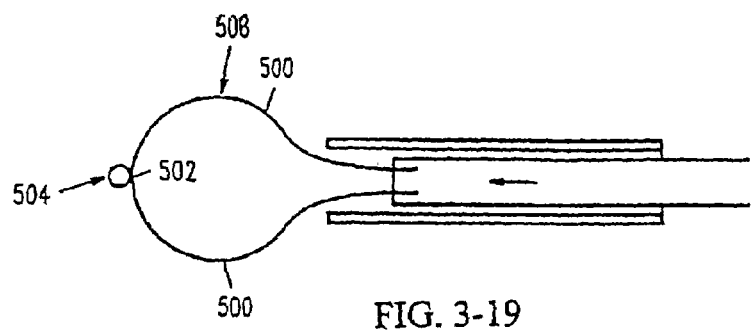
Figures 3, 4, 5, 6, 7, 8, 9, 10, 11, 12, 13, 14, 15, 16, 17, 18, 19, 20:
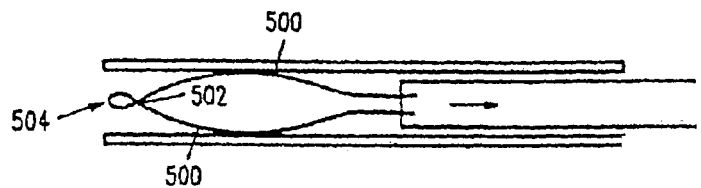
Figures 3, 4, 5, 6, 7, 8, 9, 10, 11, 12, 13, 14, 15, 16, 17, 18, 19, 20, 21:
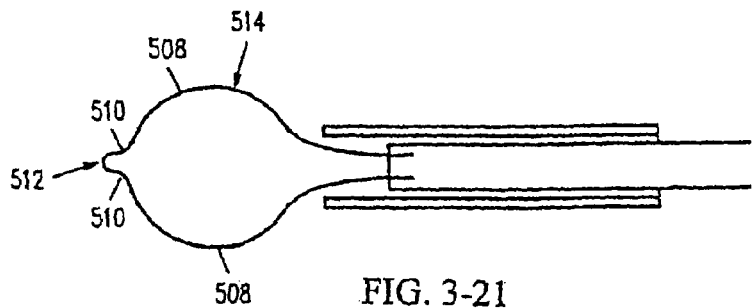
Figures 3, 4, 5, 6, 7, 8, 9, 10, 11, 12, 13, 14, 15, 16, 17, 18, 19, 20, 21, 22:
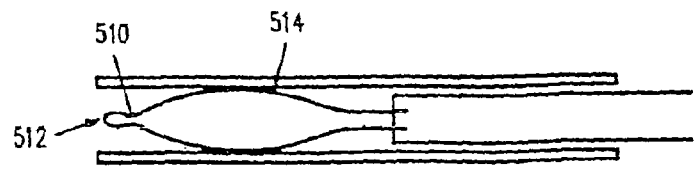

FIGS. 7-9d through 7-9f graphically represent the forces involved in FIGS. 9a through 9c, respectively, as represented in top view.

FIG. 7-9d depicts vectors for the elastic members 202a and 202b, as shown in FIG. 7-9a. Elastic member 202a is shown as a vector arrow pointing to the left; elastic member 202b is shown as a vector arrow pointing to the right.

FIG. 7-9e depicts vectors for the elastic members 202a and 202b as shown in FIG. 7-9b. The flexible sheath 204 is shown. The flexible sheath 204 does not curve, as the forces exerted by the elastic member 202a are cancelled out by the forces exerted by elastic member 202b.

FIG. 7-9f depicts vectors for the elastic members 202a and 202b, as shown in FIG. 7-9c. The flexible sheath 204 is shown. The flexible sheath 204 curves to the left represented by the resultant arrow 205. The vector forces exerted by the elastic member 202a are reinforced by the vector forces exerted by elastic member 202b.

FIG. 7-9g depicts alternate vectors for elastic members 202a and 202b. The flexible sheath 204 is shown. Elastic member 202a is represented by a vector leftward, while elastic member 202b is represented by a vector which is at a 90° angle from that of elastic member 202a. The forces exerted by the elastic member 202a are only partially reinforced by the forces exerted by elastic member 202b. The flexible sheath 204 curves to the upper left, represented by the resultant arrow 206.

FIG. 7-9h depicts another vector set for elastic members 202a and 202b. The flexible sheath 204 is shown. Elastic member 202a is represented by a vector downward, while elastic member 202b is represented by a vector to the right. The forces exerted by the elastic member 202a are only partially reinforced by the forces exerted by elastic member 202b. The flexible sheath 204 curves to the lower right, represented by the resultant arrow 207.

FIG. 7-9i depicts yet another vector set for elastic members 202a and 202b. The flexible sheath 204 is shown. Elastic member 202a is represented by a vector downward, as is elastic member 202b. The forces exerted by the elastic member 202a are reinforced by the forces exerted by elastic member 202b. The flexible sheath 204 curves to the bottom, represented by the resultant arrow 208. By rotation of one or more of the elastic members 202a and 202b, the flexible sheath 204 can be curved through a 360° circle.

FIG. 7-10 shows a device of this invention having two pivoted blades, each blade having a longitudinal slot next to the pivot.

FIG. 7-10a is a side view of an instrument in the unconstrained configuration with a partial cutaway near the bladed element. A bend of approximately 90° is present in the elastically deformable stem 210. The actuating rod 212 is enclosed within the elastic member 214. The movement of the actuating rod 212 and of the elastically deformable stem 210 are preferably independent, and each is controlled by longitudinal motion of the proximal ends. Opening and closing of the blades is caused by reciprocal motion of the proximal portion of the actuating rod 216. Deflection of the elastically deformable stem 210 is caused by reciprocal motion relative to the elongate housing 220 of the proximal portion of the elastically deformable stem 218.

FIG. 7-10b shows a cut-away top view of the instrument of FIG. 7-10a. Two blades 222a and 222b are present. As shown, each blade is V-shaped. In a preferred embodiment, not shown, each blade is substantially straight. A pivot 224 is present intermediate to the ends of the blade. The pivot allows pivotal motion of the two blades, and holds the blades in position on the elastically deformable stem. A longitudinal slot 226 is present in each blade proximal to the pivot. The two blades 222a and 222b are moveable between a closed position, wherein the axes of the distal portions of the blades are substantially parallel, and an open position, wherein the axes of the distal portions of the blades are deflected from the parallel. Pivotal movement of the blades 222 is caused by a sliding pin (not shown) which is part of the actuator rod 212, and which integrates with the longitudinal slot 226 present in each of the blades. In alternate embodiments, the blades can be located partially within the elastically deformable stem; the blades can be fixed to opposite sides of the elastically deformable stem; or the blades can be fixed to a concave, convex, or lateral edge of the elastically deformable stem. The pivotal connection shown is for demonstration purposes only, and any appropriate toggle, gear, or pivotal connection can be used.

FIG. 7-11a shows a longitudinal cross-sectional view of an instrument in the unconstrained configuration. The bladed element 228 includes two blades, two bars, and four pivots. A bend of approximately 90° is present in the elastically deformable stem 230. The actuating rod 232 is enclosed within the elastic member 234. The movement of the actuating rod 232 and of the elastically deformable stem 230 are each controlled by longitudinal motion of the proximal ends. Opening and closing of the blades is caused by reciprocal notion of the proximal portion of the actuating rod 236. Deflection of the elastically deformable stem 230 is caused by reciprocal motion of the proximal portion of the elastically deformable stem 238 relative to the elongate housing 240.

FIGS. 7-11b and 7-11c show cut-away-top views of the instrument of FIG. 7-11a. Two blades 242a and 242b are present. Two bars 244a and 244b are present. A pivot 246a is present intermediate to the ends of the blades 242a and 242b, joining the blades and attaching the blades to the elastically deformable stem 230. Two pivots 246b are present at the proximal ends of the blades 242a and 242b, where they join the distal ends of bars 244a and 244b. A pivot 246c is present at the proximal end of the bars 244a and 244b, joining the bars. Pivotal movement of the blades 242a and 242b is caused by a sliding motion of the blade actuating rod 232. FIG. 7-11b shows the blades in a relatively closed configuration. FIG. 7-11c shows the blades in a relatively open configuration.

FIGS. 7-12a through 7-12f show alternate cross-sections of an elastically deformable stem of the instrument of FIG. 7-1, taken through line 12-12.

FIG. 7-12a shows an elastic member 248 and a blade actuator rod 250 within a flexible material 252. The flexible material 252 describes a squared pyramid shape in cross-section. The elastic member 248 and the blade actuator rod 250 each comprise a strip of material which is roughly oval in cross-section.

The use of a flexible material 252 which encloses an elastic member 248 and a blade actuator rod 250 permits the easy use of one or more elastic member 248 and/or blade actuator rod 250 members which is eccentrically shaped in cross-section.

Additionally, the material of the flexible material 252 is generally less expensive and easier to work than the material of either the elastic member 248 or the blade actuator rod 250. The flexible material 252 can be, for example, a flexible polymer, or a braided, coiled, segmented, hinged, or zigzagged metal component. If made of a flexible polymeric material, the material may be reinforced, for example, with fibers, to enable it to withstand the forces exerted on it by the elastic member while it is constrained within and deformed by the elongate housing. A suitable polymeric material for the component is, for example, polytetrafluorethylene, optionally reinforced with braided fibers.

The preferred cross-sectional embodiments include the actuator rod in or close to the neutral plane, i.e., that plane which is neither compressed nor stretched during the bending of the elastically deformable stem. FIGS. 7-12a through 7-12f are each labeled with a plane z-z, representing a preferred neutral plane; and with a plane n-n, representing a preferred plane through which the elastically deformable stem bends.

FIG. 7-12b shows two elastic members 248 on either side of an actuator rod 250, within a flexible material 252. The flexible material 252 is a rounded rectangle in cross-section. The elastic members 248 are rods which are round in cross-section, and the blade actuator rod 250 comprises a strip of material which is oval in cross-section.

FIG. 7-12c shows two elastic members 248 on either side of an actuator rod 250, within a flexible material 252. The flexible material 252 has an oval cross-section. The elastic members 248 are square in cross-section. The blade actuator rod 250 is a rod which is round in cross-section.

FIG. 7-12d shows two elastic members 248 on either side of an actuator rod 250, within a flexible material 252. The flexible material 252 has an oval cross-section. The elastic members 248 are square in cross-section. The blade actuator rod 250 is a piece which resembles a rounded "H" in cross-section. In an alternate embodiment, not shown, the blade actuator rod includes a third elastic member within it, and the blade actuator rod slides freely along the third elastic member. In another embodiment, not shown, the elastic members and the actuator rod are held in position without the action of a flexible material. In yet another embodiment, the elastic member is intermediate to two blade actuator rods.

FIG. 7-12e shows an elastic member 248 and a blade actuator rod 250 within a flexible material 252. The flexible material 252 has a squared pyramid shape in cross-section. The elastic member 248 comprises a strip of material which is rectangular in cross-section. The blade actuator rod 250 comprises a strip of material which is round in cross-section.

FIG. 7-12f shows an elastic member 248, a constraining rod 254, and an actuator rod 250, within a flexible material 252. The flexible material 252 has a squared cross-section. The elastic member 248, the constraining rod 254, and the actuator rod 250 are each oval in cross-section. Note that the constraining rod is not within the neutral axis: only in the absence of the constraining rod does the elastic member 248 assume its unconstrained (bent) configuration. A configuration such as that shown in FIG. 7-7f can be used in embodiments which do not include an elongate housing. A lumen 255 is present. The lumen 255 can be used, for example, to provide access for one or more apparatus for irrigation, aspiration, cautery, and the like.

FIG. 7-13 shows a bladed element which only one pivoting blade 256 is mounted for pivotal motion. The pivoting blade 256 is biased in the open (splayed) position by a spring 258. The fixed blade 260 is mounted in a fixed position. The pivoting blade is closed by longitudinal motion of the actuator rod 262. The housing 264 is shown in partial cutaway view.

Preferred embodiments of this invention include a symmetrical blade action, so that both of the blades are actuated by the manually operated mechanism and dissection, cutting, and/or grasping is done by symmetrical motion of the two blades. However, in some situations, it may be desirable to have embodiments in which one blade is moved more by the manually operated mechanism than the other blade. In some cases, it may be desirable to have one blade function as a stationary (and therefore passive) blade, where the manually operated mechanism moves only the other blade.

The blades of this invention can be made of any appropriate material. Metals known for scissor, knife, and/or forceps use are appropriate. Stainless steel, for example, can be used. Rigid plastics can also be used.

One use of the instruments of this invention involves cutting, e.g, when one or more of the opposable blade provides a cutting edge. The honing of an edge to form a cutting blade is well known in the art. If desired, the cutting blade can be serrated. The cutting edge is preferably derived from beveling blade material itself. However, it may be desirable or necessary to provide a honed edge of a secondary material to the blade material. For example, a non-cutting plastic blade can be combined with an alloy cutting edge. A cutting surface can be provided at any desired exposed edge of the blade.

The blades can be straight, or they can be curved along their length, as shown in FIG. 7-7a. When curved blades are present the curved blades are preferably made of an elastic material as described above.

FIG. 7-13b shows a cutting blade 266 which has one longitudinal cutting edge 268.

FIG. 7-13c shows cutting blade 266 in which the perimeter of the blade provides the cutting edge 268.

FIG. 7-13d shows a blade 266 which has no cutting edges. The end portion of the blade is pointed to facilitate dissection of tissues.

FIG. 7-13e shows a blade 266 which has no cutting edges. The end portion of the blade is curved.

FIGS. 7-14a through 7-14e show various blade cross-sections, taken through line 14-14 of FIG. 7-13a. The cutting surfaces of the blades may abut one another in the manner of wire cutters, or they may cross one another in the manner of shears. The grasping surfaces of the blades may abut one another and be sufficiently blunt to avoid cutting the object to be grasped. Alternatively, the grasping surfaces need not be configured so as to contact each other in the manner of cutting devices. The object being grasped need merely be entrapped between the end portions of the blades. The grasping surfaces may be ridged or contain protuberances to assist in grasping the object.

FIG. 7-14a shows a cross-sectional view of two opposing blades. The blades are roughly rectangular in cross-section. The blades meet at a flattened surface, and are appropriate for grasping objects.

FIG. 7-14b shows a cross-sectional view of two opposing ridged blades. The blades are roughly rectangular in cross-section. The blades meet at a ridged surface, and are especially appropriate for grasping objects.

FIG. 7-14c shows a cross-sectional view of two opposing blades in which the blades are not symmetrical. One blade is roughly rectangular in cross-section, while the other blade is triangular. Such a configuration is appropriate for cutting objects.

FIG. 7-14d shows a cross-sectional view of two opposing cutting blades. The blades are roughly triangular in cross-section. The blades meet at a pointed cutting surface.

FIG. 7-14e shows a cross-sectional view of two opposing cutting blades. The blades are roughly triangular in cross-section. The blades meet and slide along their surfaces in the manner of shears.

An eighth form of the present invention provides a device for dissecting an object which comprises at least two elongate elements, positioned alongside one another, each having a body portion and an end portion, the end portions of the elements:

i being capable of being splayed apart from one another when free of transverse constraint to dissect said object from surrounding material; and ii being capable of being moved toward one another; wherein a portion of at least one of the elements is formed from a pseudoelastic material.

In another aspect, the eighth form of the present invention provides a device for grasping or cutting an object which comprises at least two elongate elements, positioned alongside one another, each having a body portion and an end portion, the end portions of the elements:

(i) being capable of being splayed outwardly apart from one another when free of transverse constraint and presenting grasping or cutting surfaces to an object to be grasped or cut that is placed between them; and (ii) being capable of being moved inwardly towards one another to grasp or cut said object;

wherein a portion of at least one of the elements is formed from a pseudoelastic material.

A further aspect of the eighth form of this invention comprises a device (or dissecting an object which comprises a. at least two elongate elements, positioned alongside one another, each having a body portion and an end portion, the end portions of the elements:

i. being capable of being splayed apart from one another when free of transverse constraint for dissecting said object from surrounding material; and ii. being capable of being moved toward one another; and b. actuating means;

wherein a portion of at least one of the elements and/or said actuating means is formed from a pseudoelastic material.

Another aspect of the eighth form of this invention comprises a device for grasping or cutting an object which comprises (a) at least two elongate elements, positioned alongside one another, each having a body portion and an end portion, the end portions of the elements:

(i) being capable of being splayed outwardly apart from one another when free of transverse constraint and presenting grasping or cutting surfaces to an object to be grasped or cut that is placed between them; and (ii) being capable of being moved inwardly towards one another to grasp or cut said object; and (b) actuating means;

wherein a portion of at least one of the elements and/or said actuating means is formed from a pseudoelastic material.

A further aspect of the eighth form of this invention comprises a device for dissecting an object which comprises a. a hollow elongate component; and b. at least two elongate elements, at least part of which are positioned within said component, said elements being positioned alongside one another, each having a body portion and an end portion, the end portions of the elements:

i. being capable of being splayed apart from one another when free of transverse constraint; and ii. being capable of being moved toward one another;

wherein the elements and the component are longitudinally slidable relative to one another so that at least the end portions of the elements can be slid into and out of said component and wherein a portion of at least one of the elements is formed from a pseudoelastic material.

Yet another aspect of the eighth form of this invention comprises a device for grasping or cutting an object which comprises (a) a hollow elongate component;

(a) at least two elongate elements, at least part of which are positioned within said component, said elements being positioned alongside one another, each having a body portion and an end portion, the end portions of the elements:

(i) being capable of being splayed outwardly apart from one another when free of transverse constraint and presenting grasping or cutting surfaces to an object to be grasped or cut that is placed between them; and (ii) being capable of being moved inwardly towards one another to grasp or cut said object;

wherein the elements and the component are longitudinally slidable relative to one another so that at least the end portions of the elements can be slid into and out of said component and wherein a portion of at least one of the elements is formed from a pseudoelastic material which can be deformed when under an applied stress.

A still further aspect of the eighth form of this invention comprises a method of dissecting an object from surrounding material, which comprises:

A. providing a device which comprises at least two elongate elements, positioned alongside one another, each having a body portion and an end portion, the end portions of the elements being capable of being splayed apart from one another when free of transverse constraint to dissect said object from surrounding material; and wherein a portion of at least one of the elements is formed from a pseudoelastic material;

B. positioning end portions adjacent the object; and

C. causing said end portions to splay apart so as to dissect said object from surrounding material.

A further aspect of the eighth form of this invention comprises a method of grasping or cutting an object, which comprises:

i. providing any one of the cutting or grasping devices as described above;

ii. positioning the object between splayed apart end portions of the elements; and iii. causing said end portions to move toward one another so as to grasp or cut said object.

The pseudoelastic material used in any of the aspects of this eighth form of the invention is preferably a shape memory alloy, such as a nickel/titanium-based alloy, as discussed hereinbefore. The pseudoelastic material may be, for example, a superelastic material, especially a superelastic shape memory alloy.

Where the device according to the invention comprises a hollow component this may be in the form of an elongate polymeric or metal tube.

According to two various aspects of the invention, at least a portion of at least one of the elongate elements exhibits pseudoelasticity. For example the end portion, or instead or in addition at least part of the body portion, of at least one of the elements, may be formed from a shape memory alloy which exhibits pseudoelasticity, especially superelasticity.

Figures 1, 8:
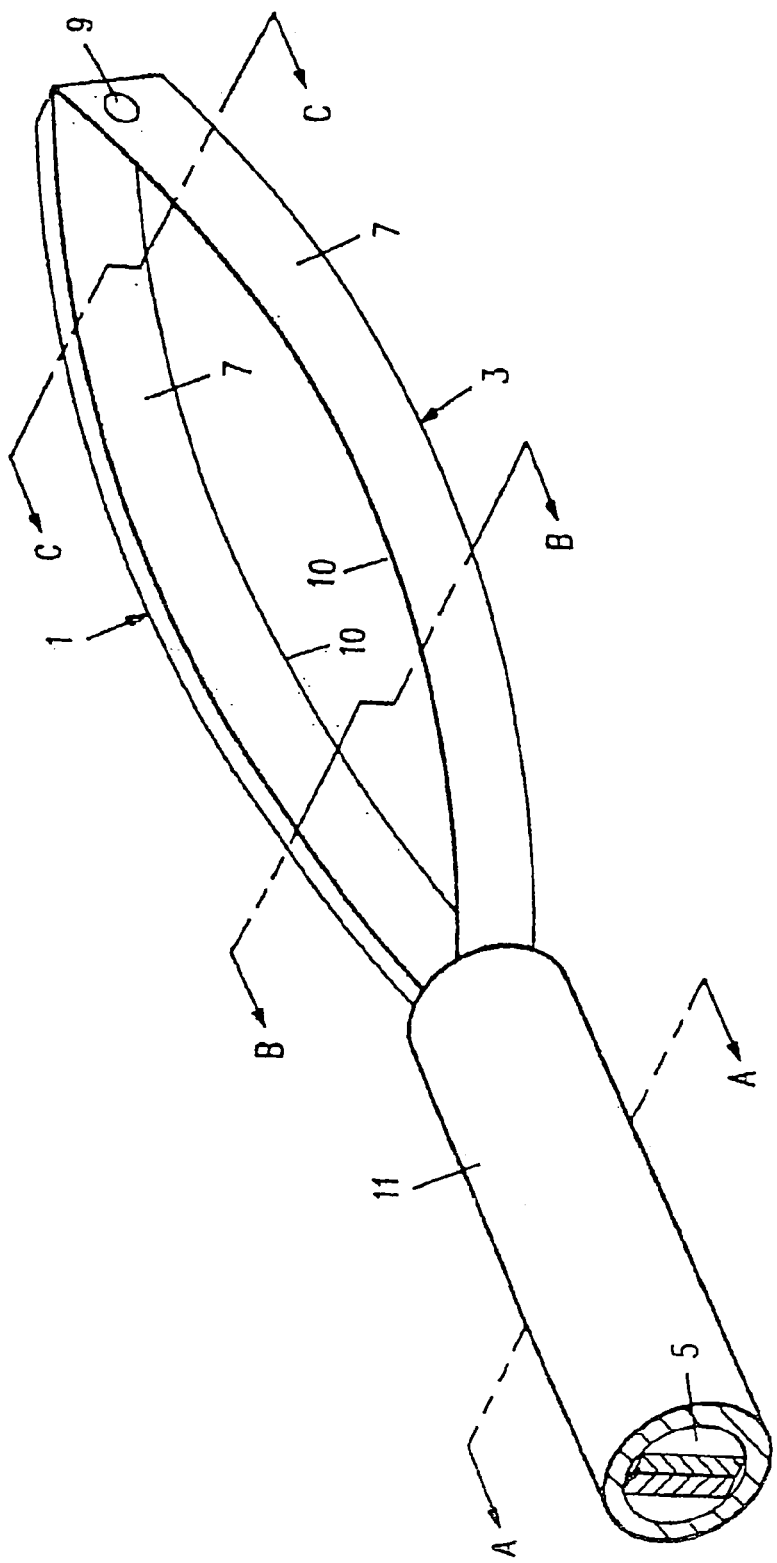
Figures 2C, 8:
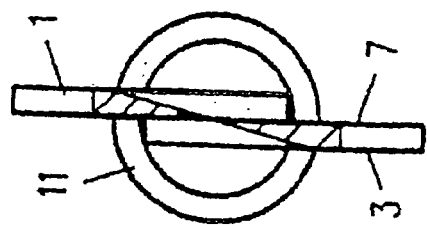
Figures 2B, 8:
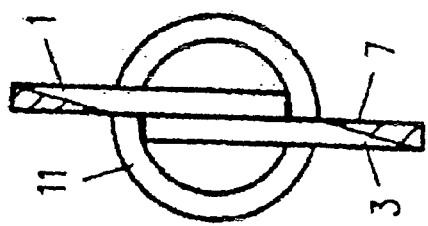
Figures 2A, 8:
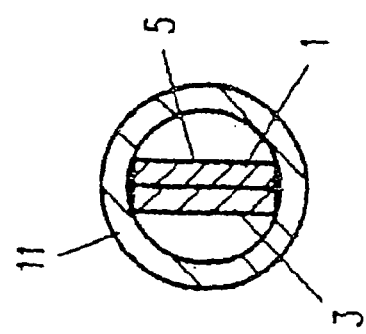
Figures 3A, 8:
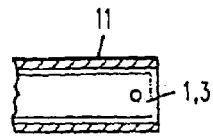
Figures 3B, 8:
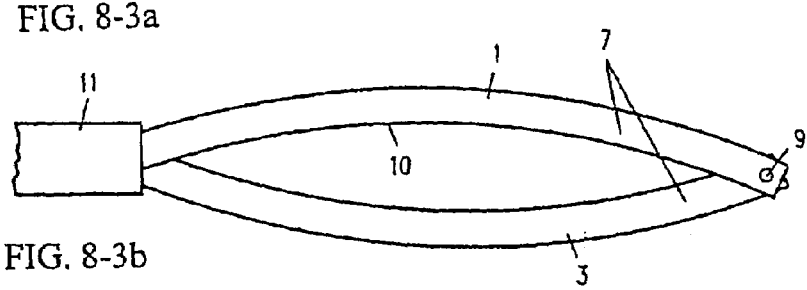
Figures 3C, 8:
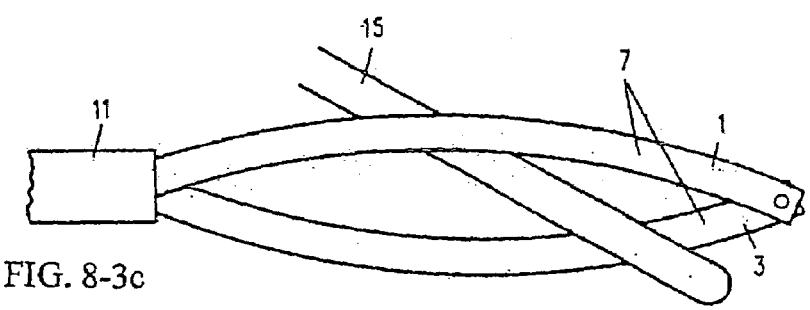
Figures 3D, 8:
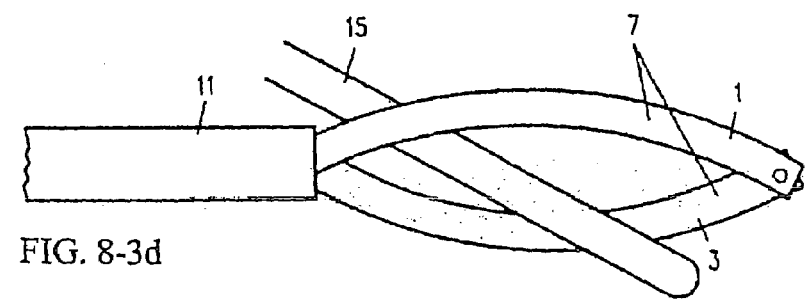
Figures 3E, 8:
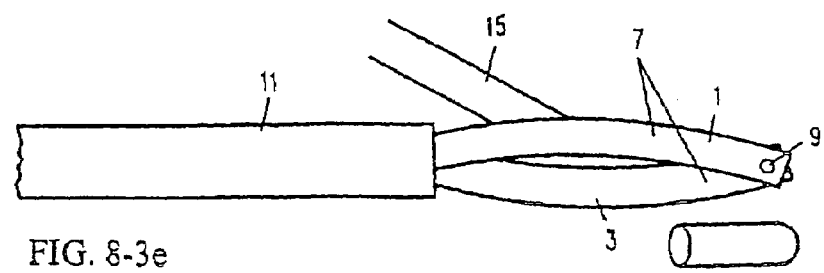
Figures 4A, 8:
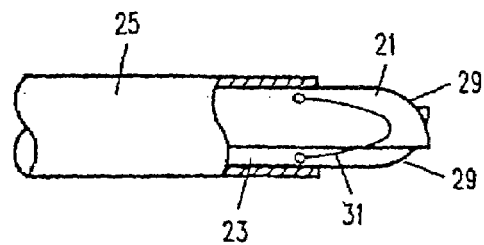
Figures 4B, 8:
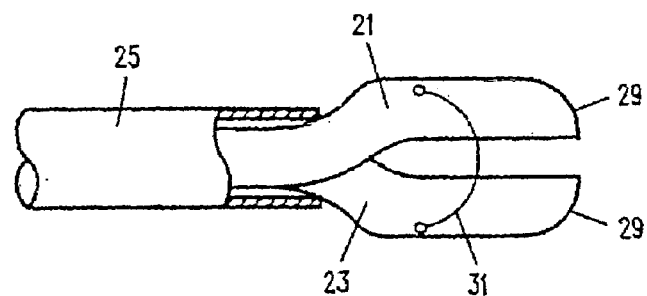
Figures 4C, 8:
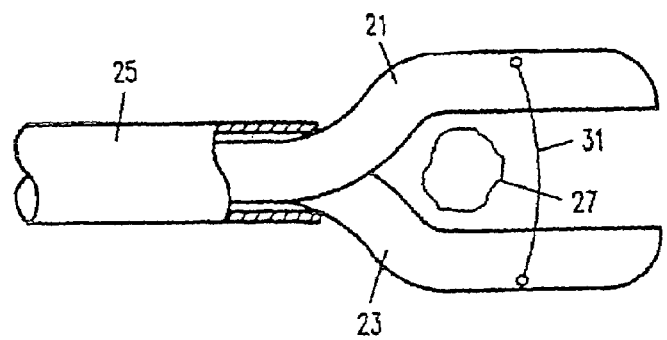
Figures 5A, 8:
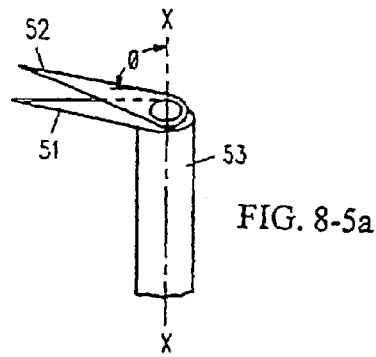
Figures 5B, 8:
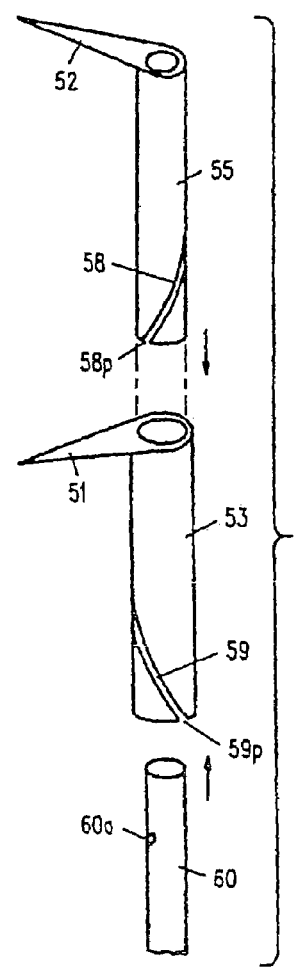

FIG. 8-1 is an isometric view of a device of the invention;

FIGS. 8-2A to 8-2C are cross-sections through the device shown in FIG. 8-1, taken at lines A-A, B-B and C-C respectively;

FIGS. 8-3A to 8-3E are elevational views of a first embodiment Of the device shown in FIG. 8-1 at various stages during a cutting operation;

FIGS. 8-4A to 8-4C are elevational views, partially in section, of another embodiment of the device at various stages during a cutting or grasping operation.

Figures 5C, 8:
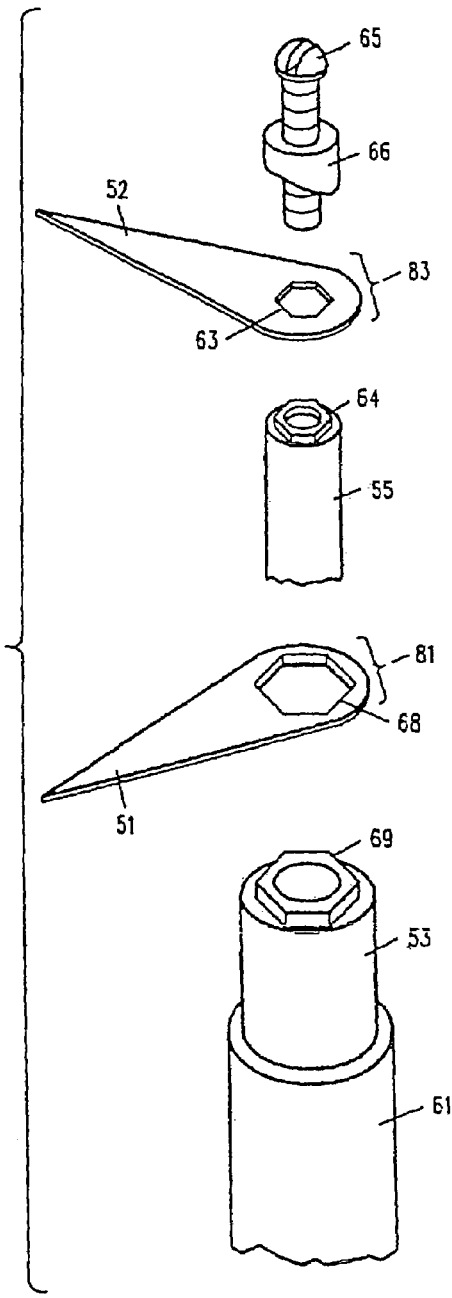
Figures 5D, 8:
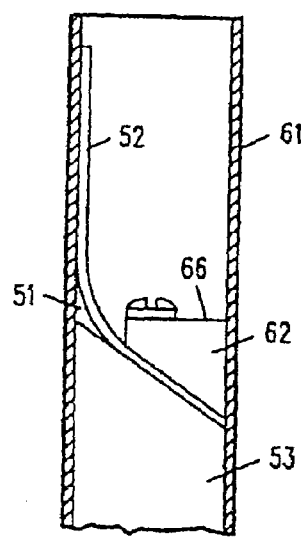
Figures 6A, 8:
Figures 6B, 8:
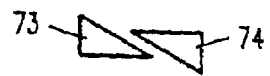
Figures 6C, 8:
Figures 6D, 8:
Figures 5E, 8:
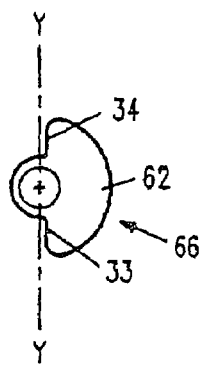

FIGS. 8-5A to 8-5E illustrate an embodiment of a device in accordance with this invention in which the end portions and body portions of the elongate elements are integral and are moved by a rotational actuator made of a material other than a pseudoelastic material.

Figures 6E, 8:
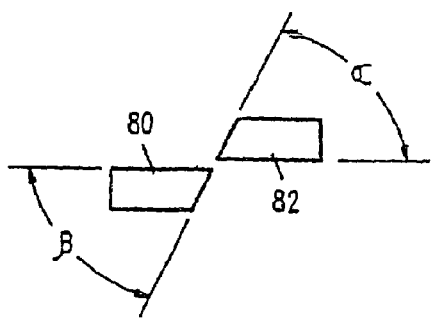
Figures 7A, 8:
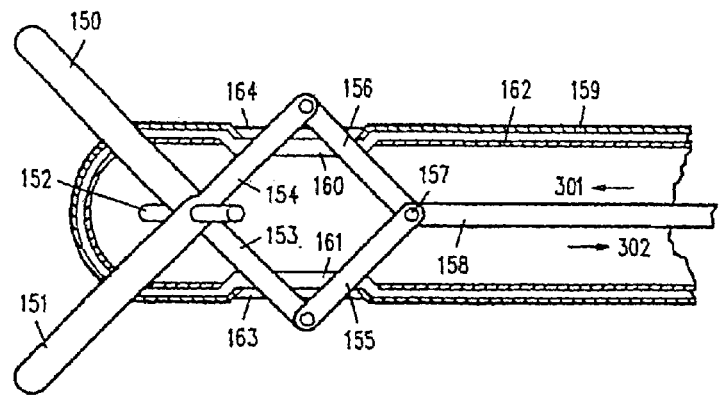
Figures 7B, 8:
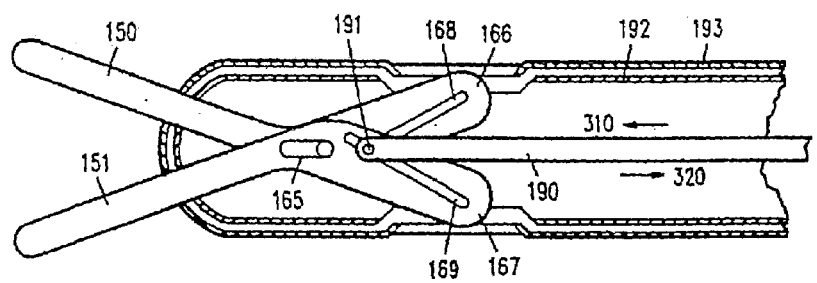
Figures 7C, 8:
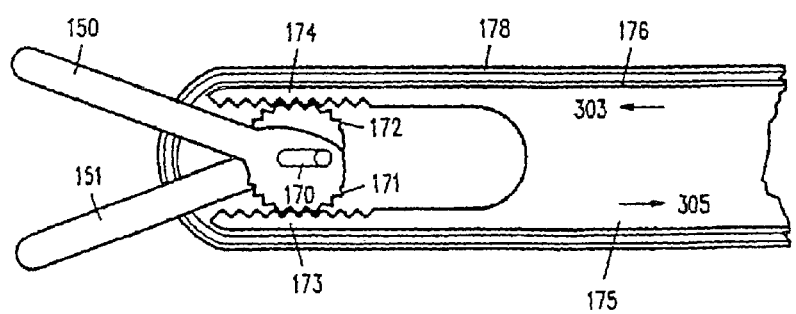
Figures 7D, 8:
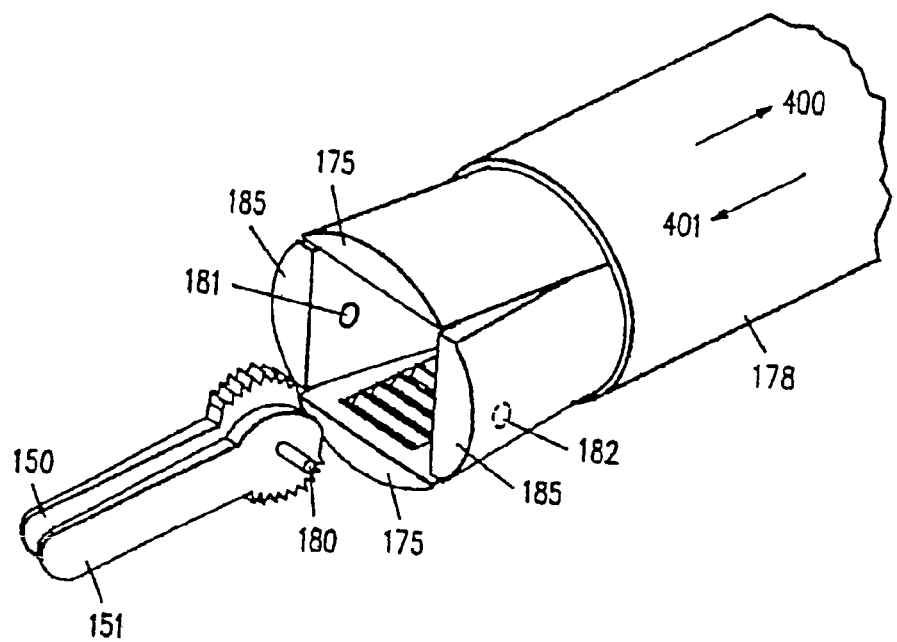
Figures 7E, 8:
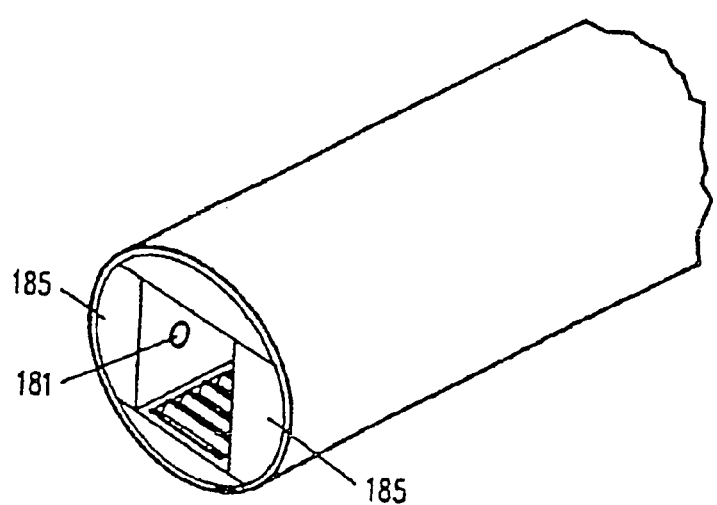
Figure 8:
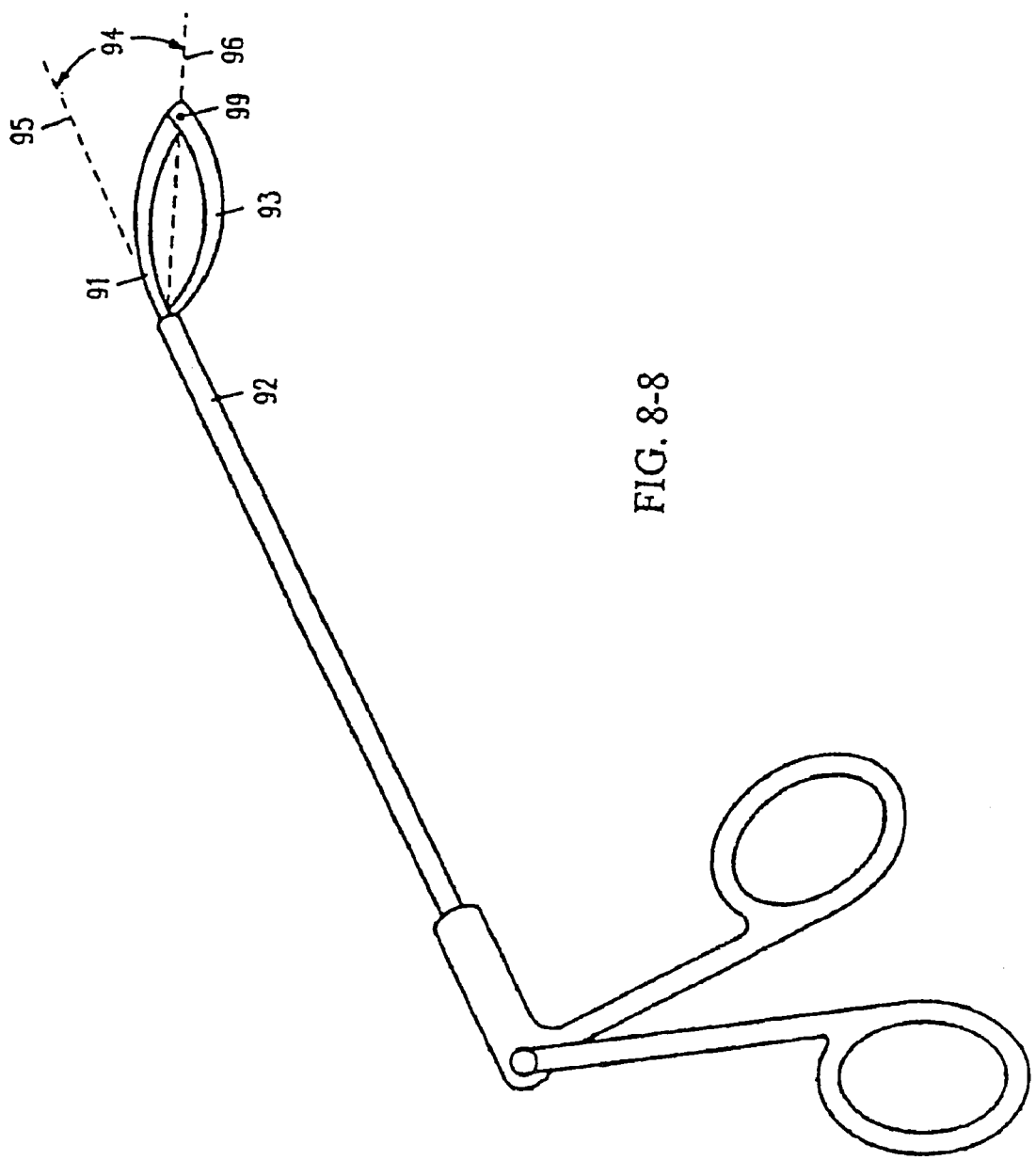
Figures 8, 9:
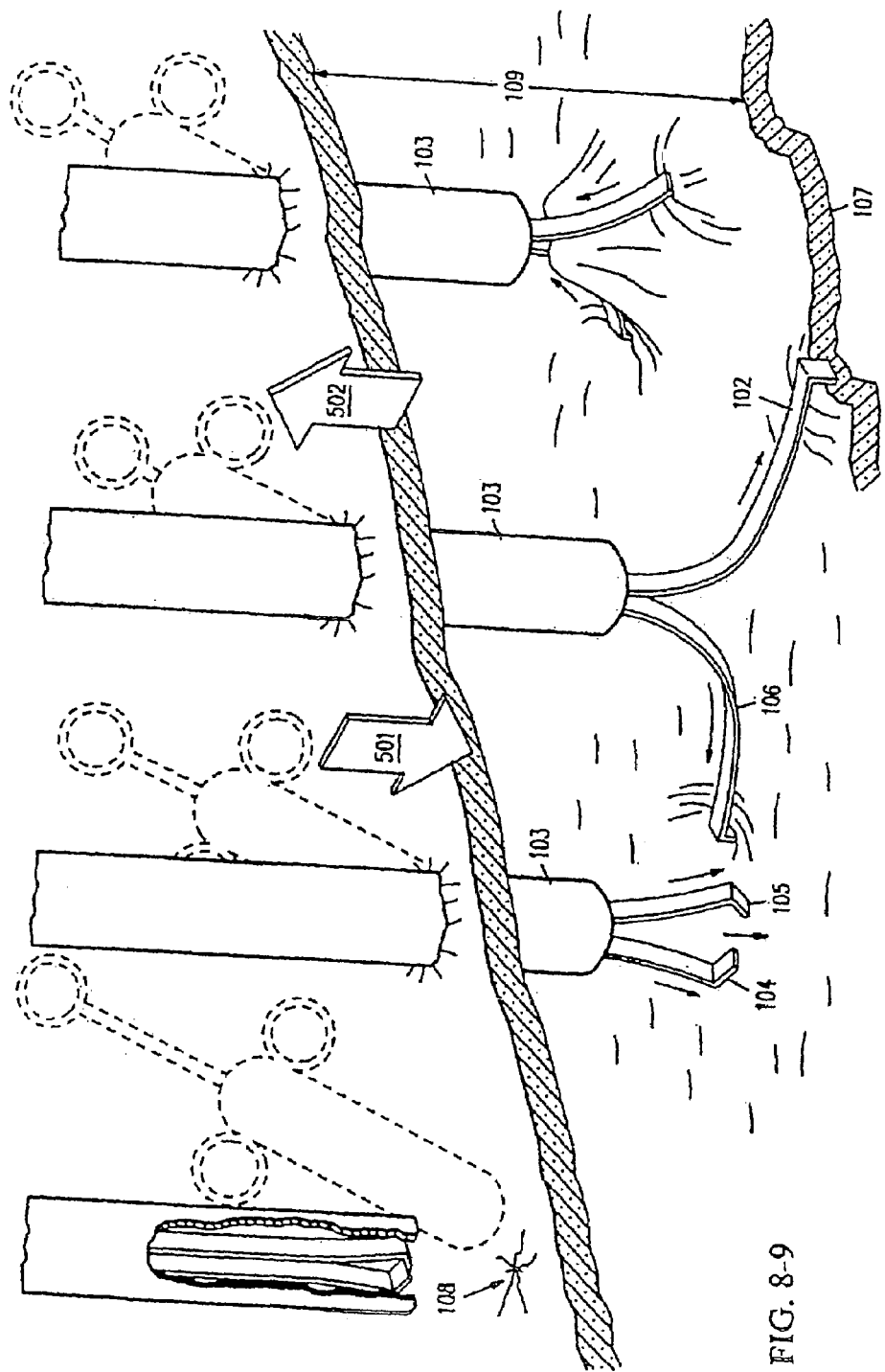
Figures 8, 9, 10, 10A:
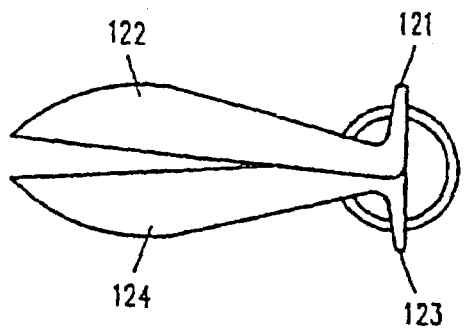
Figures 8, 9, 10, 10B:
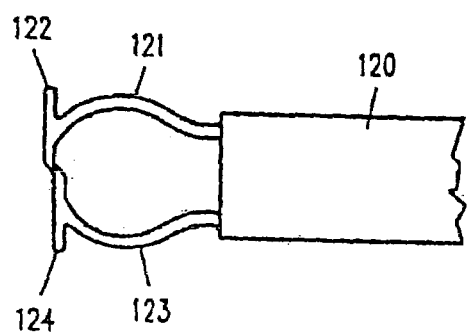
Figures 8, 9, 10, 10C:
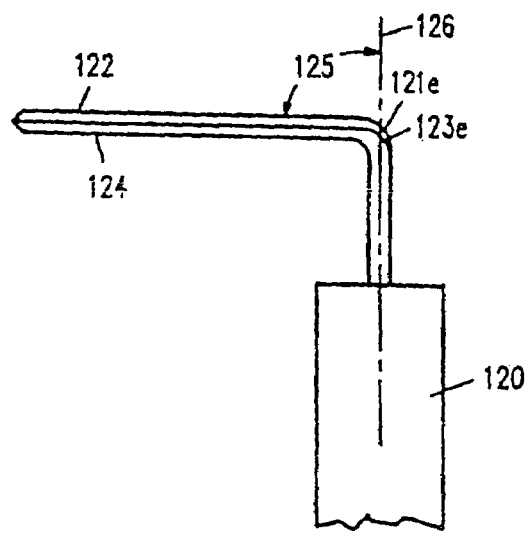
Figures 8, 9, 10, 11, 11A:
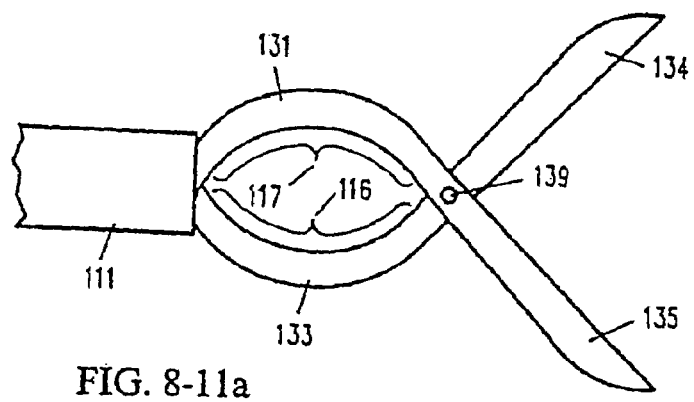
Figures 8, 9, 10, 11, 11B:
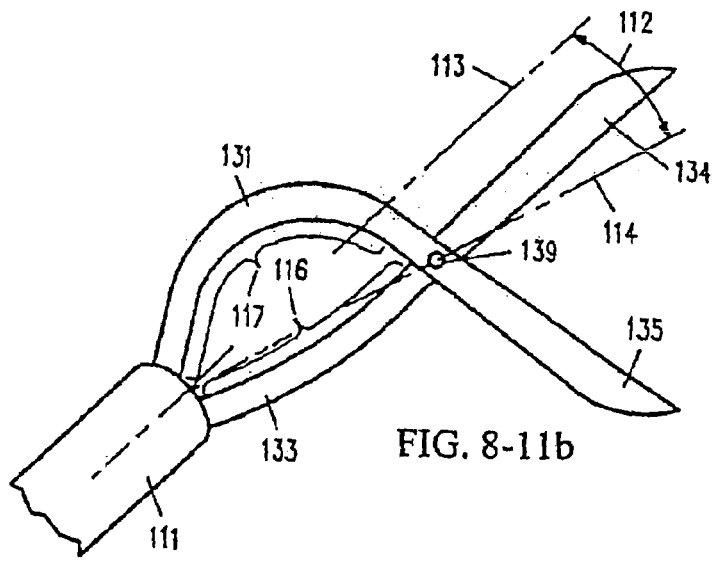
Figures 8, 9, 10, 11, 12:
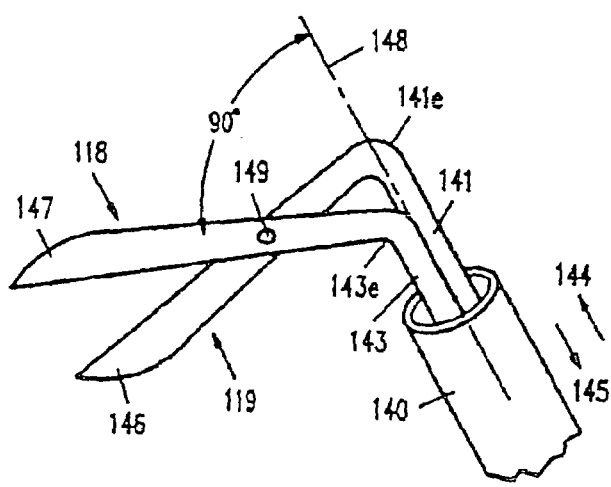
Figures 8, 9, 10, 11, 12, 13:
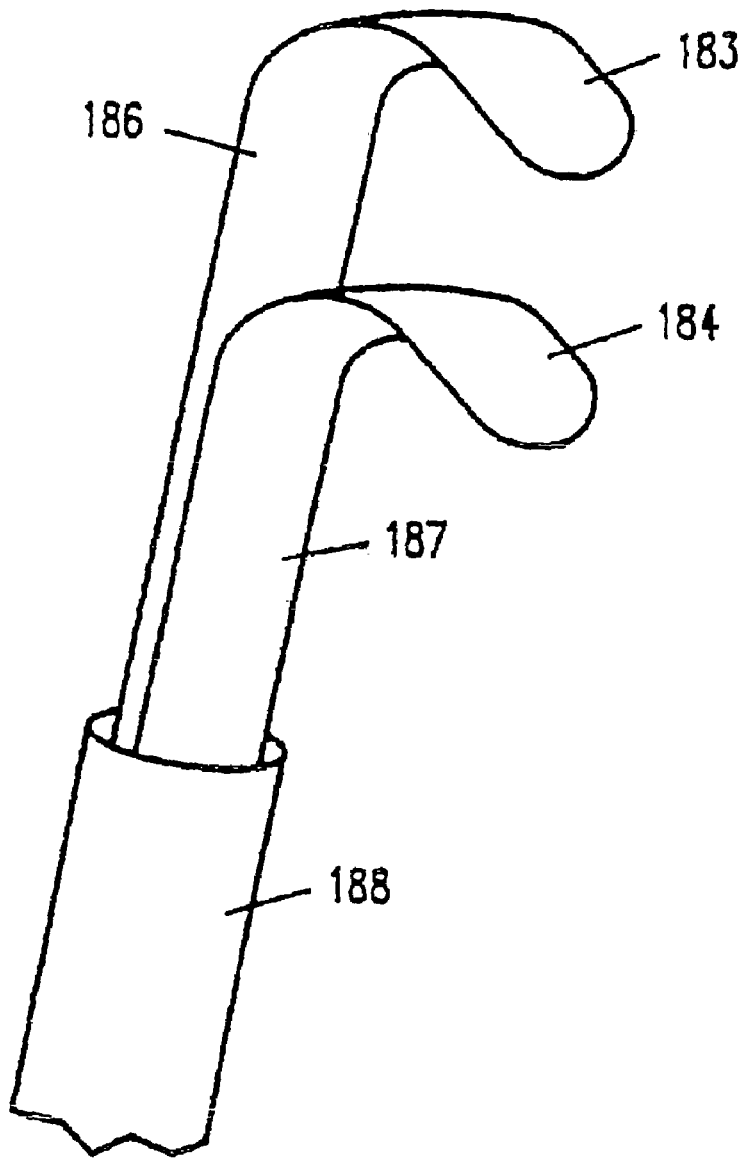

FIGS. 8-6A to 8-6E illustrate representative cross sections of end portions of the elements adapted to grasp or cut an object.

FIGS. 8-7A to 3-7E illustrate various actuating means which function to cause the elements to splay apart and come together and, optionally, rotate the elements, and/or withdraw the elements into or out of the hollow component.

FIG. 8-8 illustrates an embodiment of the device of this invention in which the end portions are curved when at least partially unconstrained and pinned together pivotally at their tips.

FIG. 8-9 demonstrates a method of using a grasping device of this invention.

FIGS. 8-10A to 8-10C illustrate an embodiment of the device of this invention in which the elements are splayed and in which the body portions of the elements are bent when the elements are unconstrained.

FIGS. 8-11A and 8-11B illustrate a device of this invention in which the elements have end portions beyond a pivot point, and in which the body portions of the elements are of pseudoelastic material and when unconstrained are bent to splay the end portions and position them at a desired angle with respect to the hollow component. The body portions act as actuating means to open and close the end portions of the elements to dissect, grasp and/or cut an object.

FIG. 8-12 illustrates a device similar to the device in FIG. 8-11B, but in which the body portions of the elements are made of a pseudoelastic material and have a bend of about 90.degree..

FIG. 8-13 illustrates another device in accordance with this invention.

The device of the eighth form this invention comprises a hollow elongate component and two elongate elements. Preferably, the hollow component is tubular. This has the advantage that the device can be operated remotely.

The material of the hollow component may be polymeric. It may be flexible or rigid. If made of polymeric material, the material may be reinforced, for example, with fibers, to enable it to withstand the forces exerted on it by the elements while they are constrained within and deformed by the component. A suitable polymeric material for the component is, for example, polytetrafluoroethylene, reinforced with braided fibers. Alternatively, the material of the hollow component may be metallic, for example stainless steel. A preferred hollow component is an elongate tube, preferably formed from stainless steel. The elongate hollow component can be, for example, a tubular housing, cannula, catheter or sheath.

The hollow component may be circular in cross-section which can have the advantage that it permits deformation of the elements substantially uniformly in all directions. Other cross-sections may be preferable in some situations. For example, it can be advantageous to use a hollow component which has the same shape in cross-section as the elements which are received within it, to minimize twisting of the elements relative to one another.

Preferably, the elements are at least partially formed from a pseudoelastic material, such as a shape memory alloy that exhibits pseudoelasticity. Shape memory alloys which exhibit superelasticity, are especially preferred. As explained above as a superelastic shape memory alloy is increasingly deformed from its unconstrained shape, some of its austenitic phase changes Into stress-induced-martensite and the stress/strain curve presents a plateau during this phase change. This means that while the alloy undergoes this phase change, it can deform greatly with only minimal increases in loading. Therefore, cutting, dissecting and grasping elements comprising superelastic shape memory alloys have a built-in safety feature. These elements can be designed (using appropriately treated alloys and appropriate dimensions) such that when they are loaded beyond a certain amount, the elements will tend to deform with a concomitant austenite to stress-induced-martensite phase change, instead of merely presenting a greater resistance with limited deformation to the load, which is seen with conventional metals.

While the alloy that is used in the devices of this eighth form of the invention may exhibit either linear pseudoelasticity or superelasticity (which is sometimes referred to as non-linear pseudoelasticity), or pseudoelasticity of an intermediate type, it is generally preferred that it exhibit superelasticity because of the large amount of deformation that is available without the onset of plasticity. Any of the materials described hereinbefore including elastically deformable materials, pseudoelastic materials, superelastic materials, and shape memory alloys can be used in this eighth form of the invention.

The device according to the eighth form of the invention has the advantage that, by use of elongate elements formed at least partially from a pseudoelastic material which can be deformed, it can be used in applications in which there is a limited amount of space. Furthermore, the device can be operated remotely or at an angle more conveniently than many previously used devices.

In certain embodiments of the invention, at least one of the end portions of the elongate elements is formed from a pseudoelastic material, preferably a pseudoelastic shape memory alloy, and that end portion may have a curved configuration when not constrained and can be deformed into a straightened configuration when within a constraint, such as a hollow component. The term "straightened configuration" means that the configuration of the element is straighter when deformed than it is when not deformed. This may be used in dissection (the separation of tissues). When the end portion of the element (or end portions of the elements if both are of a pseudoelastic material) is extruded from the hollow component it is no longer constrained and reverts or recovers to splay away from the other element. When the end portion is withdrawn back into the hollow component, or the hollow component is drawn over the end portion, it moves toward the other end portion grasping or cutting any object placed between them.

In some embodiments of the invention, the end portions of the elongate elements are formed from a pseudoelastic material, preferably a pseudoelastic shape memory alloy, and are deformed into a straightened configuration when within the hollow component and curve at an angle to the end of the component when extended therefrom.

In certain other embodiments the end portions of the elongate elements are formed from a pseudoelastic material, preferably a pseudoelastic shape memory alloy, and are deformed into a curved configuration when within the component and are substantially straight when extruded from the component.

In still other embodiments, the body portion of one or both of the elongate elements is formed from a pseudoelastic material, preferably a pseudoelastic shape memory alloy, and the body portion of the element becomes curved on exiting the component, thereby splaying the end portion away from the other end portion.

In any embodiment, an actuating means, which may be formed from a pseudoelastic material, preferably a pseudoelastic shape memory alloy, can be provided to splay the end portions apart from one another and/or to move them toward one another. In such embodiments, it is not necessary for the elongate elements to be formed from a pseudoelastic material.

In summarizing, at least a portion of at least one, preferably each, of the elongate elements is formed from a pseudoelastic material, preferably a pseudoelastic shape memory alloy. The use of a shape memory alloy which exhibits pseudoelasticity has the advantage that the amount of elastic deformation that is available is large compared with that available from many other materials. In certain preferred embodiments, the end portion of one or both of the elements is formed from a pseudoelastic shape memory alloy. In other embodiments, a section of the body portion of one or both of the elements is formed from a pseudoelastic shape memory alloy. The large amount of elastic deformation of the elements allows the device to be used to dissect, grasp and/or cut large objects, while ensuring also that the device has a small transverse dimension when the elements are deformed inwardly, allowing the device to pass through small spaces.

The end and body portions of the elongate elements may be formed from the same material, for example, both may be formed from a shape memory alloy, for convenience. Frequently, however, it may be preferable to use different materials because of the different functions that the end and body portions might have to serve. For example, the end portions may be of stainless steel or the like to provide a sharp cutting edge or a cutting edge of stainless steel may be provided on a part of end portions formed from a sharp memory alloy. The cross-sections of the end and body portions will generally be different, although this need not necessarily be the case. For example, the end portions may be rectangular to present a grasping surface or triangular to present a cutting surface, and the body portions may be rectangular for rigidity.

In some embodiments, the end portions of the elongate elements are pivotally connected to one another towards their free ends. This minimizes the possibility of an object becoming dislocated from the device before it is grasped or cut. The device may then be used to move an object once it has been positioned between the elements. This can also be achieved when the elements are not joined together at their free ends, but with less control in some situations. When the elements are not connected directly at their free ends, they may be connected by a flexible component which extends between the end portions of the elements so as, together with the end portions of the elements, to form a closed loop. Leaving the elements unattached at their free ends can facilitate positioning the device so that the object is located between the elements. The tips of the free ends may be blunt, especially when the elements are not attached at their free ends. Alternatively, the free ends may be pointed to facilitate dissection, for example.

The end portions of the elongate elements may be provided with a cutting edge of a material other than a shape memory alloy. The cutting edge may be inlaid in the end portion or can extend from the end portion of the device.

Preferably the body portions of the elongate elements are attached to one another. This can facilitate manipulation of the two elements. For example, the elements may be attached to one another by adhesive material or by fasteners such as screws or rivets, or the elements may be formed as a single body of material. Alternatively, the elements may be attached to an elongate member by which they are moved longitudinally relative to the hollow component. For example, such a member may be hollow, at least at its end, and the elements may be received within the member.

The elongate elements may be symmetrical when they are splayed outwardly apart, and preferably also when deformed inwardly. However, for some applications, it might be appropriate for the elements not to be symmetrical, or for the elements not to be deformed symmetrically (for example only one of the elements might be deformed), or both.

The cutting surfaces of the elongate elements may abut one another in the manner of wire cutters, or they may cross one another in the manner of shears. The grasping surfaces of the elements may abut one another and be sufficiently blunt to avoid cutting the object to be grasped. Alternatively, the grasping surfaces need not be configured so as to contact each other in the manner of cutting devices. The object being grasped need merely be entrapped between the end portions of the elements. The grasping surfaces may be ridged or contain protuberances to assist in grasping the object.

In certain embodiments, an object may be grasped or cut using the device of the invention by ringing the device and the object together while the elongate elements are positioned at least partially within the component, and by then moving the hollow component and the elements longitudinally relative to one another, so that the end portions of the elements extend from the object and become splayed outwardly. This action can be used to spread or dissect surrounding material from the object, if desired, to isolate the object. The object can Then be positioned between the elements to be grasped or cut in accordance with the method described above.

In other embodiments, the device is provided with means for actuating the end portions of the elongate elements, which are not necessarily formed from a pseudoelastic. Illustrative actuating means are described more fully below with reference to the drawings and include rack and pinion means, pin and slot means, four-bar linkages and the like. In certain embodiments, the actuating means may be formed of a pseudoelastic material. The actuating means may permit the elements to be rotated. The actuating means may also provide suitable means for irrigating the elements, or conduct electrical current to one or both of the elements, if desired.

The device will be particularly useful in applications in which access to an object to be dissected, cut or grasped is restricted, for example in medical applications in which the object to be dissected, cut or grasped is a part of a human or animal body. In these applications, the elongate elements may be positioned in the body by means of a hollow component in the from of a cannula, catheter or sheath introduced, for example, through an opening into a body cavity.

The device may be arranged so that the axis on which the elements dissect, cut and/or grasp the object is not coaxial with the axis of at least a significant portion of the hollow component. This may be arranged, for example, by providing the elongate elements with a suitable bend. The elements may be deformed from their bent configuration towards their straight configuration, and held in the straight configuration, by the hollow component while they are within it. Alternatively, it may be arranged by use of a hollow component which is bent towards the end from which the elements extend.

The device may also be useful in the assembly of mechanical, electrical or other equipment, for example by means of robots.

Turning now to the drawings, FIGS. 8-1 and 8-2 show a cutting or grasping device which comprises two elongate elements 1 and 3, each having a body portion 5 and an end portion 7. The end portions are joined together pivotally at their free ends by a pin 9. The end portions preferably have a triangular cross-section, where the apex of the triangle provides a cutting surface 10. Alternatively, any flat cross-sectional area may present a grasping surface. Other possible cross-sectional areas are illustrated in FIGS. 8-6A to 8-6E.

The elongate elements are preferably formed from a pseudoelastic material, preferably a shape memory alloy which has been treated so that it exhibits pseudoelasticity in the temperature range between ambient temperature and a temperature above body temperature.

Elongate elements 1 and 3 are located within an elongate housing 11 within which they can slide longitudinally, the housing preferably being a stiff tubular sheath. The elongate elements can be extended beyond the end of housing 11 by longitudinally moving them relative to housing 11 via any suitable manually operated mechanism.

FIG. 8-2 shows the cross-sectional configurations of elongate elements 1 and 3 at positions A-A, B-B, and C-C of FIG. 8-1, which illustrates the elongate elements splayed apart.

FIG. 8-3A shows a cutting device with elongate elements 1 and 3 restricted completely within housing 11, which holds the elongate elements in a deformed configuration inwardly towards one another. The housing is positioned as desired relative to an object to be cut (or dissected or grasped) while the elongate elements are in this configuration. Once so positioned, the end portions 7 of the elongate elements are caused to extend from the housing, by relative movement of the elements and the housing. Once released from the transverse constraint imposed by the housing, end portions 7 of the elements splay outwardly apart, as shown in FIG. 8-3B, allowing an object 15 to be positioned between them, as shown in FIG. 8-3C.

Object 15 is caused to engage the surfaces 10 of elongate elements 1 and 3. Relative longitudinal movement of the elongate elements and the housing will force at least parts of the elongate elements together, thereby grasping or cutting the object, as shown in FIGS. 8-3D and 8-3E. If desired, object 15 can be moved by holding the housing and moving the elongate elements. If it is desired not to move object 15, the elongate elements are held fixed and the housing is moved. The elongate elements can be retracted into the housing for removal of the device from the site of the dissecting, cutting and/or cutting operation.

The end portions 7 (or any other portion, as desired) of elongate elements 1 and 3 may represent sections of spherical surfaces to facilitate the splaying and closing. End portions 7 may be used to grasp, instead of cutting, tissues. The grasping function would be facilitated if end portions 7 do not have cutting surfaces 10, and if end portions 7 are not fully retracted back into housing 11. Furthermore, the splaying action of elongate elements 1 and 3 may be utilized to separate tissues for dissection.

FIG. 8-4 shows a device which comprises two elongate elements 21 and 23 that are preferably formed from a pseudoelastic material and more preferably a shape memory alloy which has been treated so that it exhibits superelastic behavior. The elements can slide longitudinally within a tubular housing 25. FIG. 8-4A shows the device with the elongate elements 21 and 23 positioned almost entirely within the tubular housing 25. Housing 25 constrains elongate elements 21 and 23 in straightened and deformed shapes.

As elongate elements 21 and 23 are moved longitudinally relative to housing 25, the elongate elements extend from the end of housing 25, as shown in FIGS. 8-4B and 8-40. As they extend from the end of housing 25, the elongate elements become unconstrained and recover toward their preset curved shapes pseudoelastically. They pseudoelastically splay outwardly so that they can receive an object 27 between them or, alternatively, be used to dissect surrounding material. The elongate elements may be interconnected indirectly towards their free ends 29 by a flexible component, such as a piece of wire 31, which helps to prevent dislocation of object 27 from between the elongate elements. Object 27 is cut or grasped by relative movement between housing 25 and the elongate elements, such that the elongate elements become constrained within the housing, generally as described above with reference to FIG. 8-3. The splaying action of elongate elements 21 and 23 may also be utilized to separate tissues for dissection. Elongate elements 21 and 23 may curve out of the plane of the paper.

FIG. 8-5A illustrates an embodiment of the invention in which elongate elements 51 and 52 are substantially planar and straight in their unconstrained shapes, but are located in a plane which deviates by an angle phi from a plane which includes the axis x-x of a hollow tube 53. In this embodiment, elongate elements 51 and 52 are attached to outer tube 53 and inner tube 55, respectively, as shown in FIG. 8-5B. The proximal end (i.e., the end opposite the elongate element 52) of inner tube 55 is provided with a groove 58, and inner tube 55 is positioned within outer tube 53. The proximal end of outer tube 53 is provided with a groove 59, which extends in a direction opposite to groove 58 of inner tube 55. Plunger 60 is provided with a peg 60a. The plunger may be positioned at the proximal end of the tubes. The proximal ends 58p and 59p of grooves 58 and 59, respectively, are positioned such that they overlap and are engaged by peg 60a. When peg 60a engages proximal ends 58p and 59p of grooves 58 and 59, elongate elements 51 and 52 are preferably splayed apart in the plane defined by their respective flat surfaces. When plunger 60 is pushed into inner tube 55 in a distal direction toward the elongate elements, peg 60a engages grooves 58 and 59, causing tubes 53 and 55, and thereby the elongate elements 51 and 52, to rotate in opposite directions. Preferentially, this rotation would cause the elongate elements to rotate into a more overlapped configuration. The elongate elements can thereby grasp an object placed between them. If the elongate elements have cutting edges, they could thereby cut an object placed between them. When plunger 60 is withdrawn from inner tube 55 again, peg 60a could cause tubes 53 and 55 to rotate such that elongate elements 51 and 52 splay apart from their overlapped configuration. Elongate elements 51 and 52 could thereby be used to separate tissues for dissection.

With respect to this embodiment, it should be noted that the angle .phi. between elongate elements 51 and 52 and tubes 53 and 55 can be any number of degrees desired. In addition, the elongate elements may be curved, not only within the plane generally described by their plane of motion, but also out of the plane generally described by their plane of motion. Furthermore, there may be more than one peg on plunger 60. Correspondingly there would be additional grooves (or slots) in tubes 53 and 55. The grooves may be spiraled, and longer, such that elongate elements 51 and 52 could be caused to rotate in both directions of their overlapped position in one stroke of plunger 60. The grooves may also be located anywhere along the lengths of tubes 53 and 55. Consequently, peg 60a may be appropriately located anywhere along plunder 60. Finally, grooves 58 and 59 could be made configured such that elongate elements 51 and 52 could be brought to their overlapped configuration by withdrawing plunger 60 in a proximal direction away from the elongate elements.

FIG. 8-5C shows one method of the attachment of elongate elements 51 and 52 onto inner and outer tubes 53 and 55, respectively. Elongate element 52 is provided with aperture 63 which fits over stem 64, which is integral with or is secured to the distal end of inner tube 55. The length of stem 64 is equal to or less than the thickness of elongate element 52. The cross-sectional shapes of aperture 63 and stem 64 are preferably noncircular, and they may, for example, be square, serrated, notched, etc. Screw 65 and washer 66 fasten elongate element 52 to inner tube 55. Washer 66 may have a beveled side to accommodate the angle .phi. between the axis x-x of inner tube 55 (and tube 53) and the plane of elongate elements 51 and 52 as shown in FIG. 8-5C. The distal face of tube 55 and the distal face of stem 64 should also be slanted (not shown) at f relative to the axis x-x of tube 55.

Elongate element 51 is provided with an aperture 68 which fits over stem 69, which is integral with or is secured to the distal end of outer tube 53. The length of stem 69 is preferably slightly greater than the thickness of elongate element 51, so that rotation of elongate element 51 relative to elongate element 52 is not hindered. The cross-sectional shapes of aperture 68 and stem 69 are preferably noncircular, and they may, for example, be square, serrated, notched, etc. The distal face of tube 53 and the distal face of stem 69 should be slanted (not shown) at an angle f relative to the axis x--x of tube 53.

Inner tube 55, with attached elongate element 52, fits into outer tube 53. Elongate element 51 will be captured between the base of stem 69 and elongate element 52. Outer tube 53, with inner tube 55 contained therein, and elongate elements 51 and 52 attached, can be inserted into a sheath 61. As shown in FIG. 8-5D, when elongate elements 51 and 52 are drawn into sheath 61 (shown in cross-section), they will be deformed in a direction more parallel to axis x--x. This deformation will be facilitated if elongate elements 51 and 52 are transversely curved along their longitudinal dimensions (i.e., trough shaped). Also, if the outer diameter of tube 53 is only slightly smaller than the inner diameter of sheath 61, the circumferences of elongate elements 51 and 52 along portions 81 and 83 (i.e., the circumferences of elongate elements 51 and 52 around their respective apertures 68 and 63, except for their longitudinally extended portions), should preferably not extend beyond the outer diameter of outer tube 53. When outer tube 53 is extended distally beyond the end of sheath 61, elongate elements 51 and 52 will no longer be constrained, and they will elastically recover their preset shapes again. This deformation and shape recovery is enhanced if the elongate elements are made of a pseudoelastic shape memory alloy.

FIG. 8-5E is a bottom view of a possible embodiment of washer 66. Projection 62 has an outer diameter which is equal to or smaller than the outer diameter of outer tube 53. The surface of projection 62, which holds elongate element 52, may be rough, or it may even have teeth or protrusions, in order to obtain a better grip on elongate element 52. Projection 62 preferably encompasses less than half of the circumferential arc of washer 66. The remaining circumference of washer 66 has a outer diameter which is equal to or smaller than the maximum diameter of the head of screw 65. The head of screw 65 preferably has a diameter which is equal to or less than the smallest diametral dimension of stem 64. As shown in FIG. 8-5D, projection 62 covers the back end of elongate element 52. In this manner, elongate element 52, and secondarily, elongate element 51, can be given as much bending length as possible when they are both constrained within sheath 61. The sides 33 and 34 of projection 62 are preferably parallel to axis y--y, where axis y--y is perpendicular to the longitudinal dimension of elongate element 52 and is perpendicular to the axis of symmetry of washer 66. This will permit ready bending of elongate element 52 along a zone which is perpendicular to its longitudinal dimension.

There may be any suitable means between outer tube 53 and inner tube 55 to prevent plunger 60 from pushing inner tube 55 out of outer 53 tube when plunger 60 is pushed in a distal direction in inner tube 55. In addition, there may be any suitable means between outer tube 53 and sheath 61, so that outer tube 53 can not be completely pushed out of sheath 61 once elongate elements 51 and 52 are adequately extended out of sheath 61 and plunger 60 is used to cause rotation of elongate elements 51 and 52. Plunger 60 can be pushed relative to sheath 61 and tubes 53 and 55 by any suitable manually operated mechanism. Examples of manually operated mechanisms include sliders, pistol grip handles, scissors handles, and syringe-plunger arrangements.

An alternate version of the embodiment of FIG. 8-5 would have a stiff central rod slid along an inner longitudinal bore in the plunger. In this case, the elongate elements would be attached to their respective tubes along one side of the wall of each tube, e.g. by welding or by longitudinally slitting the walls instead of being herd by a screw. The central rod could then be used to straighten the elongate elements (assuming the elongate elements do not have any apertures) and deform them to be more in line with the axis of the tubes.

While most of the specific embodiments are directed to cutting devices, it is to be understood that blunt edges can replace the cutting edges in any of the embodiments. Illustrative blunt and cutting edges are shown in FIGS. 8-6A-E. The cutting and grasping edges may be integral with the elements or may be formed separately and/or of different materials and attached thereto. FIG. 8-6A illustrates grasping surfaces 71 and 72. Surfaces 71 and 72 may be flat or they may contain ridges, protrusions or the like to aid in gripping an object. FIG. 8-6B illustrates shearing cutting edges 73 and 74 which cut an object by a shearing action. FIG. 8-6C illustrates another pair of edges for cutting. In FIG. 8-6C, surface 75 is flat, while edge 76 provides a sharp edge for cutting an object. FIG. 8-6D illustrates cutting edges 77 and 78. Sharp edges 77 and 78 of the triangular cross-sections meet to permit cutting. FIG. 8-6E illustrates cutting edges 80 and 82, which are at any desired angles .alpha. and .beta. relative to the direction of opening and closing of the elongate elements. In all of these embodiments, as well as in all of the embodiments described herein, the cutting edges or gripping surfaces could be made of any material such as steel, diamond, plastic, etc., which is attached to the elongate elements.

In any of the embodiments, dissection could be performed by providing any suitable edge opposite edges 71-78 and 80 and 82 of FIGS. 8-6A-E.

FIGS. 8-7A, B and C illustrate several different means of actuating elongate elements. In FIG. 8-7A, the body portions of elongate elements 150 and 151 are joined together at pivot 152. Also joined at pivot 152 is one end of a linkage composed of four links 153, 154, 155, and 156, which are pivotally connected to each other. Elongate elements 150 and 151 are preferably rigidly attached to links 153 and 154, respectively. Alternatively, links 153 and 154 may merely represent extensions of elongate elements 150 and 151, respectively. Pivot 152 is preferably fixed to a cannula 159. The pivot 157 at the other end of the linkage is joined to rod 158. When rod 158 is pushed in direction 301, pivot 157 is pushed closer to pivot 152. This will cause elongate elements 150 and 151 to splay apart. Since the transverse dimension of linkage 153, 154, 155, and 156 which is perpendicular to rod 158 becomes larger as pivot 157 approaches pivot 152, slots 160 and 161 may be provided in cannula 159 to permit pivot 157 to approach closer to pivot 152 if the transverse dimension of cannula 159 is small. Rod 158 may be pushed (or pulled) relative to cannula 159 by any suitable manually operated mechanism. Examples of manually operated mechanisms include sliders, pistol grip handles, scissors handles, and syringe-plunger arrangements.

Elongate elements 150 and 151 may be constrained in deformed and straightened shapes within a sheath 162. This will permit compact and relatively atraumatic entry into a body. Rod 158 can then be pushed axially in direction 301 within sheath 162. The linkage 153, 154, 155, and 156 will partially extend through slots 160 and 161 in cannula 159, but the inner surface of sheath 162 will prevent pivot 157 from fully approaching pivot 152. Therefore, cannula 159 will be forced to move in direction 301, and elongate elements 150 and 151 will extend from the end of sheath 162 in direction 301. In their extended position, elongate elements 150 and 151 will not be constrained, and they may recover toward their preset shape, which may, for example, be curved out of the plane of the paper. Slots 163 and 164 are provided in sheath 162 to permit rod 158 to push pivot 157 fully toward pivot 152 in order to fully splay elongate elements 150 and 151 apart. Slots 163 and 164 in sheath 162 may be made to overlap slots 160 and 161 in cannula 159 by simply extending cannula 159 far enough within sheath 162, or by extending cannula 159 far enough within sheath 162 and then rotating sheath 162 relative to cannula 159 to allow the respective slots to coincide. Rod 158 may then be used to splay or increasingly overlap elongate elements 150 and 151 as desired.

Rod 158 can be moved in direction 302 so that pivot 157 is moved as far away as possible from pivot 152. This will cause elongate elements 150 and 151 to be in their most overlapped configuration. Moving rod 158 further in direction 302 relative to sheath 162 will cause cannula 159 to slide in direction 302, and will cause elements 150 and 151 to be drawn into straightened (i.e. non-curved) shapes within sheath 162. This will permit the entire assembly to be withdrawn from the body in a compact and relatively atraumatic fashion.

The passive (reference) member of the manually operated mechanism would preferably be mounted on sheath 162. In this fashion, the extension and withdrawal of elongate elements 150 and 151 from or into sheath 162 can be accomplished by utilizing an expanded stroke of the same manually operated mechanism which is used to splay or increasingly overlap elongate elements 150 and 151. In this case, a means must be provided to prevent cannula 159 from sliding beyond a certain location within sheath 162 in direction 301. Also, a means may be provided to minimize relative motion between cannula 159 and sheath 162 while the linkage is being used to repeatedly move elongate elements 150 and 151 toward their splayed or overlapped configurations. Furthermore, the manually operated mechanism would preferably permit axial rotation of the entire assembly of sheath 162 and its contents relative to the manually operated mechanism, so that elongate elements 150 and 151 can be oriented in any desired direction relative to the manually operated mechanism, In the configuration illustrated in FIG. 8-7A, it will be noted that movement of rod 158 in direction 301 will tend to splay elongate elements 150 and 151 apart. As described above, one method of minimizing this splaying before the device is in the correct location is to create slots in specific locations of sheath 162. In an alternative method, links 156 and 155 are shorter than links 153 and 154, and pivot 157 is already positioned as close as possible to pivot 152 during placement of the device into a body. (In this configuration, links 155 and 156 would overlap links 153 and 154, respectively.) Moving rod 158 in direction 301 will then urge elongate elements 150 and 151 toward their overlapped configuration, even though the elongate elements can be extended beyond the end of sheath 162 by motion in direction 301 when the sheath is held fixed. Elongate elements 150 and 151 can then be splayed apart by moving rod 158 in direction 302, When the device is to be withdrawn from a body, rod 158 is moved further in direction 302, so that pivot 157 is as far as possible from pivot 152, where the configuration shown in FIG. 8-7A would be an intermediate position. Elongate elements 150 and 151 will thereby be urged back toward their overlapped configuration. Moving rod 158 even further in direction 302, relative to sheath 162, will permit withdrawal of elongate elements 150 and 151 into sheath 162.

FIG. 8-7B shows an embodiment in which elongate elements 150 and 151 have a pivot 165 and body portions 166 and 167, respectively. Body portions 166 and 167 have slots 168 and 169, respectively. A rod 190 has a peg 191 which is oriented to slidably engage slots 168 and 169. Pivot 165 is fixed to the cannula 192, and slots 168 and 169 are preferably oriented so that motion of rod 190 in direction 310 will urge elongate elements 150 and 151 toward their overlapped configuration, and motion of rod 190 in direction 320 will splay elongate elements 150 and 151 apart. However, slots 168 and 169 could be curved such that extreme motion of rod 190 in direction 320 will again bring elongate elements 150 and 151 to their overlapped configuration. Cannula 192 may be substantially the same as cannula 159 shown in FIG. 8-7A. In addition, a sheath 193, which may substantially be the same as sheath 162 shown in FIG. 8-7A, can be utilized. The function and use of the embodiment shown in FIG. 8-7B is then substantially the same as the embodiment shown in FIG. 8-7A.

A variation of the embodiment illustrated in FIG. 8-7B would include elongate elements in which the slots are placed distal to the pivot point between the elongate elements. (That is, the slots are located between the pivot point and the tips of the elongate elements). Body portions 166 and 167 as shown in FIG. 8-7B, and slots 160, 161, 163, and 164 as shown in FIG. 8-7A may then not be necessary. However, the actuating rod (such as rod 190 shown in FIG. 8-7B), would have to be designed so that it does not interfere with the pivot point between the elongate elements.

FIG. 8-7C shows another embodiment in which the elongate elements 150 and 151 may be made to splay apart or increasingly overlap each other. Elongate elements 150 and 151 are hinged at pivot 170, which is preferably fixed to a cannula 176. Surrounding pivot 170, elongate elements 150 and 151 each have a rounded body portion with teeth along edges 171 and 172, respectively. The teeth engage the corresponding grooves located in jaws 173 and 174 of sliding member 175. The degree of splaying or overlapping of elongate elements 150 and 151 may be limited by limiting the lengths of edges 171 or 172 which are toothed. Additionally, or alternatively, the degree of splaying or overlapping of elongate elements 150 and 151 may be limited by limiting the lengths of the grooved zones in jaws 173 and 174. Sliding member 175 is moved in direction 303 or 305 by any suitable manually operated mechanism. Examples of manually operated mechanisms include sliders, pistol grip handles, scissors handles, and syringe-plunger arrangements. Elongate elements 150 and 151 are preferably moved toward their overlapped configuration when sliding member 175 is moved in direction 303 and moved toward their splayed apart configuration when sliding member 175 is moved in direction 305 (not shown). However, toothed edges 171 and 172 can be located on elongate elements 150 and 151 such that moving sliding member 175 in direction 303 moves elongate elements 150 and 151 toward their splayed configuration and moving sliding member 175 in direction 305 moves elongate elements 150 and 151 toward their overlapped configuration.

Elongate elements 150 and 151 may be constrained in straightened shapes within a sheath 178. This will permit compact and relatively atraumatic entry into a body. Sliding member 175 can then be moved in direction 303 relative to sheath 178 in order to extend elongate elements 150 and 151 from the end of the sheath. In the preferred mode, this motion will also tend to keep elongate elements 150 and 151 in their overlapped configuration without splaying these elements apart in the wrong direction. (As described above, toothed edges 171 and/or 172 and/or the jaws 173 and/or 174 can be designed to prevent splaying in the wrong direction). Elongate elements 150 and 151 can then be repeatedly moved toward their splayed configuration or their overlapped configuration by moving sliding member 175 in directions 305 or 303, respectively, and a means may be provided to minimize relative motion between cannula 176 and sheath 178 during this repetitive motion.

Elongate elements 150 and 151 can be withdrawn back inside sheath 178 by forcibly moving sliding member 175 in direction 305 relative to sheath 178. In a preferred version (not shown) the end of sheath 178 would force elongate elements 150 and 151 into their overlapped configuration, as well as forcing elongate elements 150 and 151 into straightened shapes into sheath 178 in order to permit the entire assembly to be withdrawn from a body in a compact and relatively atraumatic fashion. Alternatively, sheath 178 can be extended over elongate elements 150 and 151 to straighten these elements into sheath 178 and to permit the entire assembly to be withdrawn from a body in a compact and relatively atraumatic fashion.

If a sheath 178 is utilized, it could be mounted to the passive (reference) member of the manually operated mechanism. In this fashion, the extension and withdrawal of elongate elements 150 and 151 from or into sheath 178 can be accomplished by utilizing an expanded stroke of the same manually operated mechanism which is used to move sliding member 175 in order to splay or increasingly overlap elongate elements 150 and 151. In addition, in order to permit the elongate elements 150 and 151 to be oriented in any desired direction relative to the manually operated mechanism, this mechanism would preferably permit axial rotation of the entire assembly of sheath 178 and its contents relative to the manually operated mechanism.

When elongate elements 150 and 151 are to be removed and replaced, it would be advantageous to move cannula 176 far enough in direction 303 so that pivot 170 is beyond the end of sheath 178. Then the pivot pin can be removed, sliding member 175 can be extended in direction 303 beyond the end of cannula 176, and elongate elements 150 and 151 can be simply slid out of jaws 173 and 174 in a direction perpendicular to the longitudinal axis of sliding member 175.

FIG. 8-7D shows how sliding member 175 could be configured around a pivot fixing member 185, which has holes 181 and 182. Elongate elements 150 and 151 are rotatably mounted on a pin 180. The ends of pin 180 can be placed into holes 181 and 182 when sheath 178 is pulled back in direction 400, since the ends of sliding member 175 and the ends of pivot fixing member 185 can gently splay apart when they are not held within sheath 178. When sheath 178 is moved back in direction 401, elongate elements 150 and 151 will be securely held when pin 180 is within sheath 178. The end of pivot fixing member 185 which has holes 181 and 182 can be fork shaped. Preferably a means is provided which minimizes motion of pivot fixing member 185 relative to sheath 178 when sliding member 175 is utilized to repeatedly move elongate elements 150 and 151 toward their splayed or overlapped configurations. FIG. 8-7E shows the device before sheath 178 is pulled back to permit insertion of elongate elements 150 and 151. In this configuration, pin 180 is preferably longer that the dimension between the two fork ends of pivot fixing member 185, so that pin 180 is firmly locked into place.

In the embodiments described for FIGS. 8-7A, B, C, and D, the elongate elements are preferably made of a pseudoelastic material, preferably a pseudoelastic shape memory alloy. The unconstrained shapes may be curved in directions away from the general planes of the body portions of the elongate elements (e.g. out of the plane of the paper). Also, in any of the embodiments described for FIGS. 8-7A, B, C, and D, the elongate elements can be used for cutting, grasping, and/or dissecting tissues. The end portions of the elongate elements can be fashioned appropriately for any of these functions, or separate appropriately designed parts may be attached to the end portions of the elongate elements.

FIG. 8-8 shows a cutting device, similar to the device shown in FIG. 8-1, with curved elongate elements 91 and 93 extended from a housing 92. This permits the elongate elements to be both open for dissecting, cutting and/or grasping and curved at an angle 94 away from axis 95 of housing 92. Angle 94 is defined by the axis 95 of housing 92 and the straight line 96 which passes through the point of intersection of axis 95 with the distal end of housing 92 and the pin 99. Angle 94 can be any desired angle, even greater than 90 degrees, thus permitting dissecting, cutting and/or grasping in a direction off axis 95. This provides access to difficult to reach locations in the body. Elongate elements 91 and 93 are preferably shaped so that they circumscribe spherical arcs which allow the elements to engage each other and perform the cutting or grasping function, either as they are retracted back into housing 92, or as housing 92 is extended over the elongate elements. The portions of elongate elements 91 and 93 which enter housing 92 assume a less curved shape. Elements 91 and 93 may be formed of a pseudoelastic material, preferably a pseudoelastic shape memory alloy.

FIG. 8-9 shows a device in which elongate elements 102 and 106, preferably made of a pseudoelastic material and more preferably a superelastic shape memory alloy, are first held constrained in straightened and deformed shapes inside a cannula 103. This permits compact placement into a body through tissue incision or orifice 108. Elongate elements 102 and 106 are then extended out of cannula 103 by moving elongate elements 102 and 106 in direction 501 relative to cannula 103. Since at least part of extended elongate elements 102 and 106 are no longer constrained, they will splay apart due to recovery of the pseudoelastic material into its preset curved unconstrained shape. Cannula 103 can be then be extended onto elongate elements 102 and 106 to force these elements to approach each other. Alternatively, elongate elements 102 and 106 can be withdrawn back into cannula 103 to force these elements to approach each other. In either mode, the tips of elongate elements 102 and 106 can be used to grasp tissue 107 or an object. The grasping function of elongate elements 102 and 106 can be enhanced by providing the end portions of these elements with bends 104 and 105, teeth (not shown), or the like at their tips. Elongate elements 102 and 106 may also be ribbed or toothed along their entire lengths (not shown). The described mode of action may permit the instrument to be used multiple times in each location.

In embodiments of the invention in which the elongate elements are made of a pseudoelastic shape memory alloy, the large pseudoelastic deformation (up to 11% or more) permits much wider splaying of elongate elements 102 and 106 over a much shorter distance 109 than would be possible with conventional metals. This permits working in more confined spaces, particularly in endoscopic or laparoscopic surgery. A variation of this embodiment may include more than two elongate elements.

Shape memory alloys have a special feature which is beneficial for any of the embodiments of this invention, but in particular for any of the embodiments in which a grasping action is desired (especially in the embodiment shown in FIG. 8-9). As a superelastic shape memory alloy is increasingly deformed from its unloaded shape, some of its austenitic phase changes into stress-induced-martensite. The stress strain curve presents a plateau during this phase change. This means that while the alloy undergoes this phase change, it can deform greatly with only minimal increases in loading. Therefore, elongate elements comprising superelastic shape memory alloys have a built-in safety feature. These elements can be designed (using appropriately treated alloys and appropriate dimensions) such that when they am loaded beyond a certain amount, the elements will tend to deform with a concomitant austenite to stress-induced-martensite phase change, instead of merely presenting a greater resistance with limited deformation to the load, which is seen with conventional metals.

Just as the stress strain curves of shape memory alloys present a plateau upon loading, they also present a plateau in the stress strain curve upon unloading. Unloading occurs when an elongate element made of superelastic shape memory alloy is permitted to revert from a significantly deformed shape toward its original unstressed shape, Because of the plateau, such an element can maintain an almost constant force during much of the unloading cycle until just before it is completely unloaded. This feature is especially useful for any grasper embodiment of this invention, because it means that an object held between one or more elongate elements made of a superelastic shape memory alloy can be gripped with nearly a constant force despite decreases in the amount(s) of deformation of the element(s).

FIGS. 8-10A, B, and C illustrate three views of another embodiment. As elongate elements 121 and 123 are extended outside the housing 120, they splay outward causing end portions 122 and 124 to separate also. When elongate elements 121 and 123 are partially withdrawn into housing 120, they cause end portions 122 and 124 to approach each other. If elongate elements 121 and 123 are further withdrawn into housing 120, the sections 121e and 123e of elongate elements 121 and 123 are forced to deform into straightened shapes in order to pass into housing 120, thus causing the direction of orientation of end portions 122 and 124 to approach the direction of axis 126 of housing 120, and the angle 125 approaches zero degrees (angle 125 is defined by axis 126 of housing 120 and the plane of end portions 122 and 124). End portions 122 and 124 may also be fully or partially withdrawn into housing 120, if desired. The straight configuration permits easy placement and/or removal of the instrument into or from a body in a compact and relatively atraumatic fashion. However, with elongate elements 121 and 123 in a completely extended position, angle 125 permits access to difficult to reach locations.

In the embodiments shown in FIGS. 8-10A, B, and C, the body portions of elongate elements 121 and 123 are preferably made of a pseudoelastic material and more preferably a superelastic shape memory alloy. Alternatively, sections 121e and 123e may be the only parts of elongate elements 121 and 123 which are made of a pseudoelastic material. End portions 122 and 124 may also be made of a pseudoelastic material, but they could be made of any suitable material, even if elements 121 and 123 are made at least in part of a pseudoelastic material. End portions 122 and 124 may have a cutting function or a grasping function. Also, end portions 122 and 124 may be curved. They may also be used to separate (dissect) tissues. The described mode of action may permit the instrument to be used multiple times in each location.

FIGS. 8-11A and 8-11 B show embodiments similar to the embodiments shown in FIGS. 8-1 and 8-8, respectively. In FIGS. 8-11A and 8-11B, the elongate elements 131 and 133 extend beyond the pin 139 in order to provide end portions 135 and 134. End portions 135 and 134 may be unitary extensions of elongate elements 131 and 133 or they may be separate portions bolted or attached to elongate elements 131 and 133. The action of withdrawing elongate elements 131 and 133 into housing 111 closes and deforms body portions 117 and 116, and the scissor action is transmitted to end portions 135 and 134. In this manner, the body portions of the elongate elements act as the actuating means for the end portions of the elongate elements. FIG. 8-11B illustrates a curved version of FIG. 8-11A. The angle 112 is defined by the axis 113 of housing 111 and the straight line 114 passing through the point of intersection of axis 113 with the distal end of the housing and pin 139. Angle 112 can be any number of degrees, even greater than 90 degrees, thus permitting dissection, cutting and/or grasping in a direction off axis 113. This provides access to difficult to reach locations within a body.

In the embodiments of FIGS. 8-11A and 8-11B, body portions 116 and 117 are preferably made of a pseudoelastic material, preferably a superelastic shape memory alloy. Alternatively, only end portions 134 and 135 may be made of a pseudoelastic material, but these end portions could be made of any suitable material, even if body portions 116 and 117 are made of a pseudoelastic material. End portions 134 and 135 may have a cutting function or a grasping function. They may also be used to separate and dissect tissues. The described mode of action may permit the instrument to be used multiple times in each location.

FIG. 8-12 illustrates another embodiment similar to the embodiment shown in FIG. 8-11B. Body portions 141 and 143 of elongate elements 119 and 118 are used to create both a scissors action through a pinned location 149 and also to provide the ability to direct the scissor action at an angle of about ninety degrees off the axis 148 of housing 140. Elongate elements 119 and 118 splay apart when they are outside of housing 140. As housing 140 is pushed over the body portions 141 and 143 in direction 144, sections 141e and 143e move toward one another. This action in turn causes the end portions 146 and 147 to approach each other in a scissor fashion by pivoting around pin 149, which is substantially parallel to axis 148. Because the relative movement of housing 140 in directions 144 and 145 is perpendicular to end portions 146 and 147, the position of these end portions is unchanged with respect to the tissue location. After end portions 146 and 147 have closed, withdrawal of elongate elements 119 and 118 into housing 140 (or moving housing 140 in direction 144 relative to elongate elements 119 and 118) causes sections 141e and 143e to straighten from their curved shapes. This permits end portions 146 and 147 to generally align with axis 148 of housing 140. End portions 146 and 147 may also be fully or partially withdrawn into housing 140, if desired. The straight configuration permits easy placement and/or removal of the instrument from a body in a compact and relatively atraumatic fashion.

In the embodiments of FIG. 8-12, body portions 141 and 143 of elongate elements 119 and 118 are preferably made of a pseudoelastic material, more preferably a superelastic shape memory alloy. Alternatively, sections 141e and 143e may be the only parts of body portions 141 and 143 which are made of pseudoelastic material. End portions 146 and 147 may also be made of pseudoelastic material, but they could be made of any suitable material, even if body portions 141 and 143 are made at least in pad of a pseudoelastic material. End portions 146 and 147 may have a cutting function or a grasping function. They may also be used to separate (dissect) tissues. The described mode of action may permit the instrument to be used multiple times in each location.

A variation of the embodiment shown in FIG. 8-12 would still have the bent portions 141e and 143e, but would have end portions 146 and 147 in a plane which is parallel to axis 148, so that pivot 149 is perpendicular to axis 148. In this embodiment, moving body portion 141 in direction 144 and/or moving body portion 143 in direction 145 would tend to splay end portions 146 and 147 apart. Moving body portion 141 in direction 145 and/or moving element 143 in direction 144 would tend to bring end portions 146 and 147 into a more overlapped configuration. In this manner, the body portions of the elongate elements act as the actuating means for the end portions of the elongate elements. In order to facilitate the requisite bending in sections 141e and 143e, body portions 141 and 143 would preferably be either round or made of flat material oriented in a plane perpendicular to the plane of end portions 146 and 147. If body portions 141 and 143 are made of flat material, they may include a 90 degree twist in the material between sections 141e and 143e and end portions 146 and 147, respectively.

FIG. 8-13 shows a device of this invention in which the elongate elements 186 and 187 are bent, preferably about 90 degrees, relative to the longitudinal axis of housing 188. The elongate elements are slid longitudinally along the axis of housing 188 by means of any suitable manually operated mechanism in order to separate end portions 183 and 184 from each other or to bring end portions 183 and 184 toward each other or even in contact with each other. End portions 183 and 184 can have any suitable surfaces in order to permit dissection, cutting, and/or grasping. Elongate elements 186 and 187 are preferably made of a pseudoelastic material, more preferably a superelastic shape memory alloy. This permits the bent portions of elongate elements 186 and 187 to be deformed and straightened so that the elongate elements can be withdrawn into housing 188. The straight configuration permits easy placement and/or removal of the instrument from a body in a compact and relatively atraumatic fashion. End portions 183 and 184 may be made of any suitable material, whether it is pseudoelastic or not.

In any of the embodiments of this eighth form of the invention, preferably both of the elongate elements are actuated by the manually operated mechanism, so that dissection, cutting, and/or grasping is done by an equal symmetrical motion of each elongate element. However, in some situations, it may be desirable to have embodiments in which one elongate element is moved more by the manually operated mechanism than the other elongate element. In some cases, it may even be desired to have one elongate element function as a stationary and thereby passive element, where the manually operated mechanism only moves the other elongate element.

In any of the embodiments of this eighth form of the invention, any suitable manually operated mechanism may be utilized to move the elongate elements. Possible mechanisms include sliders, pistol grip handles, scissors handles, and syringe-plunger arrangements. In any of the embodiments of this invention, it may be desirable to be able to axial rotate the elongate elements relative to the manually operated mechanism, so that the elongate elements can be pointed in a preferred direction without having to rotate the manually operated mechanism itself. This feature would enhance the comfort of using a device of this invention. However, a means is preferably provided to prevent any undesired axial rotation of the elongate elements relative to the manually operated mechanism while the manually operated mechanism is being used to splay or overlap the elongate elements.

In any of the embodiments of this invention, a suitable means may be provided for passing a fluid (liquid or gas) through the device for irrigation, aspiration, insufflation, etc. In any of the embodiments of this invention, electricity may be passed to one or both end portion(s) of the elongate element(s) for purposes of electrocautery or electrocutting.

In any of the embodiments of this invention, the tips (of the end portions) of the elongate elements may be pointed or blunt. Pointed tips may facilitate the use of the device of this invention in the separation (dissection) of tissues, while blunt tips would minimize the risk of any undesired trauma that the tips could inflict upon tissues.

While the invention has been described in connection with specific embodiments thereof, those skilled in the art will recognize that various modifications are possible within the principles described herein. Such modifications, variations; uses, or adaptations of the invention, including such departures from the present disclosure as come within known or customary practice in the art, fall within the scope of the invention and of the appended claims.

What is claimed is:

1. A surgical device comprising:
   a housing having:
   an actuator end;
   a deployment end; and
   a bore extending between the actuator end and the deployment end;
   a barrier member comprising:
   an elastically deformable curved element comprising a shape memory alloy; and
   a barrier coupled to the curved element;
   a connector coupled to the barrier member and extending through the bore; and
   an actuator coupled to the connector, the actuator being positioned outside of the actuator end;
   wherein the barrier member is reversibly moveable by the actuator through the deployment end between a first position inside of the bore where the curved element is compressed and a second position outside of the bore where the curved element is expanded.

2. The surgical device of claim 1 further comprising a seal between the housing and the connector.

3. The surgical device of claim 1 wherein the housing has an inner diameter of from about 0.25 cm to about 2.5 cm.

4. The surgical device of claim 1 wherein the housing has an inner diameter of from about 0.3 cm to about 2 cm.

5. The surgical device of claim 1 wherein the housing has an outer diameter of from about 0.4 cm to about 3 cm.

6. The surgical device of claim 1 wherein the housing has an inner diameter of from about 0.4 cm to about 1.5 cm.

7. The surgical device of claim 1 wherein the curved element is a loop.

8. The surgical device of claim 7 wherein the loop has a diameter of from about 1 cm to about 5 cm.

9. The surgical device of claim 8 wherein the barrier has a depth of from about 1 to about 7 cm.

10. The surgical device of claim 1 wherein the barrier is permeable to human body fluids.

11. The surgical device of claim 10 wherein the barrier comprises at least one of the group consisting of a net, a web, and a grid.

12. The surgical device of claim 11 wherein the barrier further comprises at least one of the group consisting of polyethylene, polyvinyl chloride, urethane, and silicone rubber.

13. The surgical device of claim 1 wherein the curved element is at least one of a wire and a strip of elastic material.

14. The surgical device of claim 1 further comprising a means to prevent rotation of the baffler member relative to the housing.

15. The surgical device of claim 1 wherein the actuator comprises a syringe plunger mechanism.

16. The surgical device of claim 1 wherein the actuator comprises a thumb actuated mechanism.

17. A method for capturing objects in a mammalian body comprising:
    positioning a device according to claim 16 in the space in the mammalian body;
    pushing the actuator to move the barrier member from the first position to the second position;
    manipulating the matter using the baffler material;
    pulling the actuator to move the barrier member from the second position to the first position; and
    removing the device from the body.

18. A method for manipulating matter in a space in a mammalian body comprising:
    positioning a device according to claim 1 in the space in the mammalian body;
    engaging the actuator to move the barrier member from the first position to the second position; and
    manipulating the matter using the barrier material.

19. The method of claim 18 further comprising:
    moving the actuator to move the baffler member from the second position to the first position; and
    removing the device from the body.

20. The surgical device of claim 1 further comprising a cautery wire coupled to the actuator and extending through the bore, the cautery wire being reversibly moveable by the actuator through the deployment end between a first position inside of the bore and a second position outside of the bore.

* * * * *